(12) United States Patent
Belanger et al.

(10) Patent No.: US 8,278,337 B2
(45) Date of Patent: Oct. 2, 2012

(54) SUBSTITUTED PYRIDINES THAT ARE JNK INHIBITORS

(75) Inventors: David B. Belanger, Cambridge, MA (US); M. Arshad Siddiqui, Newton, MA (US); Patrick J. Curran, Winthrop, MA (US); Blake Hamann, Linthicum, MD (US); Lianyun Zhao, Burlington, MA (US); Panduranga Adulla P. Reddy, Walpole, MA (US); Praveen K. Tadikonda, Norwood, MA (US); Gerald W. Shipps, Jr., Stoneham, MA (US); Umar Faruk Mansoor, Framingham, MA (US)

(73) Assignee: Merck Sharp & Dohme, Rahway, NJ (US)

( * ) Notice: Subject to any disclaimer, the term of this patent is extended or adjusted under 35 U.S.C. 154(b) by 182 days.

(21) Appl. No.: 12/519,731

(22) PCT Filed: Dec. 17, 2007

(86) PCT No.: PCT/US2007/025764
§ 371 (c)(1),
(2), (4) Date: Feb. 24, 2010

(87) PCT Pub. No.: WO2008/082487
PCT Pub. Date: Jul. 10, 2008

(65) Prior Publication Data
US 2010/0179141 A1    Jul. 15, 2010

Related U.S. Application Data

(60) Provisional application No. 60/876,104, filed on Dec. 20, 2006.

(51) Int. Cl.
*A61K 31/44* (2006.01)

(52) U.S. Cl. ........ 514/354; 544/281; 544/284; 544/333; 544/353; 544/359; 546/118; 546/121; 546/122; 546/152; 546/323; 548/146; 548/152; 548/373.1

(58) Field of Classification Search .................. 514/354; 544/281, 284, 333, 353, 359; 546/118, 121, 546/122, 152, 323; 548/146, 152, 373.1
See application file for complete search history.

(56) References Cited

U.S. PATENT DOCUMENTS

2004/0102506 A1    5/2004    Hale
2010/0298314 A1    11/2010    Reddy et al.

FOREIGN PATENT DOCUMENTS

| EP | 1 380 576 A | 1/2004 |
|---|---|---|
| WO | WO 2004/013138 A | 2/2004 |
| WO | WO 2004/028539 A | 4/2004 |
| WO | WO 2004/052880 A | 6/2004 |
| WO | WO 2005/003123 A | 1/2005 |
| WO | WO 2005/074513 A | 8/2005 |
| WO | WO 2005/085252 A | 9/2005 |
| WO | WO 2005/100342 A | 10/2005 |
| WO | WO 2006/034277 A | 3/2006 |
| WO | WO 2005/125101 A | 11/2006 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chavez, et al. Inorganic Chemistry, 36(27), 1997, 6323-6327.*
Database Beilstein Beilstein Institute for Organic Chemistry, Frankfurt-Main, DE; XP002486349 Database accession No. BRN: 606563 abstract & Journal of Chemical Society, 1965, pp. 2778-2786.
Database Beilstein Beilstein Institute for Organic Chemistry, Frankfurt-Main, DE; XP002486350 Database accession No. BRN: 4453405 abstract & Synthesis, vol. 3, 1984, pp. 263-265.
Database Beilstein Beilstein Institute for Organic Chemistry, Frankfurt-Main, DE; XP002486351 Database accession No. BRN: 515555 abstract & Journal of Heterocyclic Chemistry, vol. 15, 1978, p. 119.
Database Beilstein Beilstein Institute for Organic Chemistry, Frankfurt-Main, DE; XP002486352 Database accession No. BRN: 8067187 abstract & Angewandte Chemie, International Edition, vol. 37, No. 16, 1998, pp. 2234-2237.
Database Beilstein Beilstein Institute for Organic Chemistry, Frankfurt-Main, DE; XP002486353 Database accession No. BRN: 10160724 abstract & Tetrahedron Letters, vol. 46, No. 48, 2005, pp. 8355-8357.
English Abstract for Database Beilstein Beilstein Institute for Organic Chemistry, Frankfurt-Main, DE; XP002486354 Database accession No. BRN: 980922 abstract & Journal Fuer Praktische Chemie, vol. 313, 1971, pp. 977-985, (see reference No. 14).
Database Beilstein Beilstein Institute for Organic Chemistry, Frankfurt-Main, DE; XP002486355 Database accession No. BRN: 976835 abstract & Geterotsiklicheskikh Soedinenii, vol. 1, 1967, p. 166.
International Search Report PCT/US2007/025780 date of mailing Mar. 7, 2008, 6 pages.
Written Opinion of the International Searching Authority PCT/US2007/025780 date of mailing Mar. 7, 2008, 6 pages.

(Continued)

*Primary Examiner* — Douglas M Willis
(74) *Attorney, Agent, or Firm* — Henry C. Jeanette; David A. Muthard

(57) ABSTRACT

Disclosed are compounds of the formula (I) wherein X is N or CH, and Y is N or $CR^5$. Also disclosed are methods of treating JNK and ERK mediated diseases using the compounds of formula 1.0.

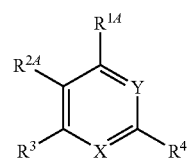

(1.0)

25 Claims, No Drawings

OTHER PUBLICATIONS

Chavarot, M. et al., Synthesis of an Adenine-Pyridinaldoxime-Acridine Conjugate for Recognition of Abasic Site Lesions in DNA, Tetrahedron, Elsevier Science Publishisers, Amsterdam, NL, vol. 53, No. 40, Oct. 6, 1997, pp. 13749-13756, XP004106254 ISSN: 0040-4020.

You, J. et al., Synthesis of New Chiral Macrocyclic Tetraoxo Polyamines Containing Pyridine Ring and Functional Arms, Synthetic Communications, Taylor & Francis, Philadelphia, PA, vol. 29, No. 14, Jan. 1, 1991, pp. 2447-2455, XP008049199, ISSN: 0039-7911.

International Search Report PCT/US2007/025764 date of mailing Oct. 29, 2008, 4 pages.

Written Opinion of the International Searching Authority PCT/US2007/025764 date of mailing Oct. 29, 2008, 7 pages.

Database Beilstein Beilstein Institute for Organic Chemistry, Frankfurt-Main, DE; XP002486354 Database accession No. BRN: 980922 abstract & Journal Fuer Praktische Chemie, vol. 313, 1971, pp. 977-985, (see reference No. 6).

\* cited by examiner

SUBSTITUTED PYRIDINES THAT ARE JNK INHIBITORS

REFERENCE TO RELATED APPLICATION

This application claims the benefit of U.S. Provisional Application No. 60/876,104 filed Dec. 20, 2006, the disclosure of which is incorporated herein by reference thereto.

FIELD OF THE INVENTION

The present invention relates to novel substituted pyridyl compounds, substituted pyrimidinyl compounds, and substituted phenyl compounds, pharmaceutical compositions comprising said compounds, and methods for treating diseases or conditions, such as, for example, inflammation, autoimmune diseases, rheumatoid arthritis (RA), psoriasis, metabolic diseases, cardiovascular disease, and neurodegenerative diseases, by administering at least one of said compounds. The novel compounds of this invention are inhibitors of Kinases, and are therefore inhibitors of MAP kinases, and in turn are therefore inhibitors of JNK, ERK1 and ERK2. Thus, for example, the novel compounds of this invention inhibit c-Jun-N-terminal kinase, and therefore the novel compounds of this invention are used to treat or inhibit diseases mediated by c-Jun-N-terminal kinase.

BACKGROUND OF THE INVENTION

Protein Kinases are divided into two families (1) tyrosine kinase family and (2) serine and threonine kinase family depending on their phosphorylation site (tyrosine, or serine and threonine. Protein kinse activity controls a wide variety of cell life such as growth, differentiation and proliferation. Some of the examples for tyrosine kinase are ALK4, Azl, Brk, EphB4, Fer, Fgr, JAK family (JAK1 and JAK2), Ret, TrkA, Tec family BTK, IKK, ITK and examples for serine and threonine kinase are Ark5, Msk1, Nek2, Pim (Pim1 and Pim2), PLK, RockI and II, SGK1,2 3, MEK, Erk, Chk, Aurrora and C-met kinases.

C-Jun-N-terminal kinases (i.e., JNKs), which belong to the mitogen activated protein kinase family, are triggered in response to cytokines, mitogens, osmotic stress and ultraviolet readiation. JNKs are divided into three (JNK1, JNK2 and JNK3) major isoforms depending on their gene sequence. Further, these JNKs are divided into 10 splicing isoforms in cells (Gupta, S., T. Barret, A. J., Whitmarsh, J. Cavanagh, H. K. Sluss, B. Derijard, and R. J. Davis 1996, EMBO J. 15, 2760-2770). JNK1 and JNK2 are ubiquitously expressed (Mohit, A. A., Martin, J. H., Miller, C. A Neuron 14, 67-70, 1995), where as JNK3 is expressed in brain and to a lesser extent in the heart and testes.

JNKs are activated by dual phosphorylation of Thr 183 and Tyr 185 by MKK4 and MKK7 kinases (Lin A., Minden A., Martinetto H., Claret F.-Z., Lange-Carter C., Mercurio F., Johnson G. L., and Karin M. Science 268: 286-289, 1995). MKK4 preferentially phosphorylates JNK on tyrosine whereas MKK7 phosphorylates JNK on threonine. Activated c-Jun-N-terminal kinase in turn activates by phosphorylating various transcription factors such as c-Jun, AP1, ATF2, IRS1, NFAT4 and Bcl-2, etc. (Karin M and Hunter T. Curr. Biol. 5,747-757, 1995 and Shaulian, E., and Karin, M., Nat. Cell Biol. 4, E131-136, 2002). Either JNK1 or JNK2 knockout studies in mice revealed a deficiency in T-helper cells (Dong, C.; Yang, D. D.; Wysk, M.; Whitmarsh, A. J.; Davis, R. J.; Flavell, R. A., Science 1998, 282, 2092-2095; Yang, D. D.; Conze, D.; Whitmarsh, A. J.; Barrett, T.; Davis, R. J.; Rincon, M.; Flavell, R. A. Immunity 1998, 9, 575-585.; Sabapathy, K.; Hu, Y.; Kallunki, T.; Schreiber, M.; David, J. P.; Jochum, W.; Wagner, E. F.; Karin, M., Curr. Biol. 1999, 9, 116-125), whereas double knockouts are embryonic lethal (Tournier, C.; Hess, P.; Yang, D. D.; Xu, J.; Turner, T. K.; Nimnual, A.; Bar-Sagi, D.; Jones, S. N.; Flavell, R. A.; Davis, R. J., Science 2000, 288, 870-874). The JNK3 knockout mouse exhibit resistance to kainic acid induced apoptosis in the hippocampus and to subsequent seizures (Yang, D. D.; Kuan, C. Y.; Whitmarsh, A. J.; Rincon, M.; Zheng, T. S.; Davis, R. J.; Rakic, P.; Flavell, R. A., Nature 1997, 389, 865-870).

Those skilled in the art know that the JNK pathway is activated in several diseases, such as, for example, inflammatory, neurodegenerative and metabolic diseases. Those skilled in the art also know that JNK activation is required for the transformation induced by RAS, an oncogene activated in many human cancers.

In view of the interest in treating diseases mediated by c-Jun-N-terminal kinase, compounds that inhibit c-Jun-N-terminal kinase would be a welcome contribution to the art. This invention provides that contribution.

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

SUMMARY OF THE INVENTION

The present invention provides novel compounds useful for treating or preventing diseases (or conditions) associated with the Kinase pathway. Thus, the present invention provides novel compounds useful for treating or preventing diseases (or conditions) associated with MAP kinases, such as, for example, JNK1, ERK1 and ERK2.

Thus, for example, the present invention provides a method of treating or preventing conditions associated with JNK activation or JNK pathway using novel compounds of formula 1.0.

This invention provides novel compounds that are inhibitors of Kinase, and therefore MAP kinases, such as, for example, inhibitors of JNK (e.g., JNK1). The novel compounds of this invention have the formula:

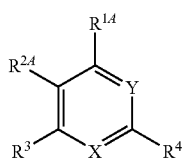

(1.0)

or pharmaceutically acceptable salts, esters or solvates thereof, wherein X, Y, $R^{1A}$, $R^{2A}$, $R^3$ and $R^4$ are as defined below.

This invention also provides the final compounds of Examples 1 to 21, 22.1 to 25, and 26.1 to 38.

This invention also provides compounds of formula 1.0 (e.g., the final compounds of Examples 1 to 21, 22.1 to 25, and 26.1 to 38) in purified and isolated form.

This invention also provides compounds of formula 1.0 (e.g., the final compounds of Examples 1 to 21, 22.1 to 25, and 26.1 to 38) in purified form.

This invention also provides compounds of formula 1.0 (e.g., the final compounds of Examples 1 to 21, 22.1 to 25, and 26.1 to 38) in isolated form.

This invention also provides pharmaceutically acceptable salts of the compounds of formula 1.0 (e.g., the final compounds of Examples 1 to 21, 22.1 to 25, and 26.1 to 38).

This invention also provides pharmaceutically acceptable esters of the compounds of formula 1.0.

This invention also provides solvates of the compounds of formula 1.0.

This invention also provides compounds of formula (1.0) selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436.

This invention also provides compounds of formula (1.0) selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436, in pure and isolated form.

This invention also provides compounds of formula (1.0) selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436, in pure form.

This invention also provides compounds of formula (1.0) selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436, in isolated form.

This invention also provides pharmaceutically acceptable salts of compounds selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436.

This invention also provides pharmaceutically acceptable esters of compounds selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436.

This invention also provides solvates of compounds selected from the group consisting of compounds: 5-78, 85-128, 129-163, 171, 174-186, 189-196, 200-203, 205, 206, 207, 210, 213, 216, 219, 222, 228, 233-235, 238, 241, 244-248, 254-258, 261, 263, 264, 267, 273-276, 287-292, 293, 295-297, 302, 303, 309, 310, 314-339, 343-347, 353-356, 362-365, 371, 372, 376-378, 380-384, 388-396, 399-402, 407, 408, 414-417, 419-422, 428-429, and 436.

This invention also provides a pharmaceutical composition comprising at least one (e.g., 1, 2 or 3, or 1 or 2, or 1, and usually 1) compound of formula 1.0, and a pharmaceutically acceptable carrier.

This invention also provides a pharmaceutical composition comprising a compound of formula 1.0, and a pharmaceutically acceptable carrier.

This invention also provides a method of inhibiting JNK (e.g., JNK1) in a patient in need of such treatment, said method comprising administering to said patient an effective amount of at least one (e.g., 1, 2 or 3, or 1 or 2, or 1, and usually 1) compound of formula 1.0.

This invention also provides a method of inhibiting JNK (e.g., JNK1) in a patient in need of such treatment, said method comprising administering to said patient an effective amount of a compound of formula 1.0.

This invention also provides a method of treating a JNK (e.g., JNK1) mediated disease in a patient in need of such treatment, said treatment comprising administering to said patient an effective amount of at least one (e.g., 1, 2 or 3, or 1 or 2, or 1, and usually 1) compound of formula 1.0.

This invention also provides a method of treating a JNK (e.g., JNK1) mediated disease in a patient in need of such treatment, said treatment comprising administering to said patient an effective amount of a compound of formula 1.0.

This invention also provides any one of the above methods for treating a JNK mediated disease wherein said JNK mediated disease is selected from the group consisting of: inflammation, autoimmune disorders (such as, for example, rheumatoid arthritis, multiple sclerosis, asthma, inflammatory bowel disease, psoriasis, pancreatitis, septic shock, transplant rejection and bronchitis), metabolic diseases (such as, for example, diabetes, insulin resistance, and obesity), neurological diseases (such as, for example, Alzheimer's, epilepsy, parkinson's disease, spinal card injury, memory and attention disorders), pain and related syndromes, cancer (such as, for example, breast, colorectal, pancreatic, ovarian, prostate and small cell lung cancer), cardiovascular diseases (such as, for example, hypertrophy and other types of left ventricular remodeling, ischemia/reperfusion injury, angiogenesis and atherogenesis), hepatic ischemia, reperfusion injury, lung fibrosism and liver fibrosis.

This invention also provides any one of the above methods for treating a JNK mediated disease wherein inflammation is treated.

This invention also provides any one of the above methods for treating a JNK mediated disease wherein rheumatoid arthritis is treated.

This invention also provides any one of the above methods for treating a JNK mediated disease wherein asthma is treated.

This invention also provides any one of the above methods for treating a JNK mediated disease wherein multiple sclerosis is treated.

This invention also provides any one of the above methods for treating a JNK mediated disease wherein inflammatory bowel disease is treated.

This invention also provides any one of the above methods for treating a JNK mediated disease wherein psorisis is treated.

This invention also provides any one of the above methods for treating a JNK mediated disease wherein diabetes is treated.

This invention also provides any one of the above methods for treating a JNK mediated disease wherein autoimmune disorders are treated.

This invention also provides any one of the above methods for treating a JNK mediated disease wherein metabolic diseases are treated.

This invention also provides any one of the above methods for treating a JNK mediated disease wherein neurological diseases are treated.

This invention also provides any one of the above methods for treating a JNK mediated disease wherein pain is treated.

This invention also provides any one of the above methods for treating a JNK mediated disease wherein cancer is treated.

This invention also provides any one of the above methods for treating a JNK mediated disease wherein cardiovascular diseases are treated.

This invention is provides any one of the above methods for treating a JNK mediated disease wherein the compound of formula 1 is administered in combination with at least one other active ingredient know in the art for the treatment of said disease. For example, in the treatment of cancer, the compound of formula 1.0 is administered in combination with at least one (e.g., 1, 2 or 3, or 1 or 2, or 1) chemotherapeutic agent. Administration "in combination with" means the drugs are administered during the same treatment protocol, for example, administration sequentially or consecutively during the treatment protocol. Examples of chemotherapeutic agents include, for example, antimetabolites, such as, for example, taxol.

This invention also provides any one of the above methods wherein said treatment comprises administering to said patient an effective amount of a pharmaceutical composition comprising at least one (e.g., 1, 2 or 3, or 1 or 2, or 1, and usually 1) compound of formula 1.0 and a pharmaceutically acceptable carrier.

This invention also provides any one of the above methods wherein said treatment comprises administering to said patient an effective amount of a pharmaceutical composition comprising a compound of formula 1.0 and a pharmaceutically acceptable carrier.

This invention also provides a method of inhibiting ERK (i.e., inhibiting the activity of ERK) in a patient in need of such treatment comprising administering to said patient an effective amount of at least one (e.g., 1, 2 or 3, 1 or 2, and usually 1) compound of formula 1.0.

This invention also provides a method of inhibiting ERK1 (i.e., inhibiting the activity of ERK1) in a patient in need of such treatment comprising administering to said patient an effective amount of at least one (e.g., 1, 2 or 3, 1 or 2, and usually 1) compound of formula 1.0.

This invention also provides a method of inhibiting ERK2 (i.e., inhibiting the activity of ERK2) in a patient in need of such treatment comprising administering to said patient an effective amount of at least one (e.g., 1, 2 or 3, 1 or 2, and usually 1) compound of formula 1.0.

This invention also provides a method of inhibiting ERK1 and ERK2 (i.e., inhibiting the activity of ERK1 and ERK2) in a patient in need of such treatment comprising administering to said patient an effective amount of at least one (e.g., 1, 2 or 3, 1 or 2, and usually 1) compound of formula 1.0.

This invention also provides a method for treating cancer in a patient in need of such treatment, said method comprising administering to said patient an effective amount of at least one (e.g., 1, 2 or 3, 1 or 2, and usually 1) compound of formula 1.0.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method of treating cancer in a patient in need of such treatment, said method comprising administering to said patient an effective amount of at least one (e.g., 1, 2 or 3, 1 or 2, and usually 1) compound of formula 1.0 in combination with at least one (e.g., 1, 2 or 3, 1 or 2, and usually 1) signal transduction inhibitor.

This invention also provides a method of treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 in combination with at least one (e.g., 1, 2 or 3, 1 or 2, and usually 1) signal transduction inhibitor.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of formula 1.0.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of at least one (e.g., 1, 2 or 3, 1 or 2, and usually 1) compound of formula 1.0, wherein said cancer is selected from the group consisting of: melanoma, pancreatic cancer, thryroid cancer, colorectal cancer, lung cancer, breast cancer, and ovarian cancer.

This invention also provides a method for treating cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent wherein said cancer is selected from the group consisting of: melanoma, pancreatic cancer, thryroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, wherein said cancer is selected from the group consisting of: melanoma, pancreatic cancer, thryroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent wherein said cancer is selected from the group consisting of: melanoma, pancreatic cancer, thryroid cancer, colorectal cancer, lung cancer, breast cancer, and ovarian cancer.

This invention also provides a method for treating melanoma in a patient in need of such treatment, said method comprising administering to said patient an effective amount of at least one (e.g., 1, 2 or 3, 1 or 2, and usually 1) compound of formula 1.0.

This invention also provides a method for treating melanoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of at least one (e.g., 1, 2 or 3, 1 or 2, and usually 1) compound of formula 1.0.

This invention also provides a method for treating pancreatic cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of at least one (e.g., 1, 2 or 3, 1 or 2, and usually 1) compound of formula 1.0.

This invention also provides a method for treating thyroid cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of at least one (e.g., 1, 2 or 3, 1 or 2, and usually 1) compound of formula 1.0.

This invention also provides a method for treating colorectal cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of at least one (e.g., 1, 2 or 3, 1 or 2, and usually 1) compound of formula 1.0.

This invention also provides a method for treating lung cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of at least one (e.g., 1, 2 or 3, 1 or 2, and usually 1) compound of formula 1.0.

This invention also provides a method for treating breast cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of at least one (e.g., 1, 2 or 3, 1 or 2, and usually 1) compound of formula 1.0.

This invention also provides a method for treating ovarian cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1)

compound of formula 1.0, in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

The methods of treating breast cancer described herein include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

The methods of treating hormone-dependent breast cancer can also be used to prevent breast cancer in patients having a high risk of developing breast cancer.

Thus, this invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 in combination with hormonal therapies (i.e., antihormonal agents), and in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) a in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0, in combination with an effective amount of a chemotherapeutic agent wherein said chemotherapeutic agent is temozolomide.

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of a chemotherapeutic agent, wherein said chemotherapeutic agent is temozolomide.

This invention also provides a method for treating prostate cancer in a patient in need of such treatment, said method comprising administering to said patient an effective amount of at least one (e.g., 1, 2 or 3, 1 or 2, and usually 1) compound of formula 1.0.

This invention also provides a method for treating prostate cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0.

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0.

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating acute myelogenous leukemia (AML)in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating acute myelogenous leukemia (AML)in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0.

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0.

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of at least one (e.g., 1, 2 or 3, 1 or 2, and usually 1) compound of formula 1.0.

This invention also provides a method for treating bladder cancer in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0.

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of at least one (e.g., 1, 2 or 3, 1 or 2, and usually 1) compound of formula 1.0.

This invention also provides a method for treating multiple myeloma in a patient in need of such treatment, said method comprising administering to said patient an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0.

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0, in combination with an effective amount of at least one (e.g., 1, 2 or 3, 1 or 2, or 1) chemotherapeutic agent.

In the methods of this invention the compounds of this invention can be administered concurrently or sequentially (i.e., consecutively) with the chemotherapeutic agents or the signal transduction inhibitor.

The methods of treating cancers described herein can optionally include the administration of an effective amount of radiation (i.e., the methods of treating cancers described herein optionally include the administration of radiation therapy).

DETAILED DESCRIPTION OF THE INVENTION

As used herein, unless indicated otherwise, the abbreviations below have the meanings indicated.
ACN Acetonitrile
AcOH Acetic acid DCC Dicyclohexylcarbodiimide
DCU Dicyclohexylurea
DCM Dichloromethane
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
EtOAc Ethyl acetate
EtOH Ethanol
HATU N,N,N',N'-Tetramethyl-O-(7-Azabenzotriazol-1-yl)Uronium hexafluorophosphate
Hex hexanes
HPLC High pressure liquid chromatography
LCMS Liquid chromatography mass spectrometry
mCPBA meta-Chloroperoxybenzoic acid
MeOH Methanol
NaH Sodium hydride
NMR Nuclear magnetic resonance
PFP Pentafluorophenol
PMB p-methoxybenzyl
Pyr Pyridine
RT Room temperature
TFA Trifluoroacetic acid
THF Tetrahydrofuran
TLC Thin layer chromatography
TMS Trimethylsilyl As herein, the following terms, unless indicated otherwise, have the following meanings indicated:

"Patient" includes both human and animals (and preferably a human being).

"Mammal" means humans and other mammalian animals.

"One or more" includes, for example, 1, 2 or 3, or 1 or 2, or 1.

"At least one" includes, for example, 1, 2 or 3, or 1 or 2, or 1.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Z$_1$Z$_2$N—, Z$_1$Z$_2$N-alkyl-, Z$_1$Z$_2$NC(O)—, Z$_1$Z$_2$NSO$_2$— and —SO$_2$NZ$_1$Z$_2$, wherein Z$_1$ and Z$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

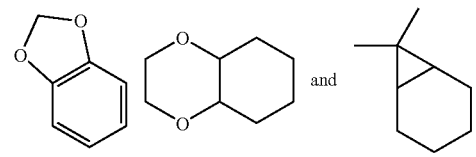

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" (e.g., "heterocycloalkyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a ring system (as described above) that is substituted with a single moiety (e.g., =O) which simultaneously replaces two available hydrogens on the same carbon atom on a ring system. An example of such a heterocyclyl is pyrrolidone:

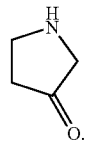

"Heterocyclylalkyl" (e.g., "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" ("e.g., heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a ring systemt (as described above) that is substituted with a single moiety (e.g., =O) which simultaneously replaces two available hydrogens on the same carbon atom on a ring system. An example of such a heterocyclenyl is pyrrolidinone:

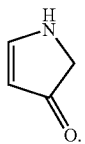

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

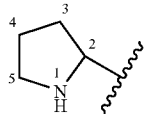

there is no —OH attached directly to carbons marked 2 and 5.

It should also be noted that tautomeric forms such as, for example, the moieties:

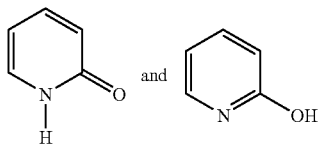

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O-group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S-group in which the alkyl group is as previously described. Non-limiting examples of suitable alkylthio groups include methylthio and ethylthio. The bond to the parent moiety is through the sulfur.

"Arylthio" means an aryl-S-group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any constituent or in Formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

"Prodrug" represents compounds that are rapidly transformed, for example, by hydrolysis in blood, in vivo to the parent compound, i.e., to the compounds of formula 1.0 or to a salt and/or to a solvate thereof; A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The scope of this invention includes Prodrugs of the novel compounds of this invention.

For example, if a compound of Formula 1.0 or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino) ethyl having from 4 to 10 carbon atoms, 3-phthalidyl, 4-crotonolactonyl, gamma-butyrolacton-4-yl, di-N,N—$(C_1-C_2)$ alkylamino$(C_2-C_3)$alkyl (such as β-dimethylaminoethyl), carbamoyl-$(C_1-C_2)$alkyl, N,N-di$(C_1-C_2)$alkyl-carbamoyl-(C1-C2)alkyl and piperidino-, pyrrolidino- or morpholino $(C_2-C_3)$alkyl, and the like.

Similarly, if a compound of Formula 1.0 contains an alcohol functional group, a prodrug can be formed by the replacement of the hydrogen atom of the alcohol group with a group such as, for example, $(C_1-C_6)$alkanoyloxymethyl, 1-$(C_1-C_6)$ alkanoyloxy)-ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-a-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of Formula 1.0 incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

This invention is also provides compounds of formula 1.0 in pure or isolated form.

This invention also includes pharmaceutically esters of the compounds of formula 1.0.

This invention also includes pharmaceutically acceptable solvates of the compounds of formula 1.0.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of formula 1.0 can form salts which are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of formula 1.0, and salts, solvates, esters and prodrugs thereof, may exist in their tautomeric form (for example, as an amide or imino ether). All such tautomeric forms are contemplated herein as part of the present invention.

The compounds of formula 1.0 may contain asymmetric or chiral centers, and, therefore, exist in different stereoisomeric forms. It is intended that all stereoisomeric forms of the compounds of formula 1.0 as well as mixtures thereof, including racemic mixtures, form part of the present invention. In addition, the present invention embraces all geometric and positional isomers. For example, if a compound of formula 1.0 incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula 1.0 may be atropisomers (e.g., substituted biaryls) and are considered as part of this invention. Enantiomers can also be separated by use of chiral HPLC column.

It is also possible that the compounds of formula 1.0 may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula 1.0 can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of formula 1.0, and of the salts, solvates, esters and prodrugs of the compounds of formula 1.0, are intended to be included in the present invention.

The compounds according to the invention have pharmacological properties; in particular, the compounds of formula 1.0 are inhibitors of JNK (e.g., JNK1, 2 or 3).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Anti-cancer agent", "chemotherapeutic agent", and "antineoplastic agent" have the same meaning, and these terms represent the drugs (medicaments) used to treat cancer.

"Antineoplastic agent" represents a chemotherapeutic agent effective against cancer.

"Compound", with reference to the antineoplastic agents, includes the agents that are antibodies.

"Concurrently" represents (1) simultaneously in time (e.g., at the same time); or (2) at different times during the course of a common treatment schedule;

"Consecutively" means one following the other;

"Different", as used in the phrase "different antineoplastic agents", means that the agents are not the same compound or structure. Preferably, "different" as used in the phrase "different antineoplastic agents" means not from the same class of antineoplastic agents. For example, one antineoplastic agent is a taxane, and another antineoplastic agent is a platinum coordinator compound.

"Effective amount" or "therapeutically effective amount" is meant to describe an amount of compound or a composition of the present invention effective in inhibiting or treating the diseases described herein, e.g., cancer, or effective in inhibiting JNK (e.g., JNK1). That is, an effective amount is that amount that produces the desired therapeutic, ameliorative, inhibitory or preventative effect. For example, the amount of the compound or composition that results in: (a) the reduction, alleviation or disappearance of one or more symptoms caused by the disease (e.g., the cancer), (b) the reduction of tumor size, (c) the elimination of the tumor, and/or (d) long-term disease stabilization (growth arrest) of the tumor.

"Sequentially" means (1) administration of one component of the method ((a) compound of the invention, or (b) chemotherapeutic agent and/or radiation therapy) followed by administration of the other component or components. After adminsitration of one component, the next component can be administered substantially immediately after the first component, or the next component can be administered after an effective time period after the first component. The effective time period is the amount of time given for realization of maximum benefit from the administration of the first component; and "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

Lines drawn into the ring systems indicate that the indicated bond may be attached to any of the substitutable ring carbon atoms of any ring when more than one ring is present.

It should also be noted that any carbon or heteroatom with unsatisfied valences in the text, schemes, examples, structural formulae, and any Tables herein is assumed to have the hydrogen atom or atoms to satisfy the valences.

This invention provides compounds of formula 1.0:

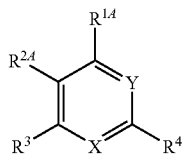

or pharmaceutically acceptable salts, esters or solvates thereof, wherein
X is N or CH;
Y is N or CR$^5$;
R$^{1A}$ is selected from the group consisting of:
(1) H,
(2) alkyl (e.g., C$_1$ to C$_6$ alkyl, such as, for example, methyl, ethyl and isopropyl),
(3) aryl (e.g., phenyl),
(4) substituted aryl (e.g., substituted phenyl), wherein said substituted aryl is substituted with 1 to 3 substitutents independently selected from the group consisting of: —NH$_2$, —NH(C$_1$ to C$_6$)alkyl, —N((C$_1$ to C$_6$)alkyl)$_2$ wherein each alkyl group is independently selected, —OH, —OR$^y$, —C(O)OR, —C(O)NR, and halo (e.g., F, Cl and Br), and wherein R$^y$ is selected from the group consisting of C$_1$-C$_6$ alkyl and C$_3$-C$_6$ cycloalkyl, and wherein R is selected from the group consisting of C$_1$-C$_6$ alkyl and C$_3$-C$_6$ cycloalkyl,
(5) heteroaryl (e.g., pyridyl and thienyl),
(6) substituted heteroaryl (e.g., substituted pyridyl and substituted thienyl) wherein said substituted heteroaryl is substituted with with 1 to 3 substituents independently selected from the group consisting of: —NH$_2$, —NH(C$_1$ to C$_6$)alkyl, —N((C$_1$ to C$_6$)alkyl)$_2$ wherein each alkyl group is independently selected, —OH, —OR$^y$, —C(O)OR, —C(O)NR, and halo (e.g., F, Cl and Br) groups (and wherein R$^y$ and R are as previously defined),
(7) halo (e.g., Cl, F, or Br),
(8) hydroxy,
(9) —O(C$_1$ to C$_6$)alkyl,
(10) —NH$_2$,
(11) —NH(C$_1$ to C$_6$)alkyl, and
(11) —N((C$_1$ to C$_6$)alkyl)$_2$ wherein each alkyl is independently selected;
R$^{2A}$ is selected from the group consisting of:
(1) H,
(2) halo (e.g., F, Cl or Br),
(3) alkyl (e.g., C$_1$ to C$_6$ alkyl),
(4) —OH,
(5) —O(C$_1$ to C$_6$)alkyl,
(6) —NH$_2$,
(7) —NH(C$_1$ to C$_6$)alkyl, and
(8) —N((C$_1$ to C$_6$)alkyl)$_2$ wherein each alkyl is independently selected;
R$^3$ is selected from the group consisting of:
(1) —C(O)NR$^8$R$^9$,
(2) —C(O)R$^{10}$,
(3) H,
(4) alkyl (e.g., C$_1$ to C$_6$ alkyl),
(5) cycloalkyl (e.g., C$_3$ to C$_6$ alkyl),
(6) aryl (e.g., phenyl),
(7) substituted aryl (e.g., substituted phenyl) wherein said substituted aryl is substituted with 1 to 3 substitutents independentlyselected from the group consisting of: —OH, —O(C$_1$ to C$_6$)alkyl, —NH$_2$, NH(C$_1$ to C$_6$)alkyl, N((C$_1$ to C$_6$)alkyl)$_2$ wherein each alkyl is independently selected, F, Cl, and Br,
(8) halo (e.g., F, Cl, Br),
(9) —NR$^{48}$R$^{50}$,
(10) heteroaryl, for example, pyrazolyl (e.g., pyrazolyl bound through a ring nitrogen to the rest of the molecule), benzoimidazolyl, benzothiazolyl,
(11) substituted heteroaryl (e.g., substituted pyrazolyl (e.g., substituted pyrazolyl bound through a ring nitrogen to the rest of the molecule) wherein said substituted heteroaryl is substituted with 1 to 3 substituents independently selected from the group consisting of: —Cl, I, CF$_3$, —(C$_1$ to C$_{10}$)alkyl (e.g., straight chain —(C$_1$ to C$_6$)alkyl, and branched chain —(C$_1$ to C$_{10}$)alkyl),
(12) —OR$^{52}$,
(13) —OH,
(14) —C(O)Oalkyl (e.g., —C(O)O(C$_{1-6}$alkyl)),
(15) —N(R$^{14A}$)$_2$ wherein each R$^{14A}$ is independently selected, and
(16) —NH—C(O)—N(R$^{14}$)$_2$ wherein each R$^{14}$ is independently selected (e.g., —NH—C(O)—NH$_2$);
R$^{2A}$ and R$^3$ taken together with the carbon atoms to which they are bound form an aryl ring (e.g, a phenyl ring); or
R$^{2A}$ and R$^3$ taken together with the carbon atoms to which they are bound form an aryl ring (e.g, a phenyl ring) wherein said aryl (e.g., said phenyl ring) is substituted with 1 to 3 substituents independently selected from the group consisting of: —OR$^{68}$ (e.g., —OH), —O(C$_1$ to C$_6$)alkyl, —NH$_2$, —NH(C$_1$ to C$_6$)alkyl, —N((C$_1$ to C$_6$)alkyl)$_2$ wherein each alkyl is independently selected, and —O—C(O)—N(R$^{14}$)$_2$ wherein each R$^{14}$ is independently selected (e.g., —O—C(O)—NHC$_2$H$_5$);
R$^4$ is selected from the group consisting of:
(1) —C(O)NR$^6$R$^7$,
(2) aryl (e.g., phenyl),
(3) substituted aryl (e.g., substituted phenyl) wherein said substituted phenyl is substituted with 1 to 3 substitutents independently selected from the group consisting of: —OH, —O(C$_1$ to C$_6$)alkyl, —NH$_2$, NH(C$_1$ to C$_6$)alkyl, N((C$_1$ to C$_6$)alkyl)$_2$ wherein each alkyl is independently selected, F, Cl, Br, and alkoxy (e.g., methoxy), and wherein examples of this moiety include o-F-phenyl and —OCH$_3$-m-F-phenyl),
(4) heteroaryl (e.g., pyridyl, pyrazolyl, benzoimidazoly, benzopyrazolyl, triazolyl, benzopyrrolyl),
(5) substituted heteroaryl (e.g., substituted pyrazolyl, substituted imidazolyl, and substituted oxadiazolyl), wherein said substituted heteroaryl is substituted with 1 to 2 substitutents independently selected from the group consisting of: (a) halo (e.g., I, Br), (b) substituted aryl, wherein said substituted aryl is substituted with 1 to 3 substituents independently selected from the group consisting of: halo (e.g., F), and wherein said substituted aryl includes, for example, substituted phenyl, such as, for example, halophenyl, such as, for example fluorophenyl, (c) heteroaryl (e.g., pyridyl), (d) alkyl (—C$_1$ to C$_6$ alkyl, such as, for example, methyl and t-butyl), (e) aryl (e.g., phenyl), and (f) heteroaryl (e.g., pyrazinyl),
(6) benzo[1,3]dioxolyl,
(7) —NR$^{58}$R$^{60}$,
(8) heterocycloalkyl (e.g., a five or six membered ring, or a five or six membered ring fused to a phenyl ring), such as, for example, pyrrolidinyl (e.g., pyrolidinyl bound through the ring N to the rest of the molecule), 2,3- dihydro-1H-isoindolyl (e.g., 2,3-dihydro-1H-isoindolyl bound through the ring N to the rest of the molecule), and morpholinyl,
(9) substituted heterocyloalkyl (e.g., a substituted five or six membered ring) wherein said substituted heterocyloalkyl is substituted with 1 to 3 substituents independently selected from the group consisting of: heteroaryl (e.g., pyridyl), heteroarylalkyl (e.g., —CH$_2$pyridyl), aryl (e.g. phenyl), —CH$_2$OH, —OH, —NH$_2$, —NH(C$_1$ to C$_6$)alkyl, and —N((C$_1$ to C$_6$)alkyl)$_2$ (wherein each alkyl is independently selected),
(10) —C(O)Oalkyl (e.g., —C(O)O(C$_{1-6}$alkyl)),
(11) —N(R$^{14A}$)$_2$ wherein each R$^{14A}$ is independently selected, and
(12) —NH—C(O)—N(R$^{14}$)$_2$ wherein each R$^{14}$ is independently selected (e.g., —NH—C(O)—NH$_2$);

R$^5$ is selected from the group consisting of: H, halo (e.g., F, Cl, and Br), —OH, —(C$_1$ to C$_6$)alkyl, —NH$_2$, NH(C$_1$ to C$_6$)alkyl, N((C$_1$ to C$_6$)alkyl)$_2$ wherein each alkyl is independently selected, alkyl (e.g., C$_1$ to C$_6$ alkyl), and CN;

R$^6$ and R$^7$ are independently selected from the group consisting of:
(1) H,
(2) heteroarylalkyl-,
(3) substituted heteroarylalkyl (for example, wherein said heteroarylalkyl moiety is as defined above in (2)), said substituted heteroarylalkyl being substituted with 1 to 3 substituents independently selected from the group consisting of:
  (a) —NH$_2$,
  (b) —NH(C$_1$-C$_6$)alkyl,
  (c) —N((C$_1$-C$_6$)alkyl)$_2$,
  (d) alkyl (e.g., C$_1$ to C$_6$ alkyl, such as, for example methyl),
  (e) halo (e.g., Cl),
  (f) aryl (e.g., phenyl),
  (g) substituted aryl (e.g., substituted phenyl) wherein said substituted aryl is substituted with 1 to 3 substituents selected from the group consisting of: (i) —SO$_2$R$^{20}$, (ii) —OR$^{21}$, (iii) -halo (e.g., Br, F and Cl), (iv) —CN, (v) —CF$_3$, (vi) aminoalkyl- (e.g., amino (C$_1$ to C$_6$ alkyl), such as, for example NH$_2$CH$_2$—), (vii) —S(O)R$^{26}$, and (viii) alkyl (e.g., C$_1$ to C$_6$ alkyl, such as, for example methyl),
  (h) heterocycloalkyl (e.g., a 5 or six membered heterocycloalkyl ring), such as, for example, pyrazolidinyl (such as, a pyrazolidinyl ring bound through the ring nitrogen to the heteroaryl moiety), and morpholinyl,
  (i) heteroaryl (e.g., pyridyl, pyrimidinyl, benzoimidazolyl quinolinyl, quinoxalinyl, thiazolyl, imidazopyridinyl (e.g., imidazo[1,2-a]pyridinyl, and 3H-imidazo[4,5-b]pyridinyl), imidazopyrimidinyl (e.g., imidazo[1,2-a]pyrimidinyl), quinazolinyl, and naphthyridinyl (e.g., [1,5]naphthyridinyl),
  (j) substituted aryl (e.g., substituted phenyl) substituted with 1 to 3 substituents independently selected from the group consisting of: alkyl (e.g., C$_1$ to C$_6$ alkyl, such as, for example methyl), and —CF$_3$,
  (k) substituted heteroaryl (e.g., substituted benzoimidazolyl, substituted quinolinyl, substituted pyridyl, and substituted thiazolo[4,5-b]pyridinyl), substituted with 1 to 3 independently substituents selected from the group consisting of: (i) alkyl (e.g., C$_1$ to C$_6$ alkyl, such as, for example methyl and isopropyl), (ii) halo (e.g., F, Br, I), (iii) —CN, (iv) —NH$_2$, (v) NH(C$_1$ to C$_6$)alkyl, (vi) —N((C$_1$ to C$_6$)alkyl)$_2$ wherein each alkyl is independently selected, (vii) —CF$_3$, (viii) substituted aryl (e.g., substituted phenyl) wherein said substituted aryl is substituted with 1 to 3 substitutents independently selected from the group consisting of: —S(O)$_2$R$^{42}$ and —CN, and (ix) —C(O)NR$^{44}$R$^{46}$ (an example of this moiety is —C(O)NHCH (CH$_3$)$_2$)),
  (l) alkylamino- (e.g., (C$_1$ to C$_6$)alkylamino-, such as, for example CH$_3$NH—, and (CH$_3$)$_2$CHNH—),
  (m) heterocycloalkyl-alkyl-amino- (e.g., a heterocycloalkyl-(C$_1$ to C$_6$ alkyl)-amino-, such as, for example, morpholinyl-(CH$_2$)$_2$—NH—),
  (n) alkylaminoalkylamino- (e.g., a —(C$_1$ to C$_6$ alkyl)-amino-(C$_1$ to C$_6$ alkyl)-amino-, such as, for example, CH$_3$NH(CH$_2$)$_2$NH—),
  (o) —NHC(O)OR$^{30}$, and (p) —NHC(O)NR$^{32}$R$^{34}$ (examples of this moiety include, for example, —NHC(O)NHCH$_2$CH$_3$, and —NHC(O)N(CH$_3$)$_2$, and —NHC(O)NH$_2$),
(4) substituted heterocycloalkyl, for example, wherein the heterocycloalkyl moiety is a five or six membered heterocycloalkyl ring, (such as substituted heterocycloalkyl wherein said substituted heterocycloalkyl is bound through a ring carbon), such as for example, substituted piperidyl (e.g., substituted piperidyl that is bound through a ring carbon), wherein said substituted heterocycloalkyl is substituted with 1 to 3 substituents independently selected from the group consisting of: (a) —C(O)(O)R$^{14}$, (b) —C(O)NR$^{15}$R$^{16}$, (c) —C(S)NR$^{15}$R$^{16}$, (d) —SO$_2$R$^{17}$, (e) heteroaryl (e.g., pyridyl, and quinolinyl), and (f) substituted heteroaryl (e.g., substituted pyrimidinyl) substituted with 1 to 3 substituents independently selected from the group consisting of: —SR$^{56}$,
(5) substituted alkyl (e.g., substituted C$_1$ to C$_6$ alkyl, such as, for example, substituted methyl and substituted ethyl), wherein said substituted alkyl is substituted with 1 to 3 substituents independently selected from the group consisting of:
  (a) —OH,
  (b) aryl (e.g., phenyl),
  (c) heterocycloalkyl (for example, wherein said heterocycloalkyl moiety is a five or six membered heterocycloalkyl ring, e.g., morpholinyl),
  (d) substituted aryl (e.g., substituted phenyl) wherein said substituted aryl is substituted with 1 to 3 substituents independently selected from the group consisting of: (i) —SO$_2$R$^{14}$, (ii) substituted heteroaryl, wherein said substituted heteroaryl is substituted with 1 to 3 substituents independently selected from the group consiting of: alkyl (e.g., C$_1$ to C$_6$ alkyl, such as, for example methyl), —NH$_2$, —NH(C$_1$ to C$_6$)alkyl, and —N((C$_1$ to C$_6$)alkyl)$_2$ wherein each alkyl is independently selected, (iii) alkyl (e.g., C$_1$ to C$_6$ alkyl, such as, for example methyl), (iv) halo (e.g., F, Cl), (v) —OR$^{19}$, (vi) heteroaryl (such as, for example, pyrazolyl), (vii) aryl (e.g., phenyl), (viii) substituted heterocycloalkyl (e.g., a substituted heterocycloalkyl ring wherein said ring is a five or six membered ring) substituted with 1 to 3 substituents independently selected from the group consisting of: =O, CH$_2$OH, OH, —O(C$_1$ to C$_6$)alkyl, —NH$_2$, —NH(C1 to C6)alkyl, and —N((C$_1$ to C$_6$)alkyl)$_2$ (wherein each alkyl is independently selected), (ix) substituted aryl (e.g., substituted phenyl) substituted with 1 to 3 substituents independently selected from the group consisting of: —CN and —SO$_2$R$^{28}$, and (x) —SO$_2$N (R$^{14}$)$_2$ wherein each R$^{14}$ is independently selected, (e) benzo(1,3)dioxo (e.g., wherein said benzodioxo is bound through a ring carbon of the benzo moiety),
(f) —C(O)OR$^{24}$, and
(g) substituted heterocycloalkyl (for example, wherein the heterocycloalkyl moiety is a five or six membered heterocycloalkyl ring), said substituted heterocycloalkyl substituted with 1 to 3 groups independently selected from the group consisting of: —C(O)OR$^{23}$, —C(O)N(R$^x$)$_2$ wherein each R$^x$ is independently selected from the group consisting of: (C$_1$ to C$_6$) alkyl,
(6) cycloalkyl (e.g., C$_3$ to C$_6$ cycloalkyl, such as, for example, cyclobutyl, cyclohexyl, cyclopentyl),
(7) alkyl (e.g., C$_1$ to C$_6$ alkyl, such as, for example, propyl, CH$_2$)$_2$CH(CH$_3$)$_2$, —CH$_2$CH(CH$_3$)$_2$, and i-propyl),
(8) substituted cycloalkyl (e.g., substituted C$_3$ to C$_6$ cycloalkyl, such as, for example, substituted cyclohexyl) wherein said substituted cycloalkyl is substituted with 1 to 3 groups independently selected from the group consisting of: —OH, and —CH$_2$OH
(9) substituted heteroaryl (e.g., substituted isooxazolyl) wherein said substituted heteroaryl is substituted with 1 to 2 substitutents independently selected from the group consisting of: alkyl (e.g., C$_1$ to C$_6$ alkyl, such as, for example, methyl, ethyl, and t-butyl), and
(10) heteroaryl (e.g., pyridyl, benzopyranzinyl, and quinoxalinyl); R$^8$ and R$^9$ are independently selected from the group consisting of:
(1) H,
(2) alkyl (e.g., C$_1$ to C$_6$ alkyl, such as, for example, methyl, ethyl, i-propyl, sec-butyl, —CH$_2$C(CH$_3$)$_2$),
(3) substituted alkyl (e.g., substituted C$_1$ to C$_6$ alkyl, such as, for example, substituted methyl and substituted ethyl), wherein said substituted alkyl is substituted with 1 to 3 substituents independently selected from the group consisting of:
(a) —OH,
(b) aryl (e.g., phenyl),
(c) heterocycloalkyl (for example, wherein said heterocycloalkyl moiety is a five or six membered heterocycloalkyl ring, e.g., morpholinyl),
(d) substituted aryl (e.g., substituted phenyl) wherein said substituted aryl is substituted with 1 to 3 substituents independently selected from the group consisting of: (i) —SO$_2$R$^{14}$, (ii) substituted heteroaryl, wherein said substituted heteroaryl is substituted with 1 to 3 substituents independently selected from the group consiting of: —NH$_2$, —NH(C$_1$ to C$_6$)alkyl, and —N((C$_1$ to C$_6$)alkyl)$_2$ wherein each alkyl is independently selected, (iii) alkyl (e.g., C$_1$ to C$_6$ alkyl, such as, for example methyl), (iv) halo (e.g., F, Cl), (v) —OR$^{19}$, (vi) heteroaryl (such as, for example, pyrazolyl, oxadiazole, and isoxazolyl), (vii) aryl (e.g., phenyl), (viii) substituted heterocycloalkyl (e.g., a substituted heterocycloalkyl ring wherein said ring is a five or six membered ring) substituted with 1 to 2 substituents independently selected from the group consisting of: =O, —CH$_2$OH, —OH, —O(C$_1$ to C$_6$)alkyl, —NH$_2$, —NH(C$_1$ to C$_6$)alkyl, and N((C$_1$ to C$_6$)alkyl)$_2$ (wherein each alkyl is independently selected), (ix) substituted aryl (e.g., substituted phenyl) substituted with 1 to 3 substituents independently selected from the group consisting of: CN, —SO$_2$R$^{28}$ and SO$_2$N(R$^{x1}$)$_2$ wherein each R$^{x1}$ is independently selected from the group consisting of: C$_1$-C$_6$ alkyl and C$_3$-C$_6$ cycloalkyl,
(e) benzo(1,3)dioxoly (e.g., wherein said benzodioxoly is bound through a ring carbon of the benzo moiety),
(f) —C(O)OR$^{24}$,
(g) substituted heterocycloalkyl (for example, wherein the heterocycloalkyl moiety is a five or six membered heterocycloalkyl ring), said substituted heterocycloalkyl substituted with 1 to 3 substituents independently selected from the group consisting of: (i) C(O)OR$^{23}$, (ii) C(O)N(R$^x$)$_2$ (wherein R$^x$ is as previously defined), (iii) aryl (e.g., phenyl), (iv) heteroaryl, (v) substituted aryl (e.g., substituted phenyl) substituted with 1 to 3 substitutents independently selected from the group consisting of: —CN, —S(O)$_2$alkyl (e.g., —S(O)$_2$CH$_3$), —S(O)$_2$N(R$^{14.4}$)$_2$ wherein each R$^{14.4}$ is independently selected, and (v) substituted heteroaryl substituted with 1 to 3 substitutents independently selected from the group consisting of: —CN, —S(O)$_2$alkyl (e.g., —S(O)$_2$CH$_3$), —S(O)$_2$N(R$^{14.4}$)$_2$ wherein each R$^{14.4}$ is independpendently selected, and
(h) substituted heteroaryl, wherein said substituted heteroaryl is substituted with 1 to 3 substituents independently selected from the group consisting of: (i) alkyl (e.g., C$_1$ to C$_6$ alkyl, such as, for example methyl), (ii) aryl (e.g., phenyl), (iii) substituted aryl wherein said substituted aryl is substituted with 1 to 3 substituents selected from the group consisting of: -(alkylene)$_{1-6}$-N(R$^{14}$)$_2$ wherein each R$^{14}$ is independently selected (e.g., —CH$_2$NH$_2$), —SO$_2$R$^{14}$ (e.g., —SO$_2$CH$_3$), —CF$_3$, halo (e.g., F and Cl), —CN, —SO$_2$N(C$_1$-C$_6$alkyl), SO$_2$N(C$_1$-C$_6$alkyl)$_2$ wherein each alkyl is independently selected, S(O)CH$_3$ and heteroaryl (e.g., quinoxalinyl, quinoline, pyrimidine, imidazopyridine, imidazopyrimidine, quinazoline, quinaxoline, naphthyridine, and thiazolyl), (iv) substituted heteroaryl wherein the substituents on the substituted substituted heteroaryl are selected from the group consisting of: alkyl (e.g., methyl) and heteroaryl (e.g., pyridyl), and wherein examples of said substituted heteroaryl moiety include, for example, -benzoimidazolylmethyl, N-phenyl-pyrazolyl-, N-(phenyl-m-CF$_3$)-pyrazolyl-, N-(m-methyl-phenyl)-pyrazolyl-, and N-(quinoxalinyl)-pyrazolyl-,
(4) heterocycloalkyl (e.g., piperidyl, such as, for example, piperidyl bound through a ring carbon),
(5) substituted heterocycloalkyl, for example, wherein the heterocycloalkyl moiety is a five or six membered heterocycloalkyl ring, also, for example, substituted heterocycloalkyl wherein said substituted heterocycloalkyl is bound through a ring carbon, examples of substituted heterocycloalkyl groups include, for example, substituted piperidyl (e.g., substituted piperidyl that is bound through a ring carbon), wherein said substituted heterocycloalkyl is substituted with 1 to 3 substituents independently selected from the group consisting of:
(a) aryl (e.g., phenyl),
(b) substituted aryl wherein said substituted aryl (e.g., substituted phenyl) is substituted with 1 to 3 substituents independently selected from the group consisting of: —CN (e.g., substituted phenyl, such as, for example, CN-phenyl-), and —C(O)OEt, such as, for example, cyanophenyl (for example, said substituted heterocycloalkyl group can be, therefore, N—(CN-phenyl)-piperidyl-),
(c) —C(O)R$^{11}$ wherein R$^{11}$ is alkyl (e.g., C$_1$ to C$_6$ alkyl, such as for example methyl), such as for example, —C(O)CH$_3$ (for example, said substituted heterocycloalkyl group can be, therefore, N—CH$_3$C(O)-piperidyl), (d) alkyl (e.g., $C_1$ to $C_6$ alkyl, such as, for example, methyl and ethyl),
(e) arylalkyl- (e.g., aryl-($C_1$ to $C_6$)alkyl), such as, for example, benzyl,
(f) heteroaryl (e.g., pyridyl (such as, for example, 2-pyridyl and 4 pyridyl), quinolinyl, and pyrimidinyl),
(g) substituted heteroaryl (e.g., substituted pyrimidinyl) substituted with 1 to 2 substituents independently selected from the group consisting of: —$SR^{56}$, F, Cl, Br, and —$CF_3$, and
(h) —$C(O)OR^{74}$, (6) cycloalkyl (e.g., $C_3$ to $C_6$ cycloalkyl, such as, for example, cyclobutyl, cyclohexyl, and cyclopentyl), (7) —$(CH_2)_m NHC(O)R^{12}$ wherein m is 1 to 7 (e.g., 2) and $R^{12}$ is selected from the group consisting of alkyl (e.g., $C_1$ to $C_6$ alkyl, such as, for example, methyl, ethyl, and isopropyl), and —$(CH_2)_2 NHC(O)CH_3$, (8) heteroarylalkyl- (e.g., heteroaryl-($C_1$ to $C_6$)alkyl-, such as, for example, heteroaryl-$CH_2$—) such as, for example, —$CH_2$-benzoimidazolyl and —$CH_2$-benzothiazolyl, (9) substituted heteroarylalkyl (for example, wherein said heteroarylalkyl moiety is as defined above in (8)), wherein said substituted heteroarylalkyl is substituted with 1 to 3 substituents independently selected from the group consisting of:
(a) —$NH_2$,
(b) —$NH(C_1$ to $C_6)$alkyl,
(c) —$N((C_1$ to $C_6)$alkyl$)_2$ wherein each alkyl is independently selected,
(d) alkyl (e.g., $C_1$ to $C_6$ alkyl, such as, for example methyl),
(e) halo (e.g., Cl),
(f) aryl (e.g., phenyl),
(g) substituted aryl (e.g., substituted phenyl) wherein said substituted aryl is substituted with 1 to 3 substituents independently selected from the group consisting of: (i) —$SO_2 R^{20}$, (ii) —$OR^{21}$, (iii) -halo (e.g., Br, F and Cl), (iv) —CN, (v) —$CF_3$, (vi) aminoalkyl- (e.g., amino($C_1$ to $C_6$ alkyl), such as, for example $NH_2 CH_2$—), (vii) —$S(O)R^{26}$, and (viii) alkyl (e.g., $C_1$ to $C_6$ alkyl, such as, for example methyl),
(h) heterocycloalkyl (e.g., a 5 or six membered heterocycloalkyl ring), such as, for example, pyrazolidinyl (such as, a pyrazolidinyl ring bound through the ring nitrogen to the heteroaryl moiety), and morpholinyl,
(i) heteroaryl (e.g., pyridyl, pyrimidinyl, benzoimidazolyl quinolinyl, quinoxalinyl, thiazolyl, imidazopyridinyl (e.g., imidazo[1,2-a]pyridinyl, 3H-imidazo[4,5-b]pyridinyl), imidazopyrimidinyl (e.g., imidazo[1,2-a]pyrimidinyl), quinazolinyl, and naphthyridinyl (e.g., [1,5]naphthyridinyl),
(j) substituted aryl (e.g., substituted phenyl) substituted with 1 to 3 substituents independently selected from the group consisting of: alkyl (e.g., $C_1$ to $C_6$ alkyl, such as, for example methyl), —$CF_3$, F, Cl, and Br,
(k) substituted heteroaryl (e.g., substituted benzoimidazolyl, substituted quinolinyl, substituted pyridyl, and substituted thiazolo[4,5-b]pyridinyl), substituted with 1 to 3 substituents selected from the group consisting of: (i) alkyl (e.g., $C_1$ to $C_6$ alkyl, such as, for example methyl and isopropyl), (ii) halo (e.g., F and Br), (iii) CN, (iv) $NH_2$, (v) —$NH(C_1$-$C_6$alkyl), (vi) —$N(C_1$-$C_6$ alkyl$)_2$ wherein each alkyl is independently selected, (vii) —$CF_3$, (viii) substituted aryl (e.g., substituted phenyl) wherein said substituted aryl is substituted with 1 to 3 substituents independently selected from the group consisting of: —$S(O)_2 R^{42}$ and —CN, and (ix) —$C(O)NR^{44}R^{46}$ (e.g., —$C(O)NHCH(CH_3)_2$)),
(l) alkylamino- (e.g., $C_1$ to $C_6$ alkylamino-, such as, for example $CH_3NH$—, and $(CH_3)_2 CHNH$—),
(m) heterocycloalkyl-alkyl-amino- (e.g., a hetero-cycloalkyl-($C_1$ to $C_6$ alkyl)-amino-, such as, for example, morpholinyl-$(CH_2)_2 NH$—),
(n) alkylaminoalkylamino- (e.g., a —($C_1$ to $C_6$ alkyl)-amino-($C_1$ to $C_6$ alkyl)-amino-, such as, for example, $CH_3 NH(CH_2)_2 NH$—), and
(o) —$NHC(O)OR^{30}$, (p) —$NHC(O)NR^{32}R^{34}$, examples of this moiety include, for example, —$NHC(O)$ $NHCH_2CH_3$, —$NHC(O)N(CH_3)_2$, and —$NHC(O)$ $NH_2$,

(10) heteroaryl (e.g., pyridyl, such as, for example, m-pyridyl), and

(11) —$NR^{36}R^{38}$, examples of said moiety include, for example, —NH-p-$SO_2 CH_3$-phenyl; or $R^8$ and $R^9$, in the substituent —$C(O)NR^8 R^9$, are taken together with the nitrogen to which they are bonded to form a heterocycloalkyl ring (for example, a heterocycloalkyl ring comprising 4 to 8 ring members (e.g., 6, i.e., a piperidyl ring)), said heterocycloalkyl ring being substituted with 1 to 2 substituents independently selected from the group consisting of: —OH, —$O(C_1$ to $C_6)$alkyl, —$CH_2 OH$, —$NH_2$, —NH ($C_1$ to $C_6)$alkyl, —$N(C_1$ to $C_6$alkyl$)_2$ wherein each alkyl is independently selected, F, —CN, aryl and aryl substituted with 1 to 2 substituents independently selected from the group consisting of —OH and —$C(O)OCH_3$ (e.g., meta and para);

$R^{10}$ is selected from the group consisting of: H, —OH, —O-alkyl (e.g., —O—($C_1$ to $C_6)$alkyl), substituted heterocycloalkyl (e.g., substituted piperidyl), wherein said substituted heterocyloalkyl is substituted with 1 to 3 substituents independently selected from the group consisting of: (1) —OH, (2) substituted aryl, wherein said substituted aryl is substituted with 1 to 3 groups independently selected from the group consisting of: —OH (e.g., hydroxyphenyl-), and —$C(O)OR^{13}$ (e.g., $CH_3 C(O)$-phenyl-), (3) hydroxy substituted alkyl (such as, for example, hydroxyalkyl, such as for example —$CH_2 OH$ and —$CH_2 CH_2 OH$), and (4) —$OR^{18}$;

$R^{11}$ is alkyl (e.g., $C_1$ to $C_6$ alkyl, such as for example methyl);

$R^{13}$ is selected from the group consisting of: alkyl (e.g., $C_1$ to $C_6$ alkyl, such as, for example, methyl, Ethyl, isopropyl);

$R^{14}$ is selected from the group consisting of: H and alkyl (e.g., $C_1$ to $C_6$ alkyl, such as, for example methyl, ethyl, and isopropyl);

$R^{14A}$ is independently selected from the group consisting of: H, alkyl (e.g., $C_1$-$C_6$alkyl), cycloalkyl, heterocycloalkyl, heteroaryl (e.g. pyrazolyl, thiazolyl, and imidazolyl) and aryl (e.g., phenyl);

$R^{15}$ and $R^{16}$ are independently selected from the group consisting of: H and alkyl (e.g., $C_1$ to $C_6$ alkyl, such as, for example methyl, ethyl, and isopropyl);

$R^{17}$ is selected from the group consisting of: hydrogen, alkyl (e.g., $C_1$ to $C_6$ alkyl, such as, for example methyl and ethyl), and arylalkyl- (e.g., aryl($C_1$ to $C_6$ alkyl)-, such as for example, phenyl($C_1$ to $C_6$ alkyl)-, such as for example, benzyl);

$R^{18}$ is selected from the group consisting of: alkyl (e.g., $C_1$ to $C_6$ alkyl, such as, for example methyl, ethyl, and isopropyl);

$R^{19}$ is selected from the group consisting of H, alkyl (e.g., $C_1$ to $C_6$ alkyl, such as, for example methyl), and heteroaryl (e.g. pyridyl);

$R^{20}$ is selected from the group consisting of: (1) alkyl (e.g., $C_1$ to $C_6$ alkyl, such as, for example methyl), (2) dialkylamino (wherein each alkyl is independently selected) (e.g., wherein said dialkylamino is —N(($C_1$ to $C_6$)$_2$alkyl wherein each alkyl is independently selected, such as, for example, wherein the alkyl is methyl and the dialkylamino is —N(CH$_3$)$_2$), (3) —NH$_2$, (4) alkylamino (e.g., wherein said alkyl is $C_1$ to $C_6$ alkyl, such as, for example methyl, and said alkylamino is, for example, —NHCH$_3$), (5) heterocycloalkyl (e.g., piperazinyl, pipiridyl and pyrrolidinyl), and (6) substituted heterocycloalkyl (e.g., substituted piperazinyl and substituted pipiridyl) wherein said substituted heterocycloalkyl is substituted with 1 to 2 substituents independently selected from the group consisting of: —C(O)OR$^{40}$;

$R^{21}$ is selected from the group consisting of: alkyl (e.g., $C_1$ to $C_6$ alkyl, such as, for example methyl, ethyl, and isopropyl);

$R^{23}$ is H, or alkyl (e.g., $C_1$ to $C_6$ alkyl, such as, for example, t-butyl);

$R^{24}$ is selected from the group consisting of: H and alkyl (e.g., $C_1$ to $C_6$ alkyl, such as, for example methyl);

$R^{26}$ is selected from the group consisting of: alkyl (e.g., $C_1$ to $C_6$ alkyl, such as, for example methyl and ethyl);

$R^{28}$ is selected from the group consisting of: alkyl (e.g., $C_1$ to $C_6$ alkyl, such as, for example methyl, ethyl, and isopropyl);

$R^{30}$ is selected from the group consisting of: alkyl (e.g., $C_1$ to $C_6$ alkyl), such as, for example, methyl);

Each $R^{32}$ and $R^{34}$ is independently selected from the group consisting of: H, alkyl (e.g., $C_1$ to $C_6$ alkyl), aryl, aryl substituted with a —OH group (e.g., phenyl substituted with a —OH), and heteroaryl;

Each $R^{36}$ and $R^{38}$ is independently selected from the group consisting of: H, aryl (e.g., phenyl), and substituted aryl, wherein said substituted aryl (e.g., substituted phenyl) is substituted with 1 to 3 substituents independently selected from the group consisting of: —SO$_2$R$^{14}$ (e.g., —SO$_2$CH$_3$), halo (F, Cl, and Br) and —CN;

$R^{40}$ is selected from the group consisting of alkyl (e.g., $C_1$ to $C_6$ alkyl, such as, for example, methyl, ethyl, and t-butyl);

$R^{42}$ is selected from the group consisting of: alkyl (e.g., $C_1$ to $C_6$ alkyl, such as, for example, hydrogen, methyl, ethyl, and isopropyl), and cycloalkyl (e.g., cyclo-propyl);

Each $R^{44}$ and $R^{46}$ is independently selected from the group consisting of: H and alkyl (e.g., $C_1$ to $C_6$ alkyl, such as for example, methyl, ethyl, and isopropyl);

Each $R^{48}$ and $R^{50}$ is independently selected from the group consisting of: (1) H, (2) arylalkyl- (e.g., aryl($C_1$ to $C_6$)alkyl-, such as, for example, phenyl($C_1$ to $C_6$)alkyl-, such as, for example, benzyl), (3) heteroaryl (e.g., pyridyl (such as, m-pyridyl), quinolinyl (e.g., quinolinyl bound through the phenyl moiety)), (4) substituted aryl (e.g., substituted phenyl) wherein said substituted aryl is substituted with 1 to 3 substituents independently selected from the group consisting of: heterocycloalkyl (e.g., a five or six membered heterocycloalkyl, such as, for example, morpholinyl), (5) substituted alkyl (e.g., $C_1$ to $C_6$ alkyl, such as, for example, —CH$_3$, —CH$_2$CH(CH$_3$)$_2$) wherein said substituted alkyl is substituted with substituents selected from the group consiting of: (a) heteroaryl (e.g., pyridyl), (b) benzo[1,3]dioxolyl, (c) alkyl (e.g., $C_1$ to $C_6$ alkyl, such as for example, methyl), and (d) heterocycloalkyl (e.g., a five or six membered ring) such as, for example piperidyl, (6) aryl (e.g., phenyl), and (7) alkyl (e.g., $C_{1-6}$alkyl, such as, for example, methyl);

$R^{52}$ is selected from the group consisting of: alkyl (e.g., $C_1$ to $C_6$ alkyl, such as, for example methyl, ethyl, and isopropyl);

$R^{56}$ is selected from the group consisting of alkyl (e.g., $C_1$ to $C_6$ alkyl, such as, for example methyl);

Each $R^{58}$ and $R^{60}$ is independently selected from the group consisting of: (1) H, (2) alkyl (e.g., $C_1$ to $C_6$ alkyl, for example, —CH$_2$CH(CH$_3$)$_2$), (3) —C(O)R$^{62}$ wherein $R^{62}$ is selected from the group consisting of: (a) alkyl (e.g., $C_1$ to $C_6$ alkyl, such as, for example methyl and i-propyl), (b) —OR$^{64}$ wherein $R^{64}$ is selected from the group consisting of: alkyl (e.g., $C_1$ to $C_6$ alkyl, such as, for example methyl), (c) substituted alkyl (e.g., substituted $C_1$ to $C_6$ alkyl, such as, for example, methyl), wherein said substituted alkyl is substituted with substituents (e.g., 1 to 3) independently selected from the group consisting of: (i) benzo[1,3]dioxolyl and (ii) substituted aryl (e.g., substituted phenyl) wherein said substituted aryl (e.g., substituted phenyl) is substituted with 1 to 3 substituents independently selected from the group consisting of: —SO$_2$R$^{66}$ wherein $R^{66}$ is selected from the group consisting of alkyl (e.g., substituted $C_1$ to $C_6$ alkyl, such as, for example, methyl);

$R^{68}$ is selected from the group consisting of: H, alkyl (e.g., substituted $C_1$ to $C_6$ alkyl, such as, for example, methyl), and —R$^{70}$R$^{72}$;

Each $R^{70}$ and $R^{72}$ is independently selected from the group consisting of: H and alkyl (e.g., substituted $C_1$ to $C_6$ alkyl, such as, for example, methyl); and $R^{74}$ is selected from the group consisting of: alkyl (e.g., substituted $C_1$ to $C_6$ alkyl, such as, for example, ethyl).

In the compounds of this invention a benzo moiety comprising a hetero ring (e.g., a heteroaryl ring) fused to a benzene ring, such as benzothiazole or benzoimidazole, may be bound to the rest of the molecule through any available atom. Thus, the benzo moiety can be bound through a ring carbon of the benzo group, a carbon atom of the hetero ring, or a hetero atom (e.g., N) of the hetero ring.

Examples of the $R^3$ substituent for formula 1 include, for example, —NH-(phenyl-morpholinyl), —NH(quinolinyl), —NH(pyridyl), —C(O)NH(CH(CH$_3$)CH$_2$OH), —C(O)NH(CH$_2$CH$_3$), —C(O)NH(CH(CH$_3$)CH$_3$), —C(O)NH(CH$_2$—N-(m-methylphenyl)-pyrazolyl, —C(O)NHCH$_2$—N-(quioxalinyl)-pyrazolyl, —C(O)—NH(CH$_2$-p-SO$_2$CH$_3$-phenyl),

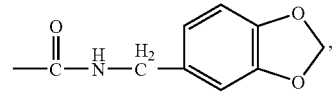

—NH—(CH$_2$-m-pyridyl), —NH—(CH$_2$-benzo[1,3]dioxolyl), —NH—(CH$_2$CH$_2$-p-pyridyl), —N(CH$_3$)—(CH$_2$CH$_2$-p-pyridyl), —NH—(CH$_2$-piperidinyl), —NH—(o-pyridyl), —C(O)NH—(N—C(O)OC$_2$H$_5$-piperidinyl), —C(O)NHCH$_3$, —C(O)NH(CH$_2$—N-(m-CN-phenyl)-piperidinyl), —C(O)NH(CH$_2$—N-(p-CN-phenyl)-piperidinyl), —C(O)NH(CH$_2$—N-(m-SO$_2$CH$_3$-phenyl)-piperidinyl), and —C(O)NH(CH$_2$—N-(p-SO$_2$CH$_3$-phenyl)-piperidinyl).

Examples of substituted heterocyloalkyl $R^4$ substituents (see (10) in the definition of $R^4$) for formula 1 include, for example, o-pyridyl-pyrrolidinyl-, such as, for example,

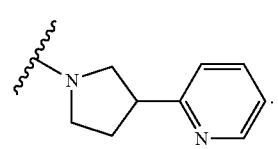

Examples of the $R^4$ substituent for formula 1 include, for example, iodopyrazolyl-, m-F-phenylpyrazolyl-, p-F-phenylpyrazolyl-, o-pyridylpyrazolyl-, t-butyloxzadiazolyl-, —C(O)NH(CH$_2$-phenyl-p-SO$_2$CH$_3$), o-F-phenyl, o-pyridyl, benzopyrazolyl-, triazolyl, dimethylpyrazolyl-, phenylpyrazolyl-, methylpyrazolyl-, bromoimidazolyl-, bromopyrazolyl, o-OCH$_3$-m-F-phenyl-, o-F-m-OCH$_3$-phenyl, o-F-p-OCH$_3$-phenyl-, N-methylpyrazolyl, o-pyridyl, pyrazinylpyrazolyl-, t-butylpyrazolyl-, benzopyrroyl-, benzoimidazolyl-, —NH(CH$_2$CH(CH$_3$)$_2$), —N(CH$_3$)(CH$_2$CH(CH$_3$)$_2$,

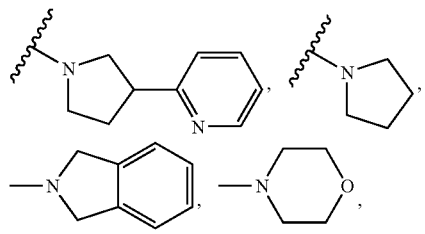

—NHC(O)CH$_3$, —NHC(O)CH(CH$_3$)$_2$, —NHC(O)OCH$_3$, —NHC(O)NH$_2$, —NHCH$_3$, —N(CH$_3$)C(O)CH$_3$, —N(C(O)CH(CH$_3$)$_2$)$_2$, —N(CH$_3$)(C(O)CH(CH$_3$)$_2$), —NHC(O)OC$_2$H$_5$, —NHC(O)—CH$_2$-benzo[1,3]dioxolyl, NHC(O)CH$_2$-(p-SO$_2$CH$_3$-phenyl), and

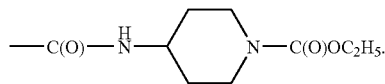

Examples of said $R^6$ and $R^7$ heteroarylalkyl-substituent (see (2) in the definition of $R^6$ and $R^7$) for formula 1 include, for example, heteroaryl-(C$_1$ to C$_6$)alkyl-(such as, for example, benzothiazolyl-(C$_1$ to C$_6$)alkyl-, sych as, for example; benzothiazolyl-CH$_2$—), —(CH$_2$)$_3$-imidazolyl (e.g, —(CH$_2$)$_3$-imidazolyl wherein said imidazolyl is bound to the alkyl group by a ring nitrogen), pyridyl-CH$_2$—, pyrazolyl-(C$_1$ to C$_6$)alkyl- (wherein said pyrazolyl is bound through the ring nitrogen to said alkyl moiety), pyrazolyl-(C$_1$ to C$_6$)alkyl- (wherein said pyrazolyl is bound through a ring carbon to said alkyl moiety), thiazolyl-(C$_1$ to C$_6$)alkyl- (e.g., wherein said thiazolyl is bound through a ring carbon to said alkyl moiety), and benzoimidiazolyl-(C$_1$ to C$_6$)alkyl- (e.g., benzoimidazolylCH$_2$—, also, for example, wherein said benzoimidazolyl is bound through a carbon of the imidazole ring to said alkyl moiety), and isooxazolyl-(C$_1$ to C$_6$)alkyl-.

Examples of said $R^6$ and $R^7$ substituted heteroarylalkyl-substituent (see (3) in the definition of $R^6$ and $R^7$) for formula 1 include, for example, substituted pyrazolylalkyl-, substituted isooxazolylalkyl-, substituted benzoimidazolylalkyl- (e.g., a substituted benzoimidazolyl ring that is bound through the benzo ring or the imidazoly ring to the alkyl moiety), substituted pyridylalkyl-, substituted thienylalkyl-, substituted benzothiazolylalkyl-, and substituted thiazolopyridinylalkyl- (e.g., substituted thiazolo[4,5-b]pyridinyl-alkyl-).

Examples of said $R^6$ and $R^7$ substituted heteroaryl-alkyl-groups (see (3) in the definition of $R^6$ and $R^7$) also include, for example, amino-benzothiazolyl-alkyl- (e.g., amino-benzothiazolyl-CH$_2$—), methyl-pyrazinyl-CH$_2$—, Cl-pyridyl-CH$_2$—, phenyl-pyrazolyl-CH$_2$— (for example, wherein said pyrazolyl moiety is bound to said —CH$_2$— moiety through a ring carbon, and said phenyl is bound to a N of said pyrazolyl moiety), NH$_2$C(O)NHbenzothiazolylCH$_2$—, N-methylbenzoimidazolylCH$_2$—, methylimidazolyl-benzoCH$_2$—, N—(CH$_3$)—(CH$_3$)$_2$-pyrazolylCH$_2$—, N—(CH$_3$)—(CH$_3$)-pyrazolylCH$_2$—, thiazolylCH$_2$—, benzoimidazolylCH$_2$—, N-methylbenzoimidazolylCH$_2$—, methylimidazolylbenzoCH$_2$—, o-NH$_2$-pyridyl-CH$_2$—, pyrazolidinyl-pyridyl-CH$_2$—, morpholinyl-pyridyl-CH$_2$—, N-methylpyrazolyl-CH$_2$—, N-isopropylpyrazolyl-CH$_2$—, pyridyl-thienyl-CH$_2$—, N-methyl-methyl-imidazolylbenzo-CH$_2$—, N-(m-methylphenyl)-pyrazolyl-CH$_2$—, methylphenyl)-pyrazolyl-CH$_2$—, N-(m-Cl-p-F-phenyl)-pyrazolyl-CH$_2$—, N-(m-Cl-phenyl)-pyrazolyl-CH$_2$—, N-(m-CN-phenyl)-pyrazolyl-CH$_2$—, N-(p-CN-phenyl)-pyrazolyl-CH$_2$—, N-(m-SO$_2$CH$_3$-phenyl)-pyrazolyl-CH$_2$—, N-(p-SO$_2$CH$_3$-phenyl)-pyrazolyl-CH$_2$—, N-(m,m-di-Cl-phenyl)pyrazolyl-CH$_2$—, N-(m-F-phenyl)-pyrazolyl-CH$_2$—, N-(m-CF$_3$-phenyl)-pyrazolyl-CH$_2$—, N-(m-pyridyl)-pyrazolyl-CH$_2$—, N-(quinolinyl)-pyrazolyl-CH$_2$— (e.g., wherein said quinolinyl moiety is bound through a ring carbon of the benzo moiety to the pyrazolyl moiety), N-(p-NH$_2$CH$_2$)-pyrazolyl-CH$_2$—, N-(quinolinyl)-pyrazolyl-CH$_2$— (e.g., wherein said quinolinyl moiety is bound through a ring carbon of the pyridyl moiety to the pyrazolyl moiety), N-(pyrimidinyl)-pyrazolyl-CH$_2$—, N-(methylimidazolylbenzo)-pyrazolyl-CH$_2$— (e.g., wherein said benzoimidazolyl moiety is bound through a ring carbon of the benzo moiety to the pyrazolyl moiety), N-(N-methyl-imidazolylbenzo)-pyrazolyl-CH$_2$— (e.g., wherein said benzoimidazolyl moiety is bound through a ring carbon of the benzo moiety to the pyrazolyl moiety), N-(methylquinolinyl)-pyrazolyl-CH$_2$— (e.g., wherein said quinolinyl moiety is bound through a ring carbon of the benzo moiety to the pyrazolyl moiety and there is a methyl substituent bound to a carbon of the pyridyl moiety), N-(m-CF$_3$-p-F-phenyl)pyrazolyl-CH$_2$—, N-(quinoxalinyl)-pyrazolyl-CH$_2$— (e.g., wherein said quinoxalinyl moiety is bound through a ring carbon of the benzo moiety to the pyrazolyl moiety), N-N-(p-(CH$_3$)$_2$SO$_2$-phenyl)-pyrazolyl-CH$_2$—, N-(m-F-pyridyl)pyrazolyl-CH$_2$—, N-(p-(CH$_3$)SO-phenyl)-pyrazolyl-CH$_2$—, N-(m-Br-m-CN-phenyl)-Pyrazolyl-CH$_2$—, N-(o-pyridyl)-pyrazolyl-CH$_2$—, N-(o-Cl-phenyl)pyrazolyl-CH$_2$—, N-(o-CN-phenyl)-pyrazolyl-CH$_2$—, N-(p-pyridyl)-pyrazolyl-CH$_2$—, N-(pyrimidinyl)-pyrazolyl-CH$_2$—, N—(CNpyridyl)-pyrazolyl-CH$_2$—, N-(m-F-m-CN-phenyl)-pyrazolyl-CH$_2$—, N-(thiazolyl)-pyrazolyl-CH$_2$—, N-(aminothiazolo[4,5-b]pyridinyl)-pyrazolyl-CH$_2$— (e.g., N-(thiazolo[4,5-b]pyridine-2-ylamine)-pyrazolyl-CH$_2$—), N-(imidazo[1,2-a]pyridinyl)-pyrazolyl-CH$_2$—, N-(imidazo[1,2-a]pyrimidinyl)-pyrazolyl-CH$_2$—, N-(quinazolinyl)-pyrazolyl-CH$_2$—, N-(3H-imidazo[4,5-b]pyridinyl)-pyrazolyl-CH$_2$—, N-([1,5]-naphthyridinyl)-pyrazolyl-CH$_2$—, N-(1-isopropyl-2-methyl-1H-benzoimidazolyl)-pyrazolyl-CH$_2$—, N-(1,2-dimethyl-1H-benzoimidazolyl)-pyrazolyl-CH$_2$—, N-(1-methyl-2-CF$_3$-1H-benzoimidazolyl)-pyrazolyl-CH$_2$—, N-(1-methyl-2-isopropyl-1H-benzoimidazolyl)-pyrazolyl-CH$_2$—, N-(1-methyl-2-pyridin-3-yl-1H-benzoimidazolyl)-pyrazolyl-CH$_2$—, N-(H$_2$NSO$_2$phenyl)-pyrazolyl-CH$_2$—, N—(CH$_3$NHSO$_2$phenyl)-pyrazolyl-CH$_2$—, N-(piperazinylSO$_2$phenyl)-pyrazolyl-CH$_2$—, N-(p-(CH$_3$)$_2$NSO$_2$)-m-Cl-phenyl)-pyrazolyl-CH$_2$—, N-(p-(N-t-butylOC (O)-piperazinyl-$SO_2$)-m-Cl-phenyl)-pyrazolyl-$CH_2$—, —(N-(p-(piperazinyl-$SO_2$)-m-Cl-phenyl)-pyrazolyl-$CH_2$—, (m-methyl-phenyl)-pyridyl-$CH_2$—, (m-F-phenyl)-pyridyl-$CH_2$—, (m-Cl-phenyl)-pyridyl-$CH_2$—, (p-methyl-phenyl)-pyridyl-$CH_2$—, (m-CN-phenyl)-pyridyl-$CH_2$—, (p-CN-phenyl)-pyridyl-$CH_2$—, (m-$SO_2CH_3$-phenyl)-pyridyl-$CH_2$—, (p-$SO_2CH_3$-phenyl)-pyridyl-$CH_2$—, (p-Cl-phenyl)-pyridyl-$CH_2$—, (m-$CF_3$-phenyl)-pyridyl-$CH_2$—, (m-Cl-p-F-phenyl)-pyridyl-$CH_2$—, (m-Cl-m-Cl-phenyl)-pyridyl-$CH_2$—, (m-methyl-phenyl)-pyridyl-$CH_2$—, quinolinyl-pyridyl-$CH_2$— (e.g., wherein the quinolinyl moiety is bound through a carbon of the benzo moiety to the pyridyl moiety), bromopyridyl$CH_2$—, (p-$SO_2CH_3$-phenyl)-pyridyl-$CH_2$—, (m-$SO_2CH_3$— phenyl)-pyridyl-$CH_2$—, (p-CN-phenyl)-pyridyl-$CH_2$—, (o-$(CH_3)_2$NHC(O))-pyridyl-$CH_2$—, ($CH_3$NH-benzothiazolyl) —$CH_2$— (for example, wherein said benzothiazolyl moiety is bound through a ring carbon of the benzo moiety to the —$CH_2$— group, and said $CH_3$NH— moiety is bound to the thiazolyl moiety), (($CH_3)_2$CHNH-benzothiazolyl)-$CH_2$— (for example, wherein said benzothiazolyl moiety is bound through a ring carbon of the benzo moiety to the —$CH_2$— group, and said $(CH_3)_2$CHNH— moiety is bound to the thiazolyl moiety), (morpholinyl-$(CH_2)_2$—NH-benzothiazolyl) —$CH_2$— (for example, wherein said benzothiazolyl moiety is bound through a ring carbon of the benzo moiety to the —$CH_2$— group, and said morpholinyl-$(CH_2)_2$—NH— moiety is bound to the thiazolyl moiety), ($CH_3$NH$(CH_2)_2$NH-benzothiazolyl) —$CH_2$— (for example, wherein said benzothiazolyl moiety is bound through a ring carbon of the benzo moiety to the —$CH_2$— group, and said $CH_3$NH$(CH_2)_2$NH— moiety is bound to the thiazolyl moiety), ($CH_3CH_2$O(O)C—NH-benzothiazolyl) —$CH_2$— (for example, wherein said benzothiazolyl moiety is bound through a ring carbon of the benzo moiety to the —$CH_2$— group, and said $CH_3CH_2$O(O)CNH— moiety is bound to the thiazolyl moiety), and ($CH_3CH_2$NH(O)C—NH-benzothiazolyl) —$CH_2$— (for example, wherein said benzothiazolyl moiety is bound through a ring carbon of the benzo moiety to the —$CH_2$— group, and said $CH_3CH_2$NH(O)C—NH— moiety is bound to the thiazolyl moiety).

Examples of said $R^6$ and $R^7$ substituted heterocycloalkyl substitutent (see (4) in the definition of $R^6$ and $R^7$) for formula 1 include, for example, substituted piperidyl wherein said substituted piperidyl is bound through a ring carbon to the rest of the molecule and the nitrogen of said substituted piperidyl ring is substituted with substituent (a), (b), (c), or (d) (see 4(a), 4(b), 4(c), or 4(d) are defined in $R^6$ and $R^7$), for example, said substituted heterocycloalkyl moiety includes: N-pyridylpiperidyl- wherein the piperidyl is bound to the amide nitrogen by a ring carbon atom, N-quinolinylpiperidyl- wherein the piperidyl is bound to the amide nitrogen by a ring carbon atom, and N—($CH_3$S-pyrimidinyl)-piperidyl-.

Examples of said $R^6$ and $R^7$ substituted alkyl substituent (see (5) in the definition of $R^6$ and $R^7$) include, for example, —$CH_2$CH($CH_3$)phenyl, —CH(CH3)C(O)OH, —CH($CH_3$)C(O)O$CH_3$, —$CH_2C_6H_4SO_2CH_3$, Clphenyl$CH_2$—, $NH_2SO_2$phenyl $CH_2$—, (m-CN-phenyl)-phenyl-$CH_2$—, (p-CN-phenyl)-phenyl-$CH_2$—, (m-$SO_2CH_3$-phenyl)-phenyl-$CH_2$—, (p-$SO_2CH_3$-phenyl)-phenyl-$CH_2$—, —$CH_2$CH(OH)phenyl, o-F-p-methyl-phenyl-$CH_2$—, o,p-di-$CH_3$-phenyl$CH_2$-phenyl-phenyl-$CH_2$—, (O=)pyrazolidinyl-phenyl-$CH_2$—, —CH($CH_3$)-p-$SO_2CH_3$-phenyl, —CH($CH_3$)-p-OH-phenyl-$CH_2$—, phenyl-phenyl-$CH_2$—, pyridyl-O-phenyl-$CH_2$—; N-substituted piperidyl-$CH_2$— (such as N—C($CH_3)_3$O(O)C-piperidyl-$CH_2$—) N-substituted pyrazolidinyl-$CH_2$— (such as N—C($CH_3)_3$O(O)C-pyrazolidinyl-$CH_2$—), and —$CH_2$-phenyl-p-$SO_2CH_3$.

Examples of said $R^8$ and $R^9$ substituted alkyl group (see (3) in the definition of $R^8$ and $R^8$) include, for example, —$CH_2$CH($CH_3$)phenyl, —CH(CH3)C(O)OH, —CH($CH_3$)C(O)O$CH_3$, —$CH_2C_6H_4SO_2CH_3$, Clphenyl$CH_2$—, $NH_2SO_2$phenyl $CH_2$—, (m-CN-phenyl)-phenyl-$CH_2$—, (p-CN-phenyl)-phenyl-$CH_2$—, (m-$SO_2CH_3$-phenyl)-phenyl-$CH_2$—, (p-$SO_2CH_3$-phenyl)-phenyl-$CH_2$—, —$CH_2$CH(OH)phenyl, o-F-p-methyl-phenyl-$CH_2$—, o,p-di-$CH_3$-phenyl$CH_2$-phenyl-phenyl-$CH_2$—, (O=)pyrazolidinyl-phenyl-$CH_2$—, —CH($CH_3$)-p-$SO_2CH_3$-phenyl, —CH($CH_3$)-p-OH-phenyl-$CH_2$—, phenyl-phenyl-$CH_2$—, pyridyl-O-phenyl-$CH_2$—; N-substituted piperidyl-$CH_2$— (such as N—C($CH_3)_3$O(O)C-piperidyl-$CH_2$—) and N-substituted pyrazolidinyl-$CH_2$— (such as N—C($CH_3)_3$O(O)C-pyrazolidinyl-$CH_2$—); —$(CH_2)_2$OH, —CH($CH_3$)$CH_2$OH, —CH($CH_2CH_3$)—$CH_2$OH, —$(CH_2)_3$OH, —$CH_2$CH($CH_3$)OH, —CH($CH_2CH(CH_3)_2$)$CH_2$OH, —CH($CH_2C_6H_5$)$CH_2$OH, —$CH_2$CH($C_6H_5$)OH, —$(CH_2)_2$morpholinyl, —$(CH_2)_2C_6H_5$, —$CH_2$-m-pyridyl, —$CH_2$-benzoimidazolyl-$CH_3$, —$CH_2$-(N-phenylpyrazolyl), —$CH_2$-pyrazolyl-N-(phenyl-p-$SO_2CH_3$), and —$CH_2$-pyrazolyl-N-(phenyl-m-$CF_3$).

Examples of said $R^8$ and $R^9$ substituted heterocycloalkyl groups (see (5) in the definition of $R^8$ and $R^9$) include, for example, substituted piperidyl wherein said substituted piperidyl is bound through a ring carbon to the rest of the molecule and the nitrogen of said substituted piperidyl ring is substituted with substituent (a), (b), (c), or (d) (see 5(a)-(d) in the definition of the $R^8$ and $R^9$ substituted heterocycloalkyl group), for example, said substituted heterocycloalkyl moiety includes: N-pyridylpiperidyl- wherein the piperidyl is bound to the amide nitrogen by a ring carbon atom, N-quinolinylpiperidyl- wherein the piperidyl is bound to the amide nitrogen by a ring carbon atom, and N—($CH_3$S-pyrimidinyl)-piperidyl-.

Examples of said $R^8$ and $R^9$ heteroarylalkyl substitutent (see (8) in the definition of $R^8$ and $R^9$) include, for example, benzothiazolyl-($C_1$ to $C_6$)alkyl- (such as, for example, benzothiazolyl-$CH_2$—), —$(CH_2)_3$-imidazolyl (e.g, —$(CH_2)_3$-imidazolyl wherein said imidazolyl is bound to the alkyl group by a ring nitrogen), pyridyl-$CH_2$—, pyrazolyl-($C_1$ to $C_6$)alkyl- (wherein said pyrazolyl is bound through the ring nitrogen to said alkyl moiety), pyrazolyl-($C_1$ to $C_6$)alkyl- (wherein said pyrazolyl is bound through a ring carbon to said alkyl moiety), thiazolyl-($C_1$ to $C_6$)alkyl- (e.g., wherein said thiazolyl is bound through a ring carbon to said alkyl moiety), benzoimidiazolyl-($C_1$ to $C_6$)alkyl- (e.g., benzoimidazolyl$CH_2$—, also, for example, wherein said benzoimidazolyl is bound through a carbon of the imidazole ring to said alkyl moiety), and isooxazolyl-($C_1$ to $C_6$)alkyl-.

Examples of said $R^8$ and $R^9$ substituted heteroarylalkyl substitutent (see (9) in the definition of $R^8$ and $R^9$) include, for example, substituted pyrazolylalkyl-, substituted isooxazolylalkyl-, substituted benzoimidazolylalkyl- (e.g., a substituted benzoimidazolyl ring that is bound through the benzo ring or the imidazoly ring to the alkyl moiety), substituted pyridylalkyl-, substituted thienylalkyl-, substituted benzothiazolylalkyl-, and substituted thiazolopyridinylalkyl- (e.g., substituted thiazolo[4,5-b]pyridinyl-alkyl-).

Examples of said $R^8$ and $R^9$ substituted heteroarylalkyl substitutent (see (9) in the definition of $R^8$ and $R^9$) also include, for example, amino-benzothiazolyl-alkyl- (e.g., amino-benzothiazolyl-$CH_2$—), methyl-pyrazinyl-$CH_2$—, Cl-pyridyl-$CH_2$—, phenyl-pyrazolyl-$CH_2$— (for example, wherein said pyrazolyl moiety is bound to said —CH₂— moiety through a ring carbon, and said phenyl is bound to a N of said pyrazolyl moiety), NH₂C(O)NHbenzothiazolylCH₂—, N-methylbenzoimidazolylCH₂—, methylimidazolylbenzoCH₂—, N—(CH₃)—(CH₃)₂-pyrazolylCH₂—, N—(CH₃)—(CH₃)— pyrazolylCH₂—, thiazolylCH₂—, benzoimidazolylCH₂—, N-methylbenzoimidazolylCH₂—, methylimidazolylbenzoCH₂—, o-NH₂-pyridyl-CH₂—, pyrazolidinyl-pyridyl-CH₂—, morpholinyl-pyridyl-CH₂—, N-methylpyrazolyl-CH₂—, N-isopropylpyrazolyl-CH₂—, pyridyl-thienyl-CH₂—, N-methyl-methyl-imidazolylbenzo-CH₂—, N-(m-methylphenyl)-pyrazolyl-CH₂—, N-(p-methylphenyl)-pyrazolyl-CH₂—, N-(m-Cl-p-F-phenyl)-pyrazolyl-CH₂—, N-(m-Cl-phenyl)-pyrazolyl-CH₂—, N-(m-CN-phenyl)-pyrazolyl-CH₂—, N-(p-CN-phenyl)-pyrazolyl-CH₂—, N-(m-SO₂CH₃-phenyl)-pyrazolyl-CH₂—, N-(p-SO₂CH₃-phenyl)-pyrazolyl-CH₂—, N-(m,m-di-Cl-phenyl) pyrazolyl-CH₂—, N-(m-F-phenyl)-pyrazolyl-CH₂—, N-(m-CF₃-phenyl)-pyrazolyl-CH₂—, N-(m-pyridyl)-pyrazolyl-CH₂—, N-(quinolinyl)-pyrazolyl-CH₂— (e.g., wherein said quinolinyl moiety is bound through a ring carbon of the benzo moiety to the pyrazolyl moiety), N-(p-NH₂CH₂)-pyrazolyl-CH₂—, N-(quinolinyl)-pyrazolyl-CH₂— (e.g., wherein said quinolinyl moiety is bound through a ring carbon of the pyridyl moiety to the pyrazolyl moiety), N-(pyrimidinyl)-pyrazolyl-CH₂—, N-(methyl imidazolylbenzo)-pyrazolyl-CH₂— (e.g., wherein said benzoimidazolyl moiety is bound through a ring carbon of the benzo moiety to the pyrazolyl moiety), N-(N-methyl-imidazolylbenzo)-pyrazolyl-CH₂— (e.g., wherein said benzoimidazolyl moiety is bound through a ring carbon of the benzo moiety to the pyrazolyl moiety), N-(methylquinolinyl)-pyrazolyl-CH₂— (e.g., wherein said quinolinyl moiety is bound through a ring carbon of the benzo moiety to the pyrazolyl moiety and there is a methyl substituent bound to a carbon of the pyridyl moiety), N-(m-CF₃-p-F-phenyl)pyrazolyl-CH₂—, N-(quinoxalinyl)-pyrazolyl-CH₂— (e.g., wherein said quinoxalinyl moiety is bound through a ring carbon of the benzo moiety to the pyrazolyl moiety), N-N-(p-(CH₃)₂SO₂-phenyl)-pyrazolyl-CH₂—, N-(m-F-pyridyl)pyrazolyl-CH₂—, N-(p-(CH₃)SO-phenyl)-pyrazolyl-CH₂—, N-(m-Br-m-CN-phenyl)-pyrazolyl-CH₂—, N-(o-pyridyl)-pyrazolyl-CH₂—, N-(o-Cl-phenyl) pyrazolyl-CH₂—, N-(o-CN-phenyl)-pyrazolyl-CH₂—, N-(p-pyridyl)-pyrazolyl-CH₂—, N-(pyrimidinyl)-pyrazolyl-CH₂—, N—(CNpyridyl)-pyrazolyl-CH₂—, N-(m-F-m-CN-phenyl)-pyrazolyl-CH₂—, N-(thiazolyl)-pyrazolyl-CH₂—, N-(aminothiazolo[4,5-b]pyridinyl)-pyrazolyl-CH₂— (e.g., N-(thiazolo[4,5-b]pyridine-2-ylamine)-pyrazolyl-CH₂—), N-(imidazo[1,2-a]pyridinyl)-pyrazolyl-CH₂—, N-(imidazo[1,2-a]pyrimidinyl)-pyrazolyl-CH₂—, N-(quinazolinyl)-pyrazolyl-CH₂—, N-(3H-imidazo[4,5-b]pyridinyl)-pyrazolyl-CH₂—, N-([1,5]-naphthyridinyl)-pyrazolyl-CH₂—, N-(1-isopropyl-2-methyl-1H-benzoimidazolyl)-pyrazolyl-CH₂—, N-(1,2-dimethyl-1H-benzoimidazolyl)-pyrazolyl-CH₂—, N-(1-methyl-2-CF₃-1H-benzoimidazolyl)-pyrazolyl-CH₂—, N-(1-methyl-2-isopropyl-1H-benzoimidazolyl)-pyrazolyl-CH₂—, N-(1-methyl-2-pyridin-3-yl-1H-benzoimidazolyl)-pyrazolyl-CH₂—, N—(H₂NSO₂phenyl)-pyrazolyl-CH₂—, N—(CH₃NHSO₂phenyl)-pyrazolyl-CH₂—, N-(piperazinylSO₂phenyl)-pyrazolyl-CH₂—, N-(p-(CH₃)₂NSO₂)-m-Cl-phenyl)-pyrazolyl-CH₂—, 4-[4-(4-Aminomethyl-pyrazol-1-yl)-2-Chloro-bezenesulfonyl]-piperazine-1-carboxylic acid tert-butylester, C-{1-[3-Chloro-4-(piperazine-1-sulfonyl)-phenyl]-1H-pyrazol-4-yl}methylamine, (m-methyl-phenyl)-pyridyl-CH₂—, (m-F-phenyl)-pyridyl-CH₂—, (m-Cl-phenyl)-pyridyl-CH₂—, (p-methyl-phenyl)-pyridyl-CH₂—, (m-CN-phenyl)-pyridyl-CH₂—, (p-CN-phenyl)-pyridyl-CH₂—, (m-SO₂CH₃-phenyl)-pyridyl-CH₂—, (p-SO₂CH₃-phenyl)-pyridyl-CH₂—, (p-Cl-phenyl)-pyridyl-CH₂—, (m-CF₃-phenyl)-pyridyl-CH₂—, (m-Cl-p-F-phenyl)-pyridyl-CH₂—, (m-Cl-m-Cl-phenyl)-pyridyl-CH₂—, (m-methyl-phenyl)-pyridyl-CH₂—, quinolinyl-pyridyl-CH₂— (e.g., wherein the quinolinyl moiety is bound through a carbon of the benzo moiety to the pyridyl moiety), bromopyridylCH₂—, (p-SO₂CH₃-phenyl)-pyridyl-CH₂—, (m-SO₂CH₃-phenyl)-pyridyl-CH₂—, (p-CN-phenyl)-pyridyl-CH₂—, (o-(CH₃)₂NHC(O))-pyridyl-CH₂—, (CH₃NH-benzothiazolyl) —CH₂— (for example, wherein said benzothiazolyl moiety is bound through a ring carbon of the benzo moiety to the —CH₂— group, and said CH₃NH— moiety is bound to the thiazolyl moiety), ((CH₃)₂CHNH-benzothiazolyl)-CH₂— (for example, wherein said benzothiazolyl moiety is bound through a ring carbon of the benzo moiety to the —CH₂— group, and said (CH₃)₂CHNH— moiety is bound to the thiazolyl moiety), (morpholinyl-(CH₂)₂—NH-benzothiazolyl) —CH₂— (for example, wherein said benzothiazolyl moiety is bound through a ring carbon of the benzo moiety to the —CH₂— group, and said morpholinyl-(CH₂)₂—NH— moiety is bound to the thiazolyl moiety), (CH₃NH(CH₂)₂NH-benzothiazolyl) —CH₂— (for example, wherein said benzothiazolyl moiety is bound through a ring carbon of the benzo moiety to the —CH₂— group, and said CH₃NH(CH₂)₂ NH— moiety is bound to the thiazolyl moiety), (CH₃CH₂O(O)C—NH-benzothiazolyl) —CH₂— (for example, wherein said benzothiazolyl moiety is bound through a ring carbon of the benzo moiety to the —CH₂— group, and said CH₃CH₂O(O) CNH— moiety is bound to the thiazolyl moiety), and (CH₃CH₂NH(O)C—NH-benzothiazolyl) —CH₂— (for example, wherein said benzothiazolyl moiety is bound through a ring carbon of the benzo moiety to the —CH₂— group, and said CH₃CH₂NH(O)C—NH— moiety is bound to the thiazolyl moiety).

Examples of said R⁸ and R⁹ heteroarylbenzoalkyl-substitutent (see (8) in the definition of R⁸ and R⁹) include, for example,

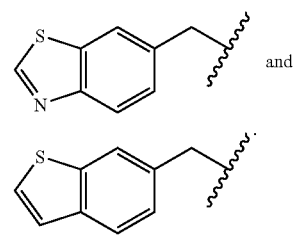

and

Examples of said R⁸ and R⁹ substituted heteroarylalkyl-substitutent (see (9) in the definition of R⁸ and R⁹) include, for example,

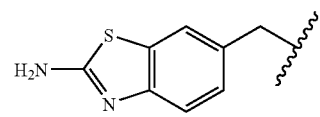

Examples of said R⁸ and R⁹ substituted heteroarylalkyl-substitutent (see (9) in the definition of R⁸ and R⁹) include, for example,

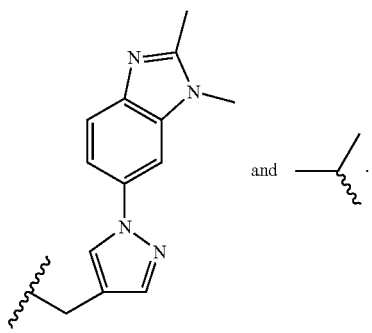 and 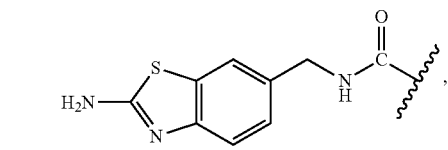

Preferably, $R^{1A}$ is selected from the group consisting of: alkyl, aryl, and heteroaryl.

More preferably, $R^{1A}$ is selected from the group consisting of: hydrogen, hydroxy, —$NH_2$, and —$NH(C_1$ to $C_6)$alkyl.

Most, $R^{1A}$ is selected from the group consisting of: hydrogen, hydroxy, and —$NH_2$.

Preferably, $R^{2A}$ is selected from the group consisting of: hydrogen, hydroxy, —$NH_2$, and —$NH(C_1$ to $C_6)$alkyl, F and Cl.

More preferably, $R^{2A}$ is selected from the group consisting of: hydrogen, hydroxy, —$NH_2$, and —$NH(C_1$ to $C_6)$alkyl.

Most preferably, $R^{2A}$ is selected from the group consisting of: hydrogen, hydroxy, and —$NH_2$.

Preferably, $R^3$ is selected from the group consisting of: heteroarylalkyl- (e.g., —$CH_2$benzothiazole and —$CH_2$benzoimidazolyl), —$NR^{48}R^{50}$ (e.g., wherein $R^{48}$ and $R^{50}$ are independently selected from H and aryl (e.g., phenyl)), halo, —$OR^{52}$ (e.g., wherein $R^{52}$ is alkyl, such as $C_1$-$C_6$ alkyl), —$C(O)NR^8R^9$ wherein $R^8$ and $R^9$ are taken together to form a heterocycloalkyl ring (e.g., a six membered ring), —$C(O)NR^8R^9$ wherein $R^8$ is H and $R^9$ is a heteroarylalkyl- (e.g., —$CH_2$benzothiazole and —$CH_2$benzothiophene), —$C(O)NR^8R^9$ wherein $R^8$ is H and $R^9$ is a substituted heteroarylalkyl- (e.g., wherein $R^9$ is (a) —$CH_2$benzothiazole wherein the benzothiazole moiety is substituted with —$NH_2$, or (b) substituted pyrazolyl-$CH_2$, such as, for example: (1) N-(dimethylimidazolyl-benzo)-pyrazolyl-$CH_2$—, (2) N-(quinoxalinyl-pyrazolyl-$CH_2$—, or (3) N-(p-$SO_2N(CH_3)_2$-m-Cl-phenyl)-pyrazolyl-$CH_2$—).

More preferably, $R^3$ is selected from the group consisting of: —NHaryl (e.g., —NHphenyl), —$CH_2$benzothiazole, —$CH_2$benzoimidazolyl, Cl, —$OCH_3$,

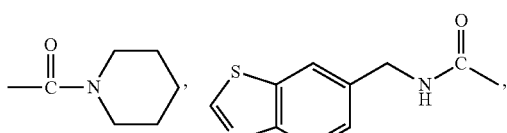

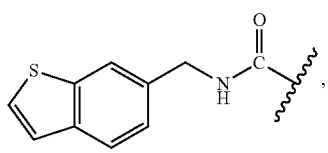

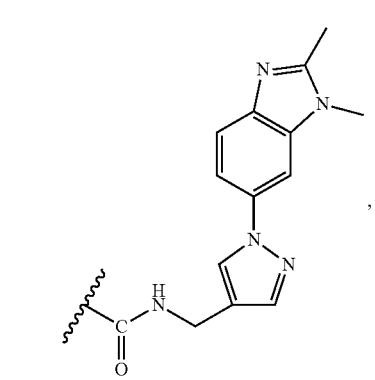

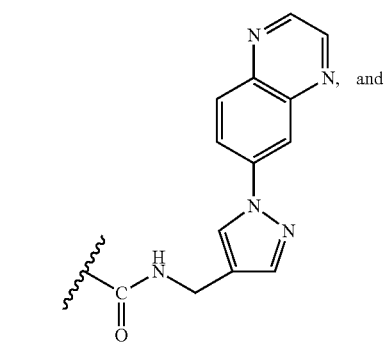

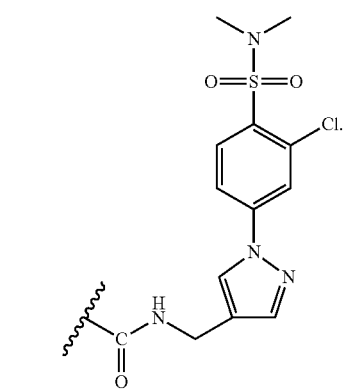

Most preferably, $R^3$ is selected from the group consisting of:

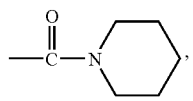

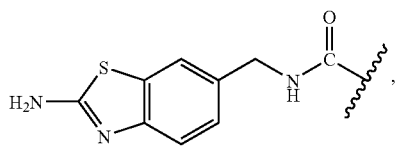

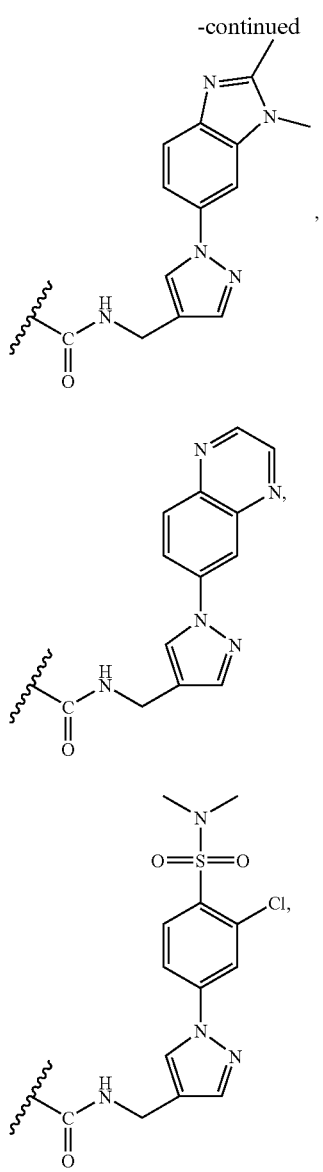

—NHaryl (e.g., —NHphenyl), Cl, and —OCH$_3$, —CH$_2$benzothiazole and —CH$_2$benzoimidazolyl.

Preferably, R$^4$ is selected from the group consisting of: (a) —C(O)NR$^6$R$^7$ wherein R$^6$ is H and R$^7$ is heterocycloalkyl (e.g., piperidyl), (b) —C(O)NR$^6$R$^7$ wherein R$^6$ is H and R$^7$ is a substituted heterocycloalkyl (e.g., a heterocycloalkyl substituted with —C(O)OR$^{14}$ (e.g., wherein R$^{14}$ is alkyl such as methyl), for example, R$^7$ is a piperidyl whose N is substituted with —C(O)OR$^{14}$, such as for example an R$^7$ that is —N—C(O)OC$_2$H$_5$-piperidyl), (c) heteroaryl (e.g., pyrazolyl), and (d) substituted heteroaryl (e.g., substituted pyrazolyl, such as pyrazolyl substituted with (a) halo (e.g., I, Br), (b) substituted aryl, wherein said substituted aryl is substituted with 1 to 3 substituents independently selected from the group consisting of: halo (e.g., F), and wherein said substituted aryl includes, for example, substituted phenyl, such as, for example, halophenyl, such as, for example fluorophenyl, (c) heteroaryl (e.g., pyridyl), (d) alkyl (—C$_1$ to C$_6$ alkyl, such as, for example, methyl and t-butyl), (e) aryl (e.g., phenyl), (f) heteroaryl (e.g., pyrazinyl), (g) —C(O)NR$^6$R$^7$ wherein R$^6$ is H and R$^7$ is alkyl, and (h) —C(O)NR$^6$R$^7$ wherein R$^6$ is H and R$^7$ is substituted alkyl).

More preferably, R$^4$ is selected from the group consisting of: —C(O)NR$^6$R$^7$ wherein R$^6$ is H and R$^7$ is selected from the group consisting of: alkyl,

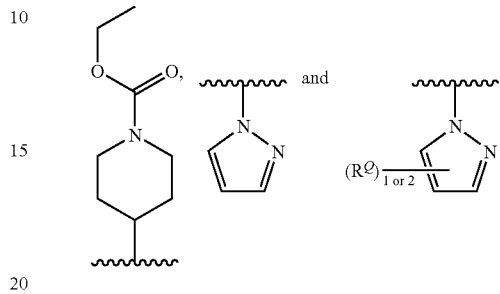

wherein each R$^Q$ is independently selected from the group consisting of: (a) halo (e.g., I, Br), (b) substituted aryl, wherein said substituted aryl is substituted with 1 to 3 substituents independently selected from the group consisting of: halo (e.g., F), and wherein said substituted aryl includes, for example, substituted phenyl, such as, for example, halophenyl, such as, for example fluorophenyl, (c) heteroaryl (e.g., pyridyl), (d) alkyl (—C$_1$ to C$_6$ alkyl, such as, for example, methyl and t-butyl), (e) aryl (e.g., phenyl), and (f) heteroaryl (e.g., pyrazinyl).

Most preferably, R$^4$ is selected from the group consisting of: —C(O)NH(i-propyl),

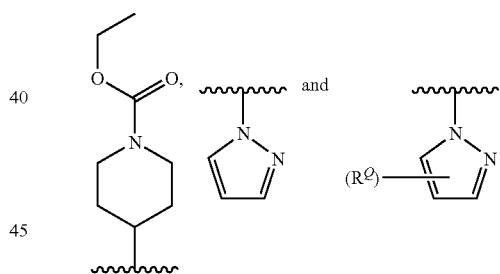

wherein R$^Q$ is as previously defined. In one embodiment R$^Q$ is iodo. In another embodiment R$^Q$ is t-butyl.

In one embodiment of the compounds of this invention, X is CH.

In another embodiment of the compounds of this invention, X is nitrogen.

In another embodiment of the compounds of this invention, Y is CR$^5$.

In another embodiment of the compounds of this invention Y is nitrogen.

In another embodiment of this invention X is nitrogen, Y is CR$^5$, R$^3$ is selected from the group consisting of: —CH$_2$benzothiazole, —CH$_2$benzoimidazole, and R$^4$ is —C(O)NR$^6$R$^7$, R$^6$ is H, and R$^7$ is a heterocycloalkyl or a substituted heterocycloalkyl. For example, R$^7$ is a substituted heterocycloalkyl, such as, for example:

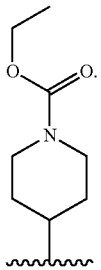

In another embodiment of this invention X is nitrogen, Y is CR$^5$, R$^3$ is selected from the group consisting of: —CH$_2$benzothiazole, —CH$_2$benzoimidazole, and R$^4$ is selected from the group consisting of: heteroaryl and substituted heteroaryl, such as, for example, pyrazolyl and substituted pyrazolyl, such as, for example,

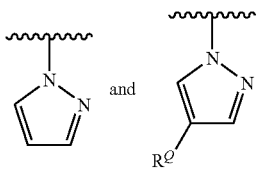

wherein R$^Q$ is as previously defined. In one embodiment R$^Q$ is iodo. In another embodiment R$^Q$ is t-butyl.

In another embodiment of this invention X is nitrogen, Y is CR$^5$, R$^3$ is selected from the group consisting of: —C(O)NR$^8$R$^9$ wherein R$^8$ is H, and R$^9$ is heteroarylalkyl or a substituted heteroarylalkyl, and R$^4$ is —C(O)NR$^6$R$^7$, R$^6$ is H, and R$^7$ is alkyl (e.g., isopropyl) or substituted alkyl. An example of R$^9$ is

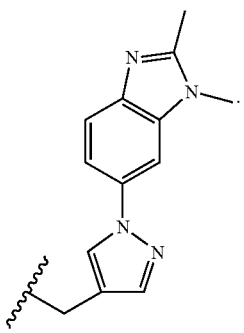

In another embodiment of the compounds of this invention, X is nitrogen, Y is CR$^5$, R$^{1A}$ is aryl or halo, R$^{2A}$ is F or Cl, R$^3$ is selected from the group consisting of: —C(O)NR$^8$R$^9$ wherein R$^8$ is H, and R$^9$ is heteroarylalkyl or a substituted heteroarylalkyl, and R$^4$ is —C(O)NR$^6$R$^7$, R$^6$ is H, and R$^7$ is alkyl (e.g., isopropyl) or substituted alkyl. An example of R$^9$ is

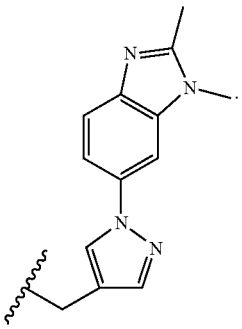

In another embodiment of the compounds of this invention, X is nitrogen, Y is CR$^5$, R$^{1A}$ is OH or H, R$^{2A}$ is H, OH, or NH$_2$, R$^3$ is selected from the group consisting of: —C(O)NR$^8$R$^9$ wherein R$^8$ is H, and R$^9$ is heteroarylalkyl or a substituted heteroarylalkyl, and R$^4$ is —C(O)NR$^6$R$^7$, R$^6$ is H, and R$^7$ is alkyl (e.g., isopropyl) or substituted alkyl. An example of R$^9$ is

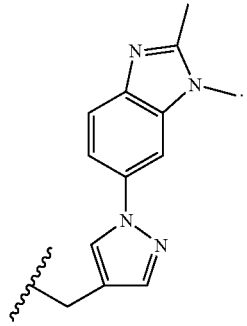

In another embodiment of the compounds of this invention, X is nitrogen, Y is CR$^5$, R$^{1A}$ is OH or H, R$^{2A}$ is H, R$^3$ is selected from the group consisting of: —C(O)NR$^8$R$^9$ wherein R$^8$ is H, and R$^9$ is heteroarylalkyl or a substituted heteroarylalkyl, and R$^4$ is —C(O)NR$^6$R$^7$, R$^6$ is H, and R$^7$ is alkyl (e.g., isopropyl) or substituted alkyl. An example of R$^9$ is

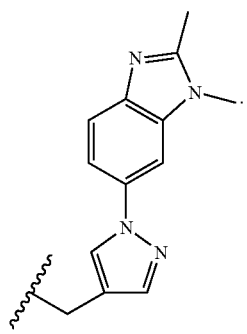

In another embodiment of the compounds of this invention, X is nitrogen, Y is CH$_2$, R$^{1A}$ is H, R$^{2A}$ is H, R$^3$ is selected from the group consisting of: —C(O)NR$^8$R$^9$ wherein R$^8$ is H, and R$^9$ is heteroarylalkyl or a substituted heteroarylalkyl, and R$^4$ is —C(O)NR$^6$R$^7$, R$^6$ is H, and R$^7$ is alkyl (e.g., isopropyl) or substituted alkyl. Examples of R$^9$ include:

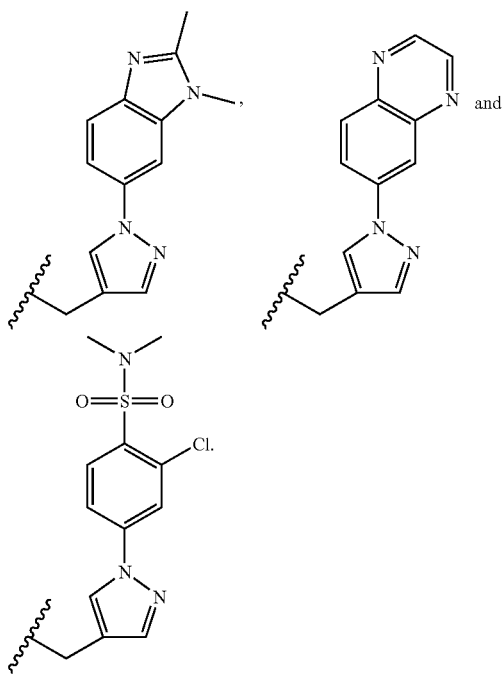

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

In the Examples below there are formulas shown with an R, $R^1$ and/or $R^2$ group. Those skilled in the art will appreciate that each particular Example with such R groups defines what those R groups are by reference to the final compounds prepared in that Example.

In the tables below EMW stands for Exact Molecular Weght. The LC-MS data for the EMW was obtained using an Agilent 1100 Series LC/MSD (quadrupole, API-ES (Atmospheric Pressure Interface Electrospray)) with a capillary voltage set to 3500 V and running in positive mode.

In the tables below, the retention time is for the purification via reverse phase chromatography which was accomplished using a C18 reverse phase column with a gradient of 0.1% trifluoroacetic acid in water to 95:5 acetonitrile:water at a flow rate of 20 mL/min. Samples were collected using a UV (Gilson, 254 nm) or mass spectra (Agilent 1100 Series LC/MSD model SL) signal Example 1

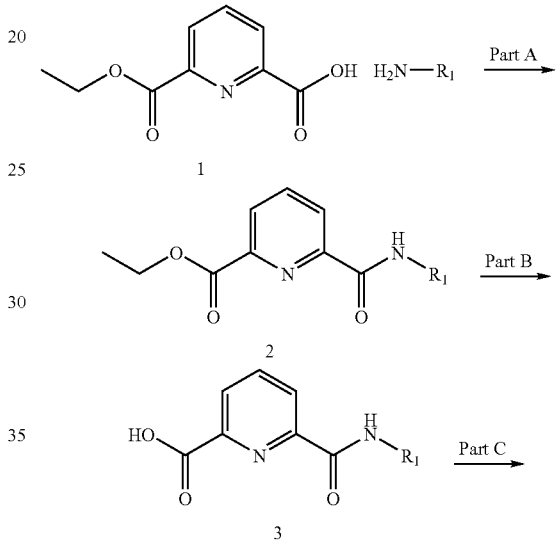

GENERAL PROCESS SCHEME

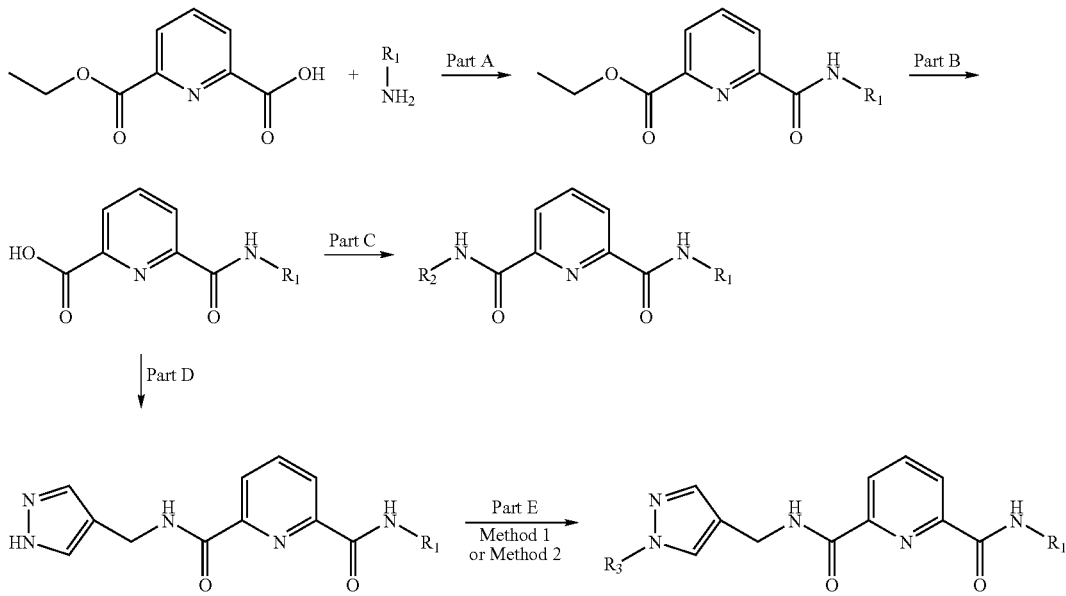

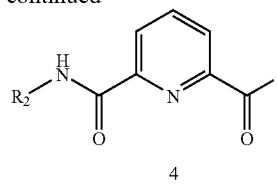

4

Part A

To a solution of compound 1 (0.050 g, 0.256 mmol) in DMF (2 mL) was added the appropriate amine building block to make the compounds in Table 1 (1.2 equivalents) and diisopropylethylamine (3 equivalents). The reaction mixture was stirred at room temperature for 10 minutes, cooled to 0° C. (ice-bath) and then added HATU (1.2 equivalents) and catalytic DMAP. The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography (SiO$_2$, ethyl acetate) afforded compound 2 as a solid in varialble yields.

Part B

To a solution of compound 2 (1 equivalent) in THF (3 mL) was added 1M LiOH (2 equivalents) at room temperature. The reaction mixture was stirred at room temperature for 2 hours at which time. Thin layer chromatography indicated that the reaction was complete. The reaction mixture was concentrated. The residue was suspended in ethyl acetate and water, and acidified to pH 4 with 1N HCl. The organic and aqueous layers were separated. The aqueous layer was extracted with ethyl acetate (×3). The combined organic layer was washed with brine, dried over sodium sulfate and concentrated to afford compound 3 as a solid.

Part C

To a solution of compound 3 (1 equivalent) in DMF (2 mL) was added the appropriate amine building block (1.2 equivalents) to make the compounds in Table 1 and diisopropylethylamine (3 equivalents). The reaction mixture was stirred at room temperature for 10 minutes, cooled to 0° C. (ice-bath) and then added HATU (1.2 equivalents) and catalytic DMAP. The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography (SiO$_2$, ethyl acetate) afforded the compounds of formula 4 given in Table 1.

TABLE 1

| Cmpd No. | Compound | Ret. Time UV$_{254}$ (min) | EMW | MS (m/z) Observed |
|---|---|---|---|---|
| 5 | | 3.62 | 369.1 | 370.1 |
| 6 | | 2.17 | 385.1 | 386.0 |
| 7 | | 3.05 | 383.1 | 384.1 |
| 8 | | 3.09 | 383.1 | 384.1 |

TABLE 1-continued

| Cmpd No. | Compound | Ret. Time UV$_{254}$ (min) | EMW | MS (m/z) Observed |
|---|---|---|---|---|
| 9 | (structure) | 2.41 | 399.1 | 400.1 |
| 10 | (structure) | 3.74 | 511.2 | 512.0 |
| 11 | (structure) | 2.89 | 381.1 | 382.1 |
| 12 | (structure) | 3.37 | 409.2 | 410.2 |
| 13 | (structure) | 3.27 | 355.1 | 356.1 |
| 14 | (structure) | 3.65 | 355.1 | 356.1 |
| 15 | (structure) | 3.20 | 371.1 | 372.1 |
| 16 | (structure) | 3.31 | 412.1 | 413.1 |

TABLE 1-continued

| Cmpd No. | Compound | Ret. Time UV$_{254}$ (min) | EMW | MS (m/z) Observed |
|---|---|---|---|---|
| 17 | | 3.28 | 385.1 | 386.1 |
| 18 | | 3.34 | 385.1 | 386.1 |
| 19 | | 3.34 | 385.1 | 386.1 |
| 20 | | 3.98 | 427.2 | 428.1 |
| 21 | | 3.98 | 427.2 | 428.1 |
| 22 | | 3.97 | 461.2 | 462.1 |
| 23 | | 3.97 | 461.2 | 462.1 |
| 24 | | 3.91 | 447.1 | 448.1 |

TABLE 1-continued

| Cmpd No. | Compound | Ret. Time UV$_{254}$ (min) | EMW | MS (m/z) Observed |
|---|---|---|---|---|
| 25 | | 3.9 | 447.1 | 448.1 |
| 26 | | 3.08 | 440.2 | 441.1 |
| 27 | | 4.21 | 431.1 | 432.1 |
| 28 | | 3.48 | 452.2 | 453.1 |
| 29 | | 3.09 | 424.2 | 425.1 |
| 30 | | 3.53 | 500.2 | 501.2 |
| 31 | | 3.52 | 503.2 | 504.1 |

TABLE 1-continued

| Cmpd No. | Compound | Ret. Time UV$_{254}$ (min) | EMW | MS (m/z) Observed |
|---|---|---|---|---|
| 32 | (structure) | 3.92 | 545.2 | 546.2 |
| 33 | (structure) | 3.93 | 545.2 | 546.2 |
| 34 | (structure) | 3.29 | 411.1 | 412.1 |
| 35 | (structure) | 3.18 | 411.1 | 412.1 |
| 36 | (structure) | 3.27 | 425.2 | 426.1 |
| 37 | (structure) | 3.42 | 425.2 | 426.1 |
| 38 | (structure) | 4.18 | 348.2 | 349.1 |

TABLE 1-continued

| Cmpd No. | Compound | Ret. Time UV$_{254}$ (min) | EMW | MS (m/z) Observed |
|---|---|---|---|---|
| 39 | | 4.41 | 348.2 | 349.1 |
| 40 | | 3.99 | 364.2 | 365.1 |
| 41 | | 4.12 | 376.2 | 377.2 |
| 42 | | 3.74 | 411.2 | 412.1 |
| 43 | | 4.45 | 488.2 | 489.1 |

TABLE 1-continued

| Cmpd No. | Compound | Ret. Time UV$_{254}$ (min) | EMW | MS (m/z) Observed |
|---|---|---|---|---|
| 44 | | 4.30 | 454.2 | 455.1 |
| 45 | | 3.90 | 424.2 | 425.1 |
| 46 | | 2.93 | 328.1 | 329.1 |
| 47 | | 3.38 | 341.09 | 342.1 |
| 48 | | 3.45 | 367.1 | 368.1 |
| 49 | | 3.34 | 385.1 | 386.2 |
| 50 | | 3.78 | 413.2 | 414.1 |

TABLE 1-continued

| Cmpd No. | Compound | Ret. Time UV$_{254}$ (min) | EMW | MS (m/z) Observed |
|---|---|---|---|---|
| 51 | | 3.96 | 447.1 | 448.1 |
| 52 | | 2.98 | 327.1 | 328.1 |
| 53 | | 3.57 | 383.1 | 384.1 |
| 54 | | 3.96 | 447.1 | 448.1 |
| 55 | | 2.58 | 459.2 | 460.1 |
| 56 | | 3.03 | 487.2 | 488.1 |
| 57 | | 3.19 | 489.2 | 490.1 |

TABLE 1-continued

| Cmpd No. | Compound | Ret. Time UV$_{254}$ (min) | EMW | MS (m/z) Observed |
|---|---|---|---|---|
| 58 | | 3.13 | 494.1 | 495.1 |
| 59 | | 3.78 | 413.2 | 414.1 |
| 60 | | 3.41 | 508.1 | 509.1 |
| 61 | | 4.21 | 570.2 | 571.1 |
| 62 | | 2.87 | 356.1 | 357.1 |
| 63 | | 1.90 | 314.1 | 315.1 |
| 64 | | 3.04 | 383.1 | 384.1 |

TABLE 1-continued

| Cmpd No. | Compound | Ret. Time UV$_{254}$ (min) | EMW | MS (m/z) Observed |
|---|---|---|---|---|
| 65 | | 2.76 | 369.1 | 370.1 |
| 66 | | 2.25 | 399.1 | 400.1 |
| 67 | | 3.08 | 395.1 | 396.1 |
| 68 | | 2.33 | 425.2 | 426.1 |
| 69 | | 1.90 | 435.1 | 436.1 |
| 70 | | 3.55 | 445.2 | 446.2 |
| 71 | | 3.39 | 397.2 | 398.2 |

TABLE 1-continued

| Cmpd No. | Compound | Ret. Time UV$_{254}$ (min) | EMW | MS (m/z) Observed |
|---|---|---|---|---|
| 72 | | 4.34 | 476.2 | 477.2 |
| 73 | | 4.88 | 442.2 | 443.2 |
| 74 | | 4.12 | 470.2 | 471.2 |
| 75 | | 2.63 | 413.1 | 414.1 |
| 76 | | 3.53 | 453.2 | 454.15 |
| 77 | | 4.23 | 481.2 | 482.18 |
| 78 | | 3.90 | 480.1 | 481.12 |

Example 2

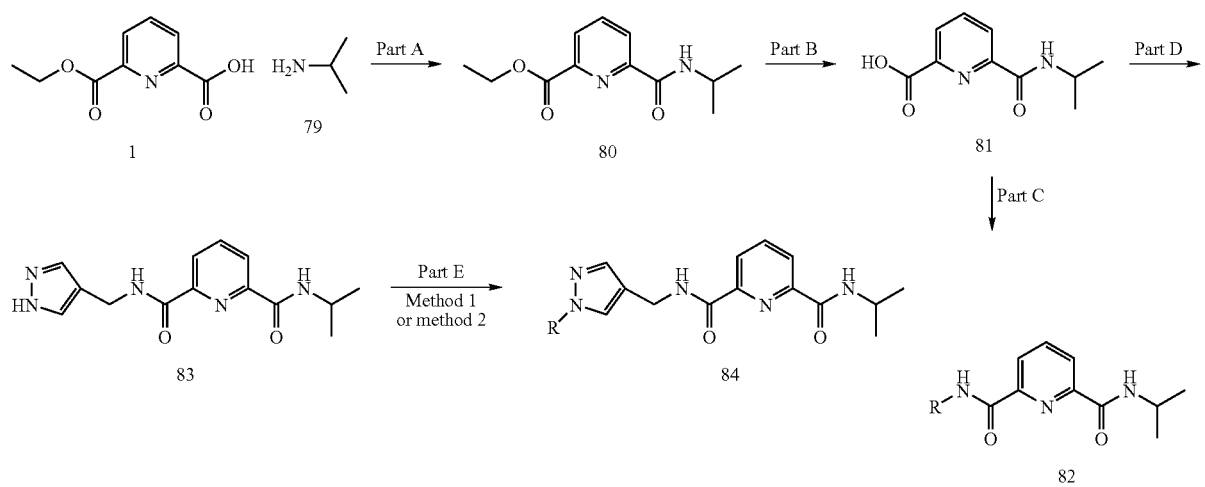

Part A

To a solution of compound 1 (3.0 g, 15.4 mmol) in DMF (25 mL) was added isopropylamine (1.09 g, 18.5 mmol) and diisopropylethylamine (8.04 mL, 46.2 mmol). The reaction mixture was stirred at room temperature for 10 minutes, cooled to 0° C. (ice-bath) and then added HATU (7.03 g, 18.5 mmol) and DMAP (0.094 g, 0.77 mmol). The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography ($SiO_2$, ethyl acetate) afforded compound 80 as a white solid (3.62 g, 99° A. yield). $^1$H NMR (400 MHz, DMSO-$d_6$) δ 8.17 (m, 3H), 4.4 (q, 2H, J=7.2 Hz), 4.15 (m, 1H), 1.37 (t, 3 H, J=7.2 Hz), 1.23 (d, 6H).

Part B

To a solution of compound 80 (3.62 g, 15.3 mmol) in THF (80 mL) was added 1M LiOH (30.6 mL, 30.6 mmol) at room temperature. The reaction mixture was stirred at room temperature for 2 hours at which time thin layer chromatography indicated that the reaction was complete. The reaction mixture was concentrated. The residue was suspended in ethyl acetate and water, and acidified to pH 4 with 1N HCl. The organic and aqueous layers were separated. The aqueous layer was extracted with ethyl acetate (×3). The combined organic layer was washed with brine, dried over sodium sulfate and concentrated to afford compound 81 as a white solid (3.02 g, 95%). $^1$H NMR (400 MHz, DMSO-$d_6$) δ 8.92 (br s, 1H), 8.21 (m, 3H), 4.15 (m, 1 H), 1.23 (d, 6H).

Part C

To a solution of compound 81 (1 equivalent) in DMF (2 mL) was added the appropriate amine building block (1.2 equivalent)) to make the compounds in Table 2 and diisopropylethylamine (3 equivalents). The reaction mixture was stirred at room temperature for 10 minutes, cooled to 0° C. (ice-bath) and then added HATU (1.2 equivalents) and DMAP (catalytic). The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography ($SiO_2$, 10% methanol/dichloromethane) afforded the compounds of general structure 82 in Table 2.

TABLE 2

| Cmpd No. | Compound | Ret. Time $UV_{254}$ (min) | EMW | MS (m/z) Observed |
|---|---|---|---|---|
| 85 | 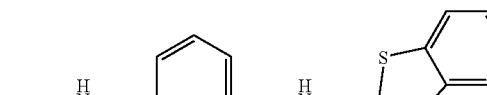 | 4.36 | 354.1 | 355.1 |
| 86 | 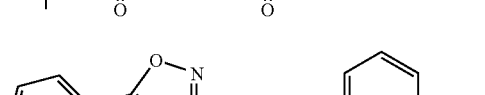 | 4.65 | 394.2 | 395.1 |

TABLE 2-continued

| Cmpd No. | Compound | Ret. Time UV$_{254}$ (min) | EMW | MS (m/z) Observed |
|---|---|---|---|---|
| 87 | | 3.21 | 412.1 | 413.1 |
| 88 | | 3.43 | 375.1 | 376.1 |
| 89 | | 4.17 | 341.1 | 342.1 |
| 90 | | 2.31 | 284.1 | 285.1 |
| 91 | | 3.77 | 335.1 | 336.1 |
| 92 | | 3.14 | 313.2 | 314.1 |
| 93 | | 4.36 | 298.1 | 299.1 |
| 94 | | 2.14 | 404.2 | 405.1 |

TABLE 2-continued

| Cmpd No. | Compound | Ret. Time UV$_{254}$ (min) | EMW | MS (m/z) Observed |
|---|---|---|---|---|
| 95 | | | 390.2 | 391.1 |
| 96 | | | 331.1 | 332.1 |
| 97 | | 4.81 | 331.1 | 332.1 |
| 98 | | 4.83 | 376.1 | 377.1 |
| 99 | | 3.1 | 332.1 | 333.1 |
| 100 | | 3.87 | 363.2 | 364.1 |
| 101 | | 4.32 | 298.1 | 299.1 |
| 102 | | 2.21 | 329.2 | 330.1 |

TABLE 2-continued

| Cmpd No. | Compound | Ret. Time UV$_{254}$ (min) | EMW | MS (m/z) Observed |
|---|---|---|---|---|
| 103 | | 2.67 | 315.2 | 316.1 |
| 104 | | 3.22 | 304.1 | 305.1 |
| 105 | | 4.25 | 391.2 | 392.1 |
| 106 | | 2.57 | 337.2 | 338.1 |
| 107 | | 2.67 | 351.2 | 352.1 |
| 108 | | 2.56 | 351.2 | 352.1 |
| 109 | | 4.15 | 363.2 | 364.1 |
| 110 | | 4.79 | 329.2 | 330.1 |

TABLE 2-continued

| Cmpd No. | Compound | Ret. Time UV$_{254}$ (min) | EMW | MS (m/z) Observed |
|---|---|---|---|---|
| 111 | (3,4-dimethoxybenzyl pyridine-2,6-dicarboxamide with isopropyl) | 3.9 | 357.2 | 358.1 |
| 112 | (biphenyl-4-ylmethyl pyridine-2,6-dicarboxamide with isopropyl) | 5.43 | 373.2 | 374.1 |
| 113 | (6-aminopyridin-3-ylmethyl pyridine-2,6-dicarboxamide with isopropyl) | 2.27 | 313.2 | 314.1 |
| 114 | (6-(pyrrolidin-1-yl)pyridin-3-ylmethyl pyridine-2,6-dicarboxamide with isopropyl) | 2.84 | 367.2 | 368.1 |
| 115 | (6-morpholinopyridin-3-ylmethyl pyridine-2,6-dicarboxamide with isopropyl) | 2.5 | 383.2 | 384.1 |
| 116 | (1-methyl-1H-pyrazol-4-ylmethyl pyridine-2,6-dicarboxamide with isopropyl) | 2.88 | 301.2 | 302.1 |
| 117 | (1-isopropyl-1H-pyrazol-4-ylmethyl pyridine-2,6-dicarboxamide with isopropyl) | 3.51 | 329.2 | 330.2 |

TABLE 2-continued

| Cmpd No. | Compound | Ret. Time UV$_{254}$ (min) | EMW | MS (m/z) Observed |
|---|---|---|---|---|
| 118 | | 3.47 | 380.1 | 381.1 |
| 119 | | 2.2 | 287.1 | 288.1 |
| 120 | | 3.69 | 380.2 | 381.1 |
| 121 | | 3.62 | 389.1 | 390.1 |
| 122 | | 3.07 | 376.1 | 377.1 |
| 123 | | 3.57 | 327.2 | 328.1 |
| 124 | | 3.57 | 327.2 | 328.1 |
| 125 | | 5.35 | 373.2 | 374.18 |

TABLE 2-continued

| Cmpd No. | Compound | Ret. Time UV$_{254}$ (min) | EMW | MS (m/z) Observed |
|---|---|---|---|---|
| 126 | | 4.41 | 390.2 | 391.17 |
| 127 | | 0.957 | 365.18 | 366.1 |
| 128 | | 2.58 | 365.18 | 366.27 |

Part D:

To a solution of compound 81 (2.0 g, 9.6 mmol) in DMF (30 mL) was added C-(1H-Pyrazol-4-yl)-methylamine (1.12 g, 11.52 mmol) and diisopropylethylamine (5.01 mL, 28.8 mmol). The reaction mixture was stirred at room temperature for 10 minutes, cooled to 0° C. (ice-bath) and then added HATU (4.38 g, 11.52 mmol) and DMAP (0.0059 g, 0.48 mmol). The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography (SiO$_2$, 10% methanol/dichlormethane) afforded compound 83 as a white solid (2.2 g, 80%). $^1$H NMR (400 MHz, DMSO-d$_6$) δ 12.63 (br s, 1H), 9.6 (t, 1H), 8.8 (d, 1H), 8.16 (m, 3H), 7.6 (d, 2H), 4.46 (d, 2H), 4.25 (m, 1H), 1.25 (d, 6H), HPLC-MS t$_R$=1.05 Min (UV$_{254\ nm}$); mass calculated for formula C14H17N5O2 287.14, observed LC/MS m/z 288.1 (M+H).

Part E—Method 1:

A mixture of compound 83 (0.040 g, 0.139 mmol), pyridine (0.0112 mL, 0.417 mmol), copper(II) acetate (0.0505 g, 0.278 mmol) and the appropriate boronic acid to make the compounds in Table 3 (3 eq.) in THF were stirred at 50° C. open to the air for 20 hours. LC-MS analysis of the reaction indicates that the reaction is complete. The crude reaction mixture was filtered to remove the solids, rinsed the solids with THF. The filtrate was concentrated. Purification by Prep-LC and conversion to a hydrochlorde salt afforded compounds 84 in Table 3 as a solid.

Part E—Method 2:

A mixture of compound 83 (0.040 g, 0.139 mmol), cesium carbonate (0.091 g, 0.278 mmol), the appropriate bromide to make the compounds in Table 3 (2 equivalents) and anhydrous dimethylacetamide (1.5 mL) were added to the reaction vessel. The reaction vessel was flushed with Argon. Added copper (I) iodide (0.026 g, 0.278 mmol) and 1,10-phenanthroline (0.05 g, 0.278 mmol). Flushed the reaction vessel again with argon and the mixture was stirred in a sealed tube for 20 hours at 140° C. LC-MS analysis of the reaction indicates that the reaction is complete. The mixture was then cooled to room temperature and filtered. The filtrate was concentrated. Purification by Prep-LC and conversion to a hydrochloride salt afforded compounds 84 in Table 3.

TABLE 3

| Cmpd No. | Compound | Ret. Time UV$_{254}$ (min) | EMW | MS (m/z) Observed |
|---|---|---|---|---|
| 129 | | 4.68 | 377.2 | 378.1 |
| 130 | | 4.67 | 377.2 | 378.1 |

TABLE 3-continued

| Cmpd No. | Compound | Ret. Time UV$_{254}$ (min) | EMW | MS (m/z) Observed |
|---|---|---|---|---|
| 131 | 3-chloro-4-fluorophenyl pyrazole derivative | 5.05 | 415.1 | 416.1 |
| 132 | 3-chlorophenyl pyrazole derivative | 4.97 | 397.1 | 398.1 |
| 133 | 4-chlorophenyl pyrazole derivative | 4.94 | 397.1 | 398.1 |
| 134 | 3-cyanophenyl pyrazole derivative | 4.23 | 388.2 | 389.1 |
| 135 | 4-cyanophenyl pyrazole derivative | 4.18 | 388.2 | 389.1 |
| 136 | 3-methylsulfonylphenyl pyrazole derivative | 3.7 | 441.1 | 442.1 |
| 137 | 4-methylsulfonylphenyl pyrazole derivative | 3.63 | 441.1 | 442.1 |
| 138 | 3,5-dichlorophenyl pyrazole derivative | 5.64 | 431.1 | 432.1 |

TABLE 3-continued

| Cmpd No. | Compound | Ret. Time UV$_{254}$ (min) | EMW | MS (m/z) Observed |
|---|---|---|---|---|
| 139 | | 4.59 | 381.2 | 382.1 |
| 140 | | 5.16 | 431.2 | 432.1 |
| 141 | | 2.77 | 364.2 | 365.1 |
| 142 | | 2.92 | 414.2 | 415.1 |
| 143 | | 2.71 | 392.2 | 393.1 |
| 144 | | 3.93 | 414.2 | 415.1 |
| 145 | | 3.13 | 365.2 | 366.1 |
| 146 | | 2.77 | 417.2 | 418.1 |
| 147 | | 2.79 | 417.2 | 418.1 |

TABLE 3-continued

| Cmpd No. | Compound | Ret. Time UV$_{254}$ (min) | EMW | MS (m/z) Observed |
|---|---|---|---|---|
| 148 | | 2.72 | 403.2 | 404.1 |
| 149 | | 2.93 | 428.2 | 429.1 |
| 150 | | 3.69 | 449.1 | 390.1 |
| 151 | | 3.72 | 415.2 | 416.1 |
| 152 | | 4.17 | 470.2 | 471.1 |
| 153 | | 3.78 | 382.2 | 383.1 |
| 154 | | 3.34 | 425.2 | 426.1 |
| 155 | | 4.92 | 466.1 | 467.1 |
| 156 | | 4.02 | 364.2 | 365.1 |

TABLE 3-continued
| Cmpd No. | Compound | Ret. Time UV$_{254}$ (min) | EMW | MS (m/z) Observed |
|---|---|---|---|---|
| 157 | 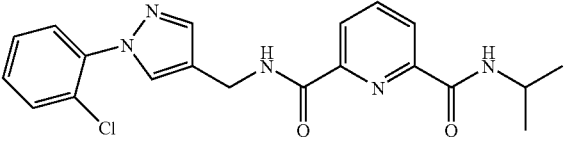 | 4.4 | 397.1 | 398.1 |
| 158 | 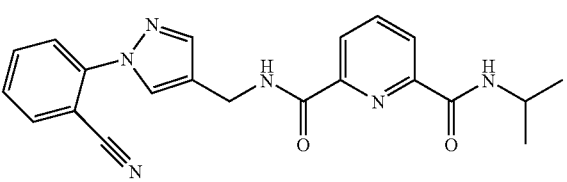 | 4.0 | 388.2 | 389.1 |
| 159 | 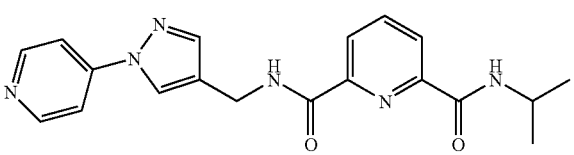 | 2.54 | 364.2 | 365.1 |
| 160 | 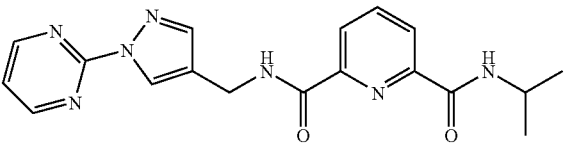 | 3.12 | 365.2 | 366.1 |
| 161 | 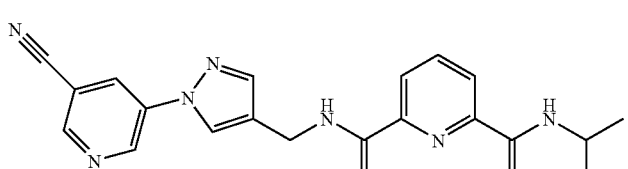 | 3.67 | 389.2 | 390.1 |
| 162 | 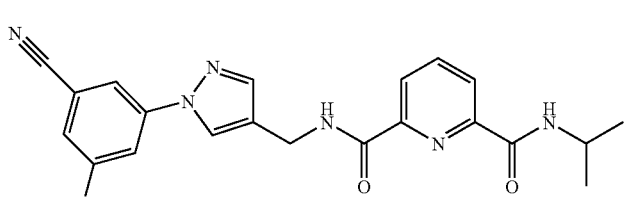 | 4.53 | 406.2 | 407.1 |
| 163 | 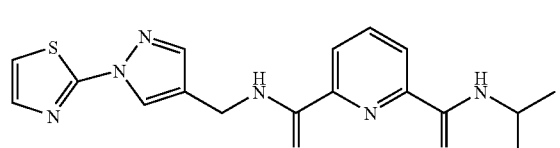 | 3.87 | 370.1 | 371.1 |

Example 2.1

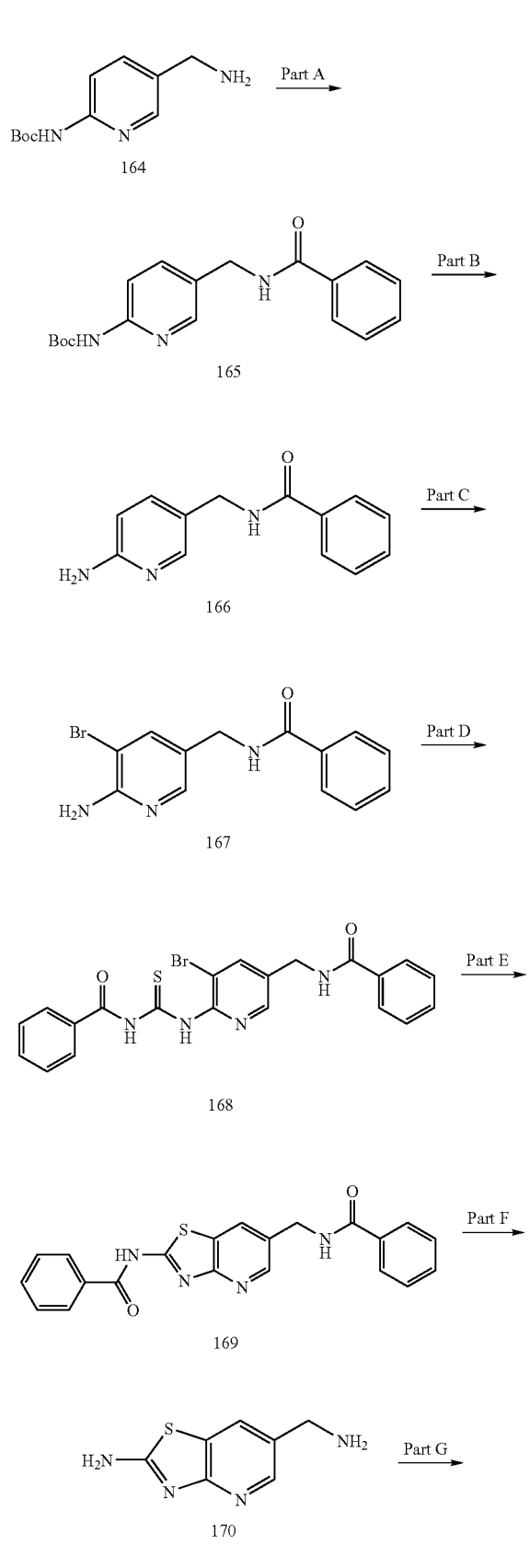

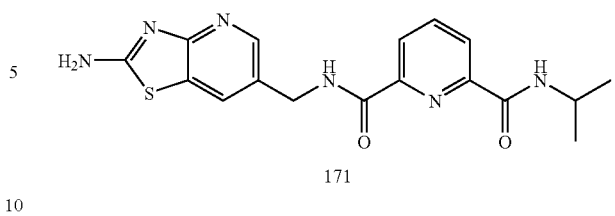

Part A:

The compound 164 (1.0 g, 4.5 mmol) was dissolved in DCM (20 mL) and TEA (1.36 mL, 10 mmol) was added. The mixture was cooled to 0° C. with ice-water bath and benzoyl chloride (0.675 g, 4.8 mmol) was added. The resulting mixture was allowed to warm to room temperature and stirred for 3 h. The mixture was diluted with EtOAc (200 mL) and washed with $H_2O$, $NaHCO_3$, and brine and dried over $Na_2SO_4$. After concentration, the crude residue was purified with short column (silica gel, hexane/EtOAc=70/30) gave the product 165 (1.31 g). HPLC-MS $t_R$=1.48 min ($UV_{254\ nm}$); mass calculated for formula C18H21N3O3 327.2, observed LCMS m/z 328.1 (M+H).

Part B:

The compound 165 (1.0 g, 3.0 mmol) was dissolved in MeOH (3 mL) and HCl (6N, 5 mL) was added. The mixture was stirred at room temperature for 1 hour and concentrated to remove MeOH. The aqueous was treated with $NaHCO_3$ (sat. aq., 30 mL) and extracted with EtOAc. The organics was dried over $Na_2SO_4$ and concentrated to give the crude product 166. It was used in the next step without further purification. HPLC-MS $t_R$=0.61 min ($UV_{254\ nm}$); mass calculated for formula C13H13N3O 227.1, observed LCMS m/z 228.1 (M+H).

Part C:

The 2-aminopyridine compound 166 (1.14 g, 5 mmol) was dissolved in HOAc (20 mL) and bromine (0.26 mL, 5.0 mmol) was added at room temperature. The mixture was stirred for 1 hour and concentrated. The resulting residue was diluted with $Na_2CO_3$ (aq.) and extracted with EtOAc. After concentration, the product was purified with column (silica gel, hexane/EtOAc=40/60) gave the pure product 167 (1.28 g) as white solid. HPLC-MS $t_R$=0.91 min ($UV_{254\ nm}$); mass calculated for formula C13H12BrN3O 305.0, observed LCMS m/z 306.0 (M+H).

Part D:

A mixture of ammonium thiocyanate (0.35 g, 4.3 mmol) and acetone (1.5 mL) was warmed to 50° C. until a clear solution was obtained. Benzoyl chloride (0.53 mL, 4.3 mmol) was then slowly dropped in and the resulting suspension refluxed 5 min. The 2-amino-3-bromopyridine 167 (1.28 g, 4.3 mmol) in acetone (1.5 mL) was added and the reaction mixture was refluxed for 1 hour. After cooling to room temperature, the solution was poured into water and the solid was collected by filtration, washed with water, ethyl ether and dried under vacuum. Gave the product 168 (1.15 g) as white solid. HPLC-MS $t_R$=1.32 min ($UV_{254\ nm}$); mass calculated for formula C21H17BrN4O2S 468.0, observed LCMS m/z 469.0 (M+H).

Part E:

The compound 168 (1.15 g, 2.5 mmol) was dissolved in NMP (10 mL) and NaOMe (810 mg, 15 mmol) was added. The mixture was heated up to 120° C. under Ar for 4 hours. After cooling down to room temperature, the mixture was diluted with EtOAc and washed with NH$_4$Cl (aq.) and brine. After drying over Na$_2$SO$_4$, the organic phase was concentrated and the residue was purified by column (silica gel, hexane/EtOAc=20/80) gave the compound 169 (0.710 g) as yellowish solid. HPLC-MS t$_R$=1.53 min (UV$_{254\ nm}$); mass calculated for formula C21H16N4O2S 388.1, observed LCMS m/z 389.0 (M+H).

Part F:

Compound 169 (0.71 g, 1.8 mmol) was treated with HCl (6N, 5 mL) and heated at reflux overnight. After cooling to room temperature, the mixture was extracted with ethyl ether. The aqueous was concentrated and dried with lyophlization gave the product 170 which was used in the next step directly without further purification. HPLC-MS t$_R$=0.18 min (UV$_{254\ nm}$); mass calculated for formula C7H8N4S 180.0, observed LCMS m/z 181.1 (M+H).

Part G:

The compound 81 (0.021 g, 0.1 mmol) was dissolved in DMF (2 mL), DIEA (0.018 mL, 0.1 mmol) and HATU (0.038 g, 0.1 mmol) were added at room temperature followed by the addition of compound 170 (0.040 g, crude, ~0.4 mmol). The mixture was stirred over night and purified with HPLC. To yield Compound 171 (Table 4) HPLC-MS t$_R$=0.91 min (UV$_{254\ nm}$); mass calculated for formula C17H18N6O2S 370.1, observed LCMS m/z 371.0 (M+H).

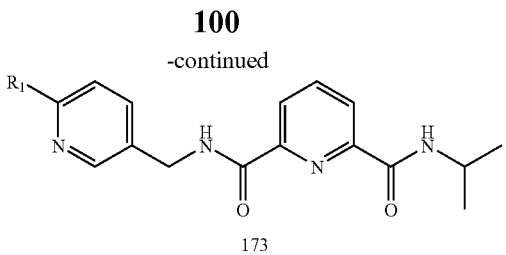

Compound 82 was synthesized via the synthetic method described in Example 2 (Part B).

Part A:

To a solution of compound 81 (0.7 g, 3.36 mmol) in DMF (20 mL) was added 5-aminomethyl-2-chloropyridine (0.57 g, 4.04mmol) and diisopropylethylamine (1.75 mL, 10.1 mmol). The reaction mixture was stirred at room temperature for 10 minutes, cooled to 0° C. (ice-bath) and then added HATU (1.54 g, 4.04 mmol) and DMAP (0.020 g, 0.16 mmol). The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography (SiO$_2$, ethyl acetate) afforded compound 172 as a white solid (0.62 g, 56%). $^1$H NMR (400 MHz, DMSO-d$_6$) δ 9.8 (t, 1H), 8.8 (d, 1H), 8.4 (d, 1H), 8.2 (m, 3H), 7.8 (dd, 1H), 7.49 (d, 1H), 4.65 (d, 2H), 4.2 (m, 1H), 1.26 (d, 6H). HPLC-MS t$_R$=1.5 Min (UV$_{254\ nm}$) calculated for formula C16H17ClN4O2 332.1, observed LC/MS m/z 333.0 (M+H).

TABLE 4

| Cmpd No. | Compound | Ret. Time UV$_{254}$ (min) | EMW | MS (m/z) Observed |
|---|---|---|---|---|
| 171 | ![structure] | 0.91 | 370.0 | 371.0 |

Example 3

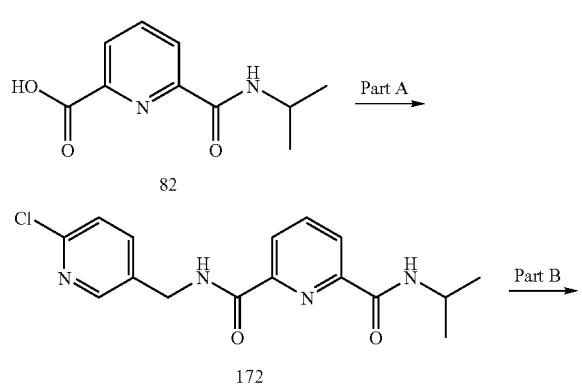

Part B:

To compound 172 (1 equivalent) in 1,4-dioxane (1 mL) was added the appropriate boronic acid (2 equivalents) to make the compounds in Table 5, dichloro[1,1'-bis(diphenylphosphino)ferrocene]palladium (II) dichloromethane adduct (10 mol %) and 2M K$_2$CO$_3$ (1 mL). The reaction vial was flushed with Argon and stirred at 80° C. overnight. LC-MS analysis of the reaction indicates that the reaction is complete. The crude reaction mixture was filtered to remove the solids, rinsed the solids with THF. The filtrate was concentrated. Purification by Prep-LC and conversion to a hydrochlorde salt afforded compounds of formula 173, as a solid, as set forth in Table 5.

TABLE 5
| Compd No. | Compound | Ret. Time UV$_{254}$ (min) | EMW | MS (m/z) Observed |
|---|---|---|---|---|
| 174 | 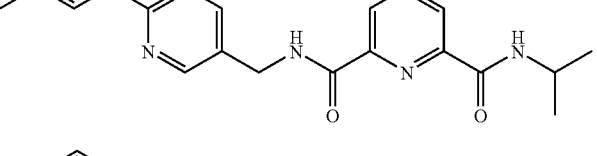 | 3.47 | 388.2 | 389.1 |
| 175 | 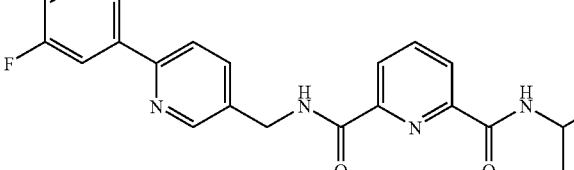 | 3.91 | 392.2 | 393.1 |
| 176 | 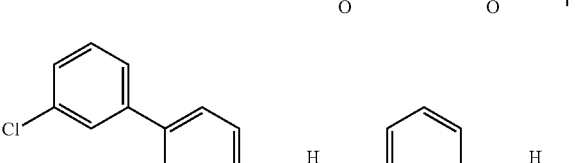 | 4.37 | 408.1 | 409.1 |
| 177 | 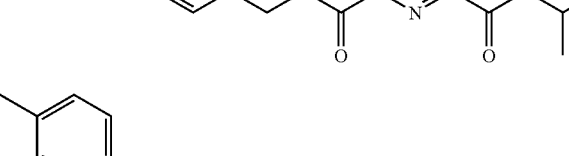 | 3.47 | 388.2 | 389.1 |
| 178 | 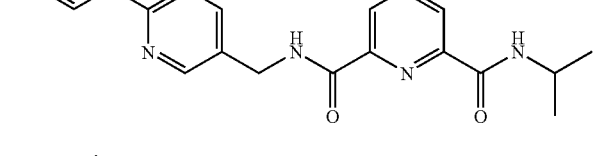 | 3.92 | 399.2 | 400.1 |
| 179 | 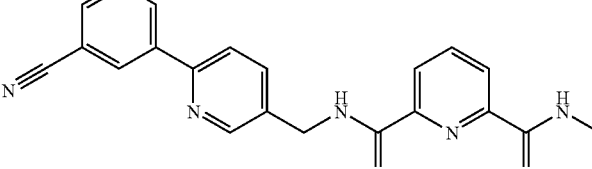 | 3.91 | 399.2 | 400.1 |
| 180 | 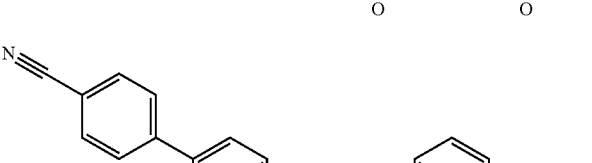 | 3.37 | 452.2 | 453.1 |

TABLE 5-continued

| Compd No. | Compound | Ret. Time UV$_{254}$ (min) | EMW | MS (m/z) Observed |
|---|---|---|---|---|
| 181 | | 3.34 | 452.2 | 453.1 |
| 182 | | 4.15 | 408.1 | 409.1 |
| 183 | | 4.8 | 442.2 | 443.1 |
| 184 | | 4.66 | 426.1 | 427.1 |
| 185 | | 5.55 | 442.1 | 443.1 |
| 186 | | 2.83 | 425.2 | 426.1 |

Example 3.1

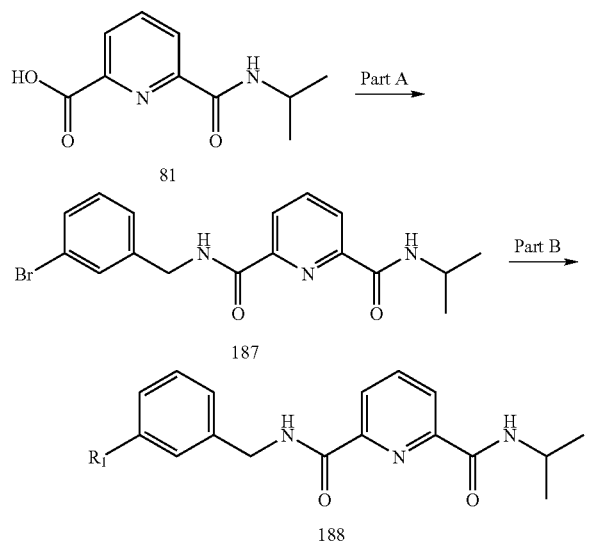

81

187

188

Compound 81 was synthesized via the synthetic method described in Example 2 (Part B).

Part A:

To a solution of compound 82 (0.20 g, 0.96 mmol) in DMF (5 mL) was added 3-bromobenzylamine hydrochloride (0.26 g, 1.15 mmol) and diisopropylethylamine (0.67 mL, 3.84 mmol). The reaction mixture was stirred at room temperature for 10 minutes, cooled to 0° C. (ice-bath) and then added HATU (0.44 g, 1.15 mmol) and DMAP (catalytic). The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over sodium sulfate and concentrated. Purification by column chromatography (SiO$_2$, ethyl acetate) afforded compound 187 as a white solid (0.32 g, 89%). $^1$H NMR (400 MHz, DMSO-d$_6$) δ 9.85 (t, 1H), 8.8 (d, 1H), 8.2 (m, 3H), 7.5 (dd, 1H), 7.45 (m, 1H), 7.3 (m, 2H) 4.65 (d, 2H), 4.2 (m, 1H), 1.26 (d, 6H). HPLC-MS t$_R$=1.85 Min (UV$_{254\ nm}$); mass calculated for formula C17H18BrN3O2 375.06, observed LC/MS m/z 376.0 (M+H).

Part B:

To compound 187 (1 equivalent) in 1,4-dioxane (1 mL) was added the appropriate boronic acid (2 equivalents) to make the compounds in Table 6, dichloro[1,1'-bis(diphenylphosphino)ferrocene]palladium (II) dichloromethane adduct (10 mol %) and 2M K$_2$CO$_3$ (1 ml). The reaction vial was flushed with Argon and stirred at 80° C. overnight. LC-MS analysis of the reaction indicates that the reaction is complete. The crude reaction mixture was filtered to remove the solids, rinsed the solids with THF. The filtrate was concentrated. Purification by Prep-LC and conversion to a hydrochloride salt afforded compounds of general formula 188 in Table 6 as a solid.

TABLE 6

| Cmpd No. | Compound | Ret. Time UV$_{254}$ (min) | EMW | MS (m/z) Observed |
|---|---|---|---|---|
| 189 | | 4.93 | 398.2 | 399.1 |
| 190 | | 4.91 | 398.2 | 399.1 |
| 191 | | 4.34 | 451.2 | 452.1 |

TABLE 6-continued

| Cmpd No. | Compound | Ret. Time UV$_{254}$ (min) | EMW | MS (m/z) Observed |
|---|---|---|---|---|
| 192 | | 4.29 | 451.2 | 452.1 |
| 193 | | 4.29 | 451.2 | 452.1 |
| 194 | | 4.92 | 398.2 | 399.1 |
| 195 | | 4.88 | 398.2 | 399.1 |
| 196 | | 4.23 | 451.2 | 452.1 |

Example 4

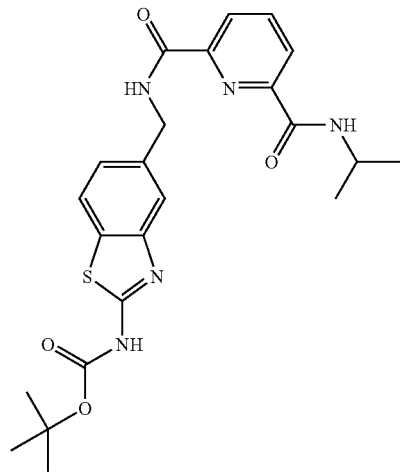

197

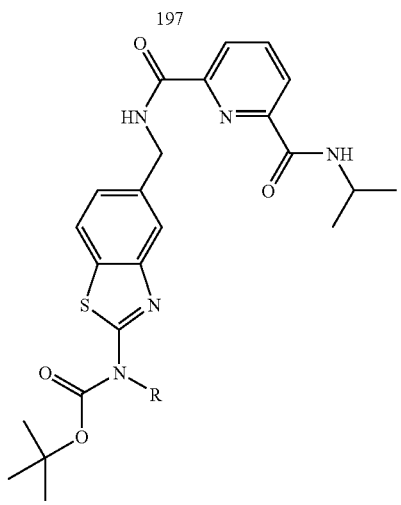

198

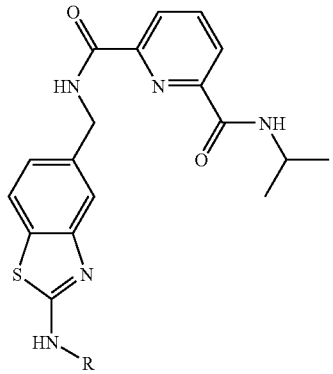

199

Part A:

Compound 197 was synthesized via the synthetic method described in Example 2 (Part C). To a solution of compound 197 (0.030 g, 0.064mmol) in anhydrous THF (1 mL) was added the respective alcohol (ROH, 1 equivalent) to make the compounds in Table 7, triphenylphosphine (1.5 equivalents) and DIAD (1.5 equivalents) at room temperature. The reaction mixture was stirred at room temperature for 5 hours at which time LC-MS analysis indicated the reaction was complete. The reaction mixture was concentrated and used in the next step without any purification.

Part B

A solution of compound 198 was stirred in 6N HCl for 1 hour at room temperature. Thin layer chromatography indicated that the reaction was complete. The reaction mixture was concentrated under vacuum. Purification by Prep-LC and conversion to a hydrochloride salt afforded compounds of general formula 199, as a solid, as set forth in Table 7. $^1$H NMR (400 MHz, DMSO-$d_6$) δ 10.0 (t, 1H), 9.3 (bs, 2H), 8.95 (d, 1H), 8.19 (m, 3H), 7.8 (s, 1H), 7.4 (m, 2H), 4.65 (d, 2H), 4.2 (m, 1H), 1.26 (d, 6H).

TABLE 7

| Cmpd No. | Structure | Ret. Time UV$_{254}$ (min) | EMW | MS (m/z) Observed |
|---|---|---|---|---|
| 200 | 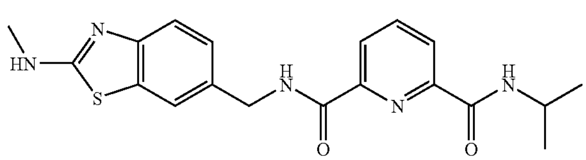 | 2.26 | 383.1 | 384.1 |
| 201 | 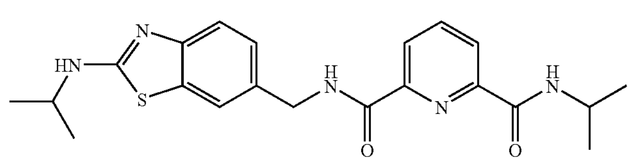 | 3.29 | 411.2 | 412.1 |

TABLE 7-continued

| Cmpd No. | Structure | Ret. Time UV$_{254}$ (min) | EMW | MS (m/z) Observed |
|---|---|---|---|---|
| 202 | 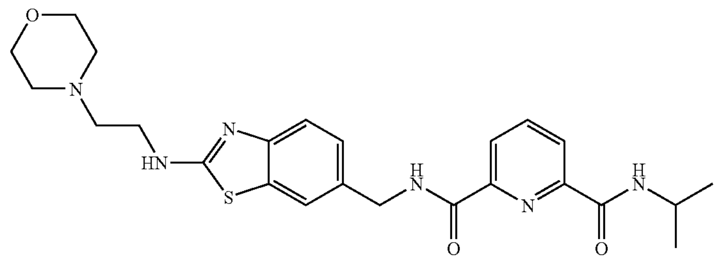 | 2.89 | 482.2 | 483.1 |
| 203 | 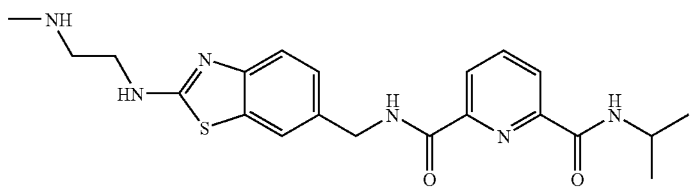 | 2.75 | 426.2 | 427.1 |

Example 5

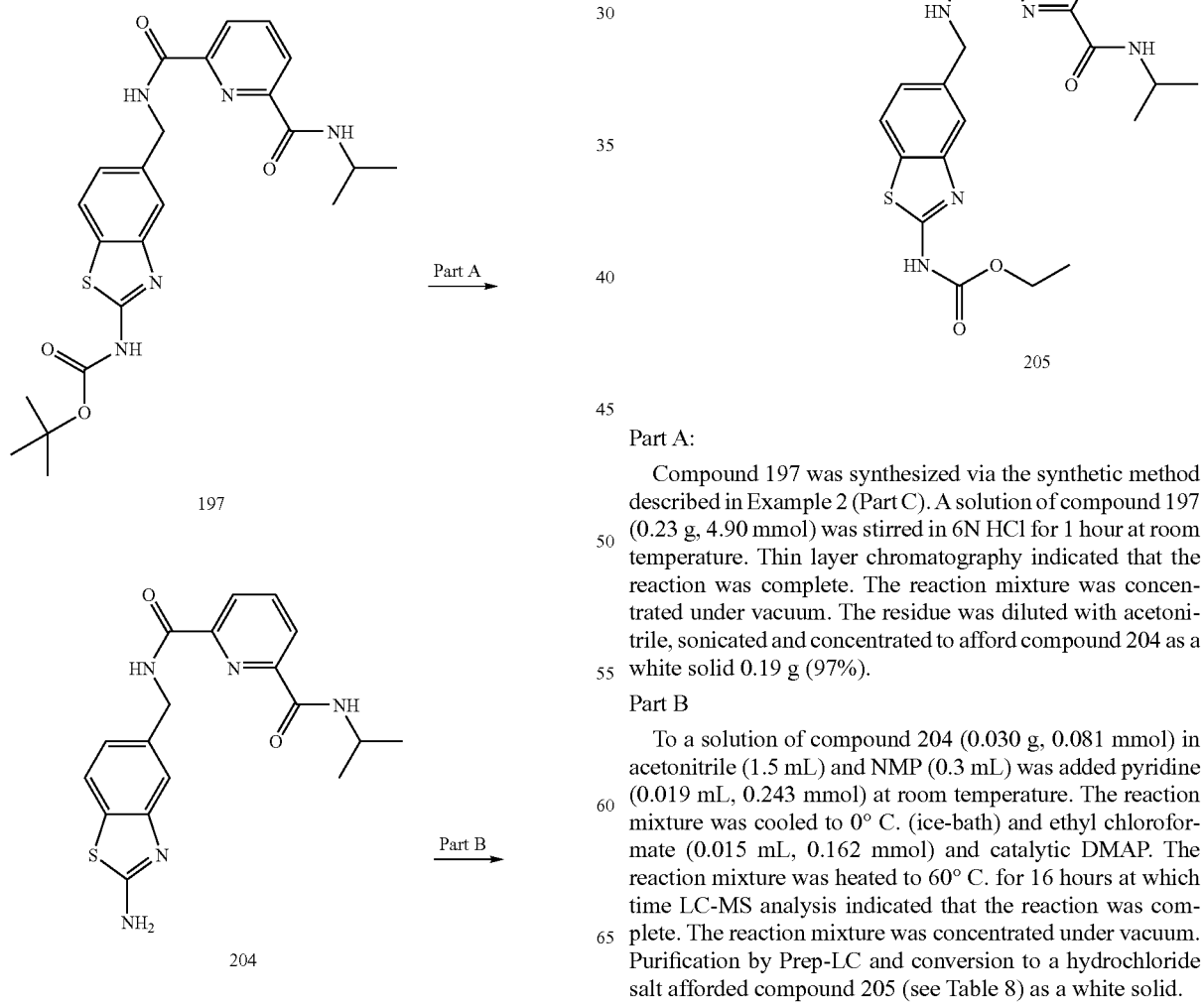

Part A:

Compound 197 was synthesized via the synthetic method described in Example 2 (Part C). A solution of compound 197 (0.23 g, 4.90 mmol) was stirred in 6N HCl for 1 hour at room temperature. Thin layer chromatography indicated that the reaction was complete. The reaction mixture was concentrated under vacuum. The residue was diluted with acetonitrile, sonicated and concentrated to afford compound 204 as a white solid 0.19 g (97%).

Part B

To a solution of compound 204 (0.030 g, 0.081 mmol) in acetonitrile (1.5 mL) and NMP (0.3 mL) was added pyridine (0.019 mL, 0.243 mmol) at room temperature. The reaction mixture was cooled to 0° C. (ice-bath) and ethyl chloroformate (0.015 mL, 0.162 mmol) and catalytic DMAP. The reaction mixture was heated to 60° C. for 16 hours at which time LC-MS analysis indicated that the reaction was complete. The reaction mixture was concentrated under vacuum. Purification by Prep-LC and conversion to a hydrochloride salt afforded compound 205 (see Table 8) as a white solid.

TABLE 8

| Cmpd No. | compound | Ret. Time UV$_{254}$ (min) | EMW | MS (m/z) Observed |
|---|---|---|---|---|
| 205 |  | 4.25 | 441.1 | 442.1 |

Example 6

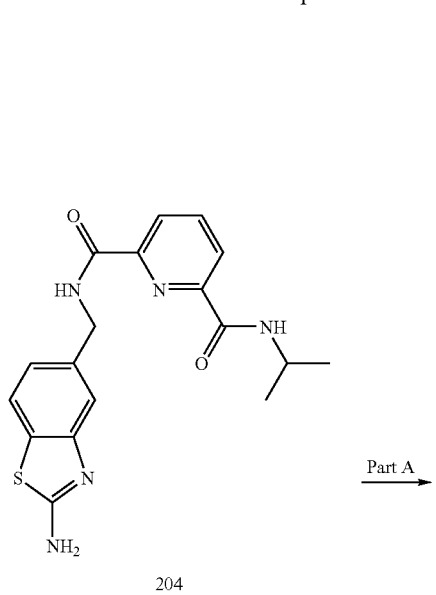

204

Part A →

-continued

206

Part A:

Compound 204 was synthesized via the synthetic method described in Example 5 (Part A). To a solution of compound 204 (0.03 g, 0.081 mmol) in acetonitrile (1 mL) and NMP (0.3 mL) was added ethyl isocyanate (0.00632 g, 0.089 mmol) followed by triethylamine (0.012 mL, 0.089 mmol) at room temperature. The reaction mixture was heated to 80° C. for 16 hours at which time LC-MS analysis indicated that the reaction was complete. The reaction mixture was concentrated under vacuum. Purification by PREP-LC and conversion to a hydrochloric salt afforded compound 206 (see Table 9) as a white solid.

TABLE 9

| Cmpd No. | Structure | Ret. Time UV$_{254}$ (min) | EMW | MS (m/z) Observed |
|---|---|---|---|---|
| 206 | 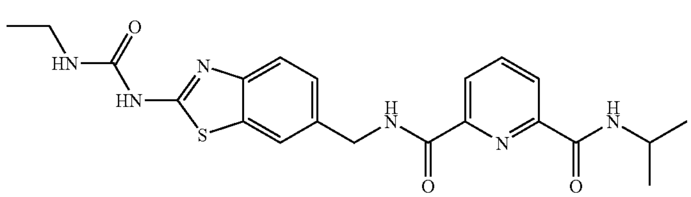 | 3.8 | 440.2 | 444.1 |

Example 7

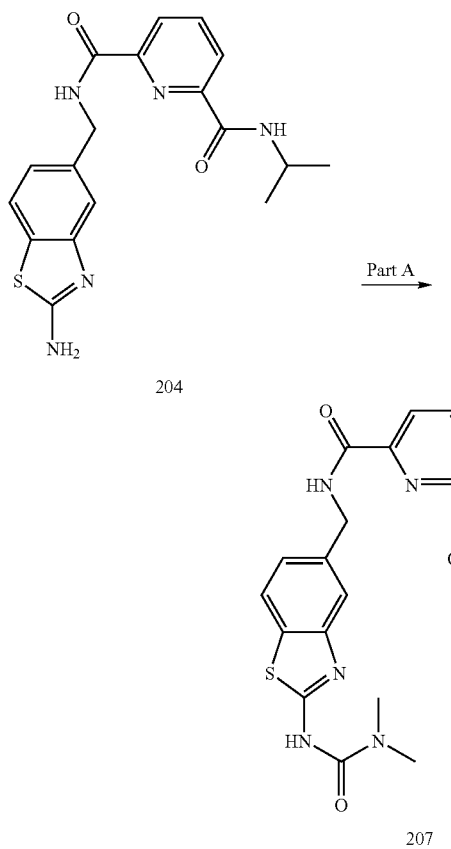

Part A:

Compound 204 was synthesized via the synthetic method described in Example 5 (Part A). To a solution of compound 1 (0.03 g, 0.081 mmol) in acetonitrile (1 mL) and NMP (0.3 mL) was added pyridine (0.019 mL, 0.243 mmol). The reaction mixture was cooled to 0° C. (ice-bath) and dimethylcarbamyl chloride (0.0145 mL, 0.162 mmol) and catalytic DMAP. The reaction mixture was heated to 60° C. for 16 hours at which time LC-MS analysis indicated that the reaction was complete. The reaction mixture was concentrated under vacuum. Purification by Prep-LC and conversion to a hydrochloric salt afforded compound 207 (see Table 10) as a white solid.

Example 8

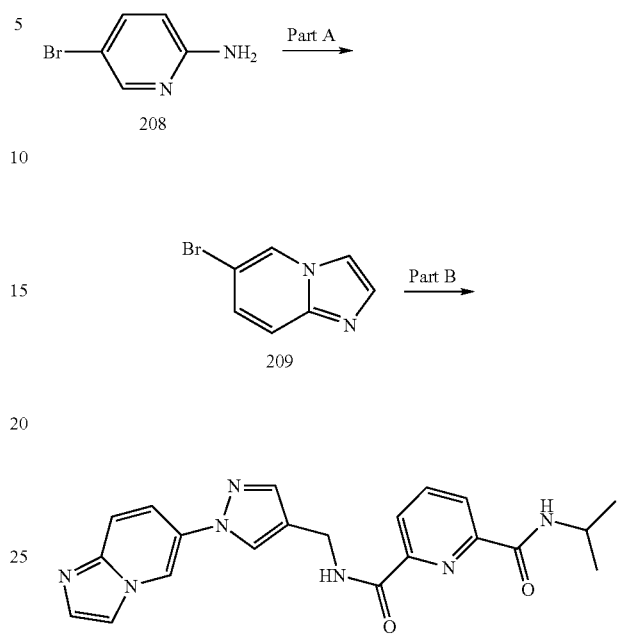

Part A:

To compound 208 (1.00 g, 5.77 mmol) in ethanol (100 mL) was added chloroacetaldehyde (50 wt % solution in water, 7.34 mL, 57.8 mmol) at room temperature. The reaction mixture was heated at reflux for 16 hours at which time LC-MS analysis indicated that the reaction was complete. The reaction mixture was concentrated under vacuum. The residue was taken back up in ethyl acetate and saturated sodium bicarbonate. The organic and aqueous layers were separated. The organic layer was washed with brine, dried over anh. sodium sulfate and concentrated to afford compound 209 as a dark brown oil. $^1$H NMR (400 MHz, DMSO-$d_6$) δ 8.89 (d, 1H), 7.9 (s, 1H), 7.56 (m, 2H), 7.31 (dd, 1H).

Part B

Compound 210 (see Table 11) was synthesized via the synthetic method described in Example 2 (Part E, method 2).

TABLE 10

| Cmpd No. | Compound | Ret. Time (min) | UV$_{254}$ EMW | MS (m/z) Observed |
|---|---|---|---|---|
| 207 | ![structure] | 3.7 | 440.2 | 441.1 |

TABLE 11

| Cmpd No. | Compound | Ret. Time UV$_{254}$ (min) | EMW | MS (m/z) Observed |
|---|---|---|---|---|
| 210 |  | 2.65 | 403.2 | 404.1 |

Example 9

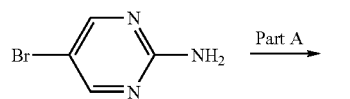

211

212

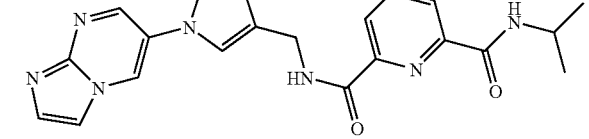

213

Example 10

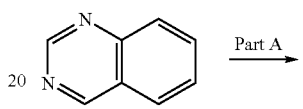

214

215

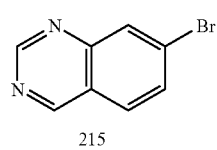

216

Part A:
To compound 211 (1.00 g, 5.74 mmol) in ethanol (100 mL) was added chloroacetaldehyde (50 wt % solution in water, 7.34 mL, 57.5 mmol) at room temperature. The reaction mixture was heated at reflux for 16 hours at which time LC-MS analysis indicated that the reaction was complete. The reaction mixture was concentrated under vacuum. The residue was taken back up in ethyl acetate and saturated sodium bicarbonate. The organic and aqueous layers were separated. The organic layer was washed with brine, dried over anh. sodium sulfate and concentrated to afford compound 212 as a beige solid. $^1$H NMR (400 MHz, DMSO-d$_6$) δ 9.32 (d, 1H), 8.56 (d, 1H), 7.85 (d, 1H), 7.74 (d, 1H).

Part B
Compound 213 (see Table 12) was synthesized via the synthetic method described in Example 2 (Part E, method 2).

Part A:
To a solution of compound 214 (1.04 g, 7.99 mmol) in concentrated sulfuric acid at room temperature was added N-bromosuccinimide (2.13 g, 11.9 mmol). The reaction mixture was stirred at room temperature for 16 hours at which time thin layer chromatography (5% MeOH/DCM) indicated the reaction was complete. The reaction mixture was poured onto crushed ice (~50 mL) and the pH adjusted to 7 using ammonium hydroxide. The resulting slurry was stirred for 1 hour at 0° C., after which it was filtered and washed with ice-cold water (3×30 mL). Purification by column chromatography (SiO$_2$, 5% MeOH/DCM) afforded compound 215 as a beige solid 0.53 g (32%). $^1$H NMR (400 MHz, DMSO-d$_6$) δ 9.57 (s, 1H), 9.32 (s, 1H), 8.46 (d, 1H), 8.14 (dd, 1H), 7.96 (d, 1H).

TABLE 12

| Cmpd No. | Compound | Ret. Time UV$_{254}$ (min) | EMW | MS (m/z) Observed |
|---|---|---|---|---|
| 213 |  | 2.55 | 404.2 | 405.1 |

Part B

Compound 216 (see Table 13) was synthesized via the synthetic method described in Example 2 (Part E, method 2).

TABLE 13

| Cmpd No. | Compound | Ret. Time UV$_{254}$ (min) | EMW | MS (m/z) Observed |
|---|---|---|---|---|
| 216 |  | 2.91 | 415.2 | 416.1 |

Example 11

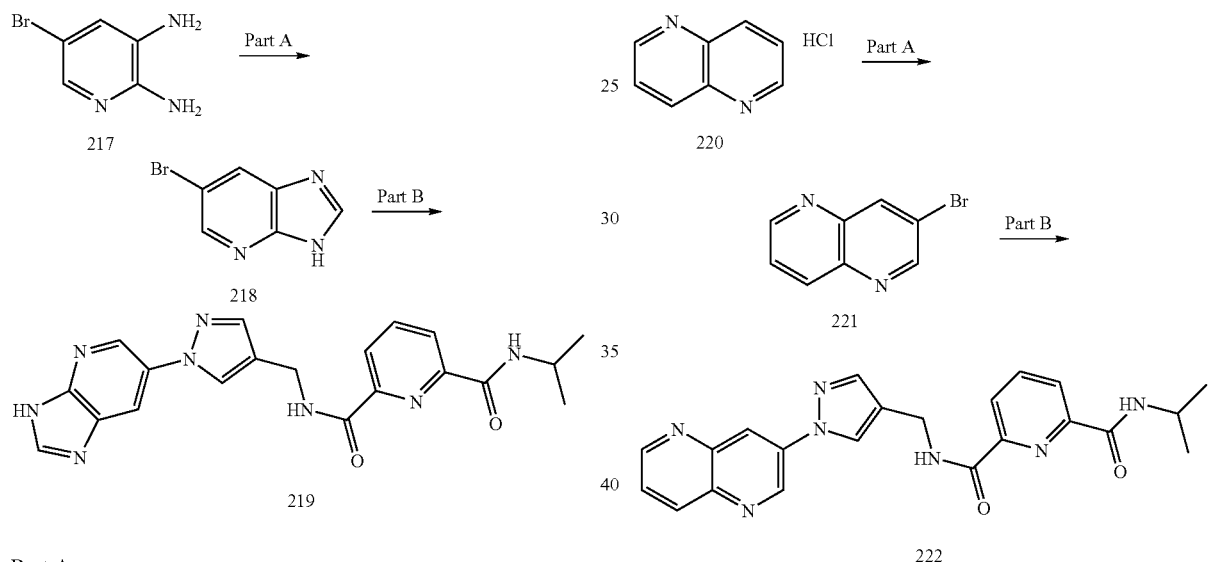

Example 12

Part A

A solution of compound 217 (1.00 g, 5.32 mmol), formic acid (0.5 mL) and triethyl orthoformate (15 mL) were stirred at 100° C. for 3 hours at which time LC-MS analysis indicated that the reaction was complete. The reaction mixture was concentrated under vacuum. Purification by column chromatography (10% MeOH/DCM) afforded compound 218 as a beige solid 1.01 g (96%). $^1$H NMR (400 MHz, DMSO-d$_6$) δ 8.46 (s, 1H), 8.41 (d, 1H), 8.27 (d, 1H).

Part B

Compound 219 (see Table 14) was synthesized via the synthetic method described in Example 2 (Part E, method 2).

Part A:

To a solution of compound 220 (1.00 g, 6.02 mmol) in carbon tetrachloride (60 mL) was added dropwise, bromine (1.15 g, 7.20 mmol) as a carbon tetrachloride solution (6 mL.). The resulting solution was refluxed for 1 hour. Pyridine (0.5 mL, 6.0 mmol) as a carbon tetrachloride solution (10 mL) was added over a period of 1 hour to the refluxing reaction mixture. The reaction was stirred at reflux for 16 hours at which time LC-MS indicated that the reaction was complete.

| Cmpd No. | Structure | Ret. Time UV$_{254}$ (min) | EMW | MS (m/z) Observed |
|---|---|---|---|---|
| 219 | 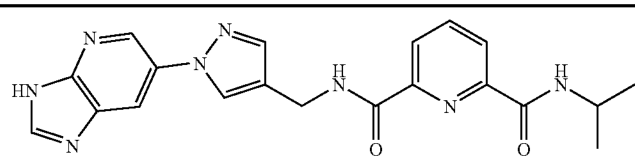 | 2.67 | 404.2 | 405.1 |

The reaction mixture was cooled to room temperature, resulting in the formation of a precipitate, which was filtered. The carbon tetrachloride filtrate was set aside. The collected brown solid was taken up in 10% NaOH (100 mL) and stirred at room temperature for 1 hour. This solution was extratcted with chloroform. The chloroform and carbon tetrachloride solutions were combined and concentrated in vacuum. Purification by column chromatography (SiO$_2$, 20% EtOAc/DCM) afforded compound 221 as a white solid 0.17 g, (14%). $^1$H NMR (400 MHz, DMSO-d$_6$) δ 9.07 (d, 1H), 9.02 (dd, 1H), 8.74 (m, 1H), 8.45 (m, 1H), 7.83 (dd, 1H).

Part B

Compound 222 (Table 15) was synthesized via the synthetic method described in Example 2 (Part E, method 2).

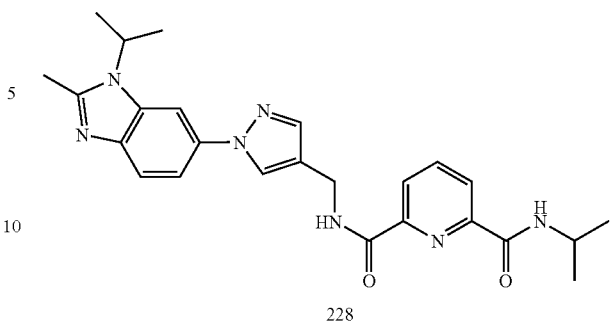

228

TABLE 15

| Cmpd No. | Structure | Ret. Time UV$_{254}$ (min) | EMW | MS (m/z) Observed |
|---|---|---|---|---|
| 222 | 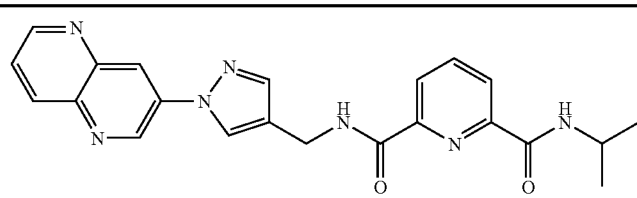 | 3.36 | 415.2 | 416.1 |

Example 13

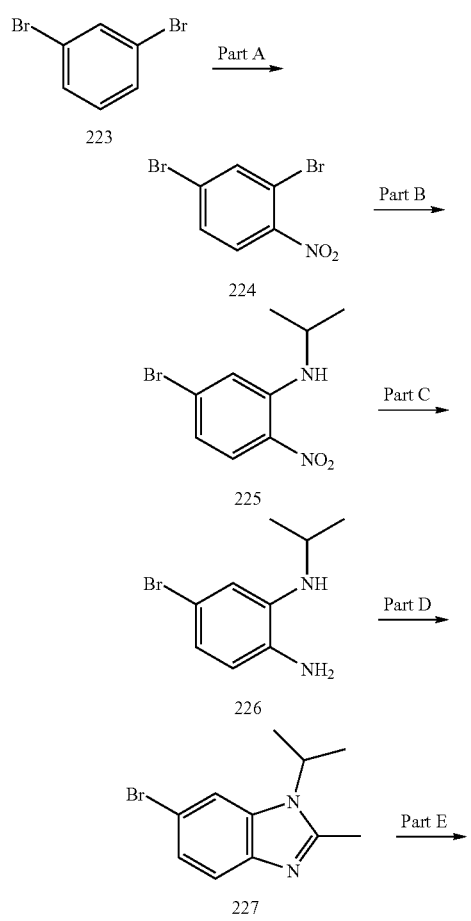

Part A:

To concentrated sulfuric acid (75 mL) at 0° C. was added concentrated nitric acid (5.5 mLl) carefully. 1,3-Dibromobenzene 223 (25.0 g, 106 mmol) was added to the acid solution at 0° C. The resulting solution was slowly warmed to room temperature and continued to stir at room temperature for 5 hours. The reaction mixture was poured into water, neutralized with solid sodium carbonate and extracted with diethyl ether (×2). The ether solution was dried over anhydrous sodium sulfate and concentrated under vacuum. Purification by column chromatography (SiO$_2$, 10% EtOAc/hexanes) afforded compound 224 as a yellow solid 17.7 g (60%). $^1$H NMR (400 MHz, DMSO-d$_6$) δ 8.22 (d, 1H), 7.97 (d, 1H), 7.85 (dd, 1H).

Part B:

To a solution of compound 224 (2.0 g, 7.17 mmol) in ethanol (50 mL) was added isopropylamine (43.0 mL, 502mmol). The resulting solution was stirred at reflux for 3 hours at which time LC-MS indicated that the reaction was complete. The reaction mixture was concentrated under vacuum to afford compound 225 as a waxy yellow solid as a mixture of regioisomers which was used without further purification. $^1$H NMR (400 MHz, DMSO-d$_6$) δ 8.22 (d, 1H), 7.97 (d, 1H), 7.85 (dd, 1H), 3.95 (m, 1H), 1.24 (d, 6H).

Part C:

To compound 225 (2.18 g, 8.43 mmol) in ethanol (100 mL) was added tin (II) chloride (7.99 g, 42.2 mmol). The resulting solution was stirred at 70° C. for 3 hours at which time LC-MS indicated that the reaction was complete. The reaction mixture was concentrated under vacuum. Ice-water was added to the residue, the pH adjusted to 10 with aqueous sodium carbonate and extracted with ethyl acetate. The organic layer was dried over sodium sulfate and concentrated under vacuum. Purification by column chromatography (SiO$_2$, DCM) afforded compound 226 as a yellow oil 0.58 g (58%) as a mixture of regioisomers.

Part D:

A solution of compound 226 (0.56 g, 2.45 mmol) in acetic acid (20 mL) was stirred at reflux for 2 hours, at which time LC-MS analysis indicated that the reaction was complete. The reaction mixture was concentrated under vacuum. Purification by column chromatography (SiO$_2$, 5% MeOH/DCM) afforded compound 227 as a red oil 0.55 g (90%). $^1$H NMR (400 MHz, DMSO-d$_6$) δ 7.82 (d, 1H), 7.44 (1H), 7.24 (dd, 1H), 4.75 (m, 1H), 2.54 (s, 3H), 1.51 (d, 6H).

Part E:

Compound 228 (Table 16) was synthesized via the synthetic method described in Example 2 (Part E, method 2).

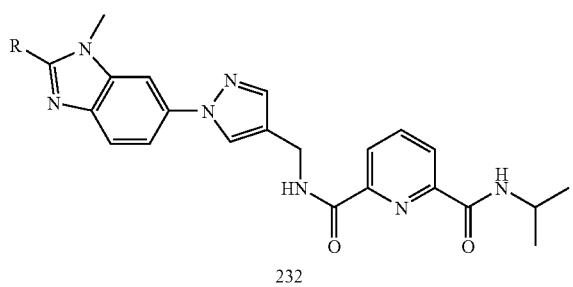

232

TABLE 16

| Cmpd No. | Compound | Ret. Time UV$_{254}$ (min) | EMW | MS (m/z) Observed |
|---|---|---|---|---|
| 228 | | 3.1 | 459.2 | 460.1 |

Example 14

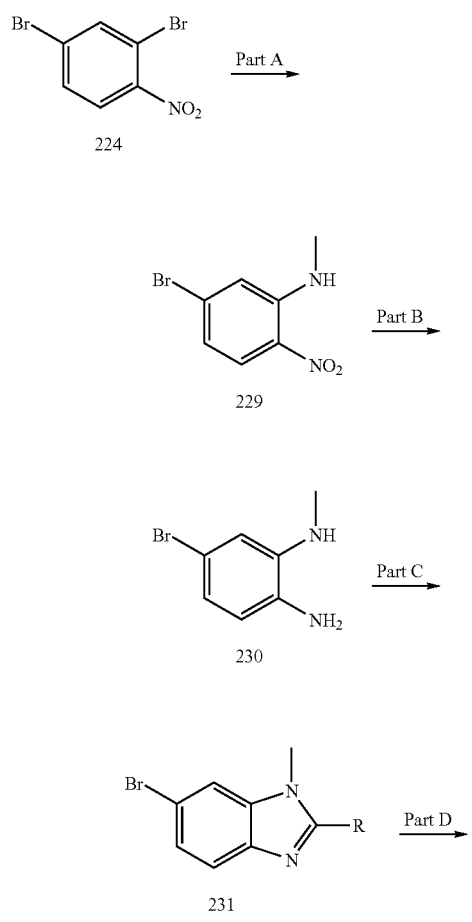

Part A:

Compound 224 was prepared via the synthetic method described in Example 13 (Part A). A solution of compound 1 (10.0 g, 35.8 mmol) and 40% aqueous methylamine (270 mL) in ethanol (270 mL) was stirred at reflux for 2 hours. The reaction mixture was cooled to room temperature, resulting in the formation of a precipitate, which was filtered and dried to afford compound 229 as a yellow solid 5.6 g (68%). $^1$H NMR (400 MHz, DMSO-d$_6$) δ 7.95 (d, 1H), 7.14 (d, 1H), 6.79 (dd, 1 H), 2.94 (d, 3H).

Part B:

To compound 229 (5.40 g, 23.4 mmol) in ethanol (200 mL) was added tin (II) chloride (22.2 g, 117 mmol). The resulting solution was stirred at 70° C. for 3 hours at which time LC-MS indicated that the reaction was complete. The reaction mixture was concentrated under vacuum. Ice-water was added to the residue, the pH adjusted to 10 with aqueous sodium carbonate and extracted with ethyl acetate. The organic layer was dried over anh sodium sulfate and concentrated under vacuum. Purification by column chromatography (SiO$_2$, 5% EtOAc/DCM) afforded compound 230 as a yellow oil 2.50 g (53%). $^1$H NMR (400 MHz, DMSO-d$_6$) δ 6.50 (dd, 1H), 6.43 (d, 1H), 6.38 (d, 1H), 4.6 (bs, 2H), 2.68 (d, 3H).

Part C:

A solution of compound 230 (2.50 g, 12.4 mmol) in the corresponding acid (100 mL) for preparing the compounds in Table 17 was stirred at reflux for 2 hours, at which time LC-MS analysis indicated that the reaction was complete. The reaction mixture was concentrated under vacuum. Purification by column chromatography (SiO$_2$, 5% MeOH/DCM) afforded compounds of general formula 231 as a solid Part D:

Compounds of formula 232 (see Table 17) were synthesized via the synthetic method described in Example 2 (Part E, method 2).

TABLE 17

| Cmpd No. | Structure | Ret. Time UV$_{254}$ (min) | EMW | MS (m/z) Observed |
|---|---|---|---|---|
| 233 | 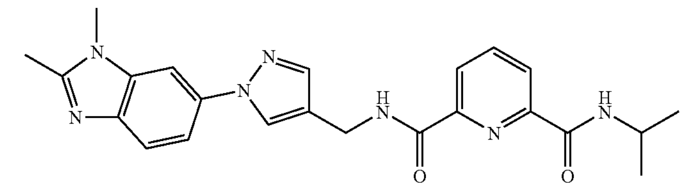 | 2.83 | 431.2 | 432.1 |
| 234 | 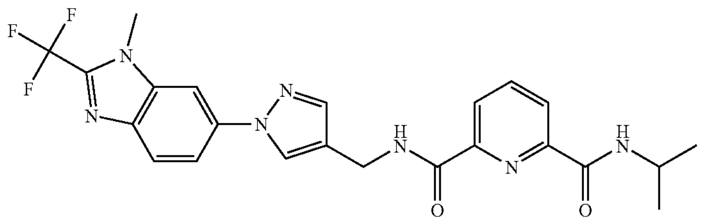 | 4.39 | 485.2 | 486.1 |
| 235 | 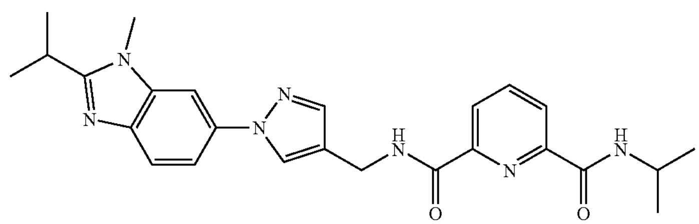 | 3.01 | 459.2 | 460.2 |

Example 15

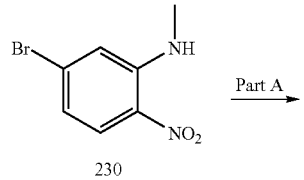

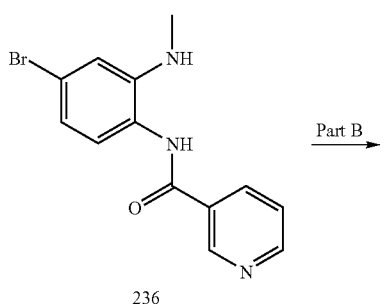

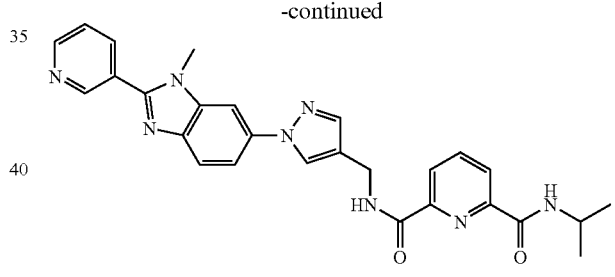

Part A:

Compound 230 was prepared via the synthetic method described in Example 14 (Part B). To a solution of nicotinic acid (0.23 g, 1.90 mmol) in DMF (10 mL) was added compound 230 (0.46 g, 2.28 mmol) and diisopropylethylamine (1.00 mL, 5.70 mmol). The reaction mixture was stirred at room temperature for 10 minutes, cooled to 0° C. (ice-bath) and then added HATU (0.87 g, 2.28 mmol) and catalytic DMAP. The reaction mixture was allowed to warm to room temperature, stirred at room temperature for 2 hours. The reaction mixture was diluted with ethyl acetate and washed with 0.1N NaOH (×1), water (×2), 0.1N HCl (×1) and brine, dried over anh sodium sulfate and concentrated. Purification by column chromatography (SiO$_2$, 10% MeOH/DCM) afforded compound 236 as a beige solid 0.60 g (100%). $^1$H NMR (400 MHz, DMSO-d$_6$) δ 9.73 (s, 1H), 9.15 (d, 1H), 8.73 (m, 1H), 8.3)m, 1H), 7.55 (m, 1H), 7.03 (d, 1H), 6.69 (m, 2H), 2.78 (s, 3H).

Part B:

Compound 237 was prepared via the synthetic method described in Example 14 (Part C). ¹H NMR (400 MHz, DMSO-$d_6$) δ 9.05 (m, 1H), 8.65 (dd, 1H), 8.27 (m, 1H), 7.97 (d, 1H), 7.65 (m, 2H), 7.39 (dd, 1H), 3.89 (s, 3H).

Part C:

Compound 238 (Table 18) was prepared via the synthetic method described in Example 2 (Part E, method 2).

TABLE 18

| Cmpd No. | Structure | Ret. Time UV$_{254}$ (min) | EMW | MS (m/z) Observed |
|---|---|---|---|---|
| 238 | 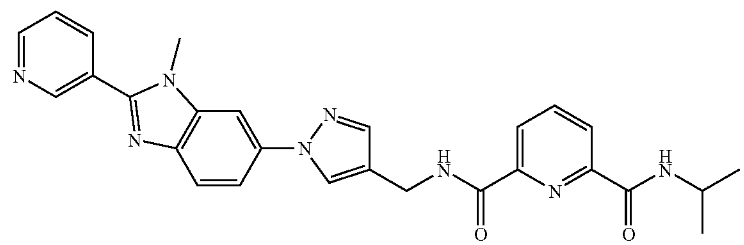 | 3.07 | 494.2 | 495.1 |

Example 16

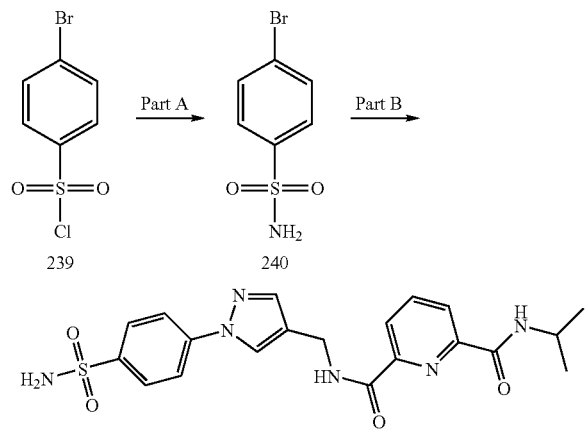

Part A:

Ammonia gas was bubbled into a solution of compound 239 (1.00 g, 3.91 mmol) in 1,4-dioxane (20 mL) at 0° C. (ice-bath) until thin layer chromatography indicated the consumption of starting material. The reaction mixture was filtered to remove the solids, rinsed the solids with dichloromethane. The filtrate was concentrated under vacuum to a white solid. This white solid was recrystallized from ethyl acetate to afford compound 240 as a white solid 0.88 g (95%). ¹H NMR (400 MHz, DMSO-$d_6$) δ 7.77 (m, 2H), 7.72 (m, 2H), 7.45 (bs, 2H).

Part B

Compound 241 (Table 19) was prepared via the synthetic method described in Example 2 (Part E, method 2).

TABLE 19

| Cmpd No. | Compound | Ret. Time UV$_{254}$ (min) | EMW | MS (m/z) Observed |
|---|---|---|---|---|
| 241 | | 3.22 | 442.1 | 443.1 |

Example 17

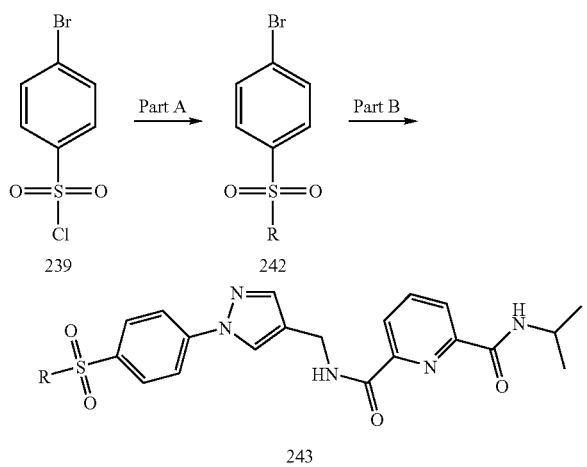

Part A:

To a solution of compound 239 (1.00 g, 3.91 mmol) in dichloromethane (20 mL) was added diisopropylethylamine (0.75 mL, 4.30 mmol) at room temperature. The reaction mixture was cooled to 0° C. (ice-bath) and the corresponding amine (1.1 equivalents) to make a compound in Table 20 was added. The reaction mixture was allowed to warm to room temperature, stirred at ambient temperature for 16 hours, at which time LC-MS analysis indicated that the reaction was complete. The reaction mixture was concentrated under vacuum. Purification of by column chromatography ((SiO$_2$, 2% ethyl acetate/dichloromethane) afforded compound of general formula 242 as a solid.

Part B

Compounds of formula 243 (see Table 20) were prepared via the synthetic method described in Example 2 (Part E, method 2).

TABLE 20

| Cmpd No. | Compound | Ret. Time UV$_{254}$ (min) | EMW | MS (m/z) Observed |
|---|---|---|---|---|
| 244 | | 3.57 | 456.2 | 457.1 |
| 245 | | 2.98 | 511.2 | 512.1 |
| 246 | | 4.44 | 504.1 | 505.0 |
| 247 | | 2.64 | 645.21 | 646.21 |

TABLE 20-continued

| Cmpd No. | Compound | Ret. Time UV$_{254}$ (min) | EMW | MS (m/z) Observed |
|---|---|---|---|---|
| 248 | 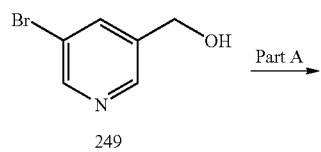 | 5.01 | 545.16 | 546.16 |

Example 18

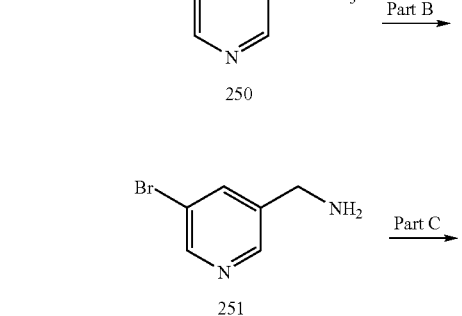

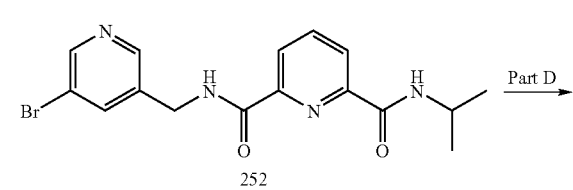

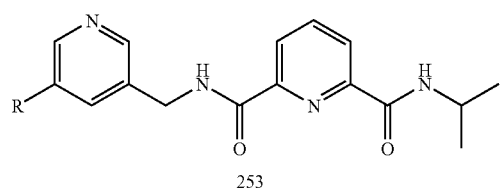

Part A:

To a solution of (5-bromo-pyridin-3-yl)-methanol 249 (1.4 g, 7.5 mmol, 1.00 equiv) and diphenylphosphoryl azide (2.4 mL, 9.0 mmol, 1.2 equiv) in THF (15 mL) at it was added 1,8-diazabicyclo[5.4.0]undec-7-ene (1.4 mL, 9.0 mmol, 1.2 equiv). The resulting solution was stirred overnight, concentrated and chromatographically purified (15% ethyl acetate in hexanes) to give 3-azidomethyl-5-bromo-pyridine 250 (1.49 g). LCMS (MH)$^+$=212.9, rt=1.50 min.

Part B:

To a solution of 3-azidomethyl-5-bromo-pyridine 250 (1.49 g, 7.00 mmol, 1.00 equiv) in 1,4-dioxane (12 mL) was added water (1 mL) and triphenylphosphine resin (2.08 g, 3 mol/g, 200-400 mesh, 1.2 equiv). The suspension was stirred overnight. Filtration and concentration afforded C-(5-bromo-pyridin-3-yl)-methylamine 251.

Part C:

To a solution of 6-isopropylcarbamoyl-pyridine-2-carboxylic acid 81 (0.17 g, 0.80 mmol, 1.00 equiv), C-(5-bromo-pyridin-3-yl)-methylamine 251 (0.16 g, 0.88 mmol, 1.2 equiv) and N,N-diisopropylethylamine (0.28 mL, 1.6 mmol, 2.0 equiv) in NMP (2 mL) at room temperature was added HATU (0.28 g, 0.88 mmol, 1.00 equiv) in one portion. The reaction mixture was stirred at room temperature for 2 hours, diluted with ethyl acetate and washed with water (three times) and brine, dried (sodium sulfate) and concentrated. Pyridine-2,6-dicarboxylic acid 2-[(5-bromo-pyridin-3-ylmethyl)-amide]6-isopropylamide 252 was used without further purification. LCMS: (MH)$^+$=377.0 (1.51 min).

Part D:

A suspension of pyridine-2,6-dicarboxylic acid 2-[(5-bromo-pyridin-3-ylmethyl)-amide]6-isopropylamide 252 (0.030 g, 0.0795 mmol, 1.00 equiv), potassium phosphate (0.051 g, 0.24 mmol, 3.0 equiv), [1,1'-bis(diphenylphosphino)ferrocene]-dichloro palladium(II) (0.003 g, 0.004 mmol, 5 mol %) and the appropriate boronic acid (to make the compounds in Table 21) (1.5 equiv) in 1,4-dioxane (1 mL) was heated at 90° C. for 2 hr. The suspension was allowed to cool, was filtered and concentrated. Purification by Prep-LC afforded the compounds in Table 21.

TABLE 21

| Cmpd No. | Compound | Ret. Time UV$_{254}$ (min) | EMW | MS (m/z) Observed |
|---|---|---|---|---|
| 254 | | 3.66 | 376.1 | 377.05 |
| 255 | | 2.82 | 452.2 | 453.15 |
| 256 | | 2.87 | 452.2 | 453.15 |
| 257 | | 3.23 | 399.2 | 400.17 |
| 258 | | 3.24 | 399.2 | 400.17 |

Example 19

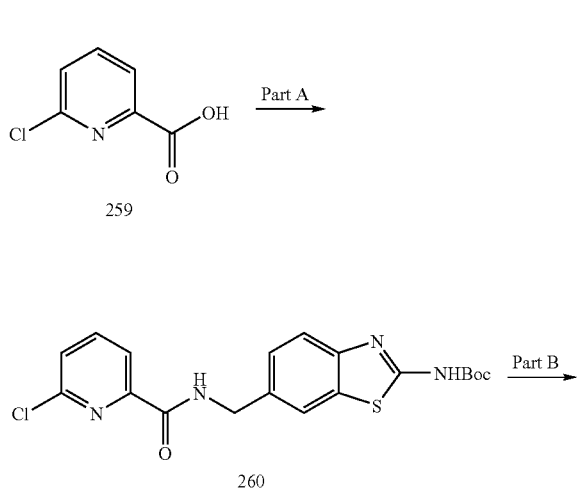

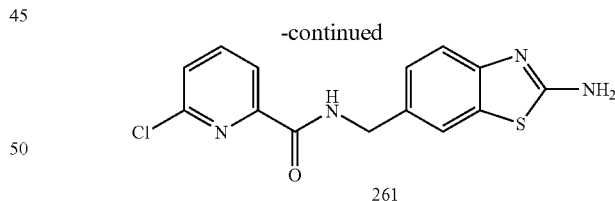

Part A:
To a solution of 6-chloropyridine-2-carboxylic acid 259 (0.16 g, 0.98 mmol, 1.00 equiv), N,N-diisopropylethylamine (0.5 mL, 1.0 mmol, 2.0 equiv) and (6-aminomethyl-benzothiazol-2-yl)-carbamic acid tert-butyl ester (0.29 g, 1.03 mmol, 1.05 equiv) in NMP (2 mL) at room temperature was added HATU (0.41 g, 1.08 mmol, 1.1 equiv) in one portion. After 3 hr at rt, the solution was diluted with ethyl acetate and washed with water, brine, dried (sodium sulfate) and concentrated. LCMS: (MH)$^+$=419.0 (2.09 min).

Part B:
The residue from 260 Part A was treated with TFA/water (95/5) for 2 hr, concentrated and purified by Prep-LC to afford the compound 261 (see Table 22).

TABLE 22

| Cmpd No. | Compound | Ret. Time UV254 (min) | EMW | MS (m/z) Observed |
|---|---|---|---|---|
| 261 | 6-chloro-pyridine-2-carbonyl-amino-methyl-benzothiazol-2-yl-amine structure | 2.64 | 318.0 | 319.03 |

Example 19.1

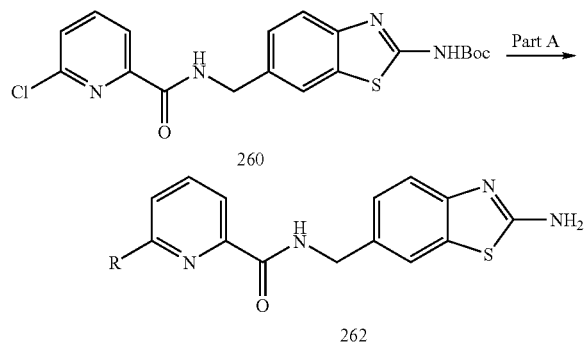

Part A:

A suspension of (6-{[(6-chloro-pyridine-2-carbonyl)-amino]-methyl}-benzothiazol-2-yl)-carbamic acid tert-butyl ester 260 (0.03 g, 1.0 equiv), palladium (II) acetate (0.0016 g, 0.1 equiv), sodium tert-butoxide (0.017 g, 2.5 equiv), benzyl amine (0.016 mL, 2.0 equiv) and 2-dicyclohexylphosphino-2'-(N,N-dimethylamino)biphenyl (0.003 g, 0.1 equiv) in toluene (1 mL) was heated under argon at 100° C. for 15 hr. The crude residue was filtered through Celite, concentrated, treated with TFA, concentrated a purified by Prep-LC to afford the title compound.

| Cmpd No. | Compound | Ret. Time UV254 (min) | EMW | MS (m/z) Observed |
|---|---|---|---|---|
| 263 | benzylamino-pyridine-carboxamide-benzothiazol-2-amine structure | 3.28 | 389.1 | 390.13 |
| 264 | pyrazolyl-pyridine-carboxamide-benzothiazol-2-amine structure | 2.97 | 350.1 | 351.1 |

Example 20

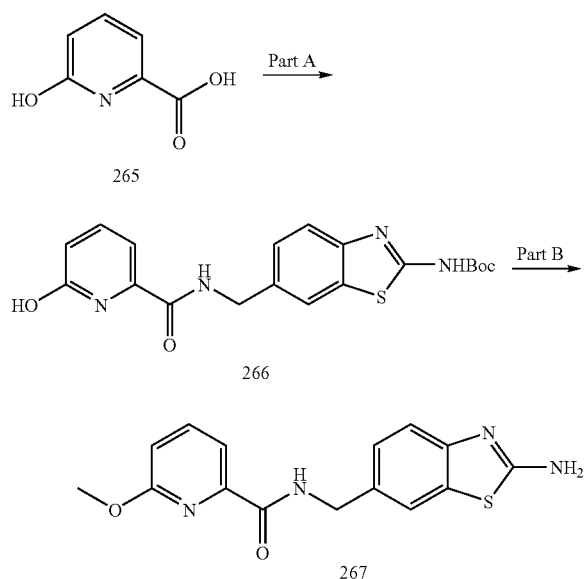

Example 21

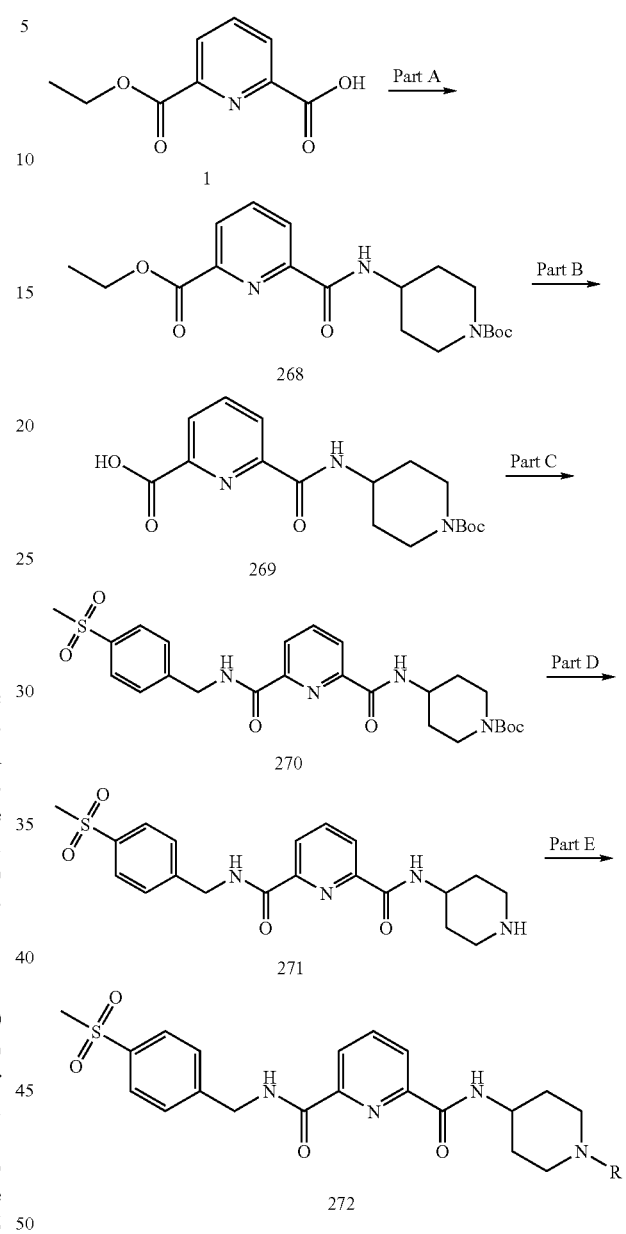

Part A:

To a solution of 6-hydroxypicolinic 265 (0.14 g, 1.0 mmol, 1.00 equiv), (6-aminomethyl-benzothiazol-2-yl)-carbamic acid tert-butyl ester (0.28 g, 1.0 mmol, 1.0 equiv) and N,N-diisopropylethylamine (0.35 mL, 2.0 mmol, 2.0 equiv) in NMP (2.5 mL) at room temperature was added HATU (0.38 g, 1.0 mmol, 1.0 equiv) in one portion. The reaction mixture was stirred at room temperature for 2 hours, diluted with ethyl acetate and washed with water, brine, dried (sodium sulfate) and concentrated affording 6-methoxy-pyridine-2-carboxylic acid (2-amino-benzothiazol-6-ylmethyl)-amide 266. LCMS: $(MH-C_4H_8)^+=345.0$ (1.55 min). (See Table 24).

Part B

The crude residue 266 from Part A (0.055 g, 0.2 mmol, 1.00 equiv) was treated with iodomethane (0.027 mL, 3.0 equiv) and potassium carbonate (0.038 g, 2.0 equiv) in DMF for 5 hr at 70° C. The resulting mixture was partitioned between ethyl acetate and water. The organic extract was washed with water, dried (sodium sulfate) and then concentrated. The Boc group was removed by treatment of the residue with TFA. The residue was purified by Prep-LC. LCMS $(MH)^+=415.1$ (1.86 min).

| Cmpd No. | Compound | Ret. Time UV$_{254}$ (min) | EMW | MS (m/z) Observed |
|---|---|---|---|---|
| 267 | | 1.79 | 314.1 | 315.08 |

Part A:

To a solution of 2,6-pyridinedicarboxylate monoethyl ester 1 (1.0 g, 6.0 mmol, 1.0 equiv), N,N-diisopropylethylamine (2.1 mL, 12.0 mmol, 2.0 equiv), and 4-amino-1-boc-piperidine (1.3 g, 6.6 mmol, 1.1 equiv) in NMP at rt was added HATU (2.5 g, 6.6 mmol, 1.1 equiv) in one portion. The reaction mixture was stirred at room temperature for 2 hours, diluted with ethyl acetate and washed with water, brine, dried (sodium sulfate) and concentrated.

Part B:

The crude residue 268 from Part A was dissolved in THF (30 mL) and treated with 1N LiOH (12 mL). The biphasic mixture was stirred at rt 2 hours, diluted with ethyl acetate and acidified to ca. pH 4 with 1N HCl. The organic phase was washed with water, dried (sodium sulfate) and concentrated. 6-(1-Tert-butoxycarbonyl-piperidin-4-ylcarbamoyl)-pyridine-2-carboxylic acid 269 was obtained as a colorless solid (0.66 g). LCMS (MH—$C_4H_8$)$^+$=294.1 (1.56 min).

Part C:

To a solution of 6-(1-tert-butoxycarbonyl-piperidin-4-ylcarbamoyl)-pyridine-2-carboxylic acid 269 (0.66 g, 1.9 mmol, 1.00 equiv), N,N-diisopropylethylamine (0.89 mL, 9.5 mmol, 5.0 equiv), and 4-methylsulfonylbenzylamine hydrochloride (0.44 g, 3.8 mmol, 2.0 equiv) in NMP (5 mL) at rt was added HATU (0.76 g, 2.0 mmol, 1.05 equiv) in one portion. The reaction mixture was stirred overnight at rt, diluted with ethyl acetate and washed with water, brine, dried (sodium sulfate) and concentrated. LCMS (MH—$C_4H_8$)$^+$= 461.1 (1.76 min).

Part D:

To a solution of the crude residue 270 from Part C in DCM (5 mL) was added trifluoroacetic acid (5 mL) at rt. The solution was stirred 2 hr and then was concentrated. The crude residue 271 was used without further purification.

Part E:

A solution of the residue 271 from Part D (0.03 g, 0.0565 mmol, 1.00 equiv), N,N-diisopropylethylamine (0.1 mL, 0.56 mmol, 10.0 equiv) and aryl chloride (5.0 equiv) in 2-methoxyethanol (0.25 mL) was heated at 120° C. for 24 hr. Concentration and purification by Prep-LC afforded the compounds in Table 25.

TABLE 25

| Cmpd No. | Structure | Ret. Time $UV_{254}$ (min) | EMW | MS (m/z) Observed |
|---|---|---|---|---|
| 273 | 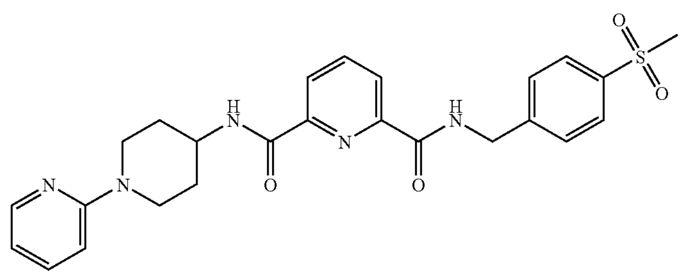 | 2.66 | 493.2 | 494.18 |
| 274 | 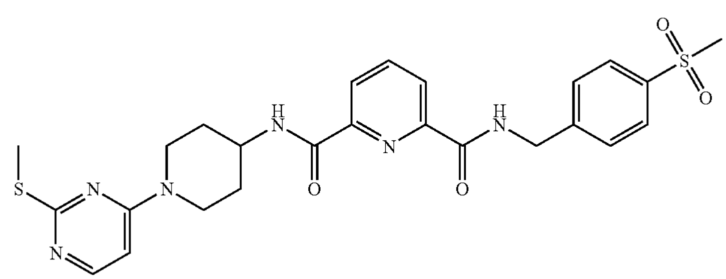 | 2.98 | 540.2 | 541.16 |
| 275 | 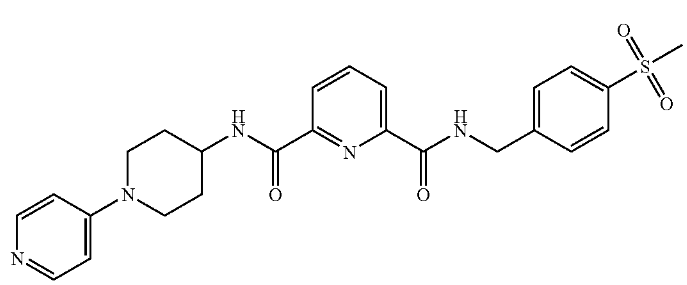 | 2.66 | 493.2 | 494.18 |

TABLE 25-continued

| Cmpd No. | Structure | Ret. Time UV$_{254}$ (min) | EMW | MS (m/z) Observed |
|---|---|---|---|---|
| 276 | 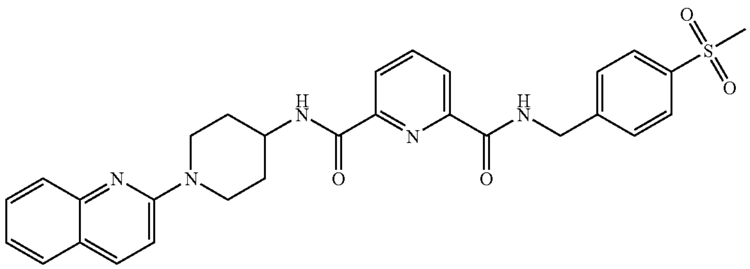 | 3.11 | 543.2 | 544.19 |

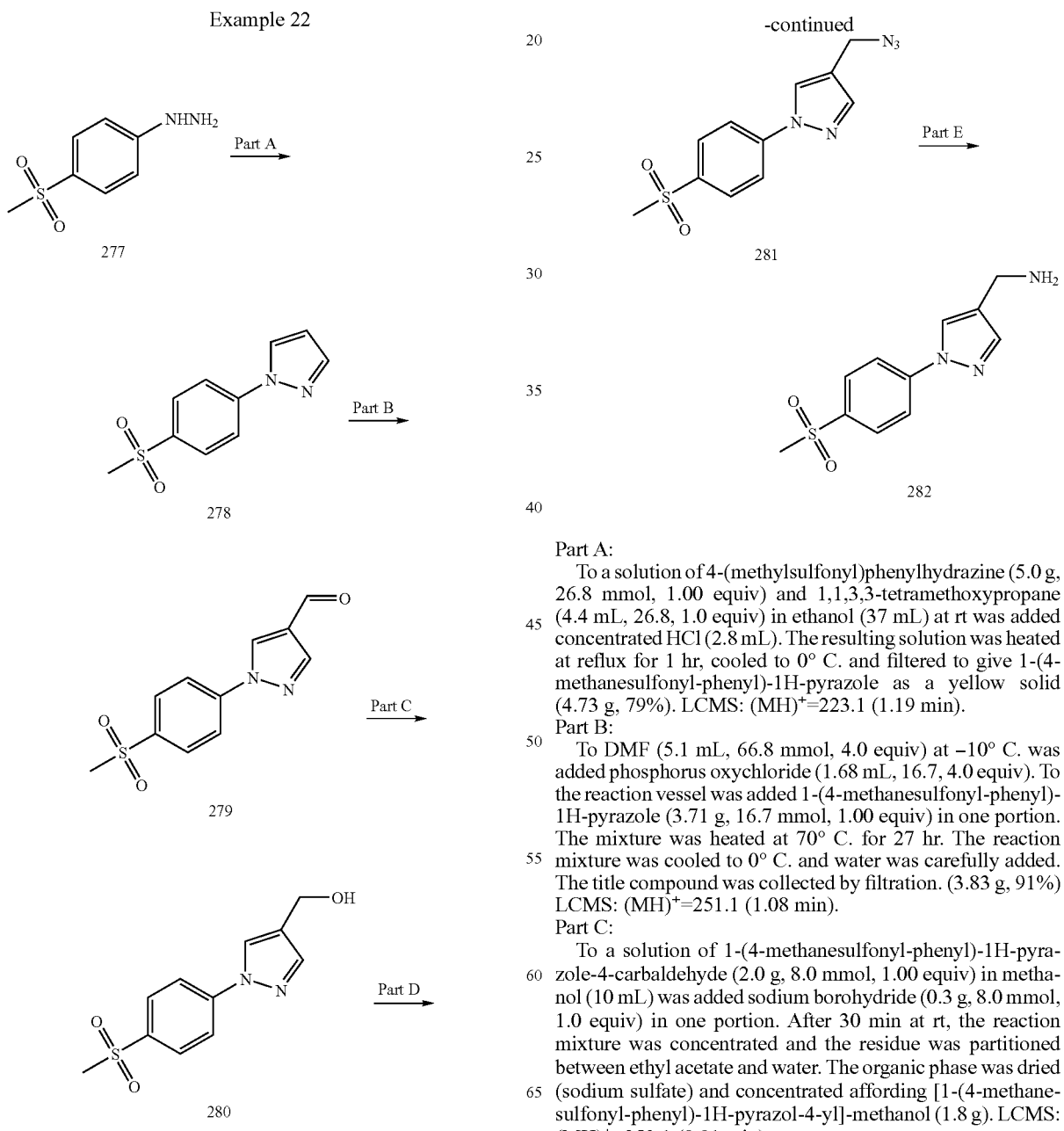

Part A:
To a solution of 4-(methylsulfonyl)phenylhydrazine (5.0 g, 26.8 mmol, 1.00 equiv) and 1,1,3,3-tetramethoxypropane (4.4 mL, 26.8, 1.0 equiv) in ethanol (37 mL) at rt was added concentrated HCl (2.8 mL). The resulting solution was heated at reflux for 1 hr, cooled to 0° C. and filtered to give 1-(4-methanesulfonyl-phenyl)-1H-pyrazole as a yellow solid (4.73 g, 79%). LCMS: (MH)$^+$=223.1 (1.19 min).

Part B:
To DMF (5.1 mL, 66.8 mmol, 4.0 equiv) at −10° C. was added phosphorus oxychloride (1.68 mL, 16.7, 4.0 equiv). To the reaction vessel was added 1-(4-methanesulfonyl-phenyl)-1H-pyrazole (3.71 g, 16.7 mmol, 1.00 equiv) in one portion. The mixture was heated at 70° C. for 27 hr. The reaction mixture was cooled to 0° C. and water was carefully added. The title compound was collected by filtration. (3.83 g, 91%) LCMS: (MH)$^+$=251.1 (1.08 min).

Part C:
To a solution of 1-(4-methanesulfonyl-phenyl)-1H-pyrazole-4-carbaldehyde (2.0 g, 8.0 mmol, 1.00 equiv) in methanol (10 mL) was added sodium borohydride (0.3 g, 8.0 mmol, 1.0 equiv) in one portion. After 30 min at rt, the reaction mixture was concentrated and the residue was partitioned between ethyl acetate and water. The organic phase was dried (sodium sulfate) and concentrated affording [1-(4-methanesulfonyl-phenyl)-1H-pyrazol-4-yl]-methanol (1.8 g). LCMS: (MH)$^+$=253.1 (0.91 min).

Part D:

To a solution of [1-(4-methanesulfonyl-phenyl)-1H-pyrazol-4-yl]-methanol (1.80 g, 7.12 mmol, 1.00 equiv) and diphenylphosphoryl azide (2.35 g, 8.54 mmol, 1.2 equiv) in THF (15 mL) at rt was added 1,8-diazabicyclo[5.4.0]undec-7-ene (1.3 g, 8.54 mmol, 1.2 equiv). The resulting solution was stirred overnight, concentrated and chromatographically purified (15% ethyl acetate in hexanes) to give 4-azidomethyl-1-(4-methanesulfonyl-phenyl)-1H-pyrazole (1.90 g, 97%). LCMS: $(MH)^+=278.0$ (1.45 min).

Part E:

To a solution of 4-azidomethyl-1-(4-methanesulfonyl-phenyl)-1H-pyrazole (1.90 g, 7.12 mmol, 1.00 equiv) in 1,4-dioxane (10 mL) was added water (1 mL) and triphenylphosphine resin (2.8 g, 3 mol/g, 200-400 mesh, 1.2 equiv). The suspension was stirred overnight. Filtration and concentration afforded C-[1-(4-methanesulfonyl-phenyl)-1H-pyrazol-4-yl]-methylamine as a colorless solid. LCMS: $(MH)^+=252.1$ (0.55 min). This compound was utilized in the following Example 22.1.

Example 22.1

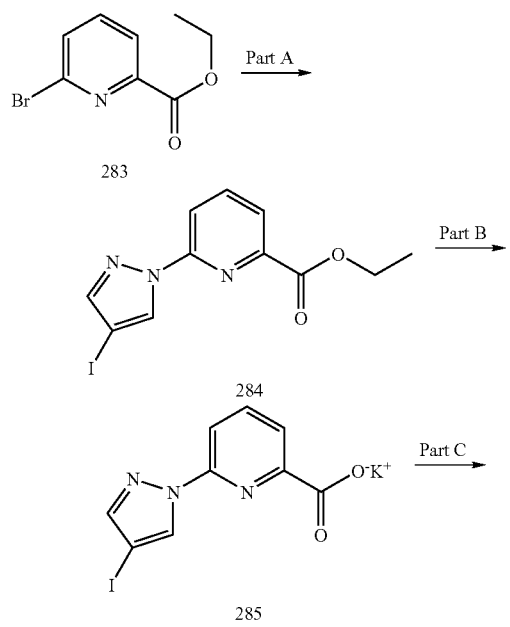

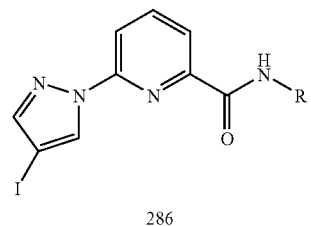

286

Part A:

To a solution of 4-iodopyrazole (0.32 g, 1.6 mmol, 1.5 equiv) in NMP (5 mL) at rt was added NaH (60% in oil, 0.065 g, 1.6 mmol, 1.5 equiv) in one portion. After 15 min at rt, ethyl-6-bromo-2-pyridinecarboxylate 283 (0.250 g, 1.09 mmol, 1.00 equiv) was added in one portion and the resulting mixture was heated overnight at 80° C. (20 h). The reaction was allowed to cool to room temperature, water was added and the resulting ppt was collected by vacuum filtration (190 mg, 51%). LCMS: $(MH)^+=343.9$ (2.16 min).

Part B:

To a solution of ester 284 (190 mg, 0.554, mmol, 1.00 equiv) in EtOH (3 mL) was added KOH (33 mg, 0.58, 1.05 equiv). After heating at 50° C. overnight, EtOH was removed under reduced pressure affording the title compound as a colorless solid. The title compound was used without further purification.

Part C:

To a solution of potassium salt 285 from Part B (0.020 g, 0.057 mmol, 1.00 equiv), N,N-diisopropylethylamine (0.029 mL, 0.17 mmol, 3.0 equiv), and amine (1.1 equiv) in NMP (5 mL) at rt was added HATU (0.86 g, 2.3 mmol, 1.1 equiv) in one portion. The reaction mixture was stirred for 2 hours at rt. The reaction mixture was stirred overnight at rt, diluted with ethyl acetate and washed with water, brine, dried (sodium sulfate) and concentrated. Purification by Prep-LC afforded the compounds in Table 26.

TABLE 26

| Cmpd No. | Compound | Ret. Time UV$_{254}$ (min) | EMW | MS (m/z) Observed |
|---|---|---|---|---|
| 287 | | 5.38 | 356.0 | 357.01 |

TABLE 26-continued

| Cmpd No. | Compound | Ret. Time UV$_{254}$ (min) | EMW | MS (m/z) Observed |
|---|---|---|---|---|
| 288 | | 3.51 | 391.0 | 391.99 |
| 289 | | 3.26 | 405.0 | 406.01 |
| 290 | | 3.59 | 458.0 | 459.04 |
| 291 | | 5.68 | 470.0 | 471.04 |
| 292 | | 4.76 | 548.0 | 549.01 |

Example 22.2

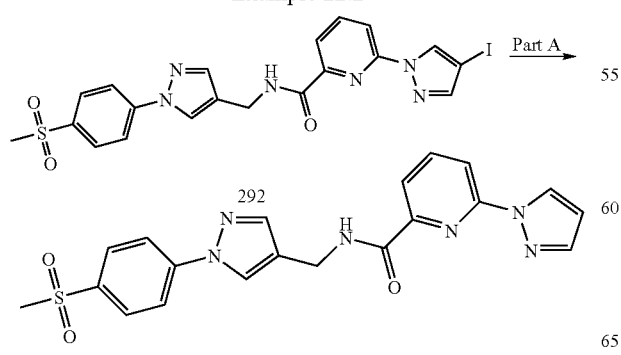

Part A

To the stirred solution of compound 292 (0.05 mmol) in Ethanol (10 mL) was added catalytic amount of 5% Pd on carbon and the flask was sealed with the rubber septum. Reaction flask was evacuated under vacuum and the balloon filled with hydrogen gas is inserted into the flask. After overnight stirring the reaction mixture was filtered through celite pad and concentrated. The crude product was purified on prep-LC (see Table 27).

TABLE 27

| Cmpd No. | Compound | Ret. Time UV₂₅₄ (min) | EMW | MS (m/z) Observed |
|---|---|---|---|---|
| 293 | | 1.469 | 422.1 | 423.1 |

Example 22.3

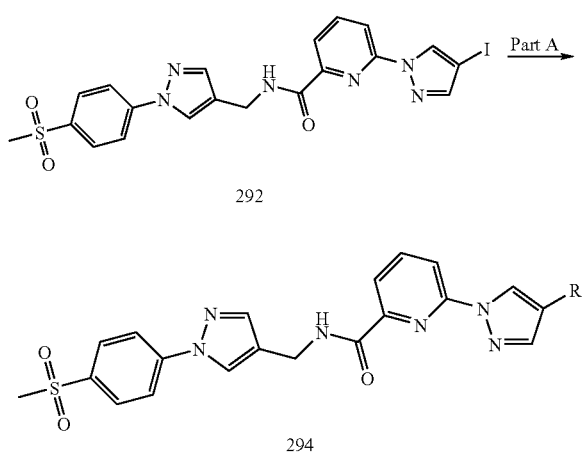

Method 1
Part A

To compound 292 (1 equivalent) in 1,4-dioxane (1 mL) was added the boronic acid (needed to make the compounds in Table 28) (2 equivalents), dichloro[1,1'-bis(diphentylphosphino)ferrocene]palladium (II) dichloromethane adduct (10 mol %) and $K_3PO_4$ (2 equivalents). The reaction vial was flushed with argon and stirred at 80° C. overnight. LC-MS analysis of the reaction indicates that the reaction is complete. The crude reaction mixture was filtered to remove the solids, rinsed the solids with THF. The filtrate was concentrated. Purification by Prep-LC and conversion to a hydrochloride salt afforded pure compounds in Table 28.

Method 2
Part A

To the stirred solution of compound 292 (0.055 mmol) in dioxane (1 mL) was added 2-pyridylzincbromide (0.5 M soln.; 1 mL) dropwise and heated to 50° C. overnight. The reaction was quenched with brine soln. and extracted with ethylacetate, dried over anhydrous $Na_2SO_4$. Filtered and concentrated. The crude product was purified on prep. LC to yield pure product 297 which was later converted to HCl salt.

The following compounds are made using procedure described in either method 1 or method 2.

TABLE 28

| Cmpd No. | Compound | Ret. Time UV₂₅₄ (min) | EMW | MS (m/z) Observed |
|---|---|---|---|---|
| 295 | | 1.903 | 516.1 | 517.1 |
| 296 | | 1.852 | 516.1 | 517.1 |
| 297 | | 3.04 | 499.1 | 500.24 |

Example 23

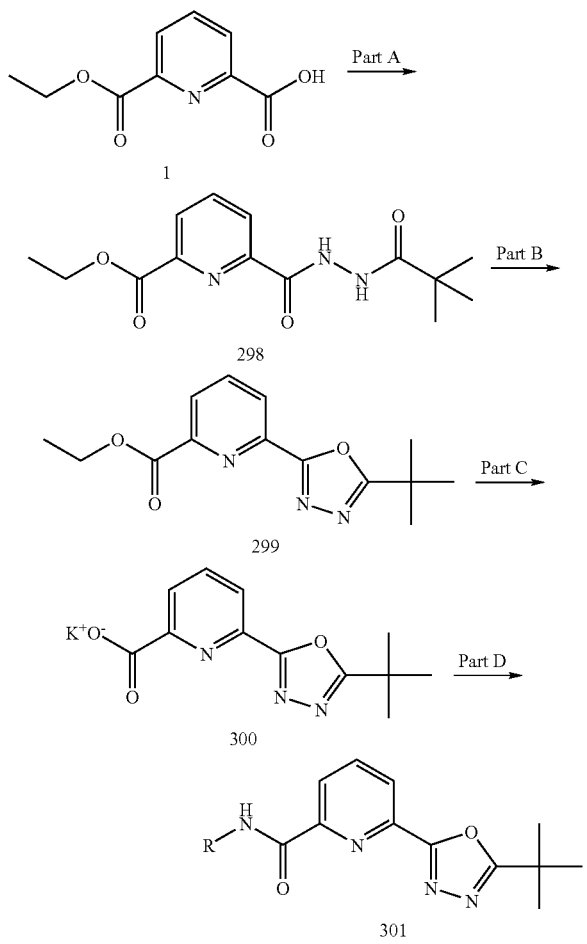

Part A

To a solution of 2,6-pyridinedicarboxylate monoethyl ester 1 (0.500 g, 2.56 mmol, 1.00 equiv), N,N-diisopropylethylamine (0.9 mL, 5.1 mmol, 2.0 equiv) and pivalic acid hydrazide (0.297 g, 2.56 mmol, 1.0 equiv) in NMP (6 mL) at it was added HATU (0.97 g, 2.6 mmol, 1.00 equiv) in one portion. After 3 hr at rt, the solution was diluted with ethyl acetate and washed with water (three times) and brine, dried (sodium sulfate) and partially concentrated. Filtration afforded 0.314 g of 6-[N',N'-(2,2-dimethyl-propionyl)hydrazinocarbonyl]-pyridine-2-carboxylic acid ethyl ester 298 as a colorless solid (42%).

Part B:

To a solution of 6-[N',N'-(2,2-dimethyl-propionyl)-hydrazinocarbonyl]-pyridine-2-carboxylic acid ethyl ester 298 (0.234 g, 0.789 mmol, 1.0 equiv) in pyridine (0.16 mL, 1.04 mmol, 1.3 equiv) at it was added thionyl chloride (0.076 mL, 1.04 mmol, 1.3 equiv). The resulting suspension was aged 15 min, diluted with toluene (8 mL) and heated at 100° C. for 1 hr. The reaction mixture was partitioned between ethyl acetate and water, washed with sodium bicarbonate, brine and dried (sodium sulfate). Concentration afforded 0.11 g (49%) of 6-(5-tert-butyl-[1,3,4]oxadiazol-2-yl)-pyridine-2-carboxylic acid ethyl ester 299 as a brown oil. The crude material was used without further purification.

Part C:

To a solution of 6-(5-tert-butyl-[1,3,4]oxadiazol-2-yl)-pyridine-2-carboxylic acid ethyl ester 300 (0.22 g, 0.80 mmol, 1.0 equiv) in ethanol (4 mL) was added KOH (46.0 mg, 0.824 mmol, 1.03 equiv). The mixture was heated at 60° C. for 1 hr, cooled to rt and concentrated. LCMS: $(MH)^+=248.2$ (1.31 min).

Part D:

To a solution of potassium carboxylate 300 from Part C (0.039 g, 0.14 mmol, 1.00 equiv), amine (1.2 equiv) and N,N-diisopropylethylamine (0.048 mL, 0.27 mmol, 2.0 equiv) in NMP (1 mL) at room temperature was added HATU (0.052 g, 0.14 mmol, 1.0 equiv) in one portion. The reaction mixture was stirred at room temperature for 2 hours, diluted with ethyl acetate and washed with water, brine, dried (sodium sulfate) and concentrated. Purification by Prep-LC afforded the products in Table 29.

TABLE 29

| Cmpd No. | Compound | Ret. Time UV$_{254}$ (min) | EMW | MS (m/z) Observed |
|---|---|---|---|---|
| 302 | | 4.07 | 480.2 | 481.16 |
| 303 | | 3.91 | 414.1 | 415.14 |

Example 24

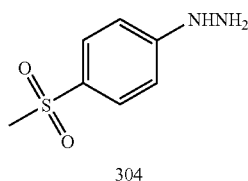

304

Part A →

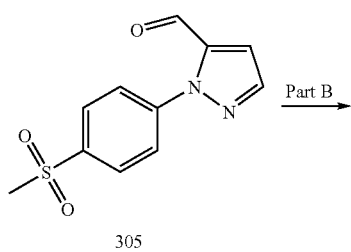

305

Part B →

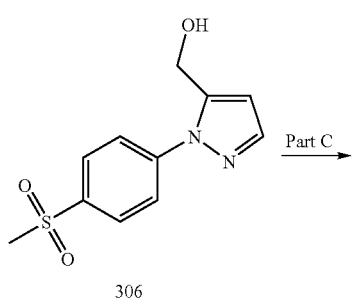

306

Part C →

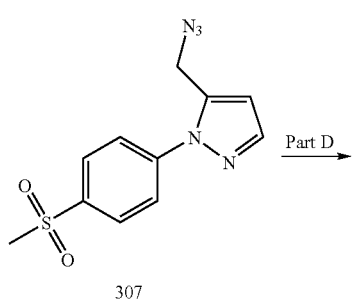

307

Part D →

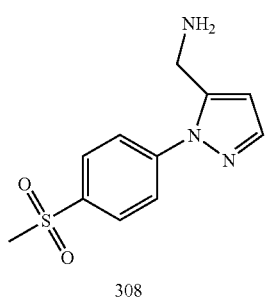

308

Part A

To a suspension of 4-(methylsulfonyl)phenylhydrazine hydrochloride (0.75 g, 4.02 mmol, 1.00 equiv) in ethanol (20 mL) was added 4-(dimethylamino)-1,1-dimethoxybut-3-en-2-one (0.7 g, 4.0 mmol, 1.0 equiv). The resulting mixture was heated at reflux (48 hr) then concentrated. To a solution of the crude residue in acetone (10 mL) was added 6N HCl (2 mL). The resulting solution was allowed to stir at room temperature for 30 min, then was partitioned between ethyl acetate and water. The organic extract was washed with water, saturated sodium bicarbonate, brine and dried (sodium sulfate). Concentration afforded 2-(4-methanesulfonyl-phenyl)-2H-pyrazole-3-carbaldehyde admixed with regioisomer 1-(4-methanesulfonyl-phenyl)-1H-pyrazole-3-carbaldehyde (ca. 10/1). The crude material was used without further purification.

Part B

To a solution of crude 2-(4-methanesulfonyl-phenyl)-2H-pyrazole-3-carbaldehyde from Part A in methanol (10 mL) was added sodium borohydride (0.15 g, 4 mmol) in one portion. After 30 min at room temperature, the reaction mixture was concentrated and the residue was partitioned between ethyl acetate and water. The organic phase was dried (sodium sulfate) and concentrated affording [2-(4-methanesulfonyl-phenyl)-2H-pyrazol-3-yl]-methanol. The crude material was used without further purification.

Part C:

To a solution of [2-(4-methanesulfonyl-phenyl)-2H-pyrazol-3-yl]-methanol (4 mmol) and diphenylphosphoryl azide (0.95 mL, 4.4 mmol, 1.1 equiv) in THF (10 mL) at rt was added 1,8-diazabicyclo[5.4.0]undec-7-ene (0.6 mL, 4.4 mmol, 1.2 equiv). The resulting solution was stirred overnight, concentrated and chromatographically purified (15% ethyl acetate in hexanes) to give 5-azidomethyl-1-(4-methanesulfonyl-phenyl)-1H-pyrazole (0.344 g, 31% based on 4-(methylsulfonyl)phenylhydrazine hydrochloride, LCMS: $(MH)^+=278.0$ (rt=1.36 min) and 3-azidomethyl-1-(4-methanesulfonyl-phenyl)-1H-pyrazole (75 mg, 7% based on 4-(methylsulfonyl)phenylhydrazine hydrochloride, LCMS: $(MH)^+=278.0$ (rt=1.48 min)).

Part D (Isomer 1)

To a solution of 5-azidomethyl-1-(4-methanesulfonyl-phenyl)-1H-pyrazole (0.344 g, 1.24 mmol, 1.00 equiv) in 1,4-dioxane (5 mL) was added water (0.5 mL) and triphenylphosphine resin (0.5 g, 3 mol/g, 200-400 mesh, 1.2 equiv). The suspension was stirred overnight. Filtration and concentration afforded C-[2-(4-methanesulfonyl-phenyl)-2H-pyrazol-3-yl]-methylamine as a colorless solid.

Part D (Isomer 2)

To a solution of 3-azidomethyl-1-(4-methanesulfonyl-phenyl)-1H-pyrazole (75 mg, 0.27 mmol, 1.00 equiv) in 1,4-dioxane (5 mL) was added water (0.5 mL) and triphenylphosphine resin (0.11 g, 3 mol/g, 200-400 mesh, 1.2 equiv). The suspension was stirred overnight. Filtration and concentration afforded C-[1-(4-methanesulfonyl-phenyl)-1H-pyrazol-3-yl]-methylamine as a colorless solid.

The compounds in Table 30 are made using the above building blocks and the methods described in Example 2.

TABLE 30

| Cmpd No. | Compound | Ret. Time UV$_{254}$ (min) | EMW | MS (m/z) Observed |
|---|---|---|---|---|
| 309 | | 3.64 | 441.1 | 442.15 |
| 310 | | 3.38 | 441.1 | 442.15 |

Example 25

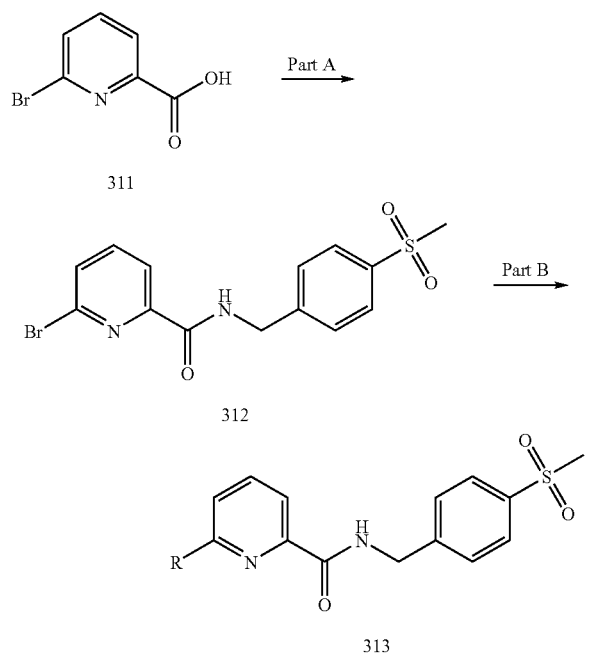

Part A:

To a solution of 6-bromopyridine-2-carboxylic acid 311 (0.44 g, 2.2 mmol, 1.00 equiv), N,N-diisopropylethylamine (1.1 mL, 6.6 mmol, 3.0 equiv), and 4-methylsulfonylbenzylamine hydrochloride (0.48 g, 2.2 mmol, 1.0 equiv) in NMP (5 mL) at rt was added HATU (0.86 g, 2.3 mmol, 1.0 equiv) in one portion. The reaction mixture was stirred overnight at rt, diluted with ethyl acetate and washed with water, brine, dried (sodium sulfate) and concentrated. $^1$H NMR (400 MHz, DMSO-$_{d6}$) δ 9.38 (t, 1H), 8.03 (dd, 1H), 7.93 (t, 1H), 7.88-7.83 (m, 3H), 7.55 (d, 2H), 4.56 (d, 2H), 3.17 (d, 2H).

Method 1

Part B

To a solution of the appropriate heterocycle (to make the compounds in Table 31) (0.065 mmol, 1.2 equiv) in NMP (0.5 mL) was added NaH (60% in oil, 0.0044 g, 0.11 mmol, 2.0 equiv). The resulting mixture was allowed to stir for 15 min, then 6-bromo-pyridine-2-carboxylic acid 4-methanesulfonyl-benzylamide (312 from Part A) (0.020 g, 0.054 mmol, 1.00 equiv) was added in one portion. The dark reaction mixture was heated at 90-100° C. for 30 minutes. The crude mixture was allowed to cool and then was partitioned between ethyl acetate and water, dried (sodium sulfate), concentrated and purified by Prep-LC.

Method 2

Part B

A suspension of 6-bromo-pyridine-2-carboxylic acid 4-methanesulfonyl-benzylamide from 312 Part A (0.020 g, 0.054 mmol, 1.00 equiv), potassium phosphate (0.034 g, 0.16 mmol, 3.0 equiv), [1,1'-bis(diphenylphosphino)-ferrocene] dichloropalladium(II) (0.004 g, 0.005 mmol, 10 mol %) and the appropriate boronic acid (to make the compounds in Table 31) (2.0 equiv) in 1,4-dioxane (1 mL) was heated at 100° C. for 17 hr. The suspension was allowed to cool, was filtered and concentrated. Purification by Prep-LC afforded the desired products.

Compounds 314, 315, 318, 319, 320, 321, 322, 323, 324, 325, 326, 327, 328, 334, 335, 336, 337, and 338 are made using method 1 part B Compounds 316, 317, 329, 330, 331, 332, 333, and 339 are made using method 2 part B

TABLE 31

| Cmpd No. | Compound | Ret. Time UV$_{254}$ (min) | EMW | MS (m/z) Observed |
|---|---|---|---|---|
| 314 | | 3.71 | 356.1 | 357.09 |
| 315 | | 4.94 | 424.1 | 425.08 |
| 316 | | 4.73 | 384.1 | 385.09 |
| 317 | | 2.44 | 367.1 | 368.10 |
| 318 | | 4.75 | 482.0 | 482.99 |
| 319 | | 4.47 | 428.1 | 429.12 |

TABLE 31-continued

| Cmpd No. | Compound | Ret. Time UV$_{254}$ (min) | EMW | MS (m/z) Observed |
|---|---|---|---|---|
| 320 | | 4.07 | 384.1 | 385.13 |
| 321 | | 5.22 | 450.1 | 451.12 |
| 322 | | 4.61 | 406.1 | 407.11 |
| 323 | | 4.18 | 370.1 | 371.11 |
| 324 | | 3.83 | 370.1 | 371.11 |
| 325 | | 4.08 | 370.1 | 371.11 |

TABLE 31-continued

| Cmpd No. | Compound | Ret. Time UV$_{254}$ (min) | EMW | MS (m/z) Observed |
|---|---|---|---|---|
| 326 | | 3.02 | 357.1 | 358.09 |
| 327 | | 3.65 | 434.0 | 435.0 |
| 328 | | 4.7 | 434.0 | 435.0 |
| 329 | | 4.86 | 414.1 | 415.11 |
| 330 | | 4.67 | 414.1 | 415.11 |
| 331 | | 4.7 | 414.1 | 415.11 |

TABLE 31-continued

| Cmpd No. | Compound | Ret. Time UV$_{254}$ (min) | EMW | MS (m/z) Observed |
|---|---|---|---|---|
| 332 | | 4.57 | 410.1 | 411.09 |
| 333 | | 3.29 | 370.1 | 371.11 |
| 334 | | 2.93 | 433.1 | 434.12 |
| 335 | | 3.86 | 434.1 | 435.12 |
| 336 | | 4.42 | 412.2 | 413.16 |
| 337 | | 2.01 | 361.1 | 362.15 |
| 338 | | 3.05 | 375.2 | 376.16 |

TABLE 31-continued

| Cmpd No. | Compound | Ret. Time UV$_{254}$ (min) | EMW | MS (m/z) Observed |
|---|---|---|---|---|
| 339 | | 5 | 405.1 | 406.11 |

Example 26

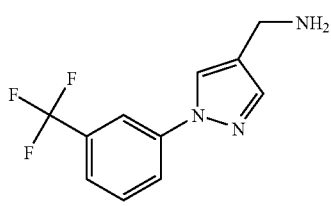

340

The title compound 340 was prepared by the methods described in Example 22. LCMS: (M$^+$+H)=242.1 (rt=0.96 min).

Example 26.1

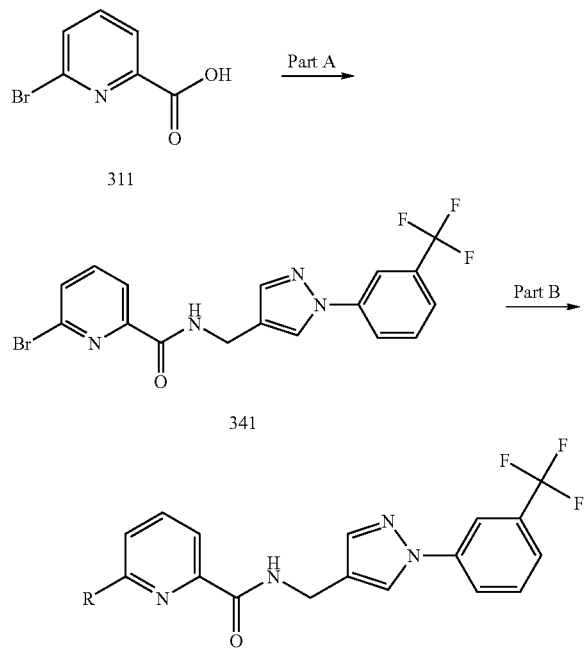

Part A

To a solution of 6-bromopyridine-2-carboxylic acid 311 (0.0.82 g, 0.41 mmol, 1.00 equiv), N,N-diisopropylethylamine (0.14 mL, 0.82 mmol, 2.0 equiv), and C-[1-(4-trifluoromethyl-phenyl)-1H-pyrazol-4-yl]-methylamine 340 (0.103 g, 0.43 mmol, 1.05 equiv) in NMP (3 mL) at rt was added HATU (0.016 g, 0.43 mmol, 1.05 equiv) in one portion. The reaction mixture was stirred overnight at rt, diluted with ethyl acetate and washed with water, brine, dried (sodium sulfate) and concentrated. LCMS (MH)$^+$=424.9 (2.12 min).

Method 1

Part B

A solution of 6-bromo-pyridine-2-carboxylic acid [1-(3-trifluoromethyl-phenyl)-1H-pyrazol-4-ylmethyl]-amide 341 from Part A (0.025 g, 0.059 mmol, 1.00 equiv), N,N-diisopropylethylamine (2.0 equiv) and the appropriate amine (to make the compounds in Table 32) (5.0 equiv) in 2-methoxyethanol (1 mL) was heated at 80° C. for 24 hr. Concentration and purification of the residue by Prep-LC afforded the desired compounds.

Part B—Synthesis of Aryl and C-Linked Heterocycles

A suspension of 6-bromo-pyridine-2-carboxylic acid [1-(3-trifluoromethyl-phenyl)-1H-pyrazol-4-ylmethyl]-amide 341 from Part A (0.035 g, 0.082 mmol, 1.00 equiv), potassium phosphate (0.055 g, 0.24 mmol, 3.0 equiv), [1,1'-bis(diphenylphosphino)ferrocene]dichloropalladium(II) (0.006 g, 0.008 mmol, 10 mol %) and the appropriate boronic acid (to make the compounds in Table 32) (2.0 equiv) in 1,4-dioxane (1 mL) was heated at 100° C. for 17 hr. The suspension was allowed to cool, was filtered and concentrated. Purification by Prep-LC afforded the desired products.

Compounds 343-346 are made by Method 1 Part B.

Compound 347 is made by Method 2 Part B.

| Cmpd No. | Compound | Ret. Time UV$_{254}$ (min) | EMW | MS (m/z) Observed |
|---|---|---|---|---|
| 343 | | 5.3 | 415.2 | 416.16 |
| 344 | | 6.42 | 463.2 | 464.16 |
| 345 | | 5.24 | 431.2 | 432.16 |
| 346 | | 4.15 | 492.2 | 493.19 |
| 347 | | 6.24 | 461.1 | 462.15 |
Example 27
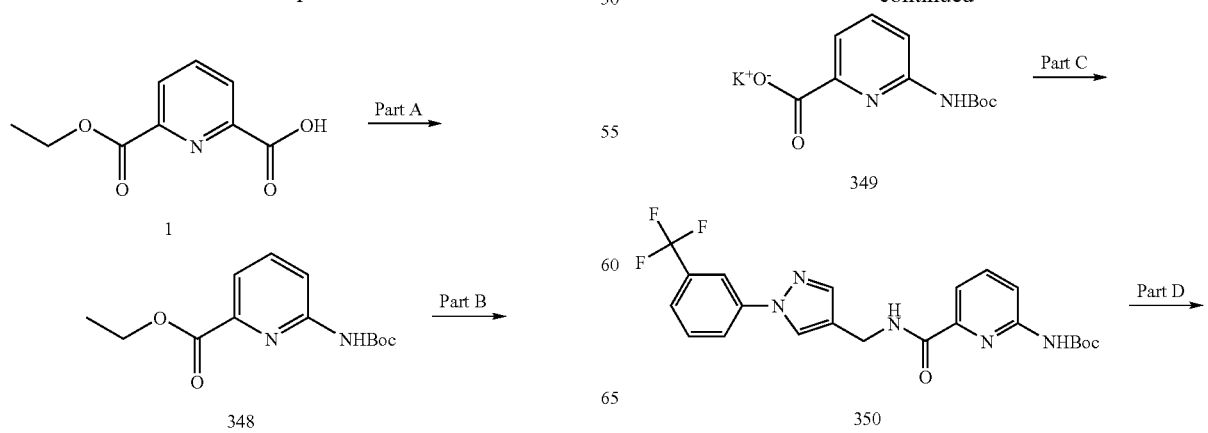

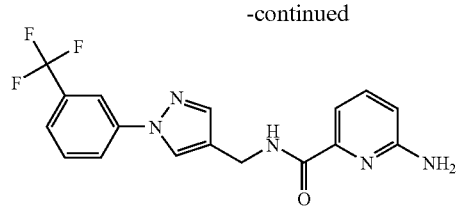

351

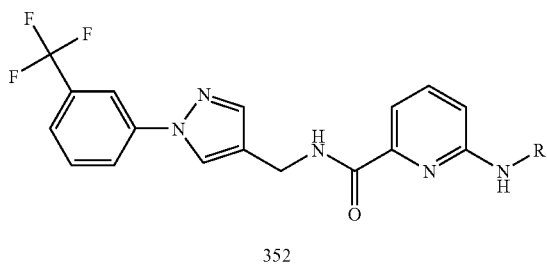

352

Part A

To a solution of 2,6-pyridinedicarboxylate monoethyl ester 1 (1.25 g, 6.40 mmol, 1.00 equiv) and N,N-diisopropylethylamine (2.2 mL, 12.8 mmol, 2.00 equiv) in toluene (38 mL) and tert-butanol (3.8 mL) was added DPPA (1.9 mL, 8.8 mmol, 1.4 equiv). The resulting solution was heated at 100° C. for 5 hr, cooled and partitioned between ethyl acetate and water, washed with brine and dried (sodium sulfate). Purification by chromatography (15% ethyl acetate in hexanes) afforded 6-tert-butoxycarbonylamino-pyridine-2-carboxylic acid ethyl ester (0.88 g, 51%) as a yellow semisolid 348. LCMS: $(MH)^+=267.1$ (rt=1.95 min).

Part B

To a solution of 6-tert-butoxycarbonylamino-pyridine-2-carboxylic acid ethyl ester 348 from Part A (0.496 g, 1.86 mmol, 1.00 equiv) in ethanol (4 mL) was added KOH (0.11 g, 1.96 mmol, 1.05 equiv). The resulting suspension was stirred for 3 hr at rt and then was concentrated. LCMS: $(MH)^+=267.1$ (rt=1.95 min).

Part C

To a solution of crude material from 349 Part B (0.200 g, 0.72 mmol, 1.00 equiv), C-[1-(3-trifluoromethyl-phenyl)-1H-pyrazol-4-yl]-methylamine (0.18 g, 0.76 mmol, 1.05 equiv) and N,N-diisopropylethylamine (0.25 ml, 1.45 mmol, 2.0 equiv) in NMP (4 mL) at rt was added HATU (0.289 g, 0.76 mmol, 1.05 equiv) in one portion. The reaction mixture was stirred at room temperature for 0.5 hours, diluted with ethyl acetate and washed with water (3×) and brine, dried (sodium sulfate) and concentrated. LCMS: $(MH)^+=462.1$ (rt=2.24 min).

Part D

To a solution of crude (6-{[1-(3-trifluoromethyl-phenyl)-1H-pyrazol-4-ylmethyl]-carbamoyl}-pyridin-2-yl)-carbamic acid tert-butyl ester 350 from Part C in DCM (3 mL) was added trifluoroacetic acid (3 mL). After 3 hr at rt, the solution was concentrated. The residue was partitioned between DCM and 1N NaOH. The aqueous extract was washed with DCM and the combined organic extracts were washed with water, brine and dried (sodium sulfate). LCMS: $(MH)^+$ 362.0 (rt=1.51 min).

Part E

To a solution of crude 6-amino-pyridine-2-carboxylic acid [1-(3-trifluoromethyl-phenyl)-1H-pyrazol-4-ylmethyl]-amide 351 from Part D (0.02 g, 0.55 mmol, 1.00 equiv) and N,N-diisopropylethylamine (2.0 equiv) in pyridine (1 mL) was added the appropriate acid chloride, isocyanate or carbamoyl chloride (to make the compounds in Table 33) (1-2 equiv). The reactions were allowed to stir at rt for 24 hr, then were concentrated. Purification by Prep-LC afforded the desired products.

TABLE 33

| Cmpd No. | Compound | Ret. Time UV$_{254}$ (min) | EMW | MS (m/z) Observed |
|---|---|---|---|---|
| 353 | 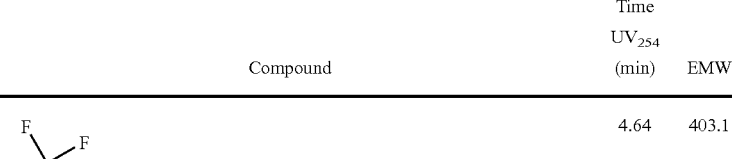 | 4.64 | 403.1 | 404.13 |
| 354 | 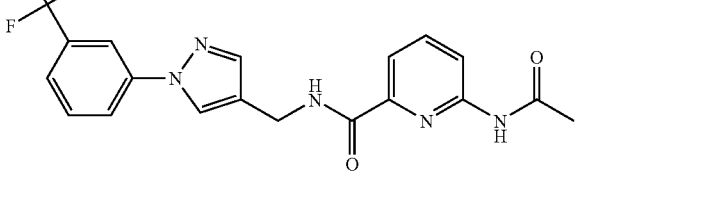 | 5.37 | 431.2 | 432.16 |

TABLE 33-continued

| Cmpd No. | Compound | Ret. Time UV$_{254}$ (min) | EMW | MS (m/z) Observed |
|---|---|---|---|---|
| 355 | 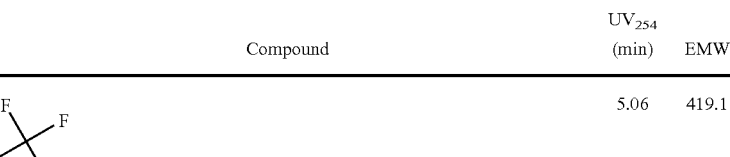 | 5.06 | 419.1 | 420.12 |
| 356 | 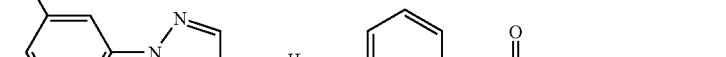 | 4.1 | 404.1 | 405.12 |

Example 28

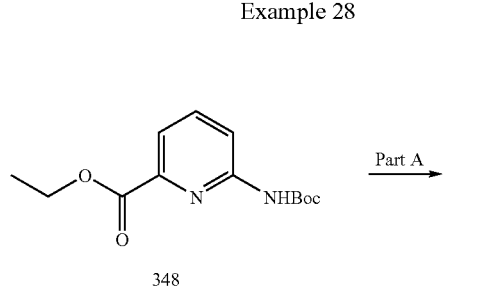

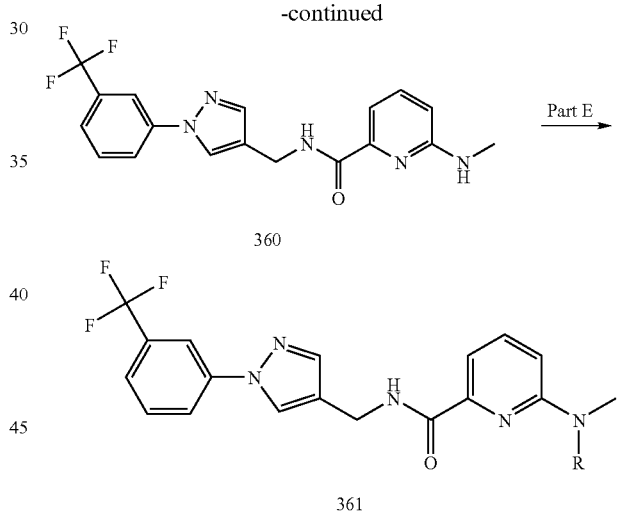

Part A

To a solution of 6-tert-butoxycarbonylamino-pyridine-2-carboxylic acid ethyl ester 348 (0.34 g, 1.5 mmol, 1.00 equiv) in NMP (4 mL) was added NaH (60% in oil, 0.090 g, 2.25 mmol, 1.5 equiv) in one portion. After stirring 15 min, iodomethane (0.1 mL, 1.65 mmol, 1.1 equiv) was added and the reaction mixture was allowed to stir 1 hr. The mixture was partitioned between ethyl acetate and water. The organic extract was washed with water, brine, dried (sodium sulfate) and concentrated. LCMS: (MH)$^+$ 281.2 (rt=2.05 min).

Part B

To a solution of 6-(tert-butoxycarbonyl-methyl-amino)-pyridine-2-carboxylic acid ethyl ester 357 from Part A (0.28 g, 1.01 mmol, 1.00 equiv) in ethanol (4 mL) was added KOH (0.06 g, 1.06 mmol, 1.05 equiv). The resulting suspension was stirred for 3 hr at rt and then was concentrated. LCMS: (MH)$^+$=253.1 (rt=1.55 min).

Part C

To a solution of crude material 358 from Part B (0.200 g, 0.69 mmol, 1.00 equiv), C-[1-(3-trifluoromethyl-phenyl)-1H-pyrazol-4-yl]-methylamine 340 (0.17 g, 0.72 mmol, 1.05 equiv) and N,N-diisopropylethylamine (0.24 ml, 1.4 mmol, 2.0 equiv) in NMP (4 mL) at it was added HATU (0.27 g, 0.72 mmol, 1.05 equiv) in one portion. The reaction mixture was stirred at room temperature for 0.5 hours, diluted with ethyl acetate and washed with water (3×) and brine, dried (sodium sulfate) and concentrated. LCMS: $(MH)^+=476.2$ (rt=2.32 min).

Part D

To a solution of crude methyl-(6-{[1-(3-trifluoromethyl-phenyl)-1H-pyrazol-4-ylmethyl]-carbamoyl}-pyridin-2-yl)-carbamic acid tert-butyl ester 359 from Part C in DCM (3 mL) was added trifluoroacetic acid (3 mL). After 3 hr at rt, the solution was concentrated. The residue was partitioned between DCM and 1N NaOH. The aqueous extract was washed with DCM and the combined organic extracts were washed with water, brine and dried (sodium sulfate). LCMS: $(MH)^+$ 376.1 (rt=1.80 min).

Part E

To a solution of crude 6-methylamino-pyridine-2-carboxylic acid [1-(3-trifluoromethyl-phenyl)-1H-pyrazol-4-ylmethyl]-amide 360 from Part D (0.02 g, 0.55 mmol, 1.00 equiv) and N,N-diisopropylethylamine (2.0 equiv) in pyridine (1 mL) was added the appropriate acid chlorides (to make the compounds in Table 34 (1-2 equiv). The reactions were allowed to stir at rt for 24 hr, then were concentrated. Purification by Prep-LC afforded the desired products.

TABLE 34

| Cmpd No. | Compound | Ret. Time UV$_{254}$ (min) | EMW | MS (m/z) Observed |
|---|---|---|---|---|
| 362 | 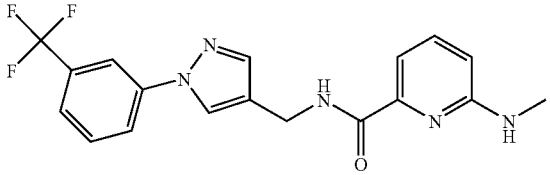 | 4.16 | 375.1 | 376.13 |
| 363 | 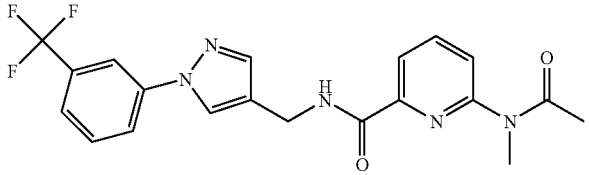 | 4.71 | 417.1 | 418.14 |
| 364 | 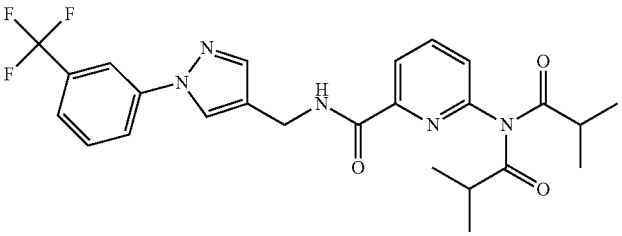 | 6.25 | 501.2 | 502.20 |
| 365 | 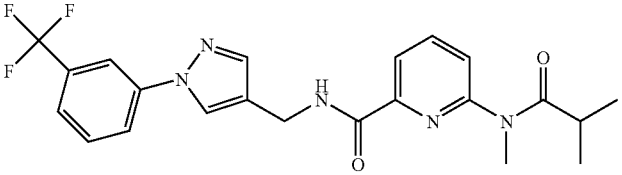 | 5.33 | 445.2 | 446.17 |

Example 29

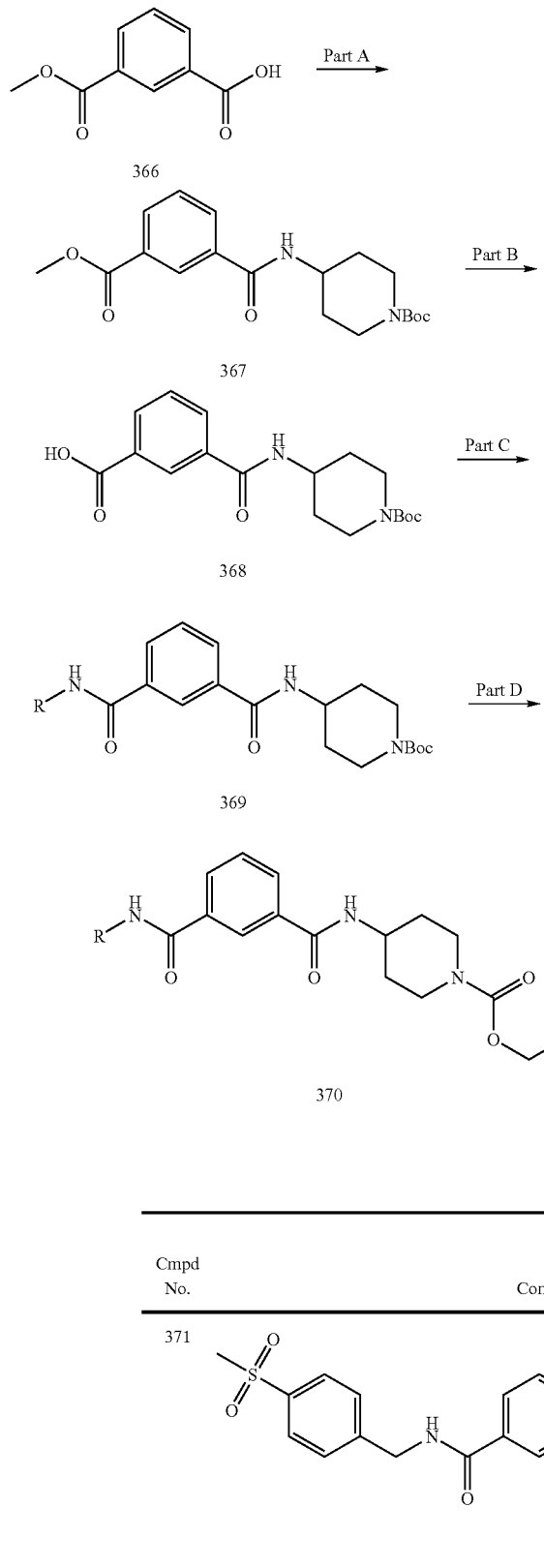

Part A

To a solution of monomethyl isophthalate 366 (1.00 g, 5.55 mmol, 1.00 equiv), 4-amino-1-boc-piperidine (1.33 g, 6.66 mmol, 1.20 equiv) and N,N-diisopropyl-ethylamine (1.9 mL, 11.1 mmol, 2.0 equiv) in NMP (15 mL) at room temperature was added HATU (2.53 g, 6.66 mmol, 1.20 equiv) in one portion. The reaction mixture was stirred at room temperature for 2 hours, diluted with ethyl acetate and washed with water (3×) and brine, dried (sodium sulfate) and concentrated. The residue 367 was used without further purification.

Part B

To a solution of the crude residue 367 from Part A in THF (36 mL) was added 1N LiOH (12 mL). The biphasic mixture was stirred at rt 2 hours, diluted with ethyl acetate and acidified to ca. pH 4 with 1N HCl. The organic phase was washed with water, dried (sodium sulfate) and concentrated. The residue 368 was used without further purification.

Part C

To a solution of 4-(3-carboxy-benzoylamino)-piperidine-1-carboxylic acid tert-butyl ester 368 (0.25 g, 0.72 mmol, 1.00 equiv), appropriate benzylamine (to make the compounds in Table 35) (0.86 mmol, 1.20 equiv) and N,N-diisopropylethylamine (0.36 ml, 2.08 mmol, 2.9 equiv) in NMP (2 mL) at room temperature was added HATU (0.33 g, 0.86 mmol, 1.20 equiv) in one portion. The reaction mixture was stirred at room temperature for 2 hours, diluted with ethyl acetate and washed with water (3×) and brine, dried (sodium sulfate) and concentrated.

Part D

The crude residue 369 from Part C was treated with 4N HCl in 1,4-dioxane for 1 hr and then concentrated. The residue was dissolved in DCM (1 mL), treated with N,N-diisopropylethylamine (0.15 mL) and ethyl chloroformate (0.011 mL, 0.12 mmol, 1.2 equiv). The crude residue was purified by Prep-LC.

TABLE 35

| Cmpd No. | Compound | Ret. Time $UV_{254}$ (min) | EMW | MS (m/z) Observed |
|---|---|---|---|---|
| 371 | ![structure] | 3.6 | 487.2 | 488.18 |

TABLE 35-continued

| Cmpd No. | Compound | Ret. Time UV$_{254}$ (min) | EMW | MS (m/z) Observed |
|---|---|---|---|---|
| 372 | 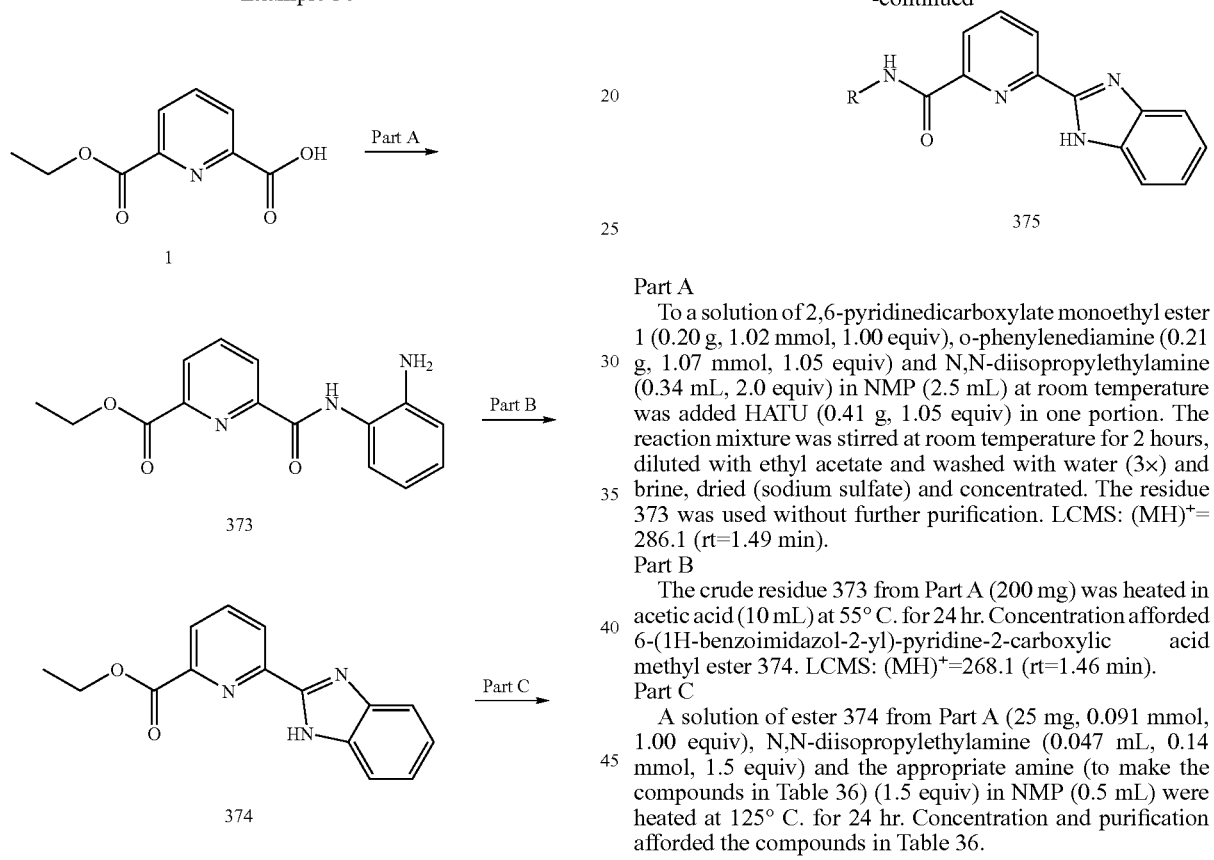 | 4.16 | 453.2 | 454.19 |

Example 30

Part A

To a solution of 2,6-pyridinedicarboxylate monoethyl ester 1 (0.20 g, 1.02 mmol, 1.00 equiv), o-phenylenediamine (0.21 g, 1.07 mmol, 1.05 equiv) and N,N-diisopropylethylamine (0.34 mL, 2.0 equiv) in NMP (2.5 mL) at room temperature was added HATU (0.41 g, 1.05 equiv) in one portion. The reaction mixture was stirred at room temperature for 2 hours, diluted with ethyl acetate and washed with water (3×) and brine, dried (sodium sulfate) and concentrated. The residue 373 was used without further purification. LCMS: (MH)$^+$= 286.1 (rt=1.49 min).

Part B

The crude residue 373 from Part A (200 mg) was heated in acetic acid (10 mL) at 55° C. for 24 hr. Concentration afforded 6-(1H-benzoimidazol-2-yl)-pyridine-2-carboxylic acid methyl ester 374. LCMS: (MH)$^+$=268.1 (rt=1.46 min).

Part C

A solution of ester 374 from Part A (25 mg, 0.091 mmol, 1.00 equiv), N,N-diisopropylethylamine (0.047 mL, 0.14 mmol, 1.5 equiv) and the appropriate amine (to make the compounds in Table 36) (1.5 equiv) in NMP (0.5 mL) were heated at 125° C. for 24 hr. Concentration and purification afforded the compounds in Table 36.

TABLE 36

| Cmpd No. | Compound | Ret. Time UV$_{254}$ (min) | EMW | MS (m/z) Observed |
|---|---|---|---|---|
| 376 | | 2.9 | 406.1 | 407.11 |

TABLE 36-continued

| Cmpd No. | Compound | Ret. Time UV$_{254}$ (min) | EMW | MS (m/z) Observed |
|---|---|---|---|---|
| 377 | 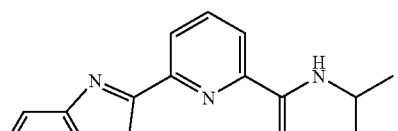 | 2.89 | 280.1 | 281.13 |
| 378 | 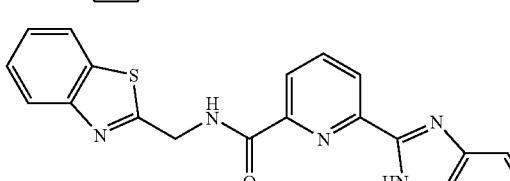 | 3.7 | 385.1 | 386.10 |

Example 31

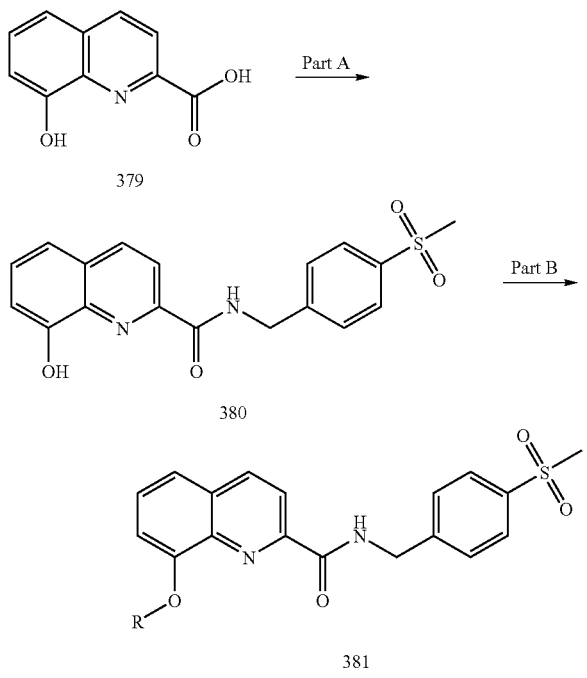

Part A

Compound 380 was synthesized starting from 379 using method described in Example 1 (Part A).

Method 1

Part B

To a solution of 8-hydroxy-quinoline-2-carboxylic acid 4-methanesulfonyl-benzylamide 380 from Part A (0.05 mg, 1.00 equiv) in acetone (1 mL) was added potassium carbonate (0.052 g, 4.5 equiv) and iodomethane (0.008 mL, 1.05 equiv). The resulting solution was stirred overnight at rt, filtered and concentrated. Purification of the residue by Prep-LC afforded compound 383. LCMS: (MH)$^+$=371.0 (rt=1.59 min).

Method 2

Part B

To a solution of 8-hydroxy-quinoline-2-carboxylic acid 4-methanesulfonyl-benzylamide 380 from Part A (0.030 g, 0.084 mmol, 1.00 equiv) in DCM (1 mL) was added ethyl isocyanate (0.008 mL, 0.101 mmol, 1.2 equiv) at rt. The resulting solution was stirred overnight at room temperature, then concentrated. Purification of the residue by Prep-LC afforded compound 384. LCMS: (MH)$^+$=428.0 (rt=1.54 min).

TABLE 37

| Cmpd No. | Structure | Ret. Time UV$_{254}$ (min) | EMW | MS (m/z) Observed |
|---|---|---|---|---|
| 380 | 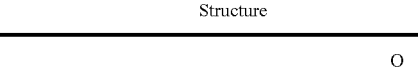 | 3.96 | 356.1 | 357.08 |

TABLE 37-continued

| Cmpd No. | Structure | Ret. Time UV$_{254}$ (min) | EMW | MS (m/z) Observed |
|---|---|---|---|---|
| 383 | 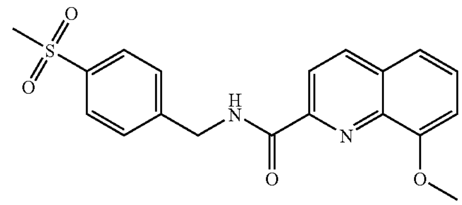 | 4.52 | 370.1 | 371.10 |
| 384 | 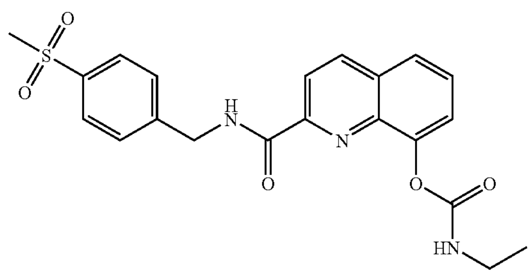 | 3.77 | 427.1 | 428.12 |

Example 32

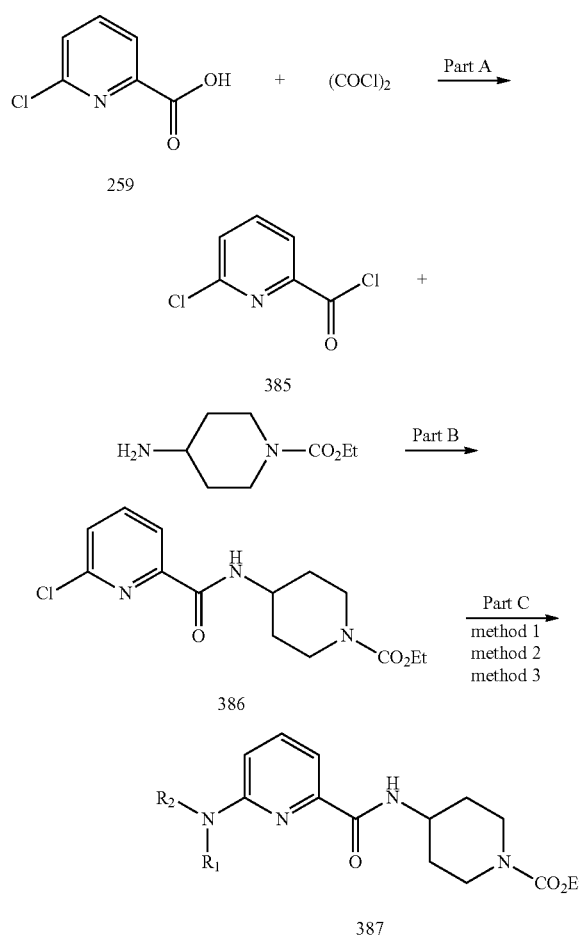

Part A

Compound 259 (0.757 g, 4.80 mmol) and DMF (0.01 mL) were dissolved in CH$_2$Cl$_2$ (25 mL) then cooled to 0° C. Oxalyl chloride (0.46 mL, 5.28 mmol) was added drop wise to the reaction. The reaction was allowed to warm to room temperature and stir for 30 minutes. The reaction was concentrated in vacuo to give crude compound 385. This material was carried on without further purification.

Part B

Compound 385 was dissolved in CH$_2$Cl$_2$ (25 mL) and cooled to 0° C. Ethyl 4-amino-1-piperidinecarboxylate (0.907 mL, 5.28 mmol) was added followed by triethyl amine (0.804 mL, 5.76 mmol). The reaction stirred for 10 minutes at 0° C. and then allowed to warm to room temperature. The reaction was concentrated in vacuo to give crude compound 386. This crude material was dissolved in ethyl acetate (50 mL), washed with 0.1 M HCl (25 mL), NaHCO$_3$ (aq., sat., 25 mL), H$_2$O (25 mL), and brine (25 mL). The organic layer was dried over sodium sulfate and concentrated in vacuo to afford compound 389 in 92% yield.

Part C: Method 1

Compound 386 (1 equivalent) was weighed into a 4 mL vial with the amine building blocks (1.1 equivalents), Pd(dppf)Cl$_2$ (0.1 equivalents), and sodium tert-butoxide (1.5 equivalents). Toluene was added, enough to produce a 0.2 M solution of compound 386. The vials were flushed quickly with N$_2$ and then capped. The reactions were then heated for 18 hours in an oil bath at 90° C. The reactions were cooled and concentrated in vacuo to obtain crude product. Products were purified via prep-LC.

The compounds in Table 38 were synthesized using this procedure:

TABLE 38

| Cmpd No. | Compound | Ret. Time UV$_{254}$ (min) | EMW | MS (m/z) Observed |
|---|---|---|---|---|
| 388 | | 2.80 | 369.2 | 370.1 |
| 389 | | 3.13 | 419.2 | 420.1 |
| 390 | | 3.44 | 453.2 | 454.1 |

Part C: Method 2

Compound 386 (1 equivalent) was weighed into a 4 mL vial with the appropriate amine building blocks (to make the compounds in Table 39) (1.5 equivalents), Pd(OAc)$_2$ (0.02 equivalents), 2-(di-tert-butylphosphino)biphenyl (0.03 equivalents) and sodium tert-butoxide (1.4 equivalents). Toluene was added, enough to produce a 0.2 M solution of compound 386. The vials were flushed quickly with N$_2$ and then capped. The reactions were then heated for 18 hours in an oil bath at 90° C. The reactions were cooled and concentrated in vacuo to obtain crude product. Products were purified via prep-LC.

The compounds in Table 39 were synthesized using this procedure:

TABLE 39

| Cmpd No. | Compound | Ret. Time UV$_{254}$ (min) | EMW | MS (m/z) Observed |
|---|---|---|---|---|
| 391 | | 2.71 | 383.2 | 384.1 |
| 392 | | 4.27 | 426.2 | 427.1 |

TABLE 39-continued

| Cmpd No. | Compound | Ret. Time UV$_{254}$ (min) | EMW | MS (m/z) Observed |
|---|---|---|---|---|
| 393 | | 2.66 | 397.2 | 398.1 |
| 394 | | 3.14 | 411.2 | 412.1 |
| 395 | | 2.44 | 389.2 | 390.1 |

Part C: Method 3

Compound 386 (1 equivalent) was weighed into a 4 mL vial with the appropriate amine building block (to make the compound in Table 40 (1.5 equivalents), Pd(OAc)$_2$ (0.05 equivalents), 2-dicyclohexylphosphino-2'-(N,N-dimethylamino)biphenyl (0.1 equivalents) and sodium tert-butoxide (1.4 equivalents). Toluene was added, enough to produce a 0.2 M solution of compound 386. The vial was flushed quickly with N$_2$ and then capped. The reaction was heated for 18 hours in an oil bath at 90° C. The reaction was cooled and concentrated in vacuo to give a black mixture containing product. The product was purified via prep-LC.

TABLE 40

| Cmpd No. | Compound | Ret. Time UV$_{254}$ (min) | EMW | MS (m/z) Observed |
|---|---|---|---|---|
| 396 |  | 2.81 | 369.18 | 370.1 |

Example 33

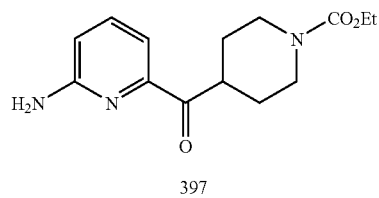

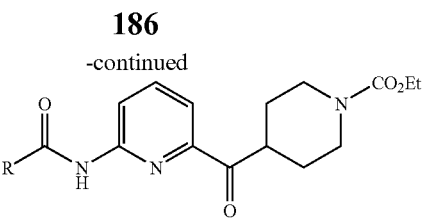

Part A

Compound 397 (1 equivalent) was mixed with the appropriate acid chloride building blocks (to make the compounds in Table 41) (5 equivalents) in pyridine to give a 0.2 M solution of compound 1. The reactions were heated at 80° C. for 20 hours. The reactions were cooled and concentrated in vacuo. Products were purified via prep-LC.

TABLE 41

| Cmpd No. | Compound | Ret. Time UV$_{254}$ (min) | EMW | MS (m/z) Observed |
|---|---|---|---|---|
| 399 | | 3.35 | 334.16 | 335.1 |
| 400 | | 4.28 | 364.17 | 365.1 |
| 401 | | 4.49 | 454.19 | 455.1 |
| 402 | | 3.82 | 488.17 | 489.1 |

Example 34

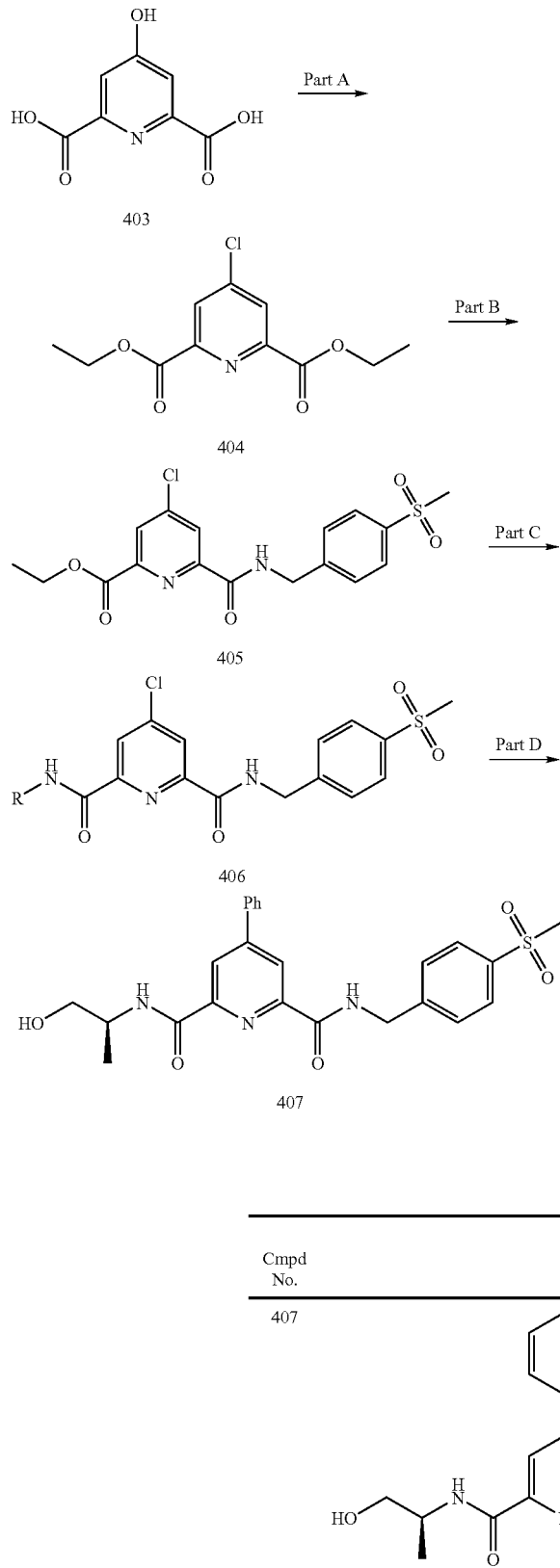

Part A

Chelidamic acid 403 (5.00 g, 27.3 mmol) was mixed with 30 mL of $POCl_3$ and heated to reflux overnight. The reaction was then concentrated in vacuo. The residue was dissolved in 50 mL of THF. This solution was added slowly to 200 mL of EtOH at 0° C. $Et_3N$ (25 mL) was carefully added to the EtOH solution. The reaction was allowed to warm to room temperature and stirred for 30 minutes. This mixture was concentrated in vacuo and the residue dissolved in 200 mL of EtOAc. The EtOAc solution was washed with $H_2O$ and brine. The organic layer was dried with $Na_2SO_4$ and concentrated in vacuo. Recrystallization from EtOH gave 6.08 g of compound 404 in 86% yields.

Part B

Compound 404 (1 equivalent) was mixed with LiOH (1.05 equivalents) in 20:5:1 THF:EtOH:$H_2O$. The reaction was heated to reflux until the starting material disappeared, as judged by TLC. The reaction was concentrated in vacuo to give the crude lithium carboxylates. The carboxylates were then dissolved in DMF with the appropriate building block amine (1.1 equivalents) and HATU (1.5 equivalents). After 1 hour at room temperature the reaction was concentrated and residue taken up in EtOAc. This solution was washed with $H_2O$ followed brine. The organic layer was dried with $Na_2SO_4$ and concentrated in vacuo. to obtain compound 405.

Part C

Compound 405 is separately reacted with ethylamine and 2-methylethanolamine to obtain compounds 406 and 406a using the method described in Example 34 (Part B).

Part D

Compound 406a (1 equivalent) was weighed in to a 4 mL vial with an phenyl boronic acid (1.2 equivalents), $Pd(OAc)_2$ (0.1 equivalents)), 2-dicyclohexyl-phosphino-2'-(N,N-dimethylamino)biphenyl (0.2 equivalents) and $K_2CO_3$ (3 equivalents). Dioxane solvent was added last, the reaction was flushed with $N_2$, capped, and heated in an oil bath at 80° C. overnight. The reaction was concentrated and purified via prep-LC.

TABLE 42

| Cmpd No. | Compound | Ret. Time $UV_{254}$ (min) | EMW | MS (m/z) Observed |
|---|---|---|---|---|
| 407 | 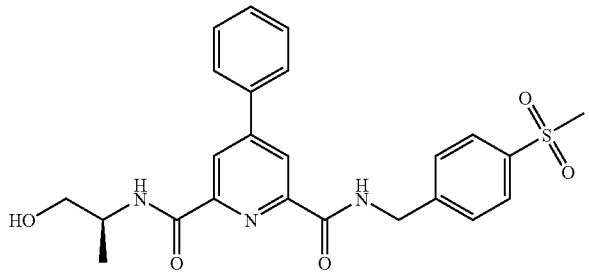 | 3.96 | 467.15 | 468.1 |

TABLE 42-continued

| Cmpd No. | Compound | Ret. Time UV254 (min) | EMW | MS (m/z) Observed |
|---|---|---|---|---|
| 408 | 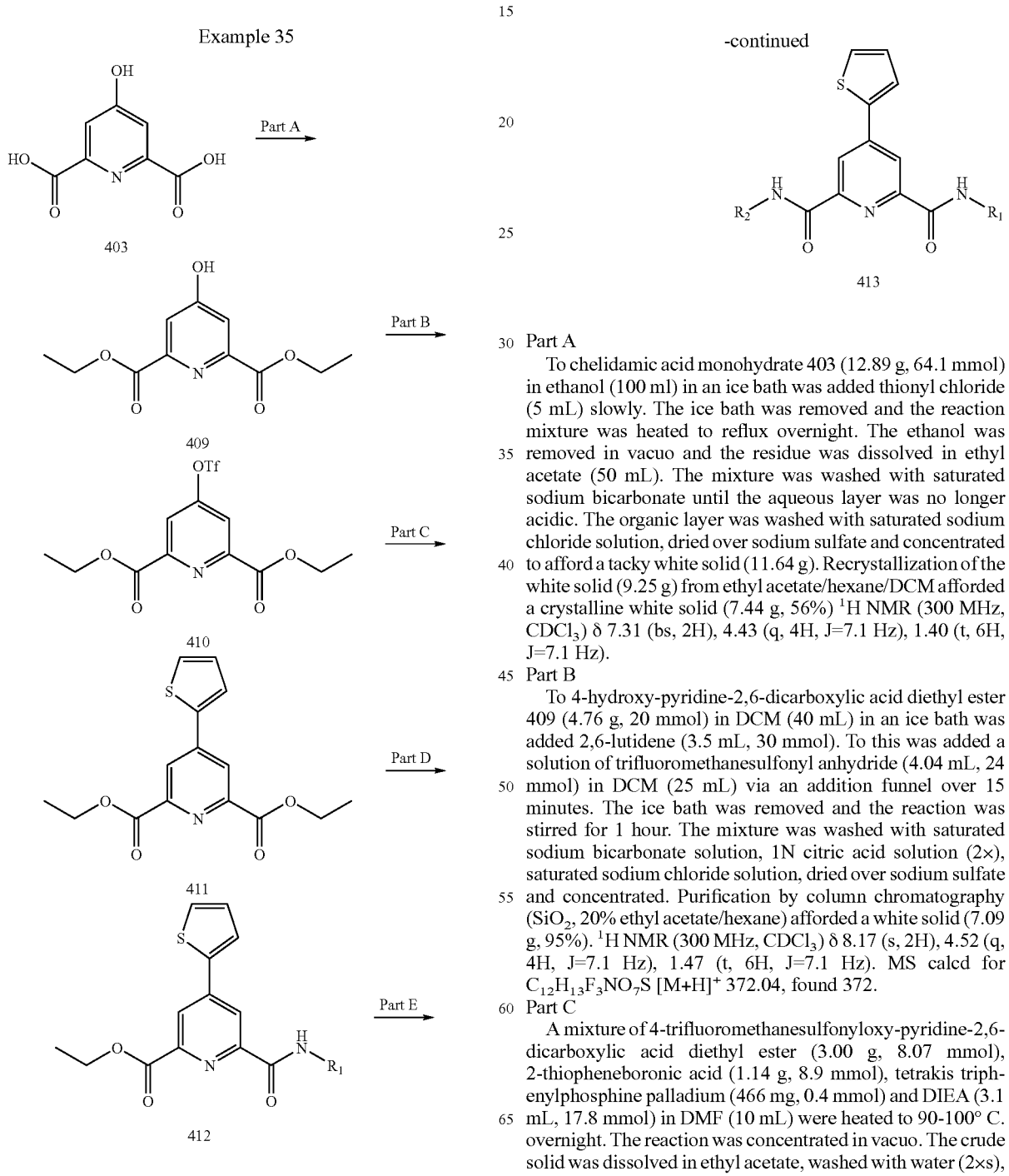 | 3.82 | 395.07 | 396.1 |

Example 35

Part A
To chelidamic acid monohydrate 403 (12.89 g, 64.1 mmol) in ethanol (100 ml) in an ice bath was added thionyl chloride (5 mL) slowly. The ice bath was removed and the reaction mixture was heated to reflux overnight. The ethanol was removed in vacuo and the residue was dissolved in ethyl acetate (50 mL). The mixture was washed with saturated sodium bicarbonate until the aqueous layer was no longer acidic. The organic layer was washed with saturated sodium chloride solution, dried over sodium sulfate and concentrated to afford a tacky white solid (11.64 g). Recrystallization of the white solid (9.25 g) from ethyl acetate/hexane/DCM afforded a crystalline white solid (7.44 g, 56%) $^1$H NMR (300 MHz, CDCl$_3$) δ 7.31 (bs, 2H), 4.43 (q, 4H, J=7.1 Hz), 1.40 (t, 6H, J=7.1 Hz).

Part B
To 4-hydroxy-pyridine-2,6-dicarboxylic acid diethyl ester 409 (4.76 g, 20 mmol) in DCM (40 mL) in an ice bath was added 2,6-lutidine (3.5 mL, 30 mmol). To this was added a solution of trifluoromethanesulfonyl anhydride (4.04 mL, 24 mmol) in DCM (25 mL) via an addition funnel over 15 minutes. The ice bath was removed and the reaction was stirred for 1 hour. The mixture was washed with saturated sodium bicarbonate solution, 1N citric acid solution (2×), saturated sodium chloride solution, dried over sodium sulfate and concentrated. Purification by column chromatography (SiO$_2$, 20% ethyl acetate/hexane) afforded a white solid (7.09 g, 95%). $^1$H NMR (300 MHz, CDCl$_3$) δ 8.17 (s, 2H), 4.52 (q, 4H, J=7.1 Hz), 1.47 (t, 6H, J=7.1 Hz). MS calcd for C$_{12}$H$_{13}$F$_3$NO$_7$S [M+H]$^+$ 372.04, found 372.

Part C
A mixture of 4-trifluoromethanesulfonyloxy-pyridine-2,6-dicarboxylic acid diethyl ester (3.00 g, 8.07 mmol), 2-thiopheneboronic acid (1.14 g, 8.9 mmol), tetrakis triphenylphosphine palladium (466 mg, 0.4 mmol) and DIEA (3.1 mL, 17.8 mmol) in DMF (10 mL) were heated to 90-100° C. overnight. The reaction was concentrated in vacuo. The crude solid was dissolved in ethyl acetate, washed with water (2×s), saturated sodium chloride solution, dried over sodium sulfate and concentrated. Purification by column chromatography (SiO$_2$, 5% ethyl acetate/dichloromethane) afforded a pale yellow solid (2.38 g, 97%). $^1$H NMR (300 MHz, CDCl$_3$) δ 8.43 (s, 2H), 7.68 (dd, 1H, J=1.0, 3.8 Hz), 7.51 (dd, 1H, J=1.0, 5.0 Hz), 7.19 (dd. 1H, J=3.7, 5.2 Hz), 4.51 (q, 4H, J=7.1 Hz), 1.48 (t, 6H, J=7.1 Hz). MS calcd for C$_{15}$H$_{16}$NO$_4$S [M+H]$^+$ 306.08, found 306.

Part D

Compounds 411 (1 equivalent) were mixed with LiOH (1.05 equivalents) in 20:5:1 THF:EtOH:H$_2$O. The reaction was heated to reflux until the starting material disappeared, as judged by TLC. The reaction was concentrated in vacuo to give the crude lithium carboxylates. The carboxylates were then dissolved in DMF with the appropriate building block amine (to obtain the compounds in Table 43) (1.1 equivalents) and HATU (1.5 equivalents). After 1 hour at room temperature the reactions were concentrated and residue taken up in EtOAc. These solutions were washed with H$_2$O followed by brine. The organic layers were dried with Na$_2$SO$_4$ and concentrated in vacuo to yield compound 412.

Part E

The Compounds 413 were synthesized with the appropriate amine using the method described in Example 34 (Part B) and purified on Prep LC. The compounds prepared are set forth in Table 43.

TABLE 43

| Cmpd No. | Compound | Ret. Time UV$_{254}$ (min) | EMW | MS (m/z) Observed |
|---|---|---|---|---|
| 414 | | 4.77 | 570.16 | 571.1 |
| 415 | | 4.30 | 443.10 | 444.1 |
| 416 | | 3.82 | 473.11 | 474.1 |
| 417 | | 3.82 | 473.11 | 474.1 |

Example 36

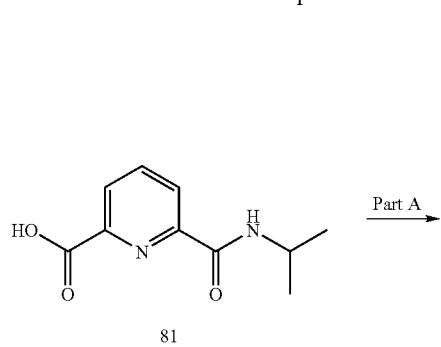

→ Part A

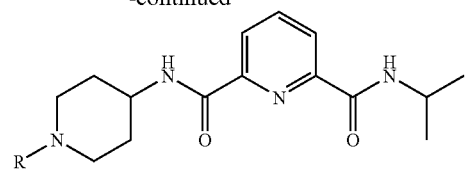

Part A

The pyridyl carboxylic acid 81 (0.020 g, 96.0 μmol) was mixed with Et₃N (40 μL, 288 μmol), and 1.2 eq of the appropriate building block amine (to make the compounds in Table 44) in DMF (2 mL). HATU (0.055 g, 144 μmol) was added last. The reactions were warmed in a sand bath at 55° C. overnight. The reactions were concentrated and purified via prep-LC.

The compounds in Table 44 were synthesized using this procedure:

TABLE 44

| Cmpd No. | Compound | Ret. Time $UV_{254}$ (min) | EMW | MS (m/z) Observed |
|---|---|---|---|---|
| 419 | | 4.51 | 405.22 | 406.1 |
| 420 | | 4.27 | 405.22 | 406.1 |
| 421 | | 3.83 | 458.20 | 459.1 |
| 422 | | 3.64 | 458.20 | 459.1 |

Example 37

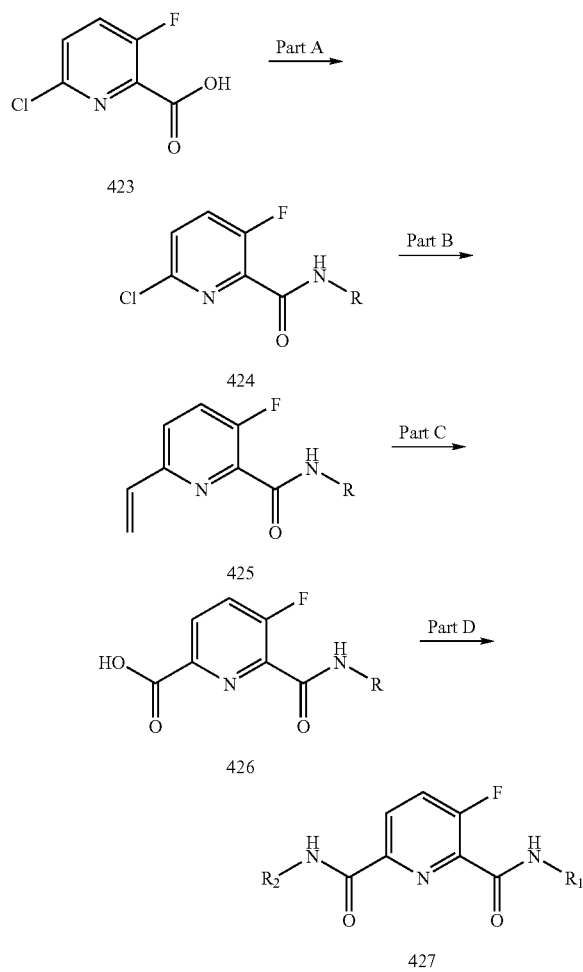

Part A

The pyridyl carboxylic acid 423 (0.969 g, 5.52 mmol) was mixed with isopropyl amine (517 μL, 6.07 mmol) and Et₃N (923 μL, 6.62 mmol) in DMF (10 mL). The coupling reagent HATU (2.517 g, 6.62 mmol) was added last. The reaction stirred at room temperature overnight. The reaction was concentrated under vacuum and yellow residue was taken up in EtOAc (100 mL). This EtOAc solution was washed with NaOH (1 M aq., 50 mL), NaHCO₃ (sat. aq., 50 mL), and brine (sat. aq. 50 mL). The organic layer was separated, dried with Na₂SO₄, and concentrated under vacuum to give the crude product. The crude was carried on without further purification.

Part B:

The amide product 424 was mixed with Pd(dppf)Cl₂·CH₂Cl₂ (355 mg, 0.435 mmol) and vinyl tributyltin (1.66 g, 5.22 mmol) in THF (15 mL) in a 40 mL screw capped vial. The vial was flushed with Ar, capped, and heated in a sand bath at 80° C. for 18 hours. The crude reaction was cooled to room temperature then filtered through celite. The filtrate was concentrated and purified via column chromatography using 5% MeOH in CH₂Cl₂. A second column using 40% EtOAc in Hexanes gave purified product in 62% yield, 0.565 g.

Part C

The olefin 425 was dissolved in acetone (10 mL) and H₂O (10 mL). KMnO₄ (0.850 g, 5.38 mmol) was added as a solid. The reaction turned black and a black precipitate formed. The reaction was shaken for 1 hour at room temperature. The reaction was filtered through celite and the celite was washed with acetone (3×20 mL). The clear filtrate was concentrated under vacuum and the residue was mixed with EtOH and concentrated again. The crude was dried overnight under vacuum. The dried crude material was take up in a 100 mL solution of 10% ⁱPrOH in CH₂Cl₂. This solution was washed with 50 mL of 0.1 M HCl. The aq. layer was washed with 10% isopropyl alcohol in CH₂Cl₂ (2×50 mL). The organic layers were combined and concentrated to give the crude product, as mixture of the desired product and the N-oxide of the product, in 92% yield, 0.561 g. The material was used without further purification.

Part D

The pyridyl carboxylic acid 426 (0.0166 g, 0.071 mmol) was mixed with 1 eq. of the appropriate building block amine (to make the compounds in Table 45) and Et₃N (19.8 μL, 0.142 mmol) in DMF (0.5 mL). The coupling reagent HATU (0.0324 g, 0.085 mmol) was added last. The reactions stirred at room temperature overnight. The reactions were concentrated and purified via prep-LC to give the compounds in Table 45.

TABLE 45

| Cmpd No. | Compound | Ret. Time UV$_{254}$ (min) | EMW | MS (m/z) Observed |
|---|---|---|---|---|
| 428 | | 4.65 | 395.18 | 396.1 |
| 429 | | 4.66 | 395.18 | 396.1 |

Example 38

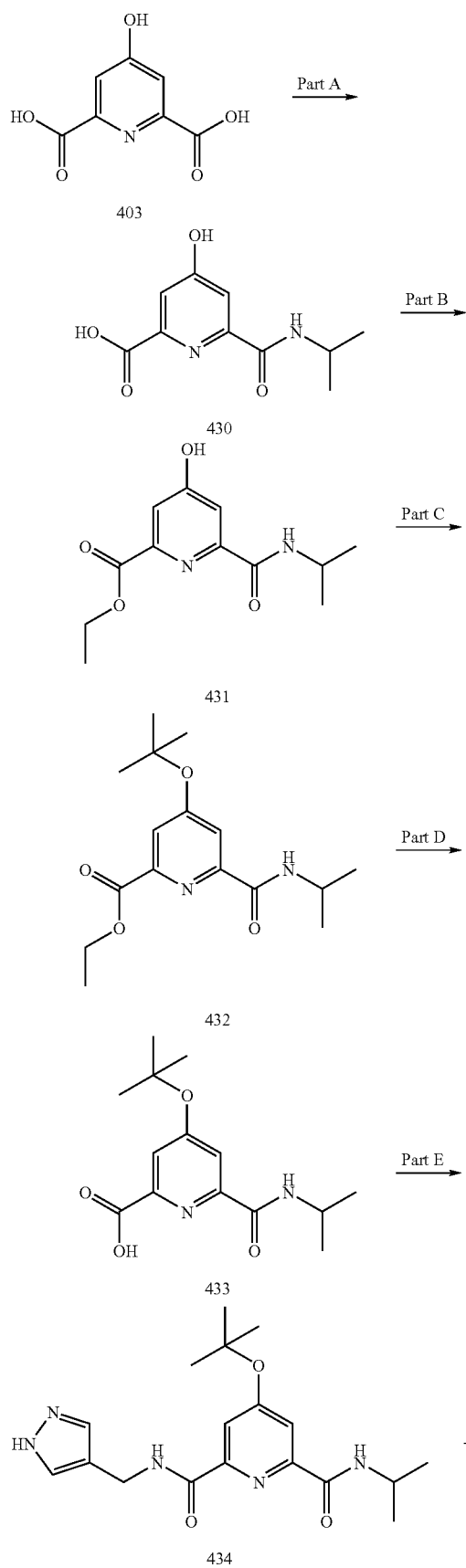

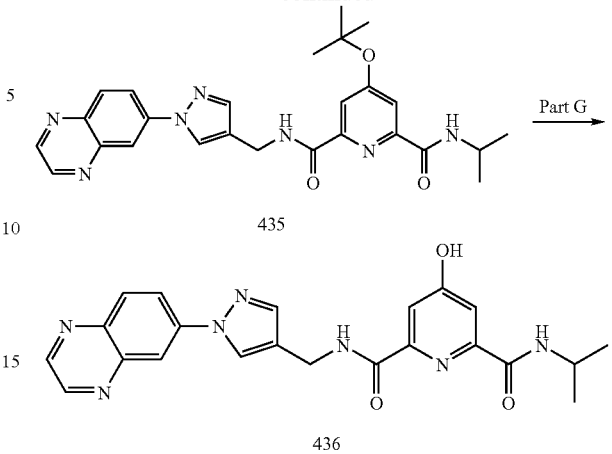

Part A

To the stirred solution of chelidamic acid 403 (1.83 g, 10 mmol) in DMF (100 mL) was added HATU (3.8 g, 10 mmol), isopropylamine (0.59 g, 10 mmol) and DIEA (20 mmol). Stirring was continued for overnight. DMF was removed under vacuum and the crude which contains mixture of products and unreacted chelidamic acid was used for the next reaction.

Part B

The crude product obtained from the above reaction was suspended in ethanol (100 mL) in an ice bath was added thionyl chloride (1 mL) slowly. The ice bath was removed and the reaction mixture was heated to reflux overnight. The ethanol was removed in vacuo and the residue was dissolved in ethyl acetate. The mixture was washed with saturated sodium bicarbonate soln, brine solution, dried over sodium sulfate and concentrated to afford product. Desired product 431 was purified by column chromatography. HPLC-MS Mass calculated for formula C12H16N2O4 252.11, observed LC/MS m/z 253.1 (M+H).

Part C

To the compound 431 (0.252 g, 1 mmol) in DCM (5 mL) and cyclohexane (1 mL) was added t-butyl-2,2,2-trichloroacetimidate (0.462 mL, 2.0 mmol) and boron trifluoride-etherate (100 μL, 6 mol %). The reaction was stirred for 4 hours and checked by TLC (2% MeOH/DCM). Added boron trifluoride-etherate (250 μL) and the reaction mixture became more cloudy. After the reaction was stirred for an additional 3 hours, sodium bicarbonate was added and the mixture was stirred for 15 minutes. The solids were removed by filtration and the organics were concentrated. The residue was redissolved in ethylacetate and the organic layer was washed with saturated sodium bicarbonate solution, water and brine. It was dried over sodium sulfate and concentrated. Purification by column chromatography (SiO2, 2% MeOH/DCM) afforded the product 432. HPLC-MS Mass calculated for formula C16H24N2O4 308.17, observed LC/MS m/z 309.1 (M+H)

Part D

Compound 433 was prepared via the synthetic method described in Example 2 (Part B). HPLC-MS Mass calculated for formula C14H20N2O4 280.14, observed LC/MS m/z 281.1 (M+H)

Part E

Compound 434 was prepared via the synthetic method described in Example 2 (Part D). HPLC-MS $t_R$=1.49 Min ($UV_{254nm}$). Mass calculated for formula C18H25N5O3 359.20, observed LC/MS m/z 360.34 (M+H)

Part F

Compound 435 was prepared via the synthetic method described in Example 2 (Part E, method 2)). HPLC-MS $t_R$=1.768 Min ($UV_{254nm}$). Mass calculated for formula C26H29N7O3 487.23, observed LC/MS m/z 488.2 (M+H)

Part G

Compound 436 (see Table 46) was prepared via the synthetic method described in Example 6 (Part B). HPLC-MS $t_R$=3.57 Min ($UV_{254nm}$). Mass calculated for formula C22H21N7O3 431.17, observed LC/MS m/z 432.24 (M+H)

Compounds 13, 14, 15, 16, 17, 19, 20, 22, 24, 26, 27, 29-39, 40-42, 45-47, 54, 56, 58-64, 66, 73, 90, 91, 92, 95, 101-105, 107, 116, 119, 122, 261, 263, 267, 274-276, 287, 288, 303, 310, 314, 315, 316, 317, 319, 320, 321, 323-327, 333, 337, 338, 339, 343-347, 363, 364, 365, 377, 382, 384, 388-396, 399-402, 371-372, 407, 408, 414-417, 419-421, and 422 had a JNK1 $IC_{50}$>1000 nM. For Example, Compounds 54, 63, 66, 73, 90-92, 95, 101-105, 107, 116, 119, 122, 275, 287, 288, 303, 310, 315-317, 319-321, 323-327, 333, 337-339, 343, 345-347, 363-365, 377, 382, 384, 399-402, 407, 408, 414-417, and 419-422 had a JNK1 $IC_{50}$ within the range of 1029 to 10,000 nM.

TABLE 46

| Cmpd No. | Compound | Ret. Time $UV_{254}$ (min) | EMW | MS (m/z) Observed |
|---|---|---|---|---|
| 436 |  | 3.57 | 431.17 | 432.24 |

Assay

DELFIA (Dissociation Enhanced Lanthanide Fluorescence Immuno-Assay) Assay:

Before initiation of kinase reactions, compounds were pre-incubated with the enzyme for 10 minutes. Pre-incubation reactions contained 50 mM HEPES pH 7.3, 10 mM $MgCl_2$, 1 mM DTT, 75 mM NaCl, 1 mM EDTA, 1 mM EGTA, 0.01% CHAPS, 2 nM JNK1, 6 ug/mL biotinylated GST-ATF2, 0.1 mg/ml BSA, 5% DMSO and 0-100 µM compound in a total volume of 40 µL. After a 10 minute room temperature pre-incubation, 10 µL of 35 µM ATP was added to start the reaction (final concentration of ATP=7 uM). Reactions were incubated at room temperature for 30 minutes. A small aliquot (10 uL) was taken and quenched by adding into 190 uL of DELFIA Assay buffer containing 100 mM EDTA. The amount of phosphate transferred to biotinylated GST-ATF2 was measured using the Dissociation Enhanced Lanthanide Fluorescence Immuno-assay (DELFIA) from Perkin Elmer according to manufacturers protocol. Briefly, biotinylated GST-ATF2 was captured on streptavidin coated plates for 1 hour, washed twice, then incubated for 1 hour with a 1:1000 dilution of rabbit-anti-phospho-ATF2 antibody and a 1:3500 dilution of Europium-labeled anti-rabbit secondary antibody. Free antibody was removed with six washes, Europium was dissociated from the antibody, and Europium fluorescence was measured using an excitation wavelength of 340 nM and an emission wavelength of 615 nM. JNK2 and JNK3 kinase reactions were carried out similarly, with the exception that the final concentration of ATP was 4 uM and 2 uM, respectively.

Compounds 18, 21, 23, 25, 28, 43, 44, 48-53, 55, 57, 65, 67-72, 74, 75, 88-89, 93, 94, 96-99, 106, 108-115, 117, 118, 120, 121, 123, 124, 126, 127, 128, 145, 156, 157, 159, 160, 162, 163, 174, 176-186, 190, 194, 195, 196, 213, 254, 264, 273, 289-291, 293, 295, 296, 302, 309, 318, 322, 328-332, 334-336, 353, 354, 355, 356, 362, 376, 378, 383, 429, had a JNK1 $IC_{50}$ within the range of 102 to 959 nM.

Compounds 5, 6, 7, 8, 9-12, 76-78, 85, 86, 87, 100, 125, 129, 130-144, 146-155, 161, 175, 189, 191-193, 200-203, 205, 206, 207, 210, 216, 219, 222, 228, 233-235, 238, 241, 244-248, 255-258, 292, 297, 428, and 436 had a JNK1 $IC_{50}$ within the range of 4 to 97 nM. Compounds 76, 129, 130, 134, 137, 138, 140, 142, 144, 149, 151, 152, 222, 228, 233, 234, 235, 238, 241, 244, 245, 246, and 248 had a JNK1 $IC_{50}$ within the range of 4 to 19 nM. Compound 246 had a had a JNK1 $IC_{50}$ 4 nM.

Compounds 5, 12, 114, 129, 130, 132-138, 140, 142, 149, 152, 154, 161, 210, 222, and 233 had a JNK1 $IC_{50}$ within the range of 6 to 162 nM, a JNK2 $IC_{50}$ within the range of 8 to 163 nM, and a JNK3 $IC_{50}$ within the range of 9 to 150 nM. Compound 142 had a JNK1 $IC_{50}$ of 6 nM, a JNK2 $IC_{50}$ of 8 nM, and a JNK3 $IC_{50}$ of 9 nM. Compound 135 had a JNK1 $IC_{50}$ of 27 nM, a JNK2 $IC_{50}$ of 48 nM, and a JNK3 $IC_{50}$ of 16 nM. Compounds 140, 142 and 152 had a JNK1 $IC_{50}$ of 13, 6, and 11 (respectively) nM, a JNK2 $IC_{50}$ of 11, 8, and 8 nM (respectively), and a JNK3 $IC_{50}$ of 9, 9, and 9 nM (respectively).

Data for compounds 134, 137, 142, 149, 152, 222, 228, 233, 246, and 248 are given in the table below. In the table below "ND" means "not determined".

| Cmpd No. | Structure | JNK1 IC$_{50}$ nM | JNK2 IC$_{50}$ nM | JNK3 IC$_{50}$ nM |
|---|---|---|---|---|
| 134 | 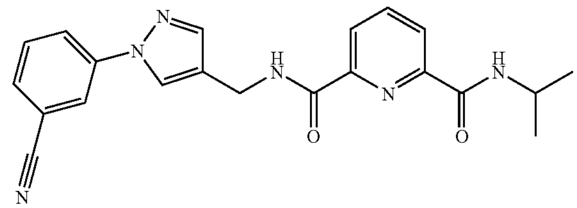 | 15 | 20 | 20 |
| 137 | 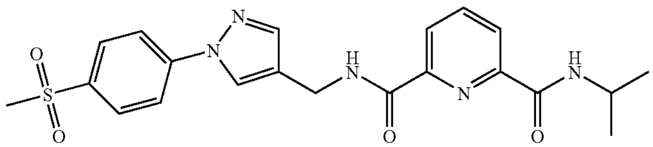 | 13 | 3 | 12 |
| 142 | 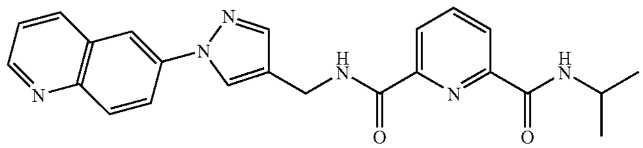 | 6 | 8 | 9 |
| 149 | 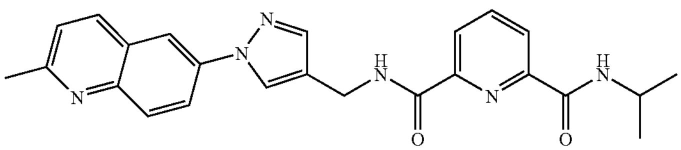 | 14 | ND | ND |
| 152 | 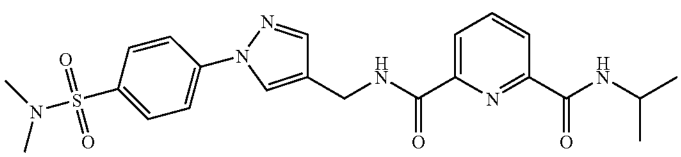 | 11 | 8 | 9 |
| 222 | 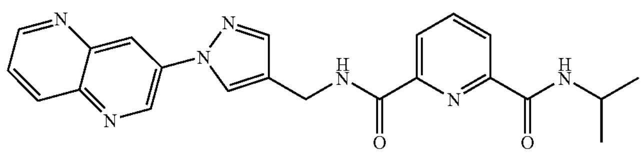 | 18 | 8 | 10 |
| 228 | 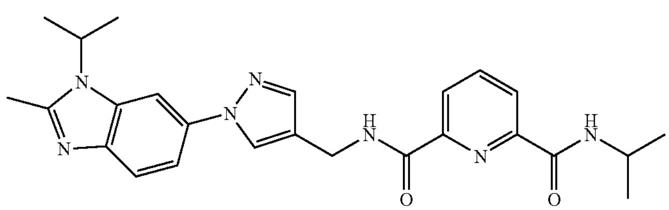 | 8 | ND | ND |
| 233 | 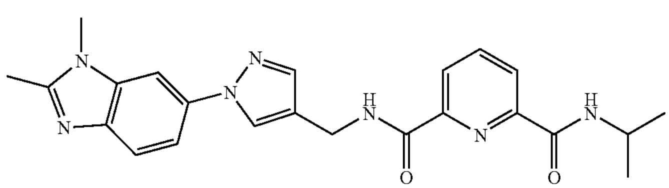 | 17 | 11 | 12 |
| 246 | 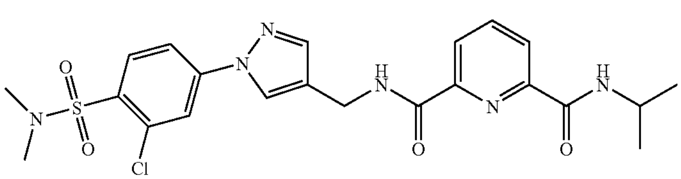 | 4 | ND | ND |

-continued

| Cmpd No. | Structure | JNK1 IC$_{50}$ nM | JNK2 IC$_{50}$ nM | JNK3 IC$_{50}$ nM |
|---|---|---|---|---|
| 248 | 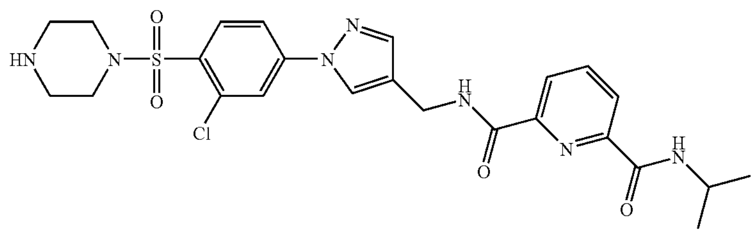 | 7 | ND | ND |

Data for Compound Numbers 76, 144, 149, 151, 222, 228, 233, 241, 246 and 248 are given in the table below.

| Compd # | Structure | JNK 1 IC$_{50}$ nM |
|---|---|---|
| 233 | 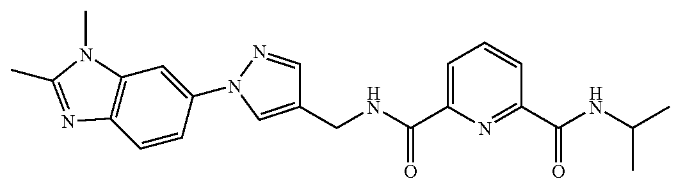 | 17 |
| 222 | 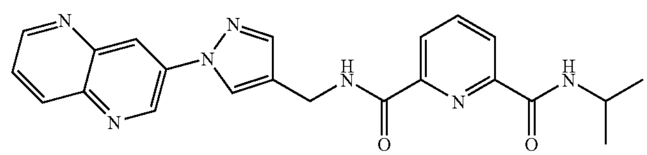 | 18 |
| 149 | 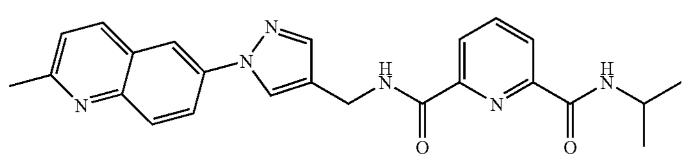 | 14 |
| 144 | 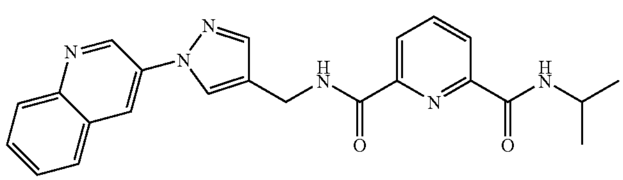 | 7 |
| 151 | 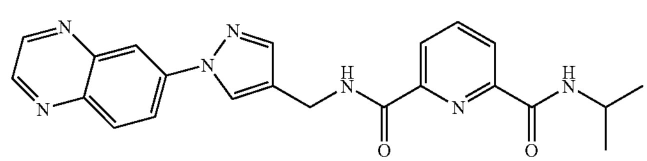 | 13 |
| 246 | 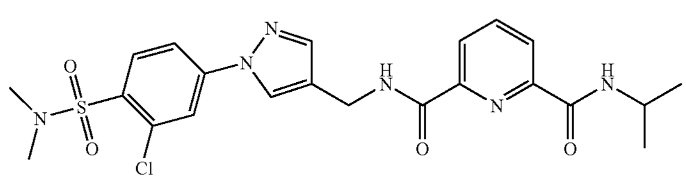 | 4 |

-continued

| Compd # | Structure | JNK 1 IC$_{50}$ nM |
|---|---|---|
| 241 | 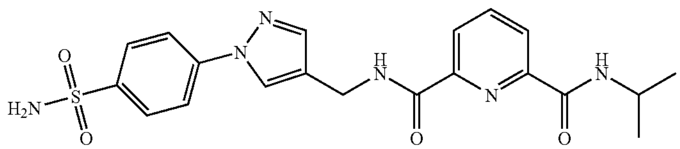 | 7 |
| 228 | 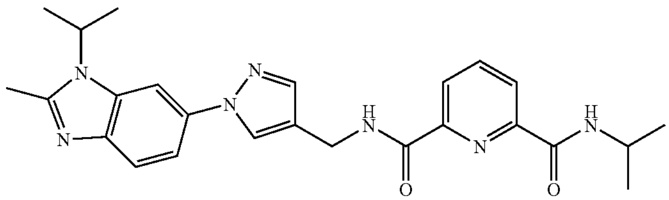 | 8 |
| 76 | 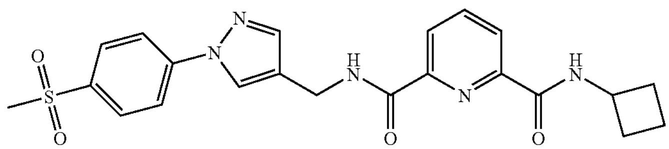 | 10 |
| 248 | 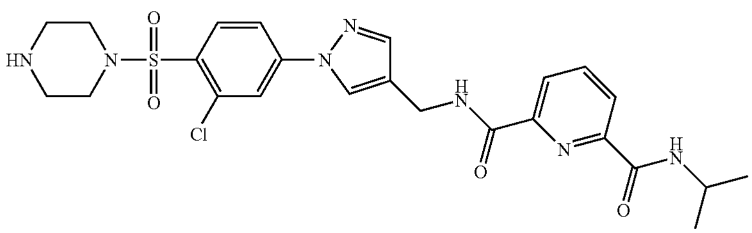 | 7 |

The compounds of this invention inhibit the activity of ERK1 and ERK2 Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK1 and/or ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention.

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy. For radiation therapy, γ-radiation is preferred.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

Chemotherapeutic agents (antineoplastic agent) include but are not limited to: microtubule affecting agents, alkylating agents, antimetabolites, natural products and their derivatives, hormones and steroids (including synthetic analogs), and synthetics.

Examples of alkylating agents (including nitrogen mustards, ethylenimine derivatives, alkyl sulfonates, nitrosoureas and triazenes) include: Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Examples of antimetabolites (including folic acid antagonists, pyrimidine analogs, purine analogs and adenosine deaminase inhibitors) include: Methotrexate, 5-Fluorouracil, Floxuridine, Cytarabine, 6-Mercaptopurine, 6-Thioguanine, Fludarabine phosphate, Pentostatine, and Gemcitabine.

Examples of natural products and their derivatives (including vinca alkaloids, antitumor antibiotics, enzymes, lymphokines and epipodophyllotoxins) include: Vinblastine, Vincristine, Vindesine, Bleomycin, Dactinomycin, Daunorubicin, Doxorubicin, Epirubicin, Idarubicin, Paclitaxel (paclitaxel is a microtubule affecting agent and is commercially available as Taxol®), Paclitaxel derivatives (e.g. taxotere), Mithramycin, Deoxyco-formycin, Mitomycin-C, L-Asparaginase, Interferons (especially IFN-a), Etoposide, and Teniposide.

Examples of hormones and steroids (including synthetic analogs) include: 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Examples of synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Examples of other chemotherapeutics include: Navelbene, CPT-11, Anastrazole, Letrazole, Capecitabinbe, Reloxafine, and Droloxafine.

A microtubule affecting agent (e.g., paclitaxel, a paclitaxel derivative or a paclitaxel-like compound), as used herein, is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents, useful in the methods of this invention, are well known to those skilled in the art and include, but are not limited to: Allocolchicine (NSC 406042), Halichondrin B (NSC 609395), Colchicine (NSC 757), Colchicine derivatives (e.g., NSC 33410), Dolastatin 10 (NSC 376128), Maytansine (NSC 153858), Rhizoxin (NSC 332598), Paclitaxel (Taxol®, NSC 125973), Paclitaxel derivatives (e.g., Taxotere, NSC 608832), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide (see Service, (1996) Science, 274:2009), Estramustine, Nocodazole, MAP4, and the like. Examples of such agents are described in, for example, Bulinski (1997) J. Cell Sci. 110:3055-3064, Panda (1997) Proc. Natl. Acad. Sci. USA 94:10560-10564, Muhlradt (1997) Cancer Res. 57:3344-3346, Nicolaou (1997) Nature 387:268-272, Vasquez (1997) Mol. Biol. Cell. 8:973-985, and Panda (1996) J. Biol. Chem. 271:29807-29812.

Chemotherapeutic agents with paclitaxel-like activity include, but are not limited to, paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Thus, in the methods of this invention wherein at least one chemotherapeutic agent is used, examples of said chemotherapeutic agents include those selected from the group consisting of: microtubule affecting agents, alkylating agents, antimetabolites, natural products and their derivatives, hormones and steroids (including synthetic analogs), and synthetics.

In the methods of this invention wherein at least one chemotherapeutic agent is used, examples of said chemotherapeutic agents also include: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

In the methods of this invention wherein at least one chemotherapeutic agent is used, examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EPO906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists, such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:

(a) Sarasar® brand of lonifarnib (i.e., 4-[2-[4-(3,10-dibromo-8-chloro-6,11-dihydro-5H-benzo[5,6]cyclohepta[1,2-b]byridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto), (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and (c) Bristol-Myers Squibb 214662:

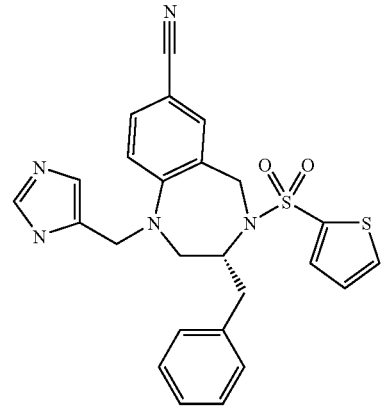

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compound of formula 1.0 (e.g., a pharmaceutical composition comprising the compound of formula 1.0); can be administered orally (e.g., as a capsule), and the chemotherapeutic agents can be administered intravenously, usually as an IV solution. The use of a pharmaceutical composition comprising more than one drug is within the scope of this invention.

The compound of formula 1.0 and the chemotherapeutic agents are administered in therapeutically effective dosages to obtain clinically acceptable results, e.g., reduction or elimination of symptoms or of the tumor. Thus, the compound of formula 1.0 and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The compounds of this invention can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The compounds of this invention can be administered in an amount of about 50 to about 400 mg once per day, and can be administered in an amount of about 50 to about 300 mg once per day. The compounds of this invention are generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m² for the taxanes; (b) about 30 to about 100 mg/m² for Cisplatin; (c) AUC of about 2 to about 8 for Carboplatin; (d) about 2 to about 4 mg/m² for EGF inhibitors that are antibodies; (e) about 50 to about 500 mg/m² for EGF inhibitors that are small molecules; (f) about 1 to about 10 mg/m² for VEGF kinase inhibitors that are antibodies; (g) about 50 to about 2400 mg/m² for VEGF inhibitors that are small molecules; (h) about 1 to about 20 mg for SERMs; (i) about 500 to about 1250 mg/m² for the anti-tumor nucleosides 5-Fluorouracil, Gemcitabine and Capecitabine; (j) for the anti-tumor nucleoside Cytarabine (Ara-C) 100-200 mg/m²/day for 7 to 10 days every 3 to 4 weeks, and high doses for refractory leukemia and lymphoma, i.e., 1 to 3 gm/m² for one hour every 12 hours for 4-8 doses every 3 to four weeks; (k) for the anti-tumor nucleoside Fludarabine (F-ara-A) 10-25 mg/m²/day every 3 to 4 weeks; (l) for the anti-tumor nucleoside Decitabine 30 to 75 mg/m² for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m² for epothilones; (o) about 1 to about 350 mg/m² for topoisomerase inhibitors; (p) about 1 to about 50 mg/m² for vinca alkaloids; (q) for the folate antagonist Methotrexate (MTX) 20-60 mg/m² by oral, IV or IM every 3 to 4 weeks, the intermediate dose regimen is 80-250 mg/m² IV over 60 minutes every 3 to 4 weeks, and the high dose regimen is 250-1000 mg/m² IV given with leucovorin every 3 to 4 weeks; (r) for the folate antagonist Premetrexed (Alimta) 300-600 mg/m² (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m² every 3 to 4 weeks (preferably used for solid tumors such as non-small cell lung cancer, colorectal cancer and ovarian cancer); (u) for the anthracycline daunorubicin 10-50 mg/m²/day IV for 3-5 days every 3 to 4 weeks; (v) for the anthracycline Doxorubicin (Adriamycin) 50-100 mg/m² IV continuous infusion over 1-4 days every 3 to 4 weeks, or 10-40 mg/m² IV weekly; (w) for the anthracycline Idarubicin 10-30 mg/m² daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m² IV weekly over 4-8 weeks for 6 months; (aa) for the alkylating agent temozolomide 75 mg/m² to 250 mg/m², for example, 150 mg/m², or for example, 200 mg/m², such as 200 mg/m² for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analogs in human multiple myeloma cells; therapeutic implications", Blood, 99(12):4525-30, Jun. 15, 2002, the disclosure of which is incorporated herein by reference thereto.

The FPT inhibitor Sarasar® (brand of lonifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®), for example, can be administered once per week in an amount of about 50 to about 100 mg/m² and in another example about 60 to about 80 mg/m². In another example Paclitaxel (e.g., Taxol®) can be administered once every three weeks in an amount of about 150 to about 250 mg/m² and in another example about 175 to about 225 mg/m².

In another example, Docetaxel (e.g., Taxotere®) can be administered once per week in an amount of about 10 to about 45 mg/m². In another example Docetaxel (e.g., Taxotere®) can be administered once every three weeks in an amount of about 50 to about 100 mg/m².

In another example Cisplatin can be administered once per week in an amount of about 20 to about 40 mg/m². In another example Cisplatin can be administered once every three weeks in an amount of about 60 to about 100 mg/m².

In another example Carboplatin can be administered once per week in an amount to provide an AUC of about 2 to about 3. In another example Carboplatin can be administered once every three weeks in an amount to provide an AUC of about 5 to about 8.

In another embodiment this invention is directed to a method of treating cancer in a patient in need of such treatment, said method comprising administering to said patient an effective amount of at least one (1, 2 or 3, or 1 or 2, or 1, and usually 1) compound of formula 1.0.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 and an effective amount of a chemotherapeutic agent.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 and an effective amount of a chemotherapeutic agent, wherein the chemotherapeutic agent is selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 and an effective amount of a chemotherapeutic agent, wherein the chemotherapeutic agent is selected from the group consisting of: paclitaxel, docetaxel, carboplatin, cisplatin, navelbine, gemcitabine, and Herceptin.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 and an effective amount of a chemotherapeutic agent, wherein the chemotherapeutic agent is selected from the group consisting of: Cyclophasphamide, 5-Fluorouracil, Temozolomide, Vincristine, Cisplatin, Carboplatin, and Gemcitabine.

Another embodiment of this invention is directed to a method of treating cancer in a patient in need of such treatment, said method comprising administering to said patient an effective amount of at least one (1, 2 or 3, or 1 or 2, or 1, and usually 1) compound of formula 1.0 and an effective amount of a chemotherapeutic agent, wherein the chemotherapeutic agent is selected from the group consisting of: Gemcitabine, Cisplatin and Carboplatin.

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0, and therapeutically effective amounts of at least one (e.g., 1, 2 or 3, or 1 or 2, or 2, or 1) chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0, and therapeutically effective amounts of at least two (e.g., 2 or 3, or 2, and usually 2) different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said method comprising administering to said patient therapeutically effective amounts at least one (e.g., 1, 2 or 3, or 1 or 2, or 1, and usually 1) compound of formula 1.0, and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with this above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment, said method comprising administering to said patient therapeutically effective amounts at least one (e.g., 1, 2 or 3, or 1 or 2, or 1, and usually 1) compound of formula 1.0, and: (1) Gleevec and interferon to treat CML; (2) Gleevec and pegylated interferon to treat CML; (3) Gleevec to treat CML; (4) an anti-tumor nucleoside derivative (e.g., Ara-C) to treat AML; or (5) an anti-tumor nucleoside derivative (e.g., Ara-C) in combination with an anthracycline to treat AML.

This invention also provides a method of treating non-Hodgkin's lymphoma in a patient in need of such treatment, said method comprising administering therapeutically effective amounts at least one (e.g., 1, 2 or 3, or 1 or 2, or 1, and usually 1) compound of formula 1.0 and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment, said method comprising administering to said patient therapeutically effective amounts of at least one (e.g., 1, 2 or 3, or 1 or 2, or 1, and usually 1) compound of formula 1.0 and: (1) a proteosome inhibitor (e.g., PS-341 from Millenium); or (2) Thalidomide (or related imid).

This invention also provides a method of treating cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) carboplatin, and (c) paclitaxel.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0, (b) cisplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) carboplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0, (b) Carboplatin, and (c) Docetaxel.

This invention also provides a method of treating cancer in a patient in need of such treatment, said method comprising administering therapeutically effective amounts of: (a) at least one (e.g., 1, 2 or 3, or 1 or 2, or 1, and usually 1) compound of formula 1.0, and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, and (2) platinum coordinator compounds.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0, and (b) at least one (e.g., 1, 2 or 3, or 1 or 2, or 2, or 1) antineoplastic agent selected from the group consisting of: (1) taxanes, (2) platinum coordinator compounds, and (3) anti-tumor nucleoside derivatives (e.g., 5-Fluorouracil).

This invention also provides a method of treating CML in a patient in need of such treatment, said method comprising administering therapeutically effective amounts of: (a) at least one (e.g., 1, 2 or 3, or 1 or 2, or 1, and usually 1) compound of formula 1.0, (b) Gleevec, and (c) interferon (e.g., Intron-A).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0, (b) Gleevec; and (c) pegylated interferon (e.g., Peg-Intron, and Pegasys).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 161) and (b) Gleevec.

This invention also provides a method of treating CMML in a patient in need of such treatment, said method comprising administering to said patient therapeutically effective amounts of at least one (e.g., 1, 2 or 3, or 1 or 2, or 1, and usually 1) compound of formula 1.0.

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0, and (b) an anti-tumor nucleoside derivative (e.g., Cytarabine (i.e., Ara-C)).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0, (b) an anti-tumor nucleoside derivative (e.g., Cytarabine (i.e., Ara-C)), and (c) an anthracycline.

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Rituximab (Rituxan).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Genasense (antisense to BCL-2).

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0, and (b) a proteosome inhibitor (e.g., PS-341 (Millenium)).

This invention also provides a method of treating multiple myeloma in a patient in need of such treatment, said method comprising administering to said patient therapeutically effective amounts of: (a) at least one (e.g., 1, 2 or 3, or 1 or 2, or 1, and usually 1) compound of formula 1.0, and (b) Thalidomide or related imid.

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0, and (b) Thalidomide.

This invention is also directed to the methods of treating cancer described herein, particularly those described above, wherein in addition to the administration of the compound of formula 1.0 and antineoplastic agents, radiation therapy is also administered prior to, during, or after the treatment cycle.

This invention also provides a method for treating cancer (e.g., lung cancer, prostate cancer and myeloid leukemias) in a patient in need of such treatment, said method comprising administering to said patient (1) an effective amount of at least one (e.g., 1, 2 or 3, or 1 or 2, or 1, and usually 1) compound of formula 1.0, in combination with (2) at least one (e.g., 1, 2 or 3, or 1 or 2, or 2, or 1) antineoplastic agent, microtubule affecting agent and/or radiation therapy.

This invention also provides a method of treating cancer in a patient in need of such treatment, said method comprising administering to said patient an effective amount of at least one (e.g., 1, 2 or 3, or 1 or 2, or 1, and usually 1) compound of formula 1.0 in combination with an effective amount of at least one (e.g., 1, 2 or 3, or 1 or 2, or 1, and usually 1) signal transduction inhibitor.

Thus, in one example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Carboplatin is administered once per week in an amount to provide an AUC of about 2 to about 3.

In another example (e.g., treating non small cell lung cancer): (1) the compound of formula 1.0 is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Cisplatin is administered once per week in an amount of about 20 to about 40 mg/m$^2$.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Carboplatin is administered once per week in an amount to provide an AUC of about 2 to about 3.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Cisplatin is administered once per week in an amount of about 20 to about 40 mg/m$^2$.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m$^2$, and in yet another example 175 mg/m$^2$, and (3) Carboplatin is administered once every three weeks in an amount to provide an AUC of about 5 to about 8, and in another example 6.

In another example of treating non small cell lung cancer: (1) the compound of formula 1.0 is administered in an amount of 100 mg administered twice a day, (2) Paclitaxel (e.g., Taxol® is administered once every three weeks in an amount of 175 mg/m$^2$, and (3) Carboplatin is administered once every three weeks in an amount to provide an AUC of 6.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m$^2$, and (3) Cisplatin is administered once every three weeks in an amount of about 60 to about 100 mg/m$^2$.

In another example (e.g., treating non small cell lung cancer): (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Carboplatin is administered once every three weeks in an amount to provide an AUC of about 5 to about 8.

In another example (e.g., treating non small cell lung cancer): (1) the compound of formula 1.0 is administered in an amount of about 50 mg to about 200 mg twice a day, in another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Cisplatin is administered once every three weeks in an amount of about 60 to about 100 mg/m$^2$.

In another example for treating non small cell lung cancer using the compounds of formula 1.0, Docetaxel and Carboplatin: (1) the compound of formula 1.0 is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 75 mg/m$^2$, and (3) Carboplatin is administered once every three weeks in an amount to provide an AUC of about 6.

In another example of the treatments of non-small cell lung cancer described above the Docetaxel (e.g., Taxotere® and Cisplatin, the Docetaxel (e.g., Taxotere® and Carboplatin, the Paclitaxel (e.g., Taxol® and Carboplatin, or the Paclitaxel (e.g., Taxol® and Cisplatin are administered on the same day.

In another example (e.g., CML): (1) the compound of formula 1.0 is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the compound of formula 1.0 is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the compound of formula 1.0 is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the compound of formula 1.0 is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341—Millenium) is administered in an amount of about 1.5 $mg/m^2$ twice weekly for two consecutive weeks with a one week rest period.

In another example (e.g., multiple myeloma): (1) the compound of formula 1.0 is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In one embodiment of the methods of treating cancer of this invention, the chemotherapeutic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

In another embodiment of the methods of treating cancer of this invention, the chemotherapeutic agents are selected from the group consisting of: paclitaxel, docetaxel, carboplatin, cisplatin, navelbine, gemcitabine, and Herceptin.

Thus, one embodiment of this invention is directed to a method of treating cancer comprising administering to a patient in need of such treatment therapeutically effective amounts of the compound of formula 1.0, a taxane, and a platinum coordination compound.

Another embodiment of this invention is directed to a method of treating cancer comprising administering to a patient in need of such treatment therapeutically effective amounts of the compound of formula 1.0, a taxane, and a platinum coordination compound, wherein said compound of formula 1.0 is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0, a taxane, and a platinum coordination compound, wherein said compound of formula 1.0 is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the compound of formula 1.0, paclitaxel, and carboplatin. In another embodiment, said compound of formula 1.0 is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0, paclitaxel, and carboplatin. In another embodiment, said compound of formula 1.0 is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the compound of formula 1.0, administering a therapeutically effective amount of carboplatin once a week per cycle, and administering a therapeutically effective amount of paclitaxel once a week per cycle, wherein the treatment is given for one to four weeks per cycle. In another embodiment said compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of a compound of formula 1.0, administering a therapeutically effective amount of carboplatin once every three weeks per cycle, and administering a therapeutically effective amount of paclitaxel once every three weeks per cycle, wherein the treatment is given for one to three weeks. In another embodiment compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of a compound of formula 1.0 twice a day, administering carboplatin once per week per cycle in an amount to provide an AUC of about 2 to about 8 (and in another embodiment about 2 to about 3), and administering once per week per cycle about 60 to about 300 $mg/m^2$ (and in another embodiment about 50 to 100 $mg/m^2$, and in yet another embodiment about 60 to about 80 $mg/m^2$) of paclitaxel, wherein the treatment is given for one to four weeks per cycle. In another embodiment said compound of formula 1.0 is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of a compound of formula 1.0 twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said compound of formula 1.0 is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments (i.e., the embodiments directed to treating cancer and to treating non small cell lung cancer with a taxane and platinum coordinator compound) except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m$^2$. In the another embodiment of the methods of this invention docetaxel is used in amounts of about 30 to about 100 mg/m$^2$.

In another embodiment this invention is directed to a method of treating cancer comprising administering to a patient in need of such treatment therapeutically effective amounts of a compound of formula 1.0, a taxane, and an EGF inhibitor that is an antibody. In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of said compound of formula 1.0 and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m$^2$ (in another embodiment about 4 mg/m$^2$), and then is administered in a maintenance dose of about 2 mg/m$^2$ once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) a compound of formula 1.0, (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of said compound of formula 1.0 and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m$^2$.

In another embodiment this invention is directed to a method of treating cancer comprising administering to a patient in need of such treatment therapeutically effective amounts of a compound of formula 1.0, an anti-tumor nucleoside derivative, and a platinum coordination compound.

Another embodiment of this invention is directed to a method of treating cancer comprising administering to a patient in need of such treatment therapeutically effective amounts of a compound of formula 1.0, an anti-tumor nucleoside derivative, and a platinum coordination compound, wherein said compound of formula 1.0 is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0, an anti-tumor nucleoside derivative, and a platinum coordination compound, wherein said compound of formula 1.0 is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and cisplatin. In another embodiment, said compound of formula 1.0 is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and cisplatin. In another embodiment, said compound of formula 1.0 is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of a compound of formula 1.0, gemcitabine, and carboplatin. In another embodiment said compound of formula 1.0 is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of a compound of formula 1.0, gemcitabine, and carboplatin. In another embodiment said compound of formula 1.0 is administered every day, said gemcitabine is administered once per week per cycle, and said carboplatin is administered once every three weeks per cycle. In another embodiment the treatment is for one to seven weeks per cycle.

In the above embodiments using gemcitabine, the compound of formula 1.0 and the platinum coordinator compound are administered as described above for the embodiments using taxanes. Gemcitabine is administered in an amount of about 500 to about 1250 mg/m$^2$. In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient a compound of formula 1.0 and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compound of formula 1.0 is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of a compound of formula 1.0 and antineoplastic agents in the embodiments described above. Radiation is administered according to techniques and protocols well know to those skilled in the art.

Another embodiment of this invention is directed to a pharmaceutical composition comprising at least two different chemotherapeutic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Other embodiments of this invention are directed to the use of a combination of at least one (e.g., one) compound of formula 1.0 and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula 1.0 and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula 1.0 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one (e.g., one) compound of formula 1.0 and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one (e.g., one) compound of formula 1.0, at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 and at least one aromatase inhibitor.

Another embodiment of this invention is directed to a method of treating or preventing breast cancer in a patient in need of such treatment wherein said treatment comprises administering a therapeutically effective amount of at least one (e.g., one) compound of formula 1.0, at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; and (2) at least one aromatase inhibitor selected from the group consisting of Anastrozole, Letrozole, Exemestane, Fadrozole and Formestane.

Another embodiment of this invention is directed to a method of treating or preventing, breast cancer in a patient in need of such treatment wherein said treatment comprises administering a therapeutically effective amount of: (1) at least one (e.g., one) compound of formula 1.0; (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0; (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 and and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 and Formestane.

Another embodiment of this invention is directed to a method of treating or preventing breast cancer in a patient in need of such treatment wherein said treatment comprises administering a therapeutically effective amount of at least one (e.g., one) compound of formula 1.0 and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 and Goserelin.

Another embodiment of this invention is directed to a method of treating or preventing breast cancer in a patient in need of such treatment wherein said treatment comprises administering a therapeutically effective amount of at least one (e.g., one) compound of formula 1.0 and and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Goserelin, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Letrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Exemestane.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0, Goserelin and Formestane.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Letrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Exemestane.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0, Leuprolide and Formestane.

Another embodiment of this invention is directed to the treatment or prevention of breast cancer in a patient in need of such treatment, said treatment comprising the administration of a therapeutically effective amount of at least one (e.g., one) compound of formula 1.0 and Anastrozole.

Another embodiment of this invention is directed to the treatment or prevention of breast cancer in a patient in need of such treatment, said treatment comprising the administration of a therapeutically effective amount of at least one (e.g., one) compound of formula 1.0 and Letrozole.

Another embodiment of this invention is directed to the treatment or prevention of breast cancer in a patient in need of such treatment, said treatment comprising the administration of a therapeutically effective amount of at least one (e.g., one) compound of formula 1.0 and Exemestane.

Another embodiment of this invention is directed to the treatment or prevention of breast cancer in a patient in need of such treatment, said treatment comprising the administration of a therapeutically effective amount of at least one (e.g., one) compound of formula 1.0 and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Anastrozole, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Letrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Exemestane, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0, Anastrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0, Letrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0, Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment or prevention of Breast Cancer wherein the method is directed to the treatment of breast cancer.

The compound of formula 1.0, antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, 57th Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula 1.0 can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered in the above treatments for breast cancer, is generally administered according to known protocols before administration of the compound of formula 1.0, antihormonal agents and optional chemotherapeutic agents.

Treatment according to the methods of treating breast cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for breast cancer can be changed to a discontinuous treatment schedule if, in the judgment of the skilled clinician, the patient would benefit from a discontinuous treatment schedule with one or more of the administered drugs. For example, the compound of formula 1.0 can be given using a discontinuous treatment schedule while the remaining drugs used in the treatment are given as described herein. An example of a discontinuous treatment protocol for the compound of formula 1.0 is a repeating cycle of three weeks with the compound of formula 1.0 followed by one week without the compound of formula 1.0.

After a complete response is achieved with the breast cancer treatment, maintenance therapy with the compound of formula 1.0 can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of breast cancer described above, the compound of formula 1.0 is administered continuously in a total daily dose of about 100 mg to about 600 mg. Usually this amount is administered in divided doses, and in one embodiment this amount is administered twice a day. In one embodiment the compound of formula 1.0 is dosed twice a day in an amount of about 50 mg to about 300 mg per dose. In another embodiment the compound of formula 1.0 is dosed twice a day in an amount of about 100 mg to about 200 mg per dose. Examples include the compound of formula 1.0 being dosed twice a day at 100 mg per dose. Examples also include the compound of formula 1.0 being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula 1.0 orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula 1.0, one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula 1.0 is dosed twice a day in an amount of about 100 mg per dose.

Other embodiments of the treatment of Breast Cancer are directed to the methods of treating Breast Cancer described above wherein the compound of formula 1.0 is dosed twice a day in an amount of about 200 mg per dose.

Other embodiments of the treatment of Breast Cancer are directed to the methods of treating Breast Cancer described above wherein a chemotherapeutic agent is administered in addition to the compound of formula 1.0 and antihormonal agent (or antihormonal agents). In these embodiments the dosage ranges of the compound of formula 1.0 and antihormonal agents are as those described above in the combination therapies, or those described above for the individual compound of formula I and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula 1.0 and at least one antihormonal agent and a pharmaceutically acceptable carrier.

Other embodiments of this invention are directed to pharmaceutical compositions comprising the compound of formula 1.0, at least one antihormonal agent, at least one chemotherapeutic agent, and a pharmaceutically acceptable carrier.

Other embodiments of this invention are directed to pharmaceutical compositions comprising the compound of formula 1.0, at least one chemotherapeutic agent, and a pharmaceutically acceptable carrier.

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compound of formula 1.0, a taxane, and a platinum coordination compound, includes within its scope a method of treating cancer comprising administering to a patient in need of such treatment therapeutically effective amounts of a pharmaceutical composition comprising the compound of formula 1.0, a pharmaceutical composition comprising a taxane, and a pharmaceutical composition comprising a platinum coordination compound.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the disease (e.g., cancer) being treated and the response of the patient to the treatment.

The amount and frequency of administration of the compound of formula 1.0 and the chemotherapeutic agents (in the methods wherein cancer is treated) will be regulated according to the judgment of the attending clinician (physician) considering such factors as age, condition and size of the patient as well as severity of the disease (e.g., cancer) being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of the disease (e.g. for cancer, the relief of cancer-related symptoms (e.g., pain, cough (for lung cancer), and shortness of breath (for lung cancer), inhibition of tumor growth, actual shrinkage of the tumor, or inhibition of metastasis). Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, $20^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

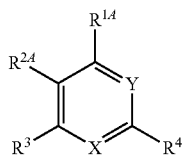

(1.0)

or pharmaceutically acceptable salts or esters thereof, wherein
X is N;
Y is $CR^5$ wherein $R^5$ is H;
$R^{1A}$ is H;
$R^{2A}$ is H;
$R^3$ is —$C(O)NR^8R^9$;
$R^4$ is —$C(O)NR^6R^7$;
$R^6$ is H;
$R^7$ is alkyl;
$R^8$ is H;
$R^9$ is selected from the group consisting of:
  (1) heteroarylalkyl-, and
  (2) substituted heteroarylalkyl wherein said substituted heteroarylalkyl is substituted with 1 to 3 substituents independently selected from the group consisting of:
    (a) —$NH_2$,
    (b) —$NH(C_1$ to $C_6)$alkyl,
    (c) —$N((C_1$ to $C_6)$alkyl$)_2$ wherein each alkyl is independently selected,
    (d) alkyl,
    (e) halo,
    (f) aryl,
    (g) substituted aryl wherein said substituted aryl is substituted with 1 to 3 substituents independently selected from the group consisting of: (i) —$SO_2R^{20}$, (ii) —$OR^{21}$, (iii) -halo, (iv) —CN, (v) —$CF_3$, (vi) aminoalkyl-, (vii) —$S(O)R^{26}$, and (viii) alkyl,
    (h) heterocycloalkyl,
    (i) heteroaryl,
    (j) substituted aryl substituted with 1 to 3 substituents independently selected from the group consisting of: alkyl, —$CF_3$, F, Cl, and Br,
    (k) substituted heteroaryl, substituted with 1 to 3 substituents selected from the group consisting of: (i) alkyl, (ii) halo, (iii) CN, (iv) $NH_2$, (v) —$NH(C_1$-$C_6$ alkyl), (vi) —$N(C_1$-$C_6$ alkyl$)_2$ wherein each alkyl is independently selected, (vii) —$CF_3$, (viii) substituted aryl wherein said substituted aryl is substituted with 1 to 3 substitutents independently selected from the group consisting of: —$S(O)_2R^{42}$ and —CN, and (ix) —$C(O)NR^{44}R^{46}$,
    (l) alkylamino-,
    (m) heterocycloalkyl-alkyl-amino-,
    (n) alkylaminoalkylamino-,
    (o) —$NHC(O)OR^{30}$, and
    (p) —$NHC(O)NR^{32}R^{34}$;

$R^{20}$ is selected from the group consisting of: (1) alkyl, (2) dialkylamino (wherein each alkyl is independently selected), (3) —$NH_2$, (4) alkylamino, (5) heterocycloalkyl, and (6) substituted heterocycloalkyl wherein said substituted heterocycloalkyl is substituted with 1 to 2 substitutents independently selected from the group consisting of: —$C(O)OR^{40}$;

$R^{21}$ is alkyl;

$R^{26}$ is alkyl;

$R^{30}$ is alkyl;

Each $R^{32}$ and $R^{34}$ is independently selected from the group consisting of: H, alkyl, aryl, aryl substituted with a —OH group, and heteroaryl;

$R^{40}$ is alkyl; and

Each $R^{44}$ and $R^{46}$ is independently selected from the group consisting of: H and alkyl.

2. The compound of claim 1 wherein $R^4$ is —C(O)NH(i-propyl).

3. The compound of claim 1 wherein $R^9$ is heteroarylalkyl.

4. The compound of claim 1 wherein $R^9$ is heteroarylalkyl and said heteroarylalkyl is pyrazolyl-($C_1$ to $C_6$)alkyl-.

5. The compound of claim 1 wherein $R^9$ is substituted heteroarylalkyl.

6. The compound of claim 1 wherein $R^9$ is substituted heteroarylalkyl and said substituted heteroarylalkyl is substituted pyrazolylalkyl-.

7. The compound of claim 1 wherein $R^9$ is substituted heteroarylalkyl and said substituted heteroarylalkyl is selected from the group consisting of: phenyl-pyrazolyl-$CH_2$—, N-methylpyrazolyl-$CH_2$—, N-isopropylpyrazolyl-$CH_2$—, N-(m-methylphenyl)-pyrazolyl-$CH_2$—, N-(p-methylphenyl)-pyrazolyl-$CH_2$—, N-(m-Cl-p-F-phenyl)-pyrazolyl-$CH_2$—, N-(m-Cl-phenyl)-pyrazolyl-$CH_2$—, N-(m-CN-phenyl)-pyrazolyl-$CH_2$—, N-(p-CN-phenyl)-pyrazolyl-$CH_2$—, N-(m-$SO_2CH_3$-phenyl)-pyrazolyl-$CH_2$—, N-(p-$SO_2CH_3$-phenyl)-pyrazolyl-$CH_2$—, N-(m,m-di-Cl-phenyl)pyrazolyl-$CH_2$—, N-(m-F-phenyl)-pyrazolyl-$CH_2$—, N-(m-$CF_3$-phenyl)-pyrazolyl-$CH_2$—, N-(quinolinyl)-pyrazolyl-$CH_2$—, N-(pyrimidinyl)-pyrazolyl-$CH_2$—, N-(methylquinolinyl)-pyrazolyl-$CH_2$—, N-(m-$CF_3$-p-F-phenyl)pyrazolyl-$CH_2$—, N-(quinoxalinyl)-pyrazolyl-$CH_2$—, N-(p-($CH_3$)SO-phenyl)-pyrazolyl-$CH_2$—, N-(m-Br-m-CN-phenyl)-pyrazolyl-$CH_2$—, N-(o-Cl-phenyl)pyrazolyl-$CH_2$—, N-(o-CN-phenyl)-pyrazolyl-$CH_2$—, N-(pyrimidinyl)-pyrazolyl-$CH_2$—, N—(CNpyridyl)-pyrazolyl-$CH_2$—, N-(m-F-m-CN-phenyl)-pyrazolyl-$CH_2$—, N-(thiazolyl)-pyrazolyl-$CH_2$—, N-(aminothiazolo[4,5-b]pyridinyl)-pyrazolyl-$CH_2$—, N-(imidazo[1,2-a]pyridinyl)-pyrazolyl-$CH_2$—, N-(imidazo[1,2-a]pyrimidinyl)-pyrazolyl-$CH_2$—, N-(quinazolinyl)-pyrazolyl-$CH_2$—, N-(3H-imidazo[4,5-b]pyridinyl)-pyrazolyl-$CH_2$—, N-([1,5]-naphthyridinyl)-pyrazolyl-$CH_2$—, N-(1-isopropyl-2-methyl-1H-benzoimidazolyl)-pyrazolyl-$CH_2$—, N-(1,2-dimethyl-1H-benzoimidazolyl)-pyrazolyl-$CH_2$—, N-(1-methyl-2-$CF_3$-1H-benzoimidazolyl)-pyrazolyl-$CH_2$—, N-(1-methyl-2-isopropyl-1H-benzoimidazolyl)-pyrazolyl-$CH_2$—, N-(1-methyl-2-pyridin-3-yl-1H-benzoimidazolyl)-pyrazolyl-$CH_2$—, N—($H_2NSO_2$ phenyl)-pyrazolyl-$CH_2$—, N—($CH_3NHSO_2$phenyl)-pyrazolyl-$CH_2$—, N-(piperazinyl$SO_2$phenyl)-pyrazolyl-$CH_2$—, N-(p-($CH_3$)$_2$$NSO_2$)-m-Cl-phenyl)-pyrazolyl-$CH_2$—

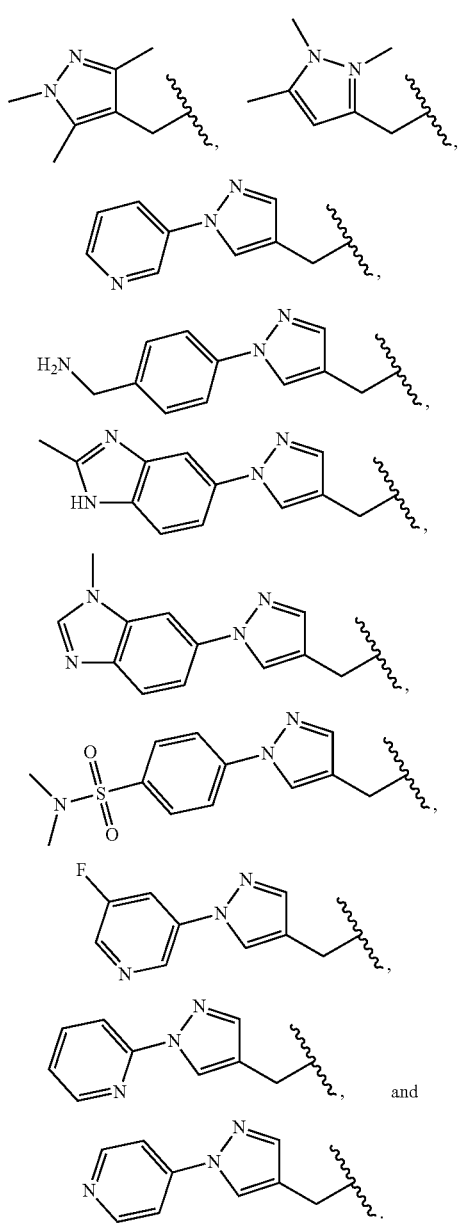

8. The compound of claim 1 wherein $R^9$ is a substituted heteroarylalkyl and said substituted heteroarylalkyl is substituted pyrazolyl-$CH_2$—.

9. The compound of claim 1 wherein $R^9$ is substituted heteroarylalkyl and said substituted heteroarylalkyl is N-(methylquinolinyl)-pyrazolyl-$CH_2$—.

10. The compound of claim 1 wherein $R^3$ is selected from the group consisting of:

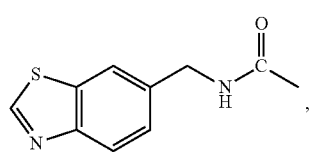

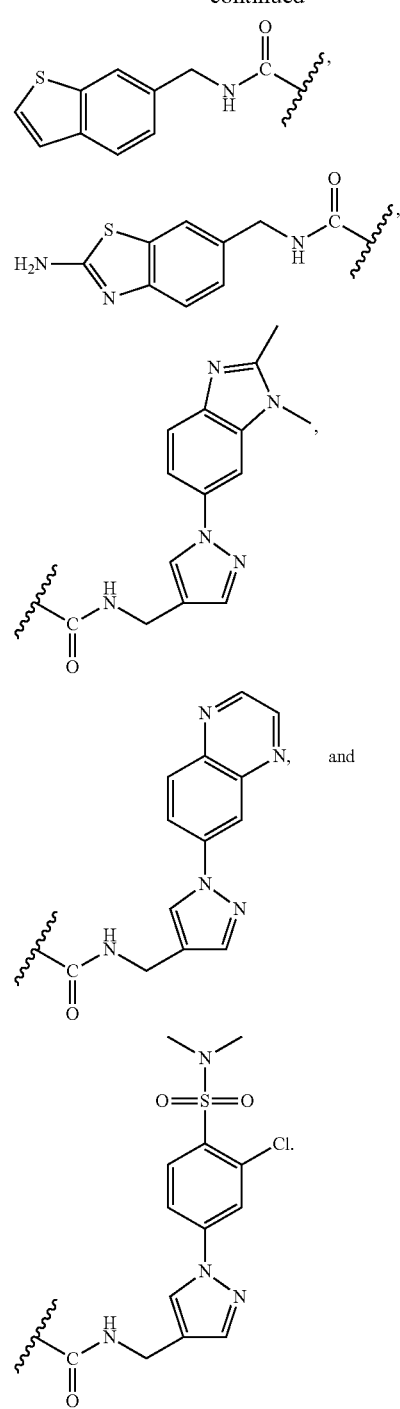

11. The compound of claim 1 wherein $R^3$ is selected from the group consisting of:

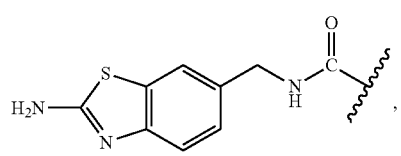

249
-continued
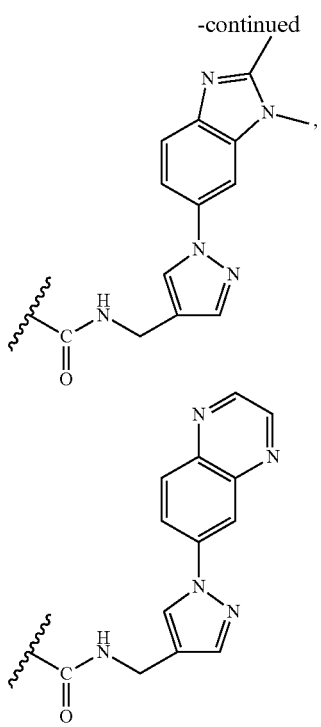
and
250
-continued
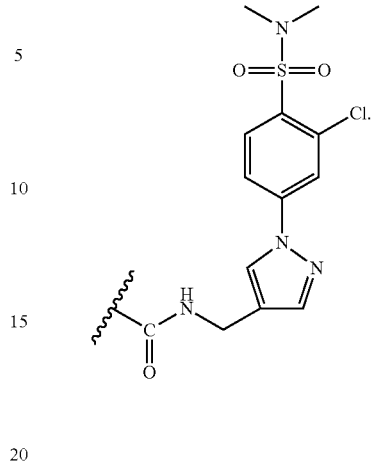
12. A pharmaceutical composition comprising an effective amount of at least one compound of claim 1 and a pharmaceutically acceptable carrier.
13. A compound selected from the group consisting of:
| Compound |
| --- |
| 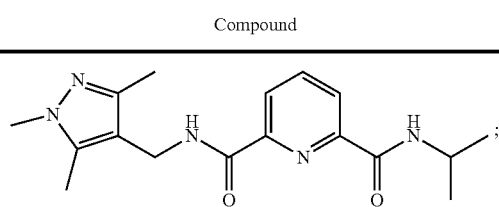<br>102 |
| 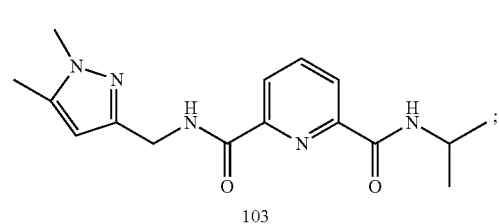<br>103 |
| 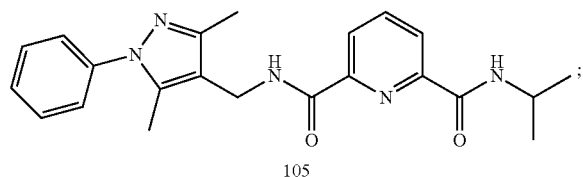<br>105 |
| 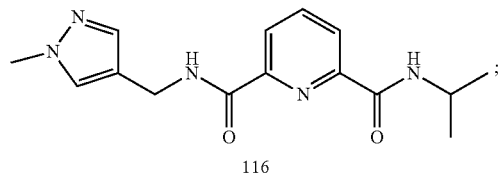<br>116 |

-continued
| Compound |
|---|
| 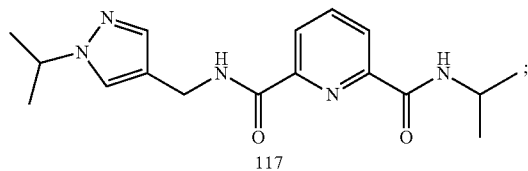<br>117 |
| 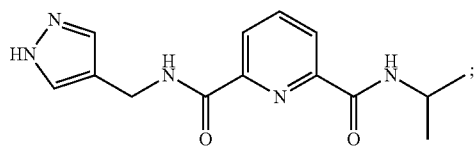<br>119 |
| 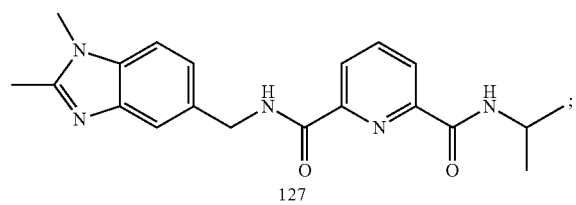<br>127 |
| 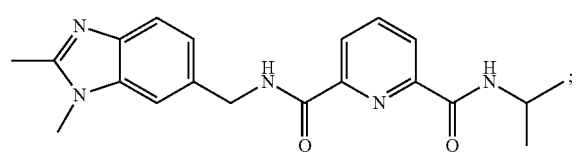<br>128 |
| 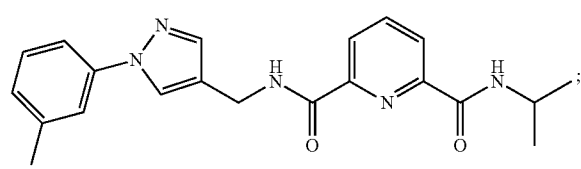<br>129 |
| 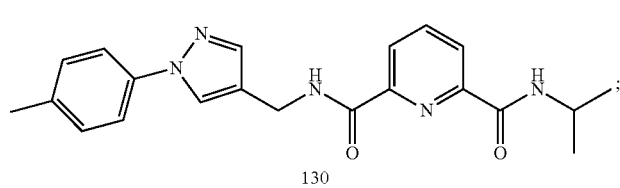<br>130 |
| 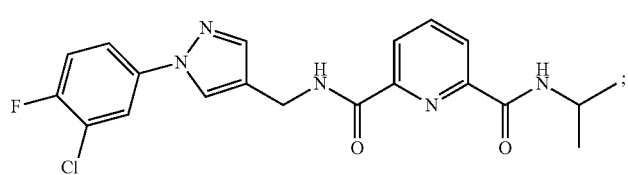<br>131 |
| 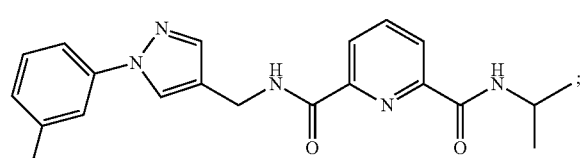<br>132 |

-continued
Compound
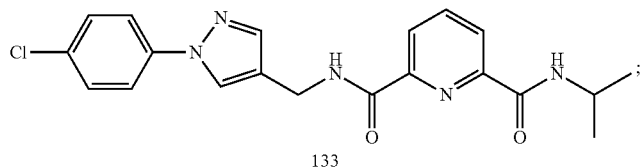
133
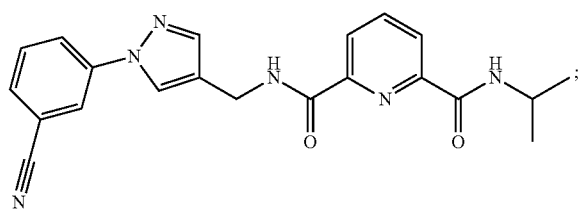
134
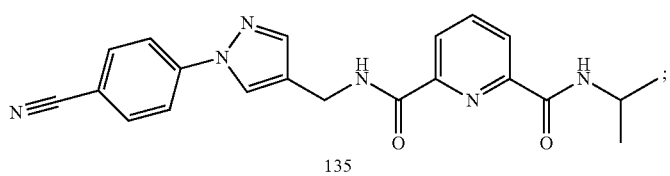
135
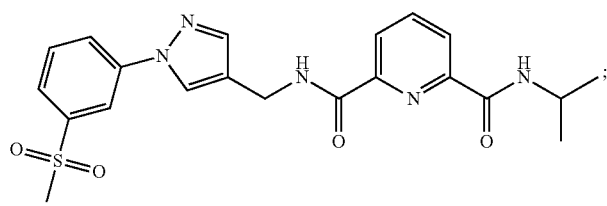
136
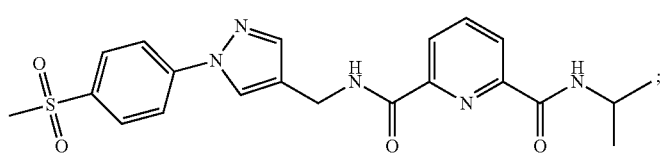
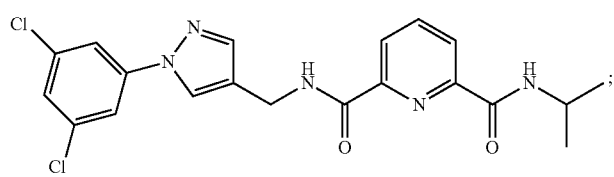
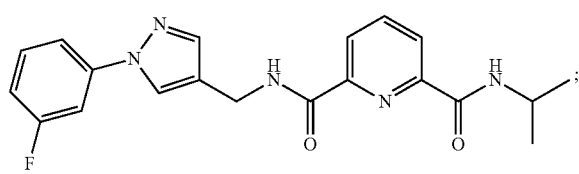
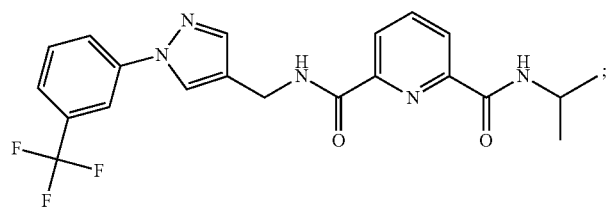

-continued
Compound
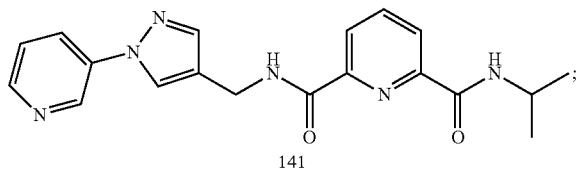
141
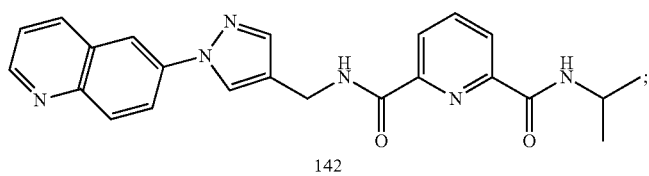
142
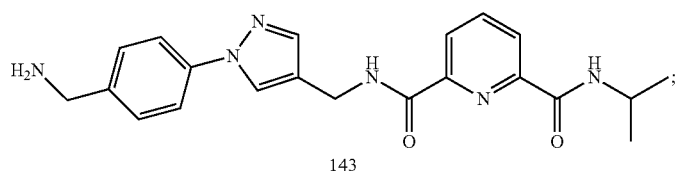
143
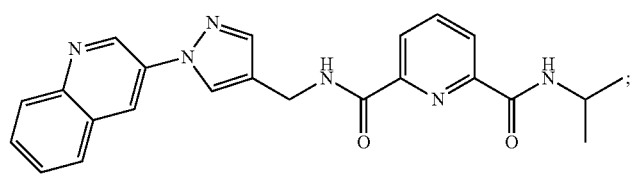
144
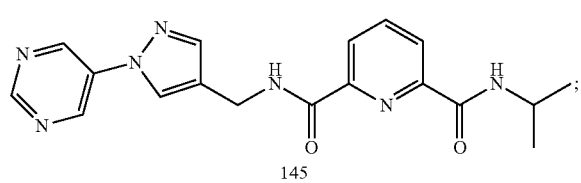
145
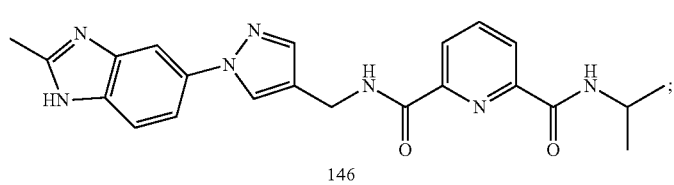
146
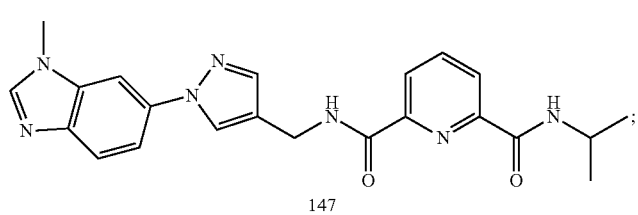
147
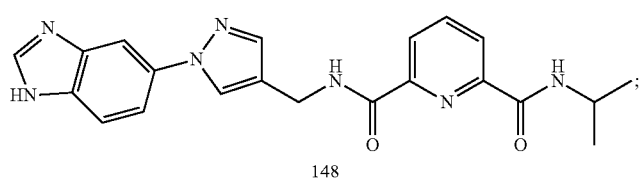
148

-continued
Compound
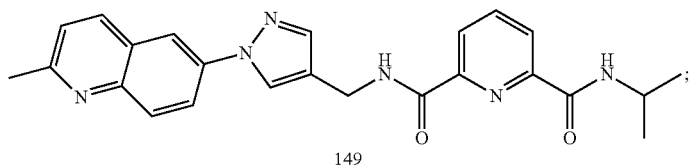
149
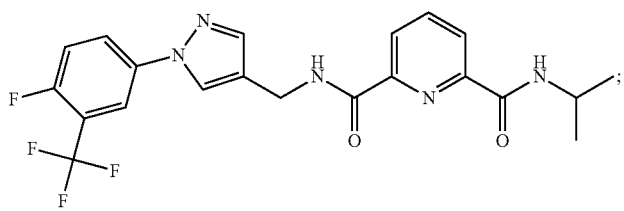
150
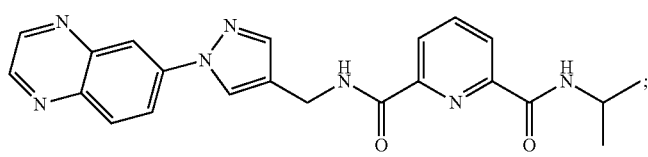
151
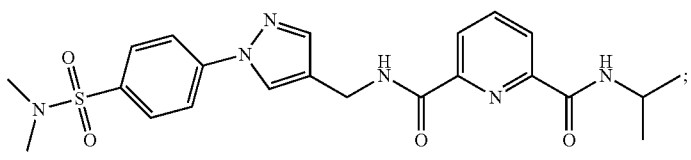
152
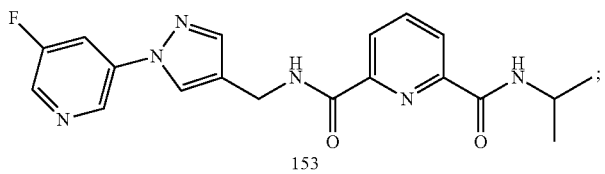
153
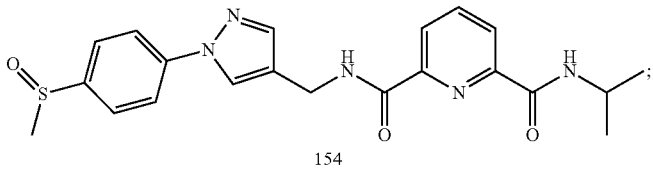
154
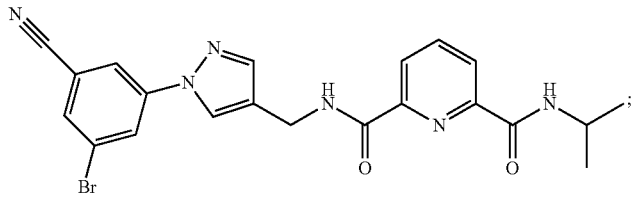
155
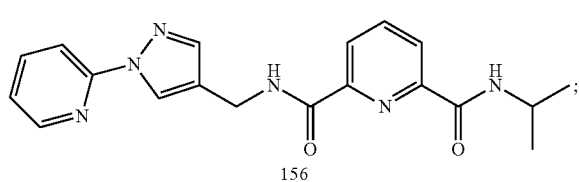
156

-continued
Compound
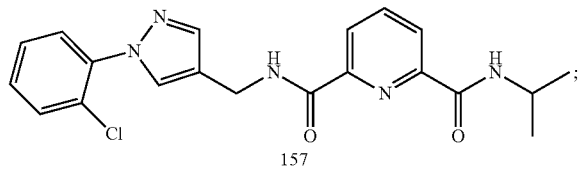
157
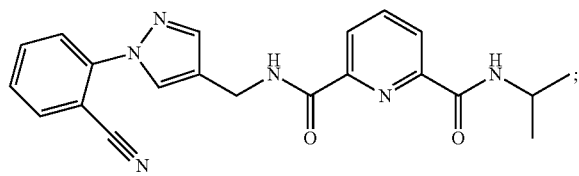
158
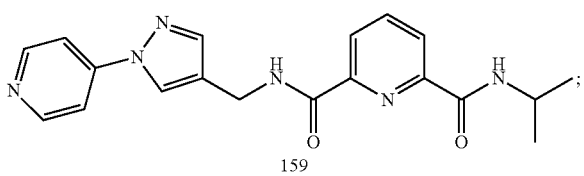
159
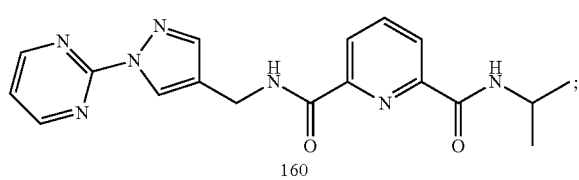
160
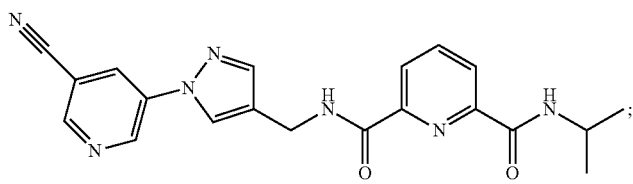
161
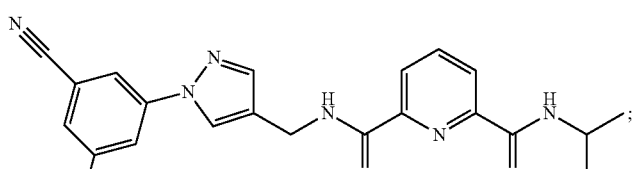
162
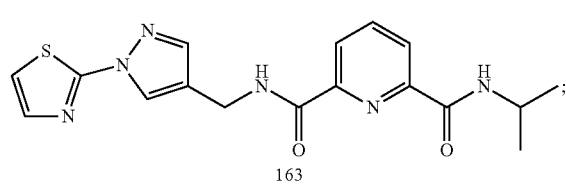
163
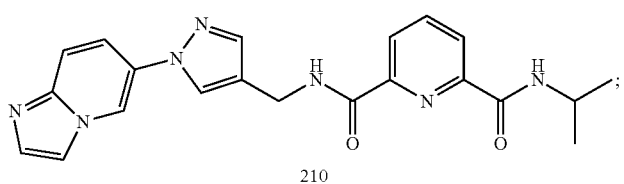
210

-continued
Compound
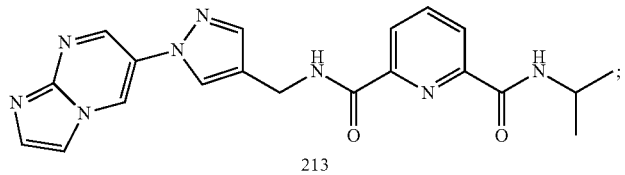
213
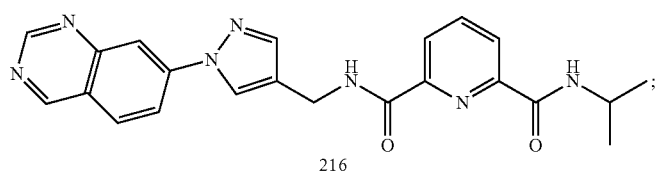
216
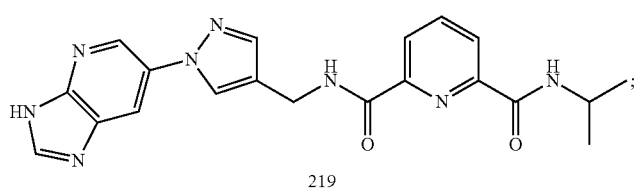
219
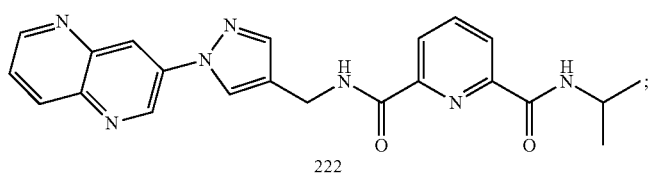
222
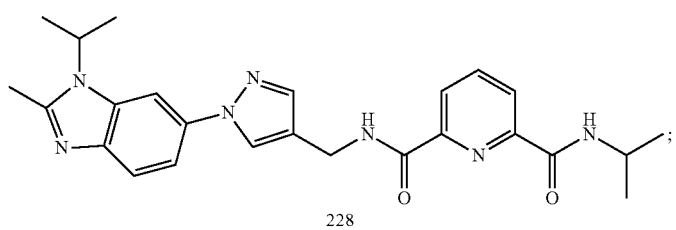
228
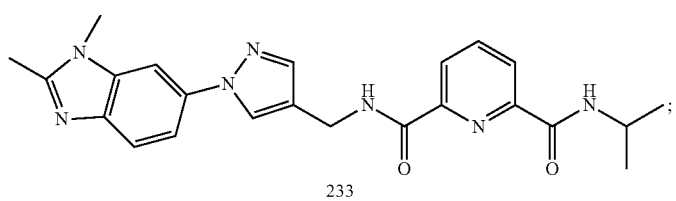
233
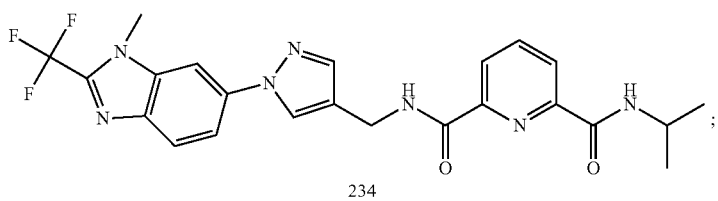
234
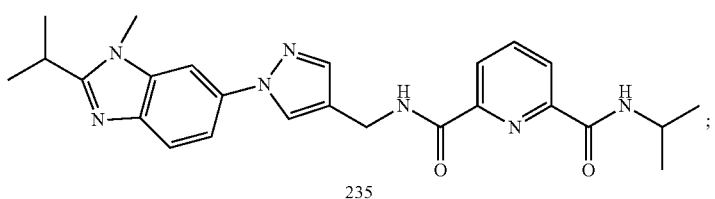
235

| Compound |
|---|
| 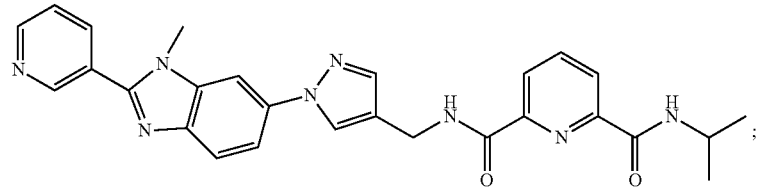 236 |
| 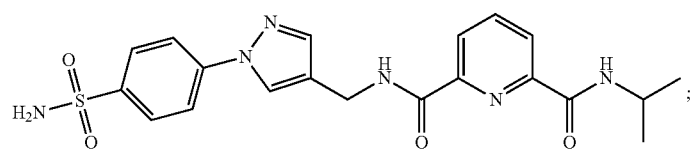 241 |
| 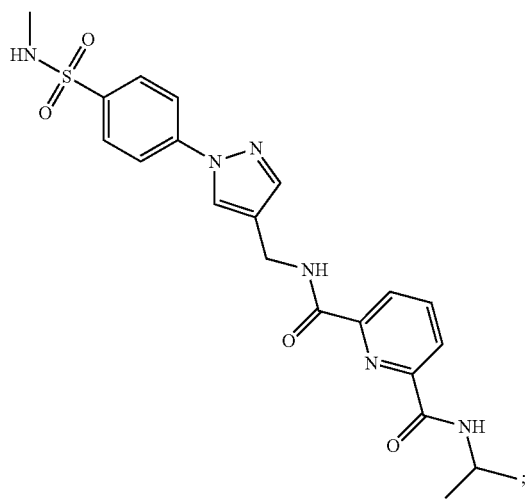 244 |
| 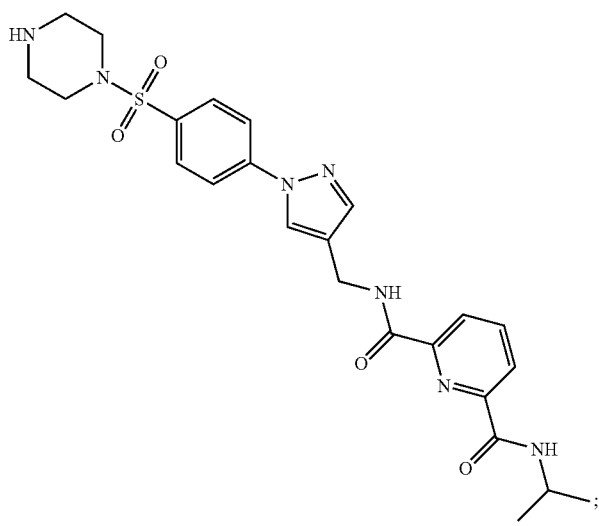 245 |

-continued
Compound
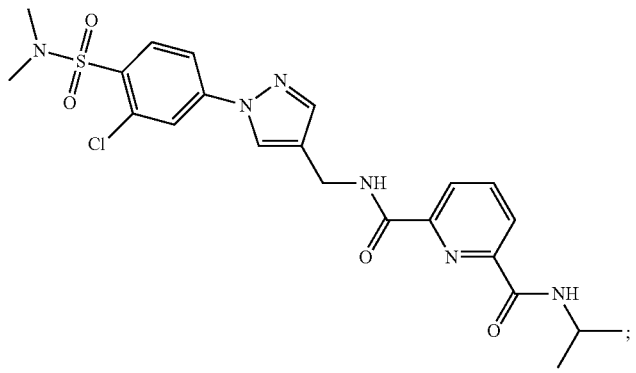
246
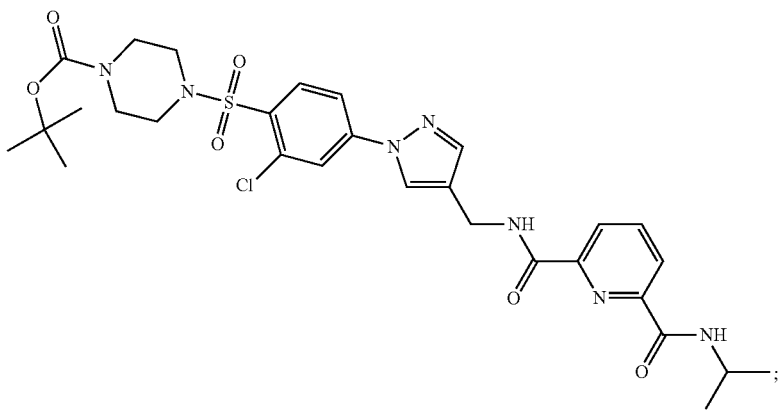
247
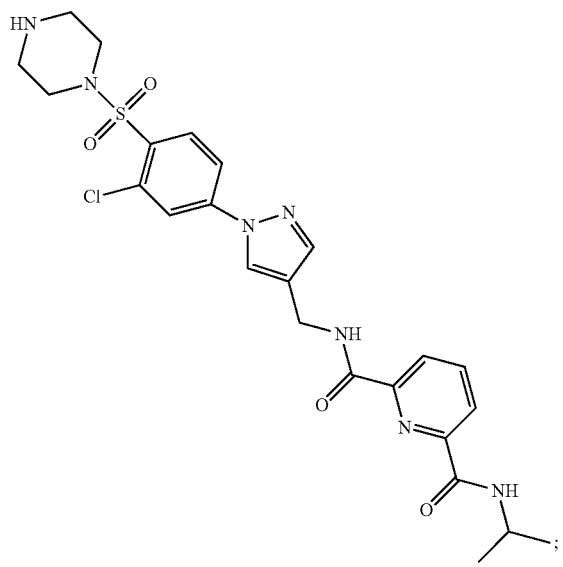
248
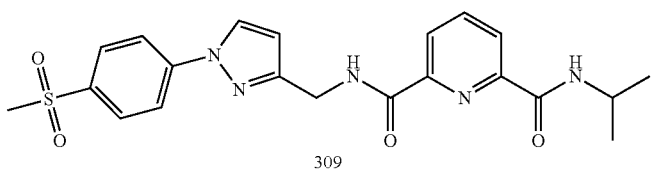
309

-continued
Compound
and
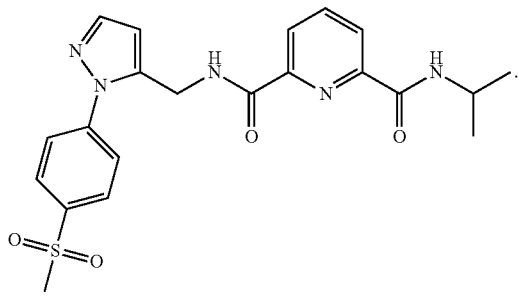
310
14. The compound of claim 13 selected from the group consisting of:
Compound
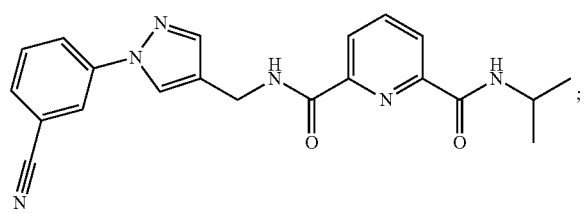
134
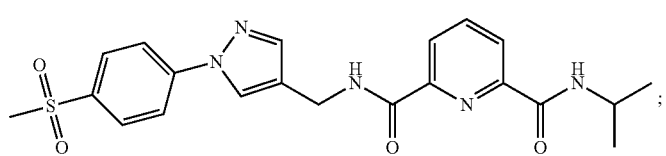
137
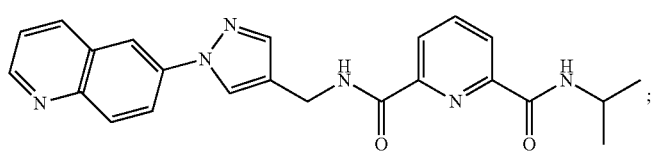
142
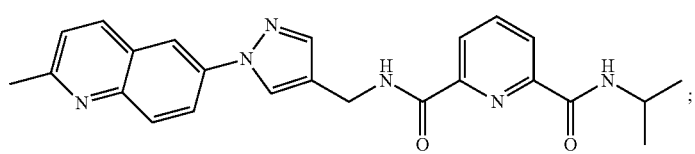
149
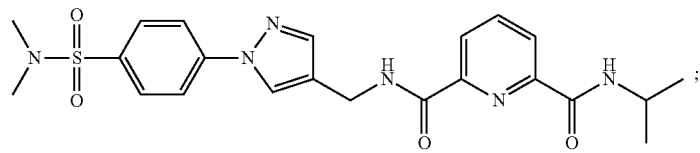
152

-continued
Compound
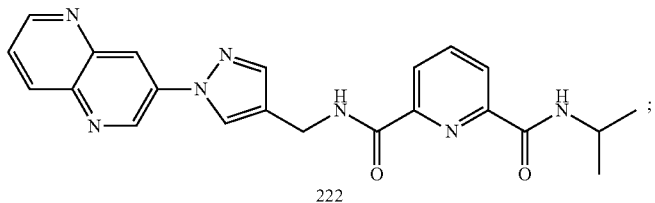
222
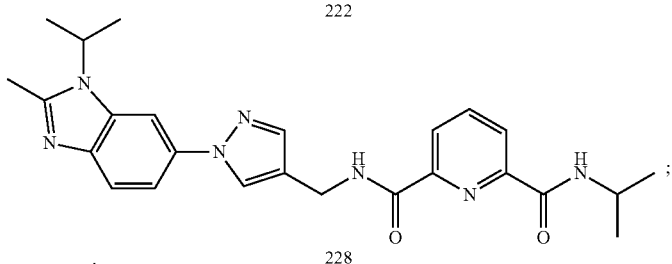
228
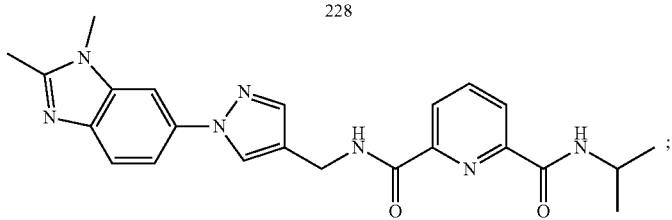
233
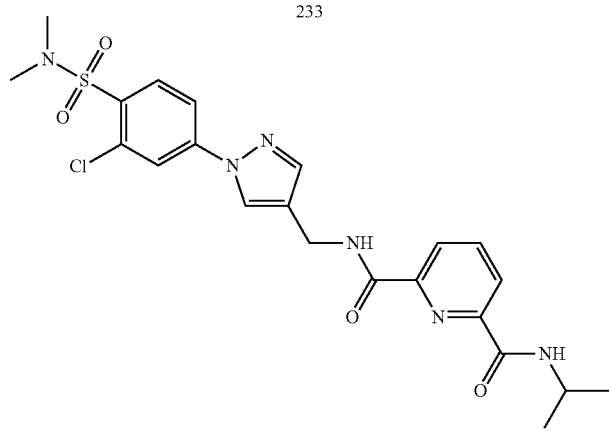
246
and
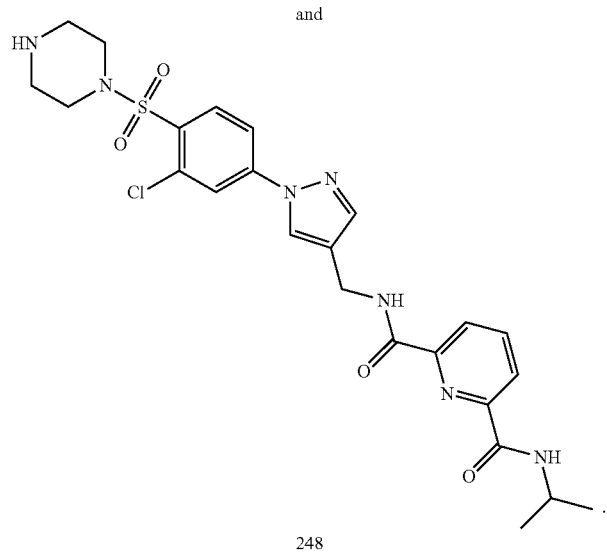
248

15. A compound selected from the group consisting of:
| Compound |
|---|
| 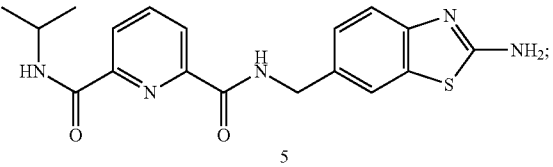 |
| 5 |
| 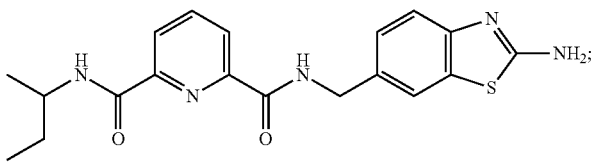 |
| 7 |
| 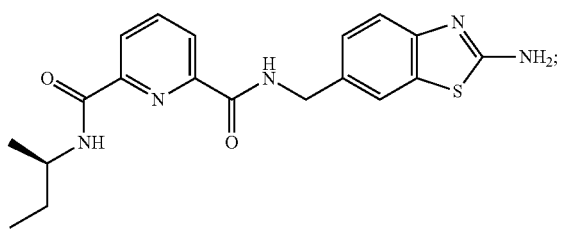 |
| 8 |
| 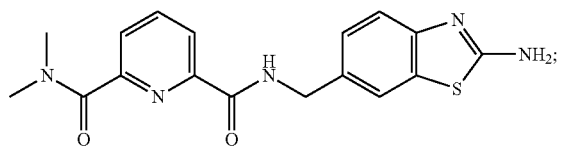 |
| 13 |
| 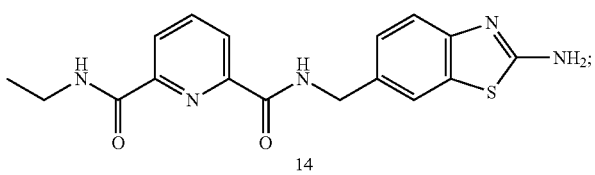 |
| 14 |
| 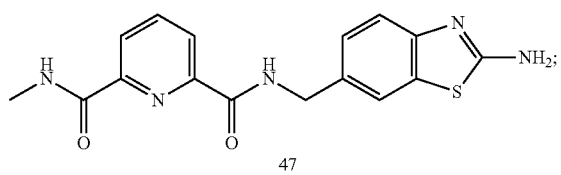 |
| 47 |
| 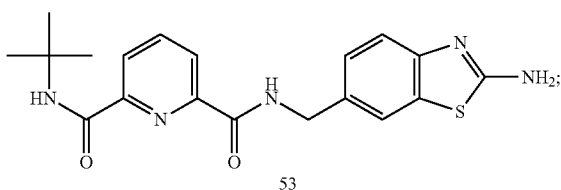 |
| 53 |
| 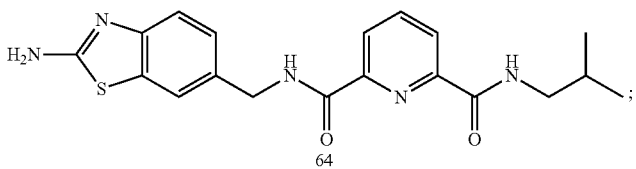 |
| 64 |

-continued
| Compound |
|---|
| 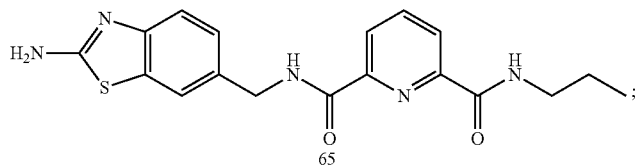 65 |
| 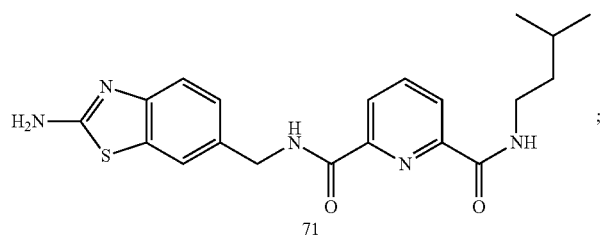 71 |
| 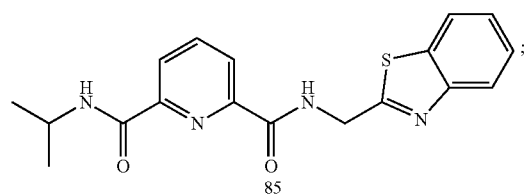 85 |
| 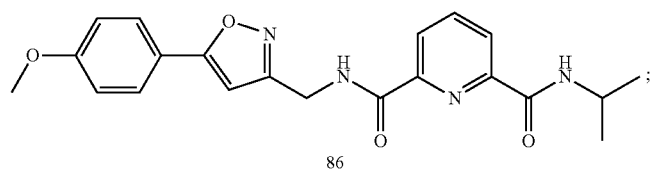 86 |
| 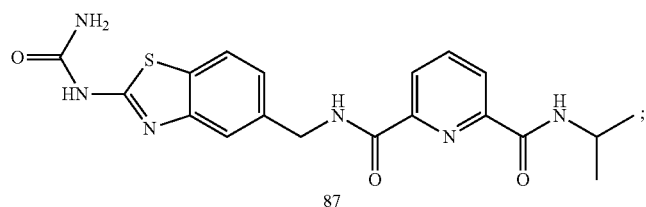 87 |
| 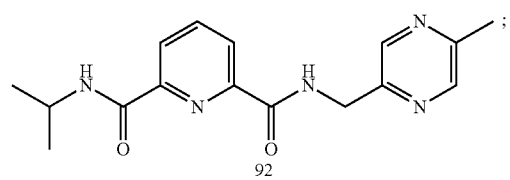 92 |
| 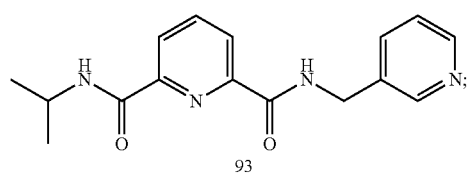 93 |
| 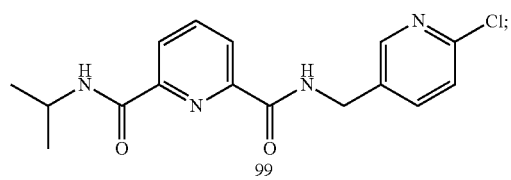 99 |

-continued
Compound
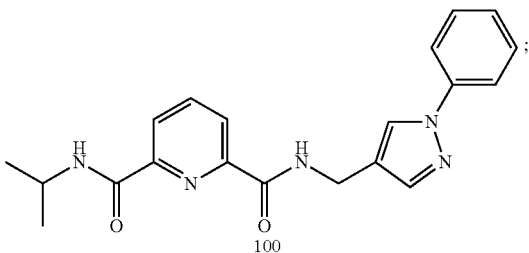
100
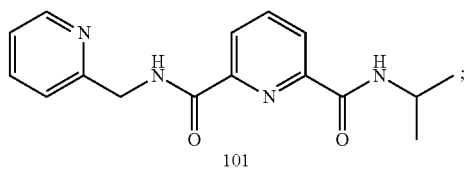
101
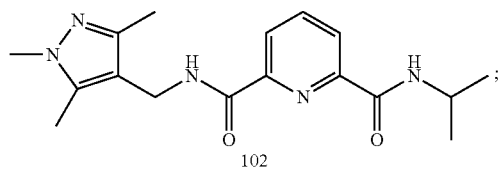
102
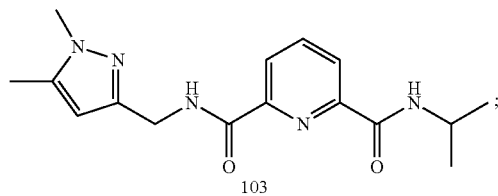
103
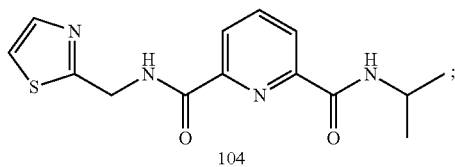
104
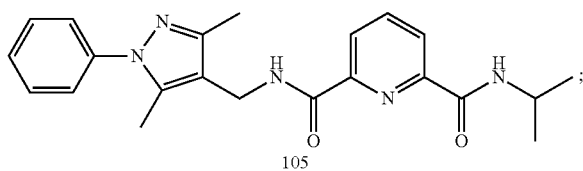
105
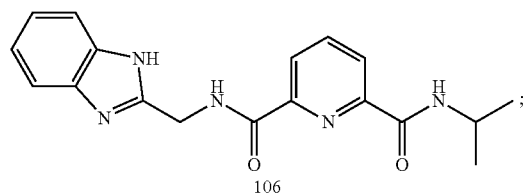
106
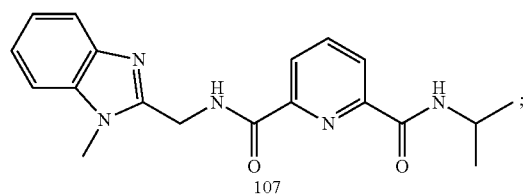
107

-continued
| Compound |
|---|
| 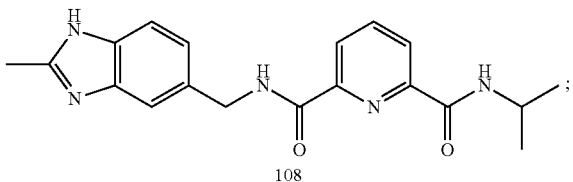 108 |
| 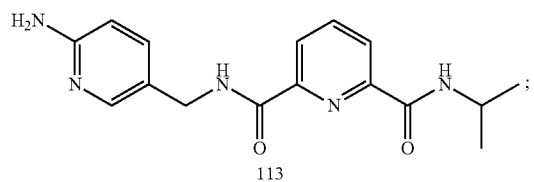 113 |
| 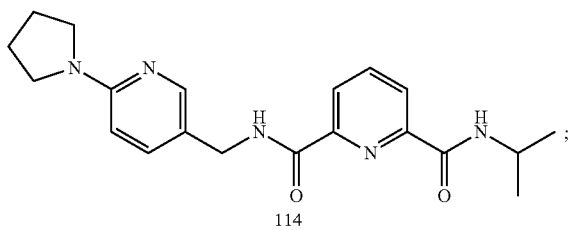 114 |
| 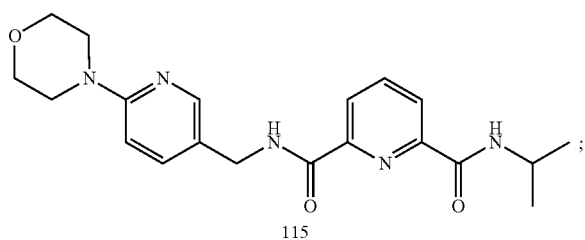 115 |
| 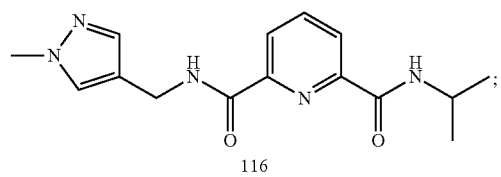 116 |
| 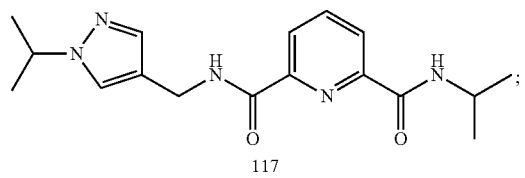 117 |
| 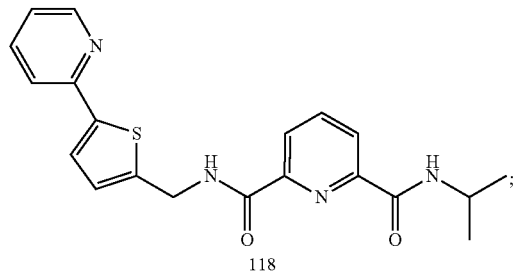 118 |

-continued
| Compound |
|---|
| 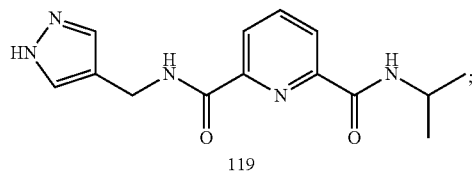 119 |
| 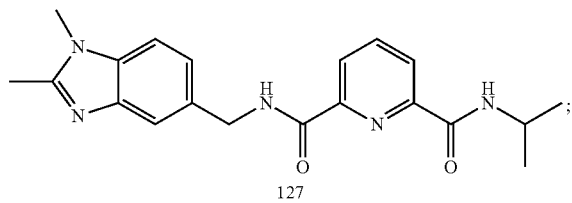 127 |
| 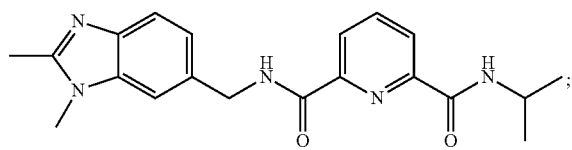 128 |
| 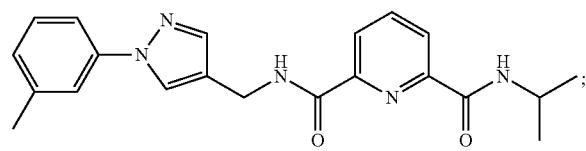 129 |
| 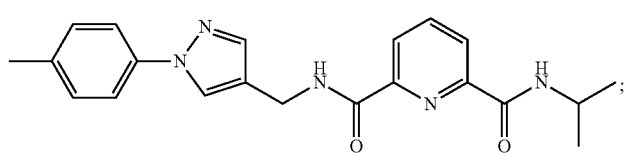 130 |
| 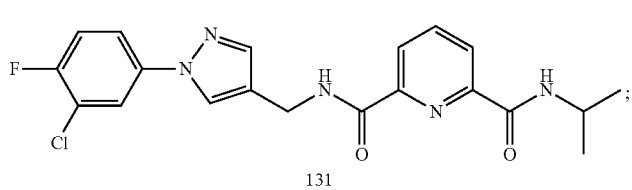 131 |
| 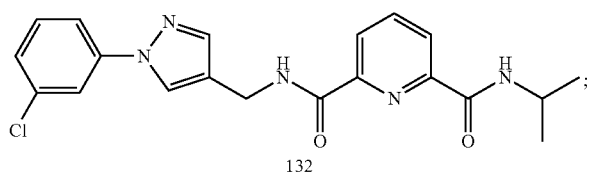 132 |
| 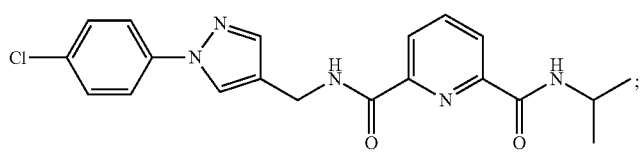 133 |

-continued
Compound
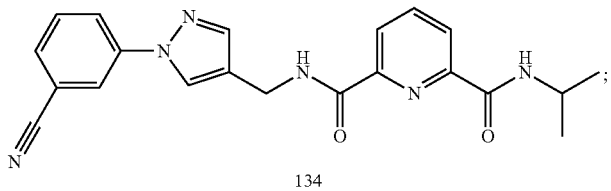
134
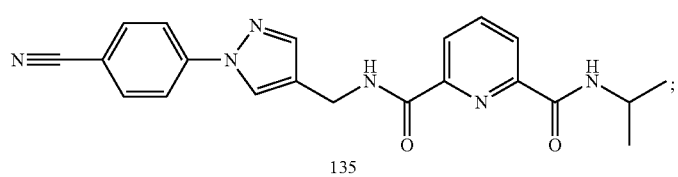
135
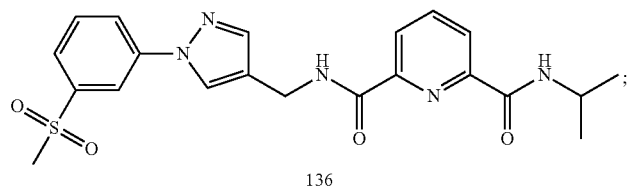
136
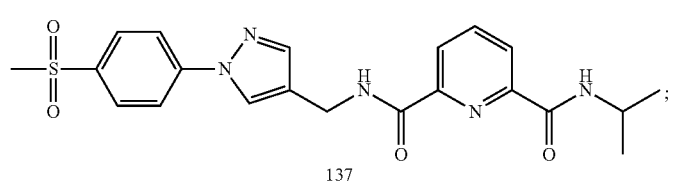
137
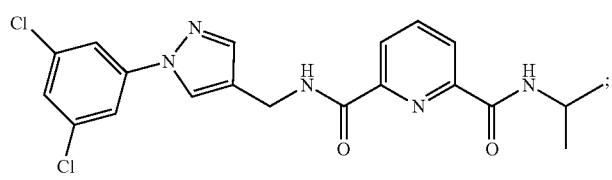
138
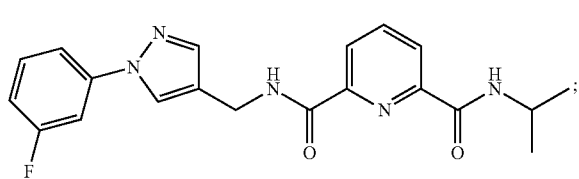
139
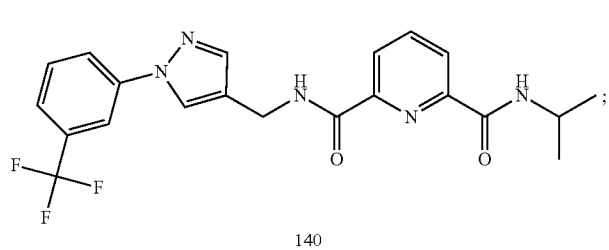
140
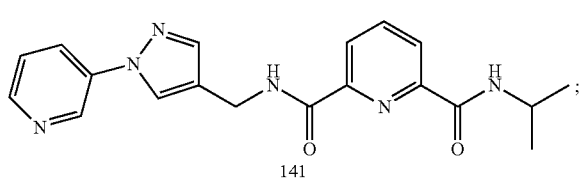
141

-continued
| Compound |
|---|
| 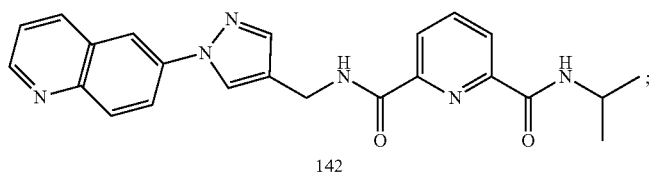 142 |
| 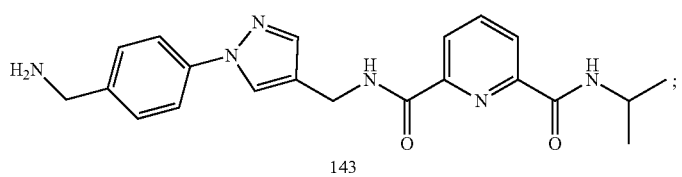 143 |
| 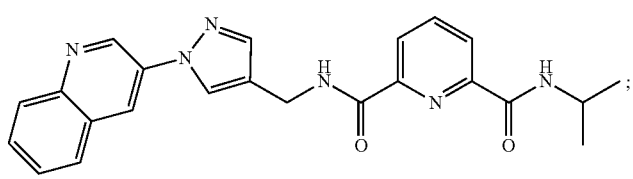 144 |
| 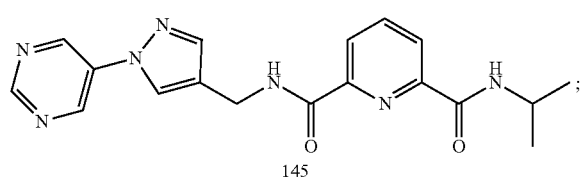 145 |
| 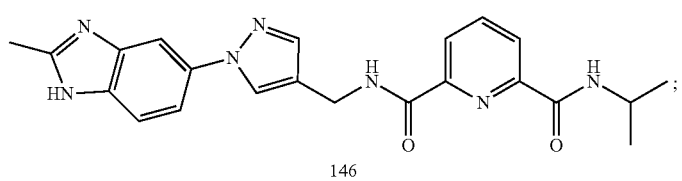 146 |
| 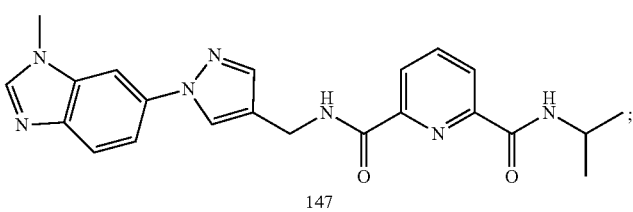 147 |
| 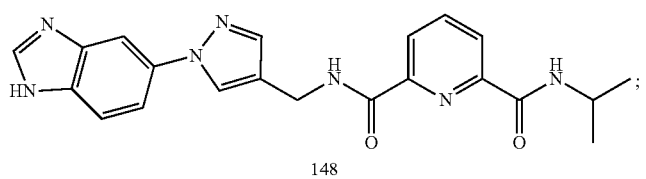 148 |
| 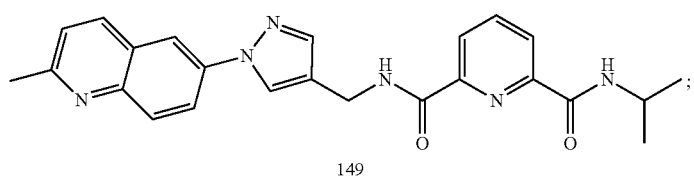 149 |

-continued

Compound

-continued
| Compound |
|---|
| 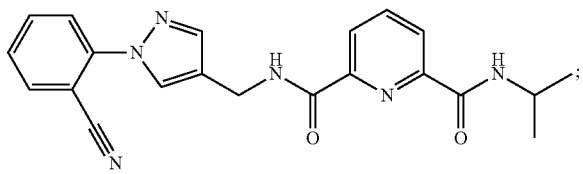 158 |
| 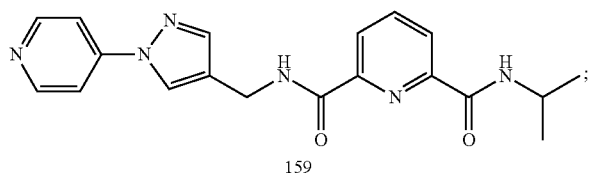 159 |
| 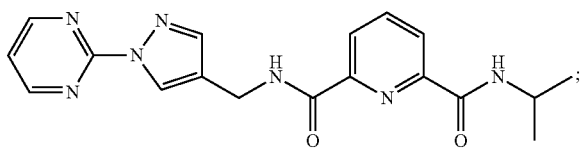 160 |
| 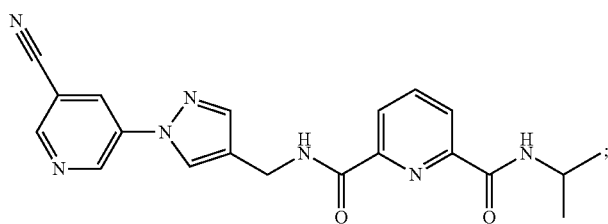 161 |
| 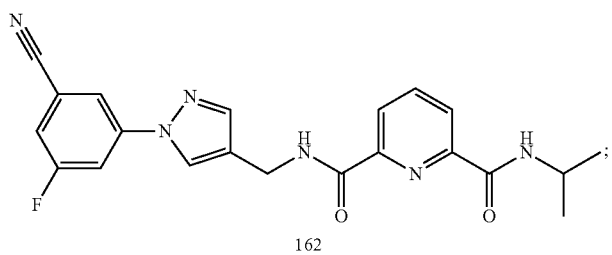 162 |
| 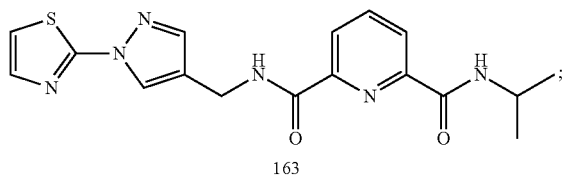 163 |
| 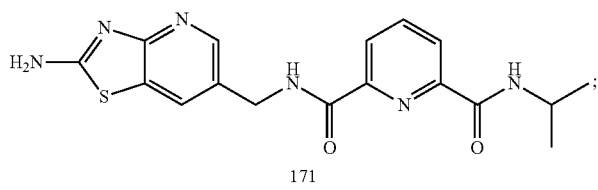 171 |

-continued
| Compound |
|---|
| 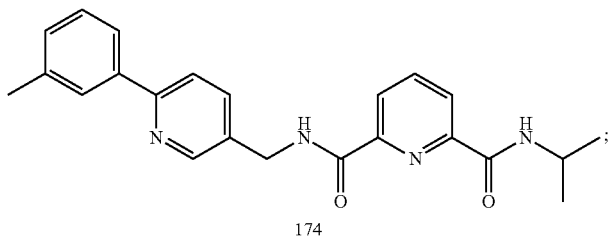<br>174 |
| 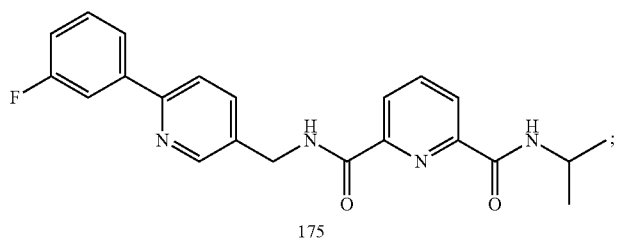<br>175 |
| 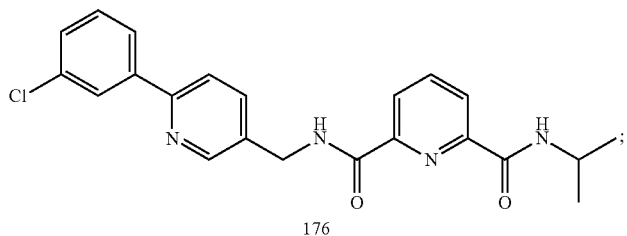<br>176 |
| 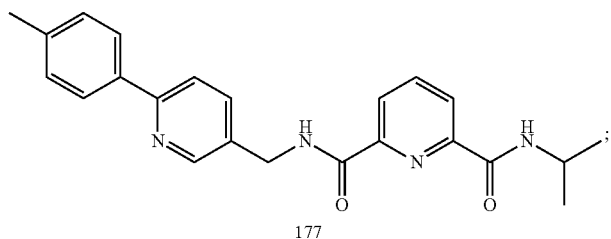<br>177 |
| 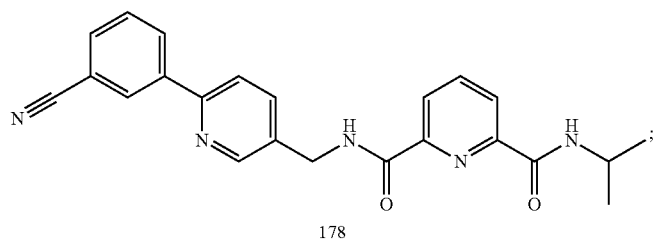<br>178 |
| 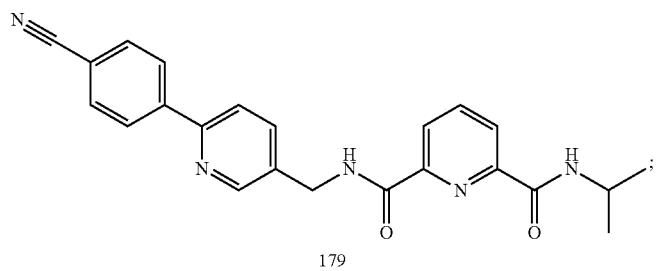<br>179 |

| Compound |
|---|
| 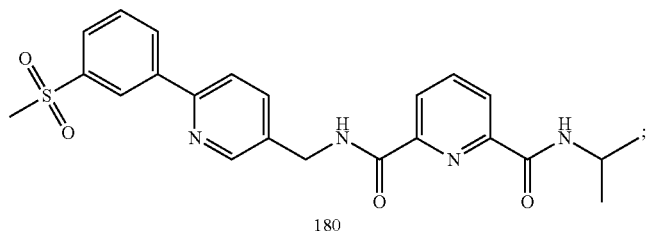 180 |
| 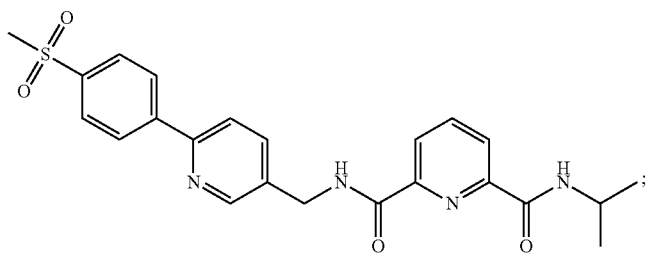 181 |
| 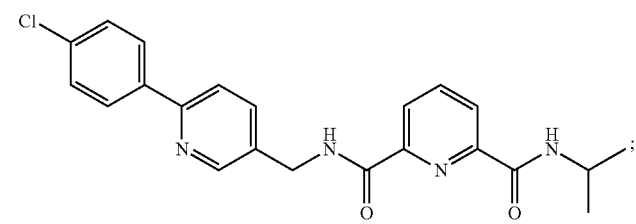 182 |
| 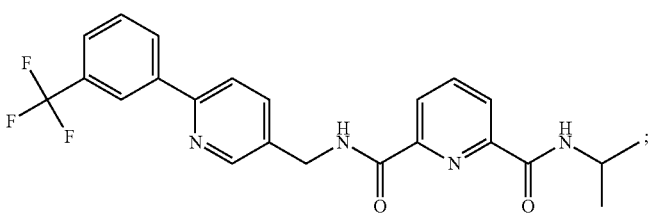 183 |
| 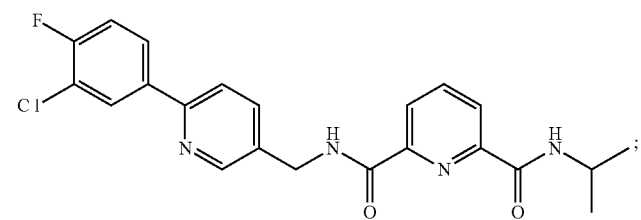 184 |
| 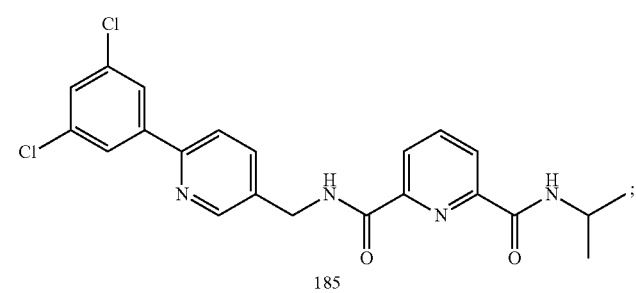 185 |

-continued
Compound
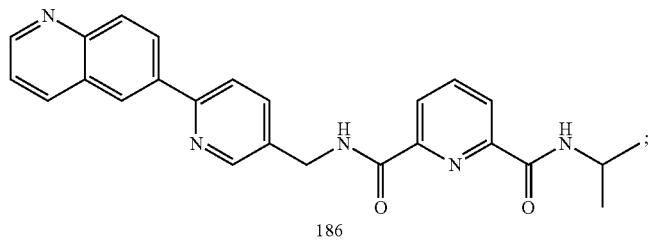
186
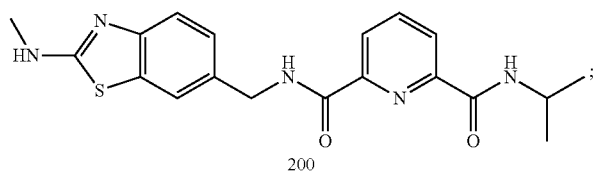
200
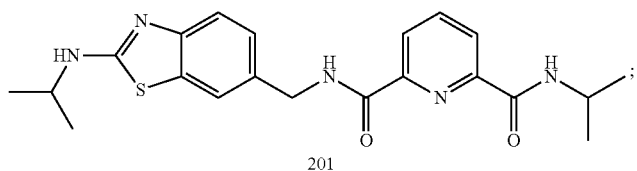
201
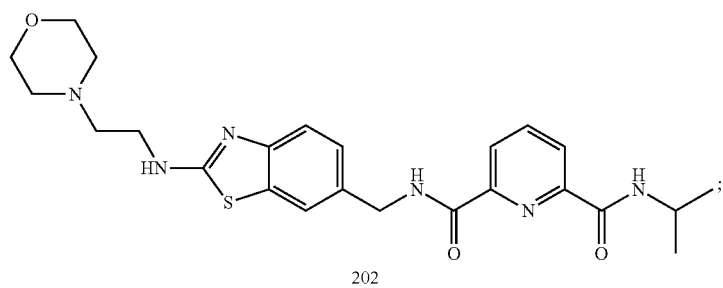
202
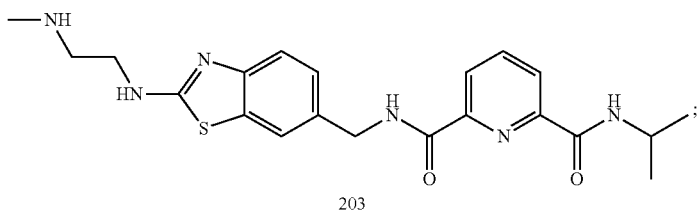
203
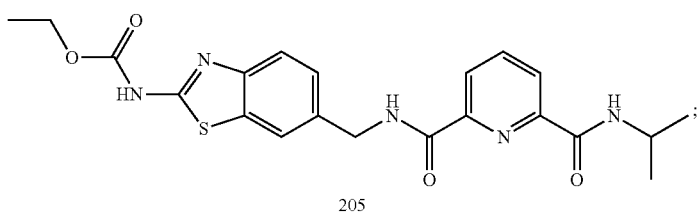
205
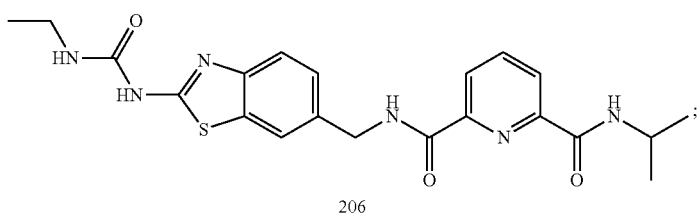
206

-continued
Compound
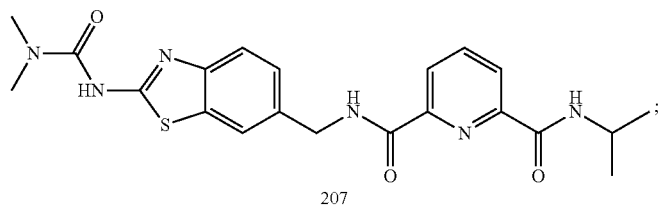
207
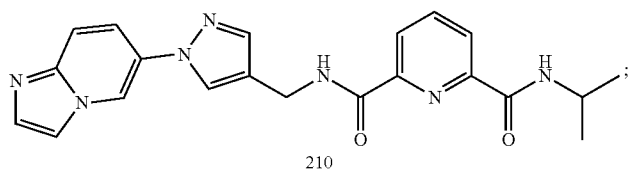
210
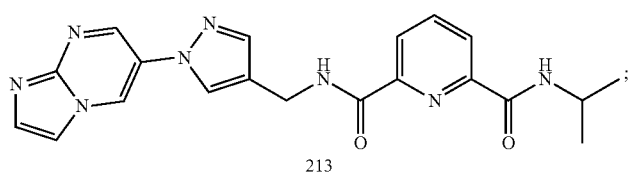
213
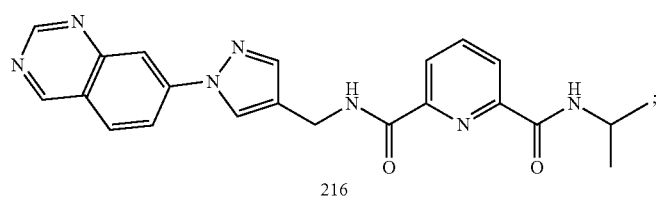
216
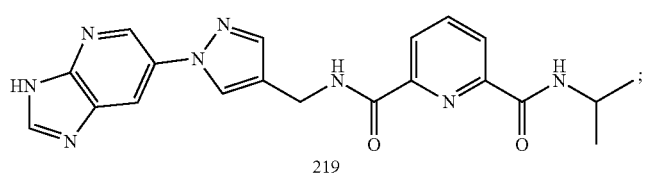
219
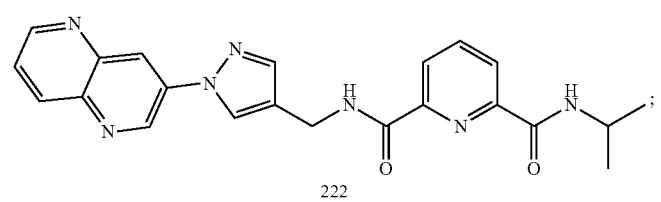
222
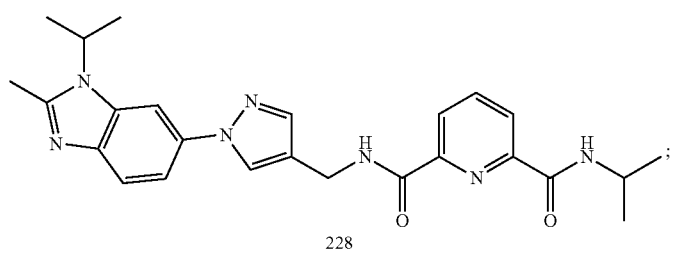
228
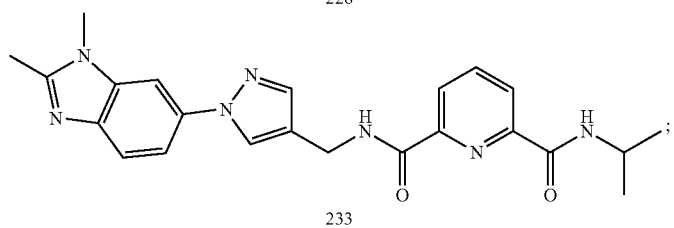
233

-continued
| Compound |
|---|
| 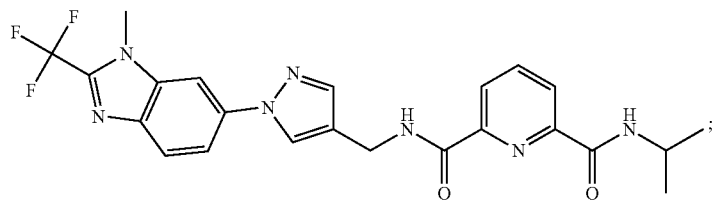 234 |
| 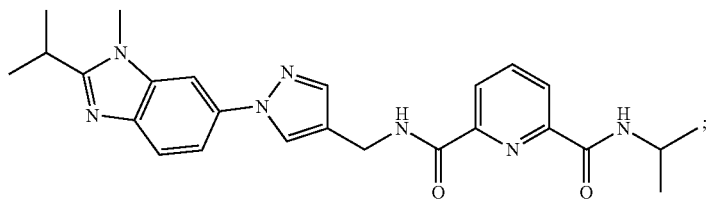 235 |
| 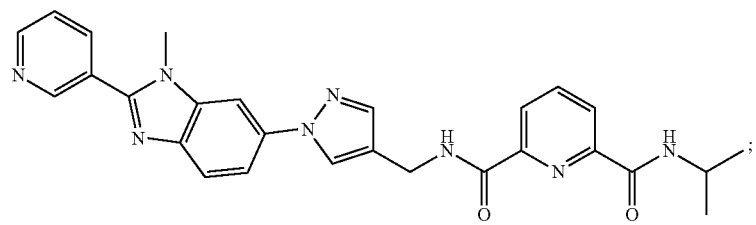 238 |
| 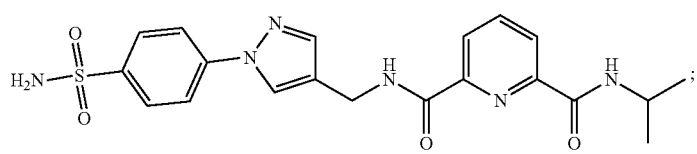 241 |
| 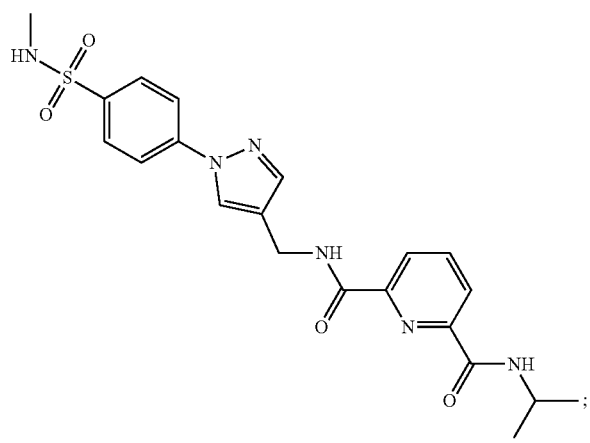 244 |

-continued
| Compound |
|---|
| 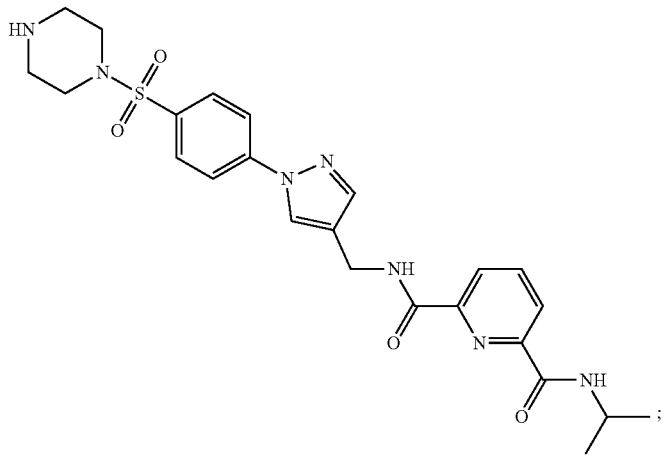 245 |
| 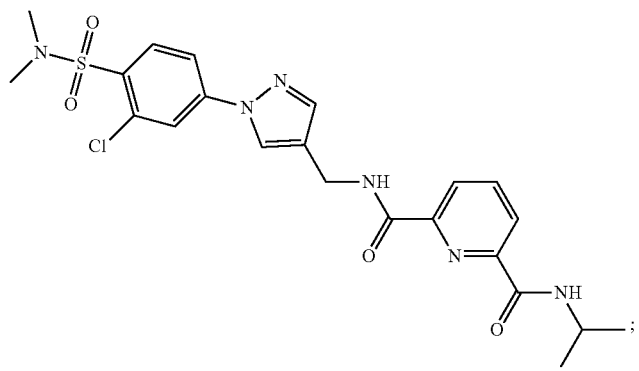 246 |
| 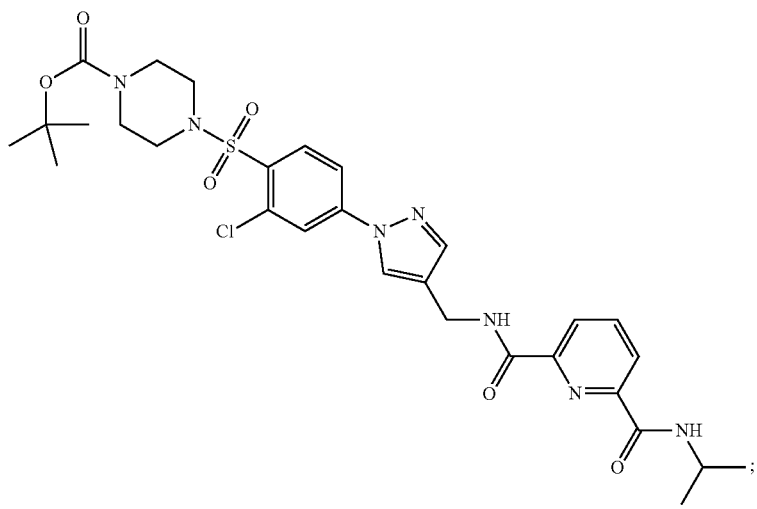 247 |

-continued
Compound
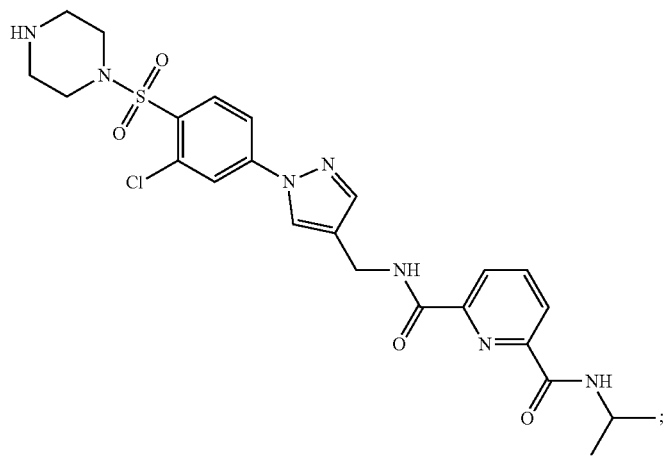
248
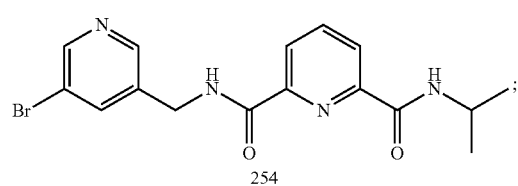
254
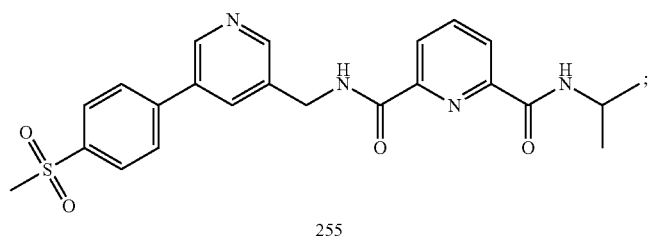
255
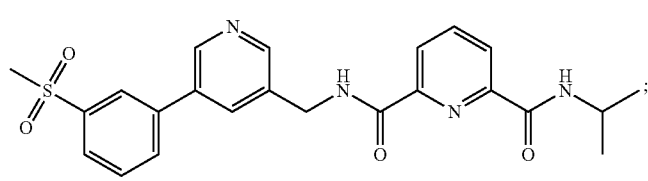
256
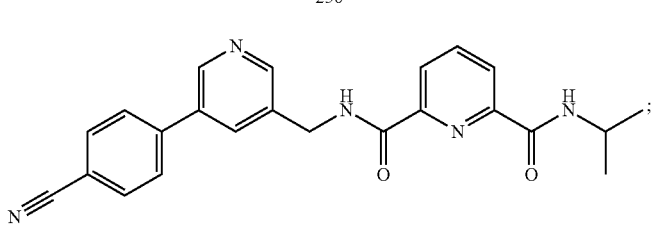
257
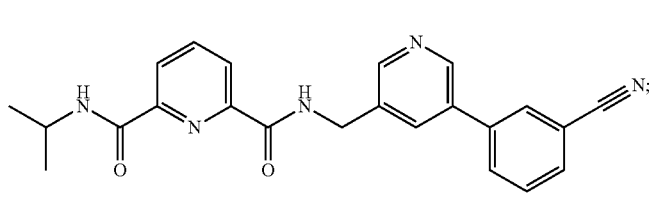
258

| Compound |
|---|
| 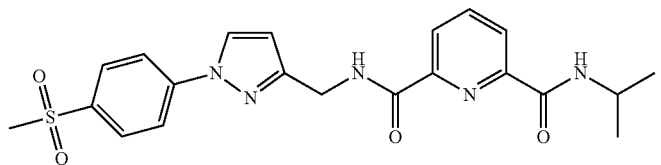 |
| 309 |
| and |
| 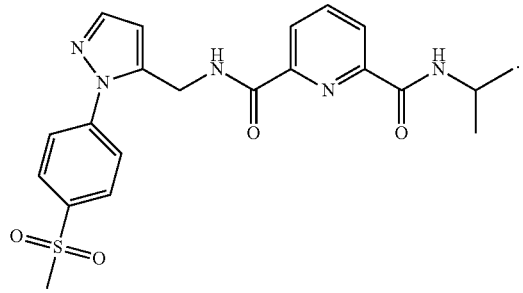 |
| 310 |
16. The compound of claim 15 selected from the group consisting of:
| Compound |
|---|
| 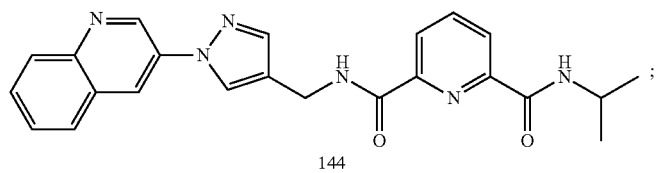 |
| 144 |
| 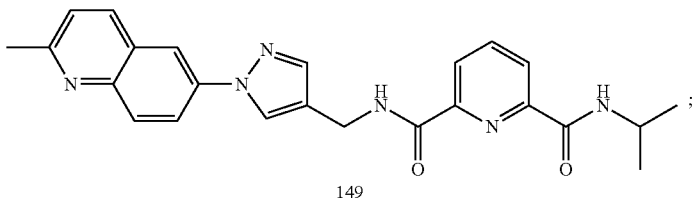 |
| 149 |
| 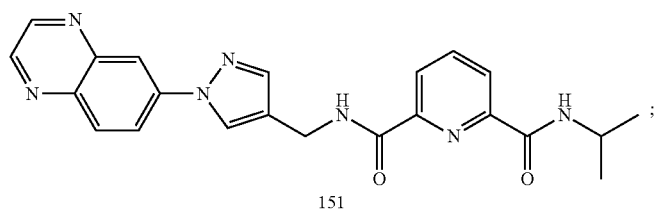 |
| 151 |
| 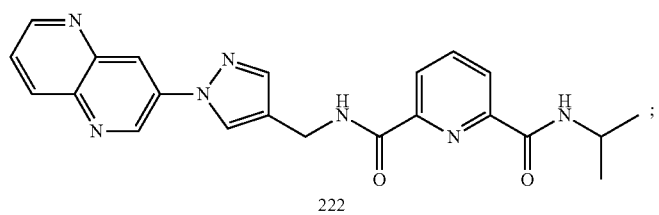 |
| 222 |

-continued
Compound
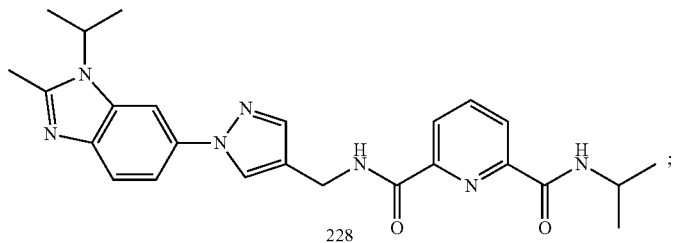
228
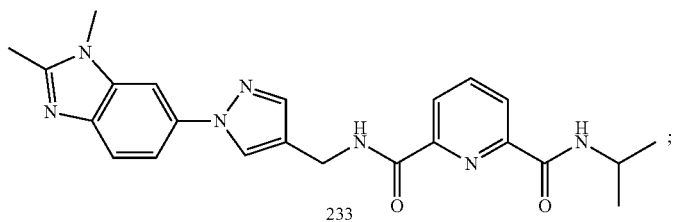
233
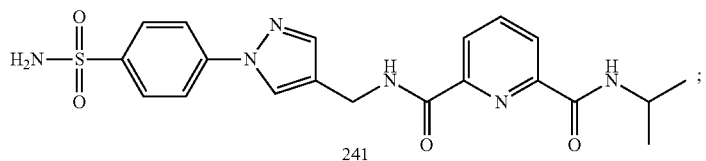
241
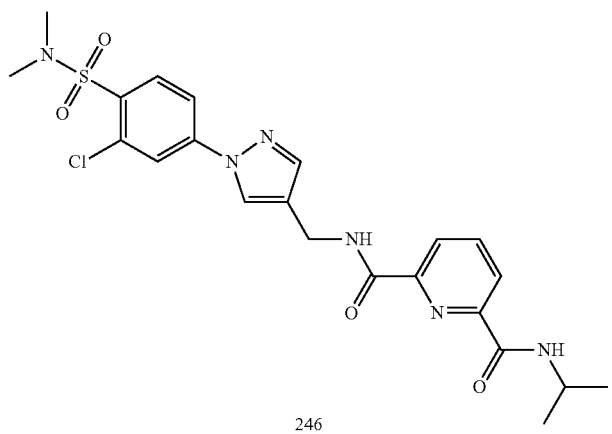
246
and
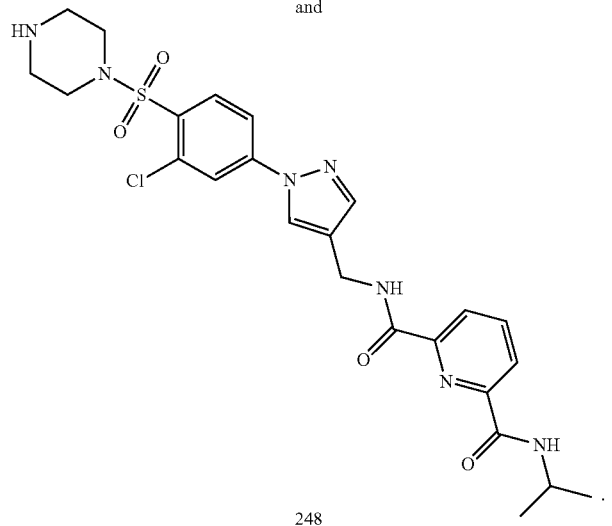
248

17. The compound of claim 16 wherein said compound is compound 144:

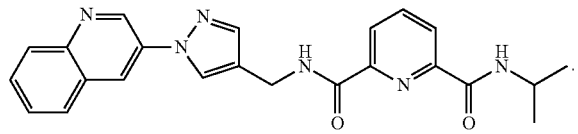

18. The compound of claim 16 wherein said compound is compound 149:

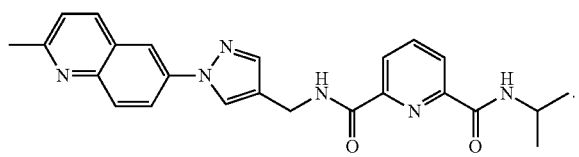

19. The compound of claim 16 wherein said compound is compound 151:

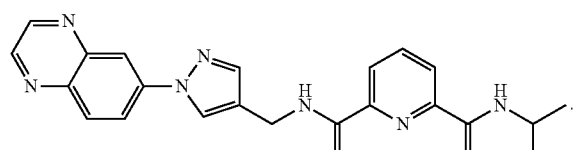

20. The compound of claim 16 wherein said compound is compound 222:

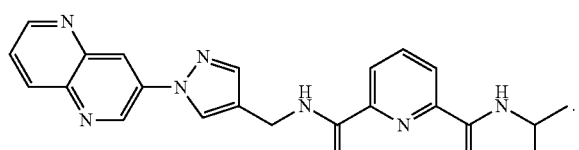

21. The compound of claim 16 wherein said compound is compound 228:

22. The compound of claim 16 wherein said compound is compound 233:

23. The compound of claim 16 wherein said compound is compound 241:

24. The compound of claim 16 wherein said compound is compound 246:

25. The compound of claim 16 wherein said compound is compound 248:

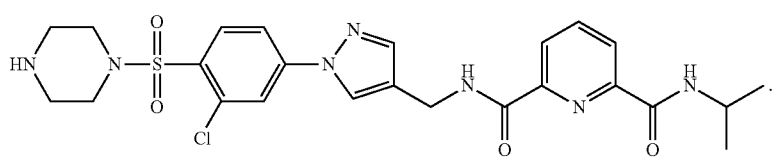

* * * * *